United States Patent
Kim et al.

(10) Patent No.: US 10,064,843 B2
(45) Date of Patent: Sep. 4, 2018

(54) BIS-AMIDE DERIVATIVE AND USE THEREOF

(71) Applicant: University-Industry Cooperation Group of Kyung Hee University, Gyeonggi-do (KR)

(72) Inventors: Sung Soo Kim, Seoul (KR); Won Jea Cho, Gwangju (KR)

(73) Assignee: University-Industry Cooperation Group of Kyung Hee University, Gyeonggi-do (KR)

(*) Notice: Subject to any disclaimer, the term of this patent is extended or adjusted under 35 U.S.C. 154(b) by 0 days.

(21) Appl. No.: 15/021,001

(22) PCT Filed: Sep. 5, 2014

(86) PCT No.: PCT/KR2014/008402
§ 371 (c)(1),
(2) Date: Jun. 21, 2016

(87) PCT Pub. No.: WO2015/037892
PCT Pub. Date: Mar. 19, 2015

(65) Prior Publication Data
US 2016/0297751 A1    Oct. 13, 2016

(30) Foreign Application Priority Data

Sep. 10, 2013 (KR) .......................... 10-2013-0108748

(51) Int. Cl.
*A61K 31/404* (2006.01)
*C07D 209/42* (2006.01)
(Continued)

(52) U.S. Cl.
CPC .......... *A61K 31/404* (2013.01); *A23L 33/175* (2016.08); *A61K 31/167* (2013.01); 
(Continued)

(58) Field of Classification Search
CPC .......................... A61K 31/404; C07D 209/04
(Continued)

(56) References Cited

U.S. PATENT DOCUMENTS

2013/0184222 A1* 7/2013 Popovici-Muller ..........................
C07C 237/22
514/19.3

FOREIGN PATENT DOCUMENTS

DE      2259567 A1 * 6/1974  ......... C07D 207/337
WO   WO 2009-150248      12/2009
(Continued)

OTHER PUBLICATIONS

Popovici-Mullet et al, Medicinal Chemistry Letters (2012), vol. 3, pp. 850-855.*
(Continued)

*Primary Examiner* — Craig D Ricci
*Assistant Examiner* — Janet L. Coppins
(74) *Attorney, Agent, or Firm* — Cesari and McKenna, LLP

(57) ABSTRACT

The present invention relates to a novel bis-amide derivative compound or a pharmaceutically acceptable salt thereof; a method of preparation thereof; and a pharmaceutical composition for preventing or treating diseases caused by hepatitis C virus infection and health functional food for preventing or ameliorating diseases caused by hepatitis C virus infection, containing the bis-amide derivative compound or a pharmaceutically acceptable salt thereof as an active ingredient.

The novel bis-amide derivative compound of the present invention, particularly WJCPA-126, specifically binds to the catalytic site of CypA to effectively inhibit the activity of an isomerase, and the duration of the inhibitory effect can be increased because WJCPA-126 binds to CypA with high (Continued)

binding affinity exhibiting a low dissociation rate ($K_{off}$). Accordingly, WJCPA-126 has nontoxic and non-immunosuppressive characteristics and can effectively inhibit HCV replication in vitro and in vivo model systems. Additionally, WJCPA-126 reactivates the host interferon response through an increase in the expression of IFN-stimulated genes (ISGs) and the inhibition of interleukin-8 (IL-8) secretion. Therefore, a series of the bis-amide derivatives including WJCPA-126 can be useful as a novel type CypA inhibitor exhibiting antiviral effect.

16 Claims, 20 Drawing Sheets

Specification includes a Sequence Listing.

(51) Int. Cl.
| | |
|---|---|
| C07C 237/22 | (2006.01) |
| C07D 209/18 | (2006.01) |
| A61K 31/167 | (2006.01) |
| A61K 31/357 | (2006.01) |
| A61K 31/44 | (2006.01) |
| A61K 31/7056 | (2006.01) |
| A61K 38/07 | (2006.01) |
| A61K 38/21 | (2006.01) |
| C07C 231/06 | (2006.01) |
| C07D 213/82 | (2006.01) |
| C07D 317/60 | (2006.01) |
| C07D 405/12 | (2006.01) |
| A23L 33/175 | (2016.01) |

(52) U.S. Cl.
CPC ............ *A61K 31/357* (2013.01); *A61K 31/44* (2013.01); *A61K 31/7056* (2013.01); *A61K 38/07* (2013.01); *A61K 38/212* (2013.01); *C07C 231/06* (2013.01); *C07C 237/22* (2013.01); *C07D 209/18* (2013.01); *C07D 209/42* (2013.01); *C07D 213/82* (2013.01); *C07D 317/60* (2013.01); *C07D 405/12* (2013.01); *C07C 2601/14* (2017.05)

(58) Field of Classification Search
USPC ...................................................... 514/252.1
See application file for complete search history.

(56) References Cited

FOREIGN PATENT DOCUMENTS

| WO | WO 2009150248 A1 * | 12/2009 | ........... C07C 237/22 |
|---|---|---|---|
| WO | WO-2012/033525 A2 | 3/2012 | |
| WO | WO 2012-129452 | 9/2012 | |
| WO | WO-2013/107405 A1 | 7/2013 | |

OTHER PUBLICATIONS

Jacobs et al "Discovery, Synthesis, and Structure-Based Optimization of a Series of N-(tert-Butyl)-2-(N-arylamido)-2-(pyridine-3-yl) Acetamides (ML188) as Potent Noncovalent Small Molecules Inhibitors of the Severe Acute Respiratory Syndrome Coronavirus (SARS-CoV) 3CL Protease" Journal of Medicinal Chemistry vol. 56, pp. 534-546, 2013.
Zuo et al "Synthesis of 4-Methyl-1,2,3-thiadiazole Derivatives via Ugi Reaction and Their Biological Activities" Journal of Agriculture and Food Chemistry vol. 58, pp. 2755-2762, 2010.
Drouet, et al., "Ugi four-component reaction of alcohols: Stoichiometric and catalytic oxidation/MCR sequences", Organic Letters, vol. 15, No. 11, pp. 2854-2857, Jun. 7, 2013.
Kumar, et al., "An expedient route to imidazo[1,4]diazepin-7-ones via a post-Ugi gold-catalyzed heteroannulation", Organic Letters, Vol, 15, No. 8, pp. 1874-1877, Apr. 19, 2013.
Kumar, et al., "Cold(I)-catalyzed post-Ugi hydroarylation: an approach to pyrrolopyridines and azepinoindoles", European Journal of Organic Chemistry, Issue 12, pp. 2288-2292, Apr. 2013.
Pramitha, et al., "Stereoselective synthesis of bio-hybrid amphiphiles of coumarin derivatives by Ugi-Mannich triazole randomization using copper catalyzed alkyne azide click chemistry" Bioorganic & Medicinal Chemistry Letters, 22, pp. 2598-2603, 2012.
Vachhani, et al., "Diversely substituted triazolo[1,5-a][1,4]benzodiazepinones: A post-Ugi copper-catalyzed tandem azide-alkyne cycloaddition/Ullmann C-N coupling approach", European Journal of Organic Chemistry, Issue 7, pp. 1223-1227, Mar. 2014.

* cited by examiner

[FIG. 1]
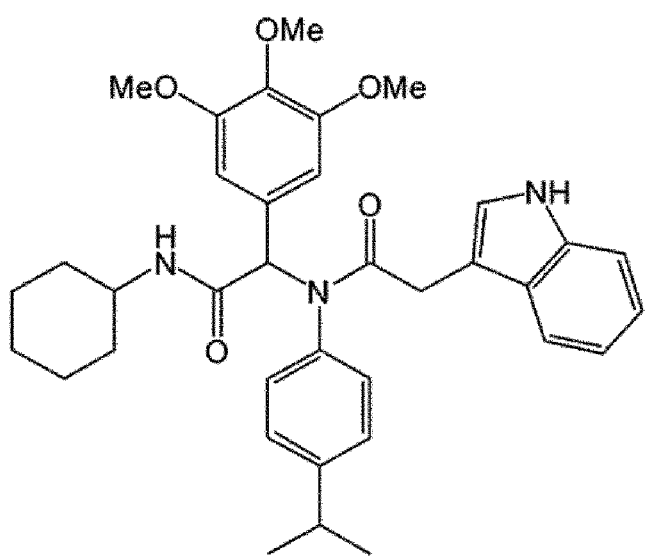
WJCPA-126
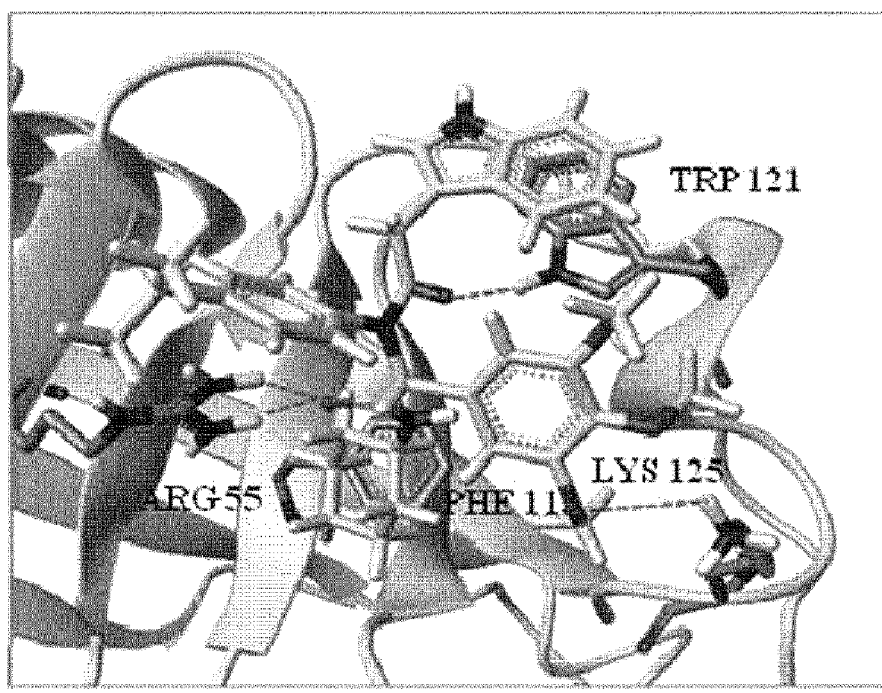

[FIG. 2]
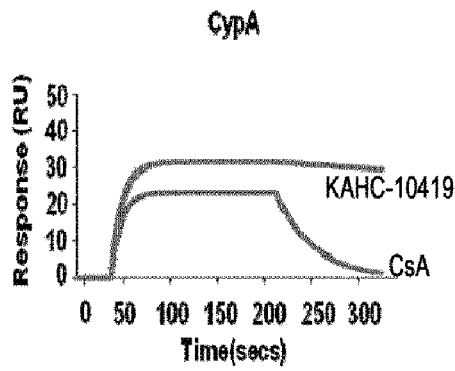
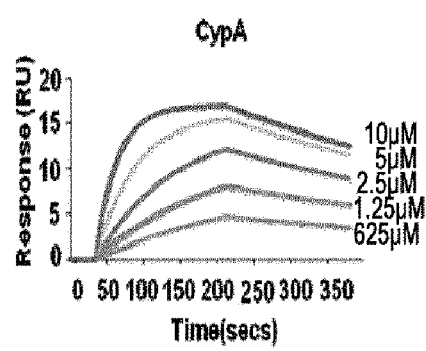
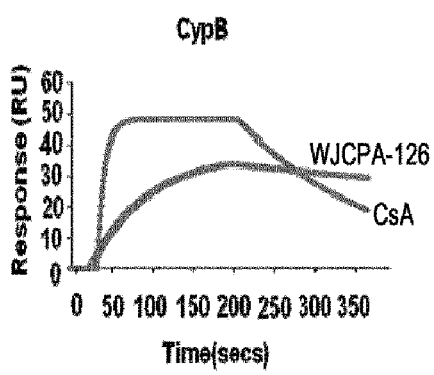
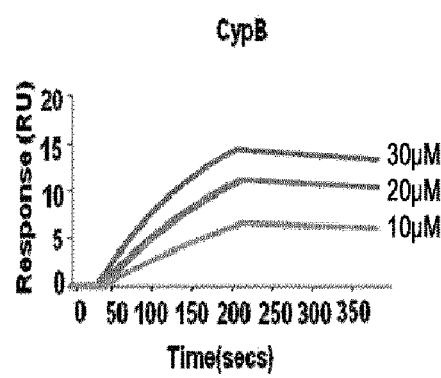

[FIG. 3]
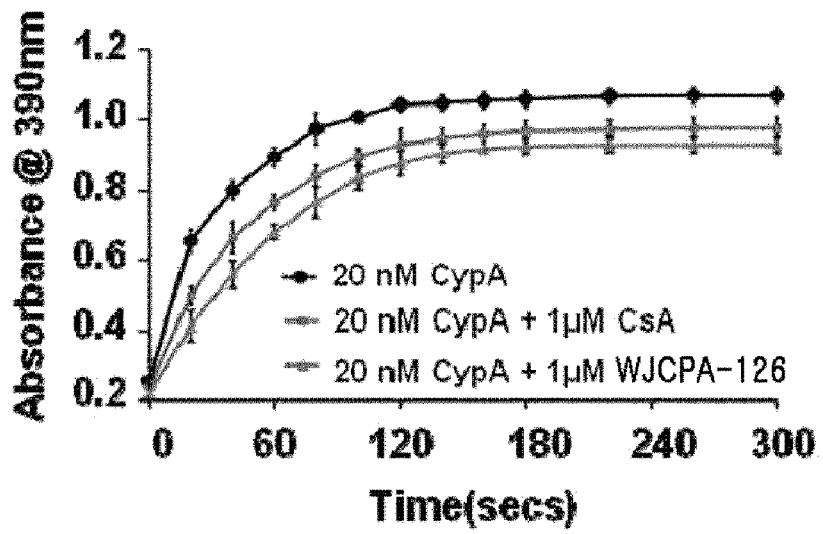
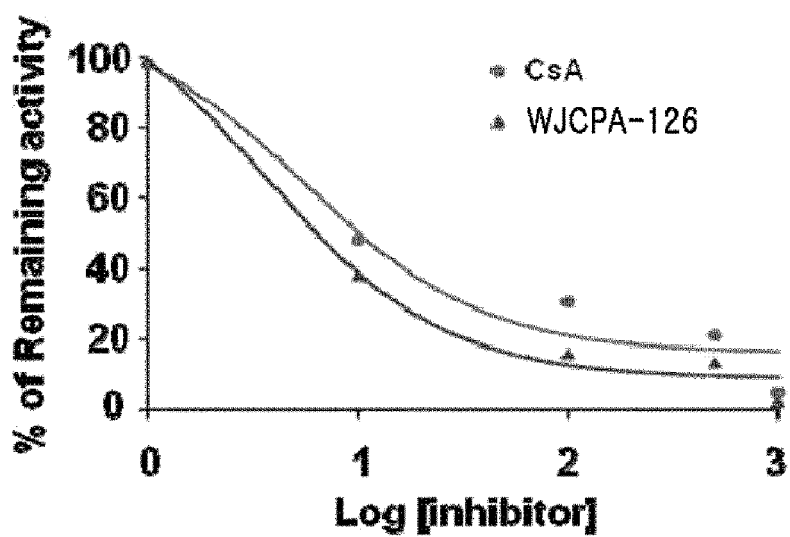
| Name | LogIC$_{50}$ | IC$_{50}$ (nM) |
|---|---|---|
| CsA | 0.744 | 5.55 |
| WJCPA-126 | 0.553 | 3.57 |

[FIG. 4]
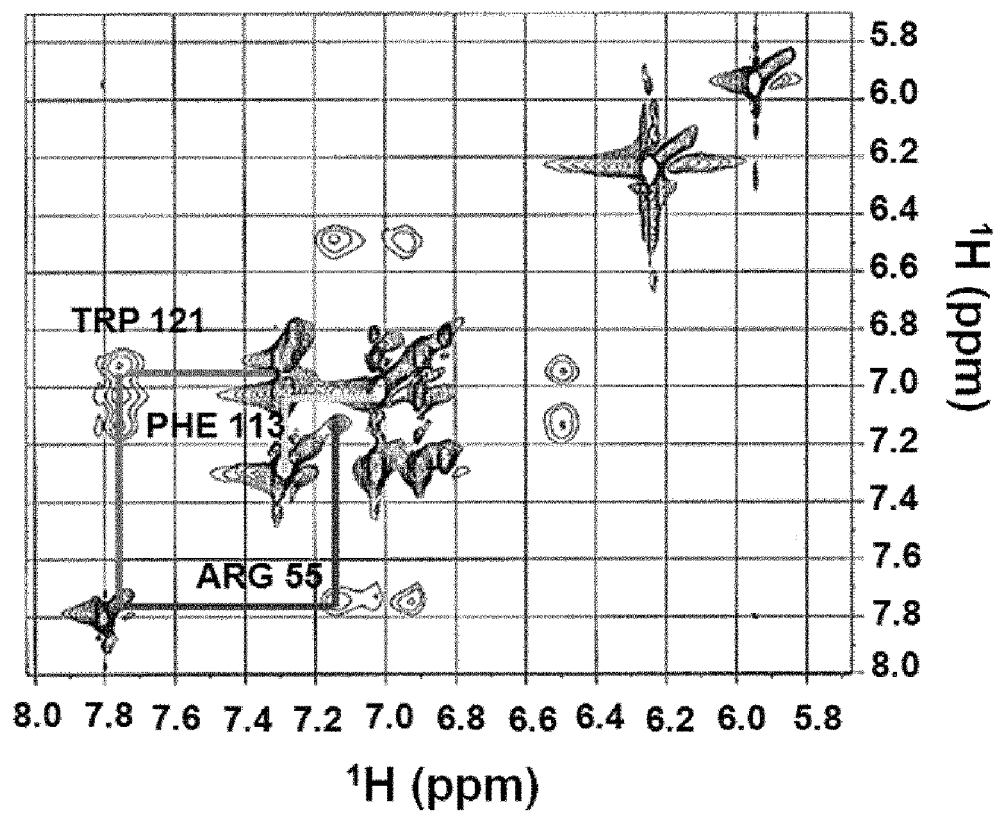

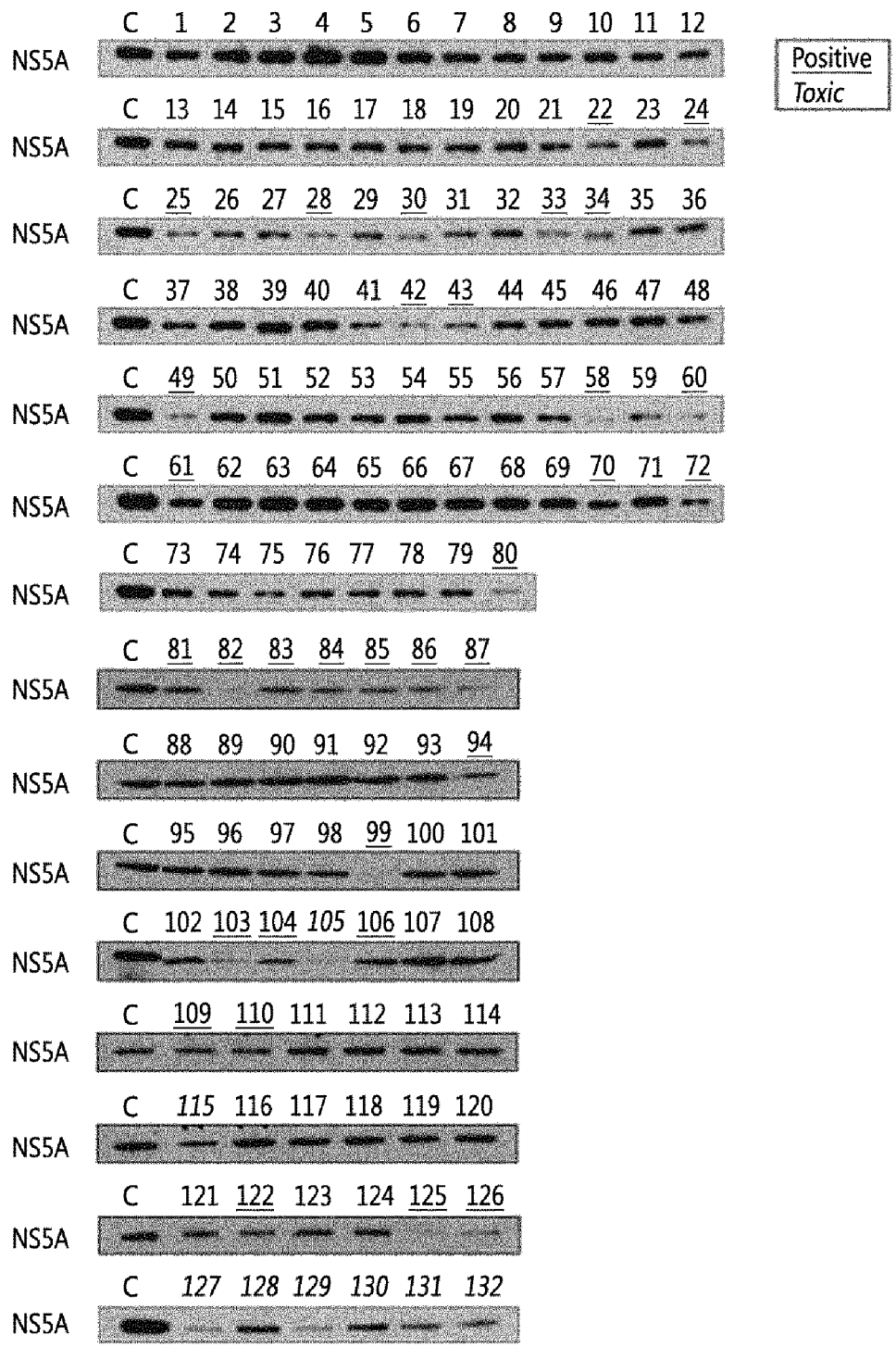
[FIG. 5]

[FIG. 6]
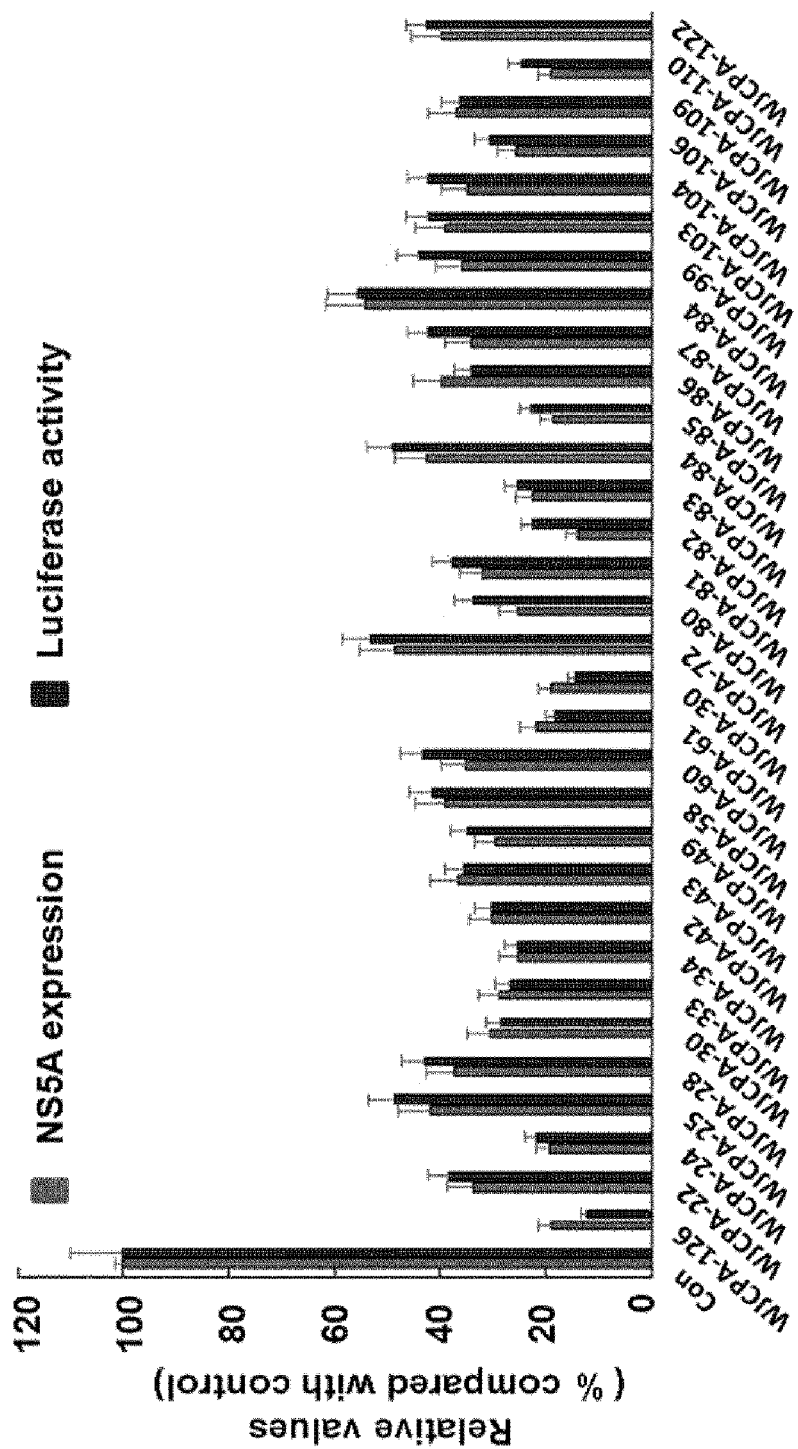

[FIG. 7]
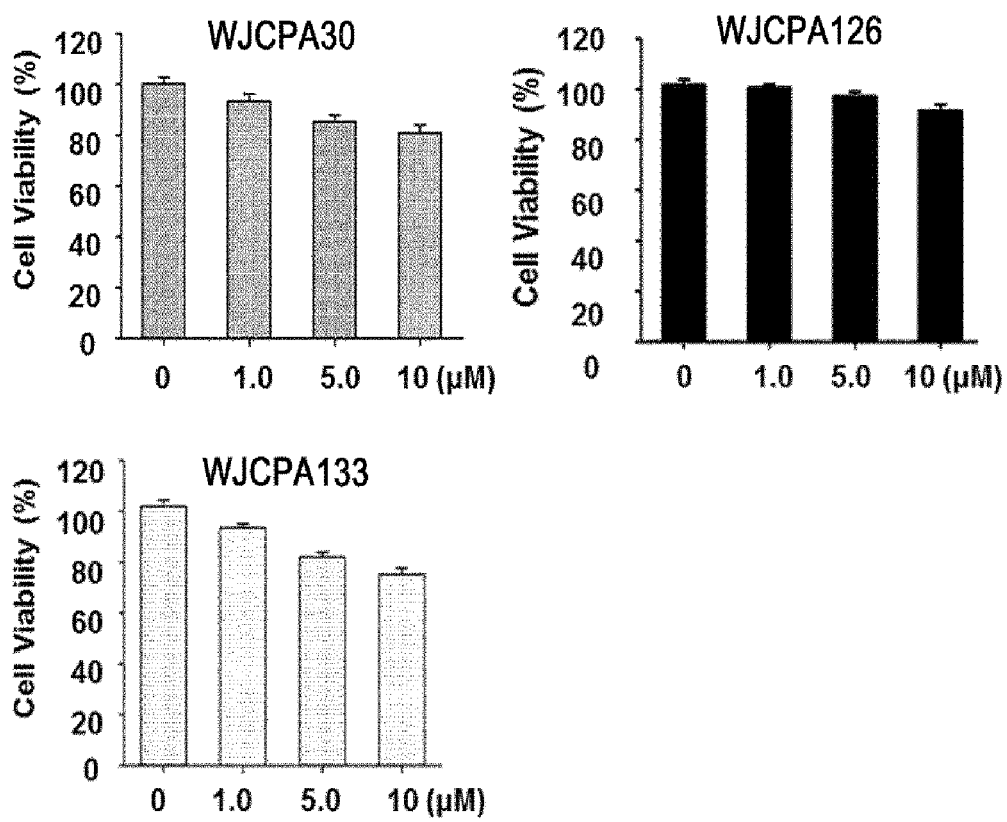

[FIG. 8]
a
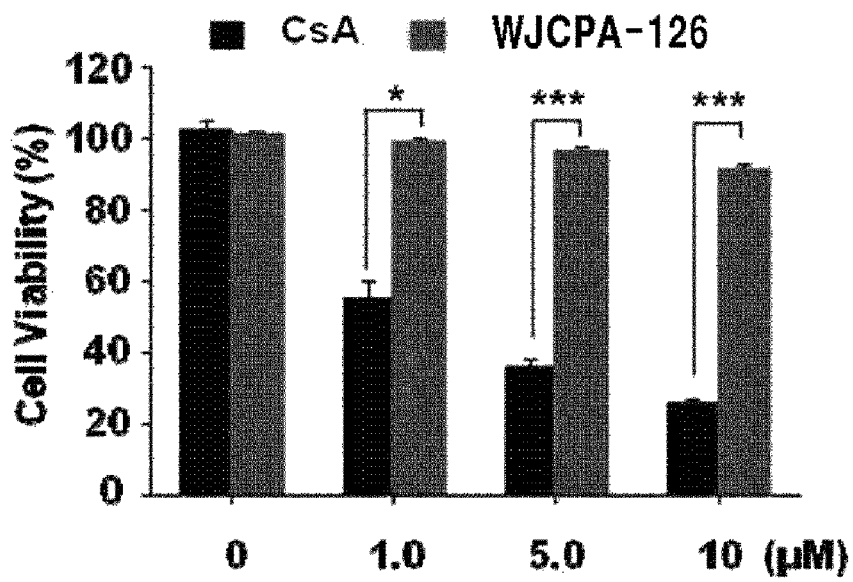
b
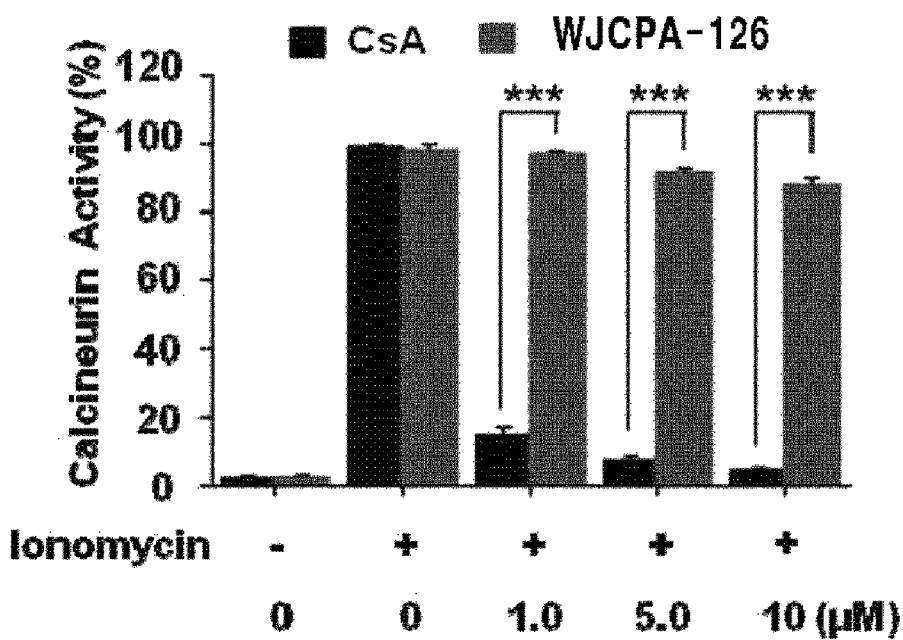

[FIG. 9]
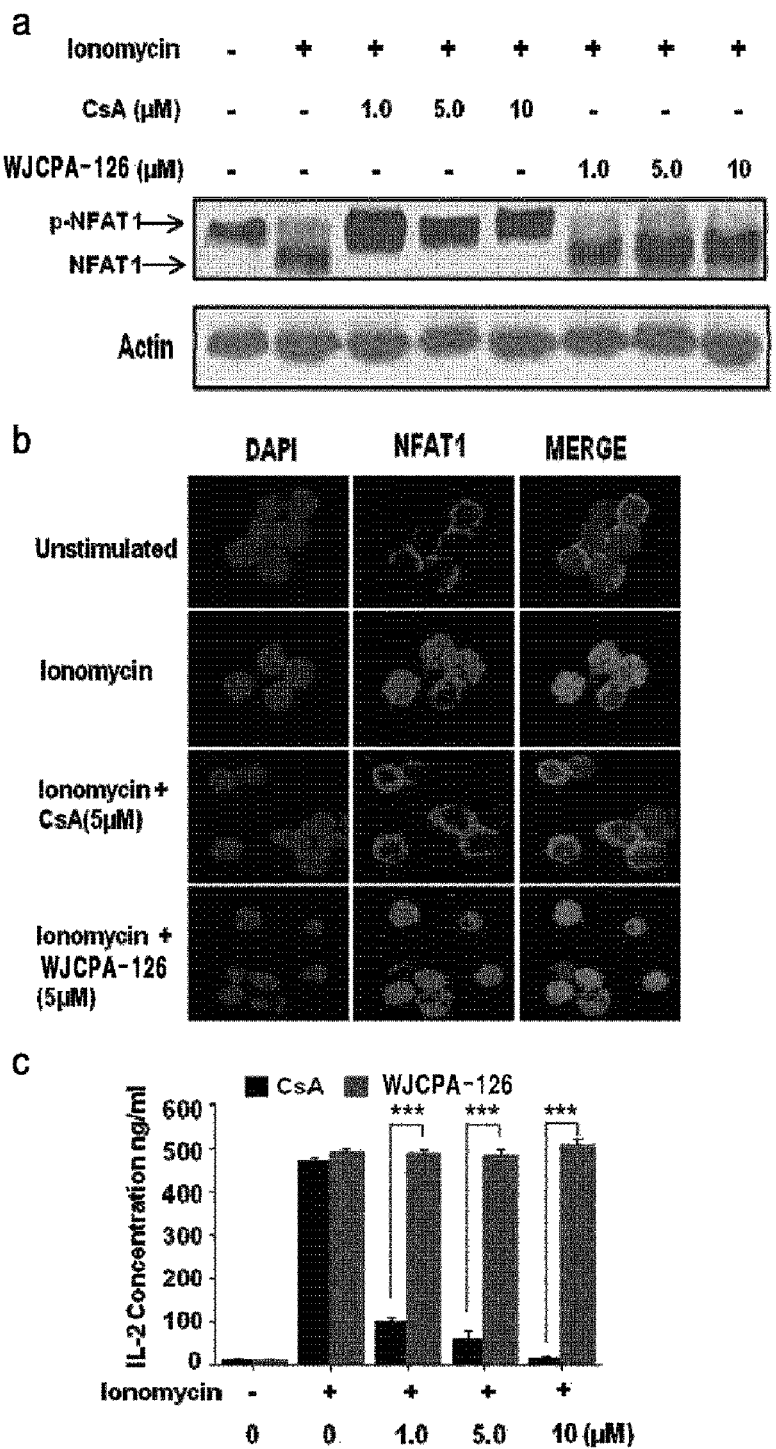

[FIG.10]
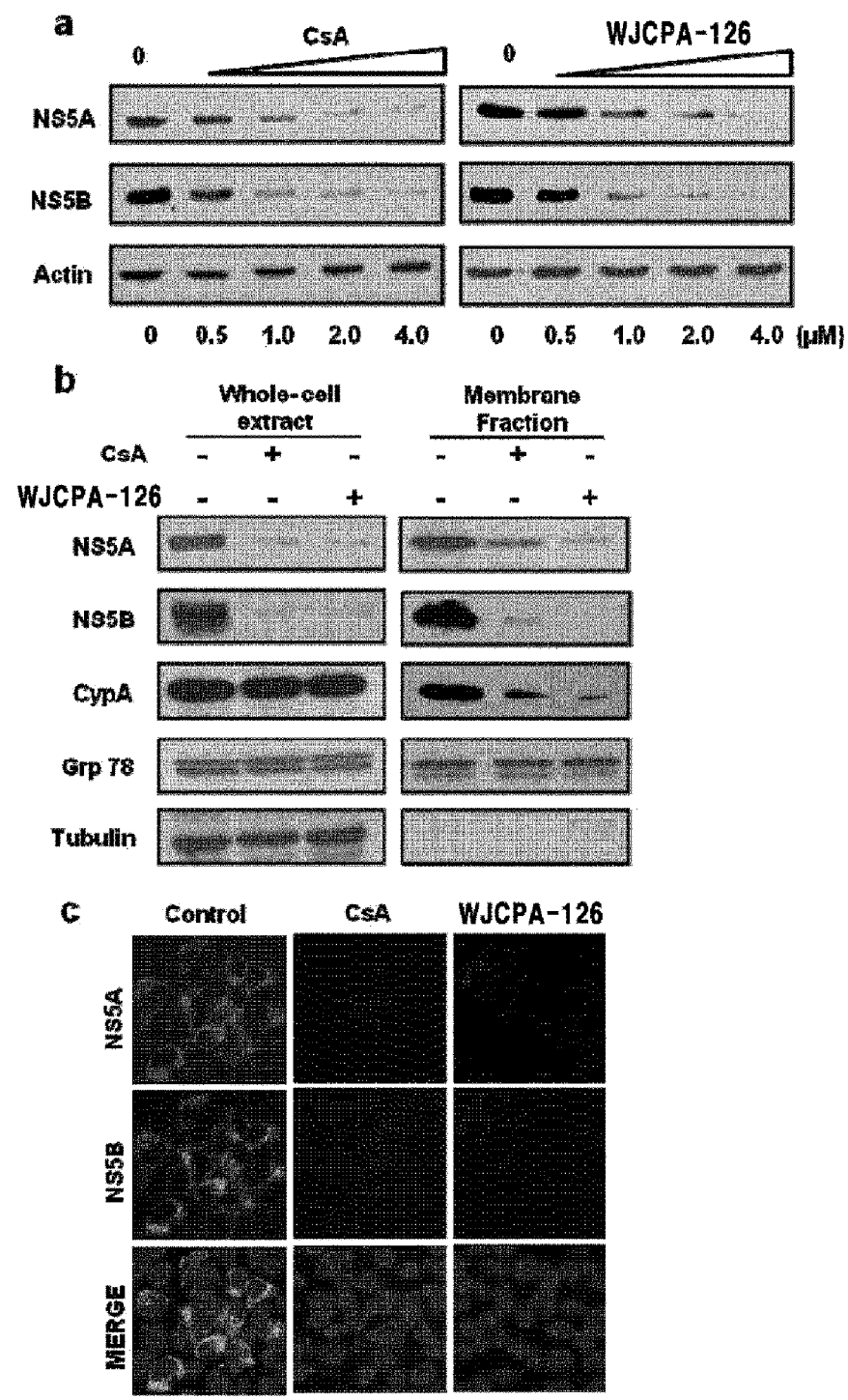

[FIG. 11]
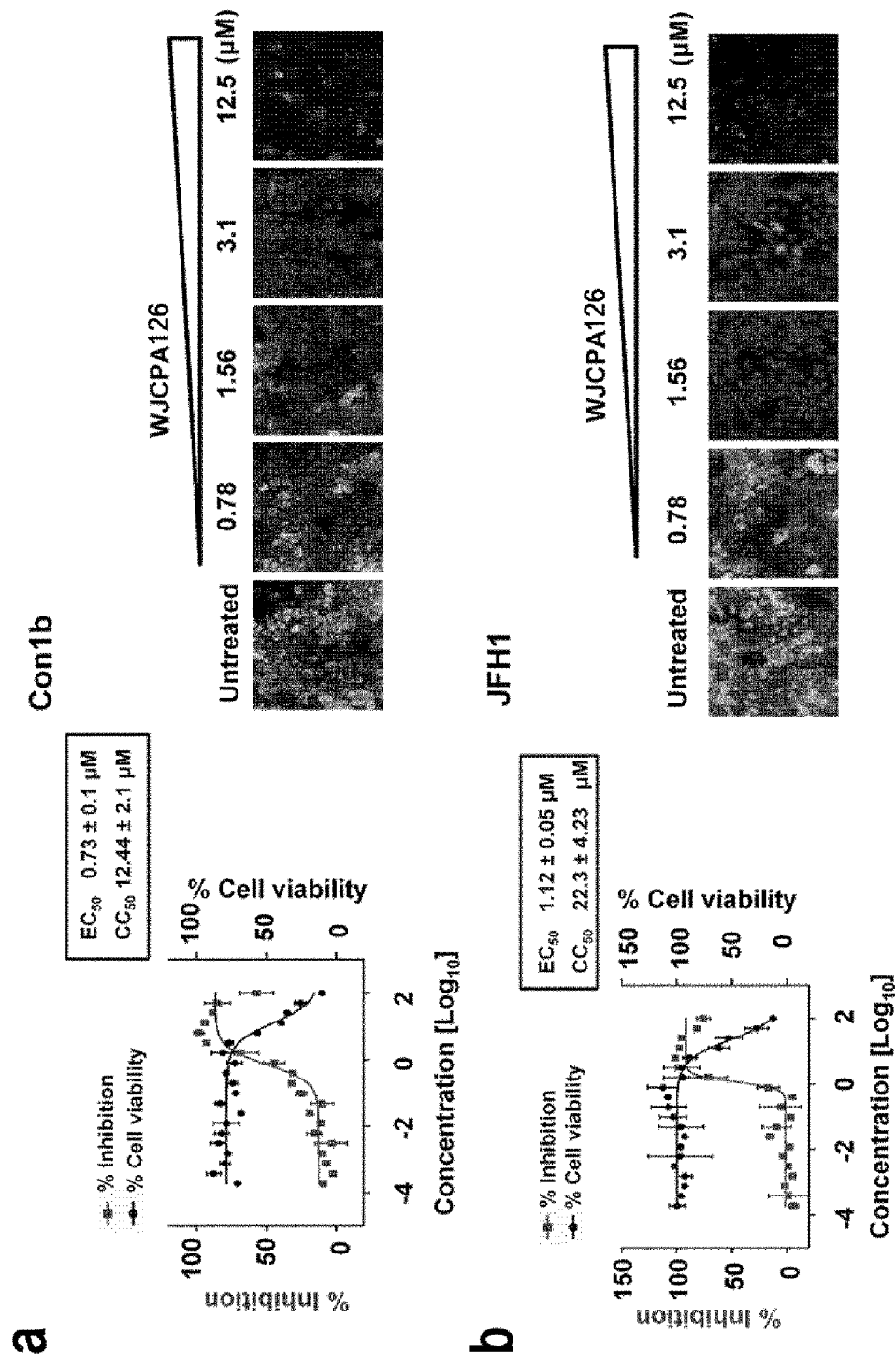

[FIG. 12]
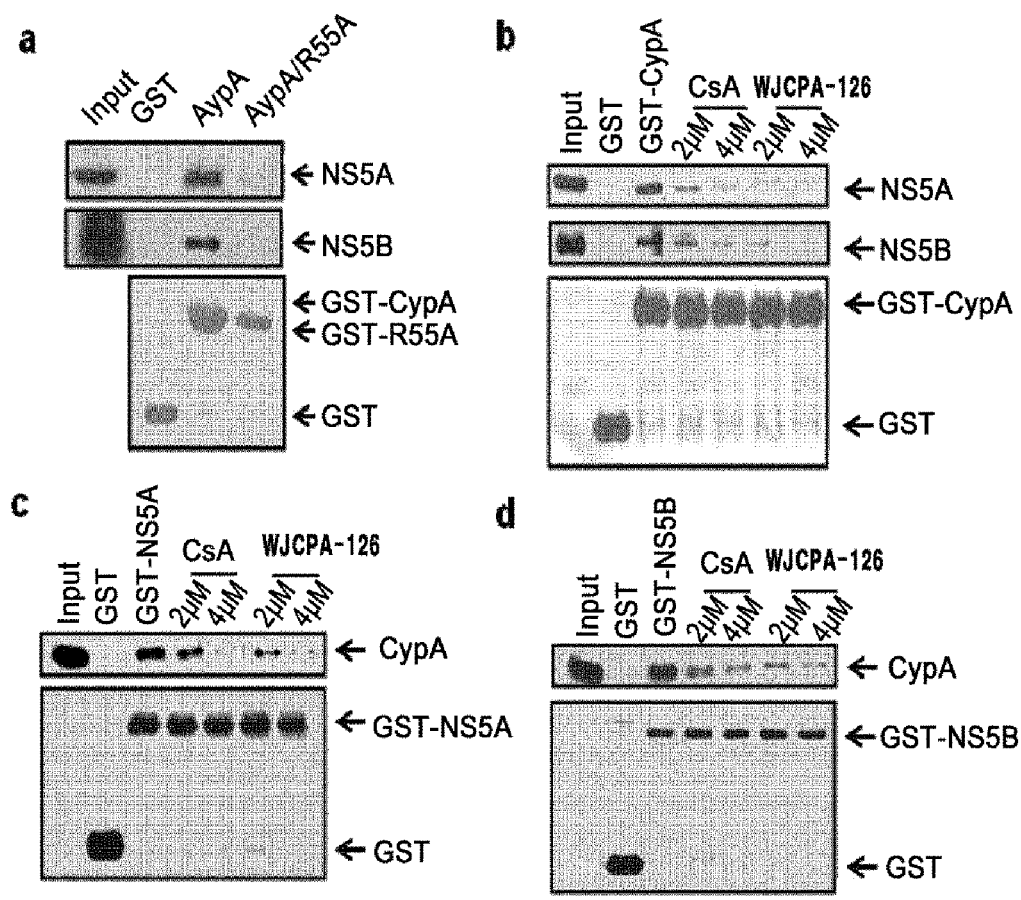

[FIG. 13]
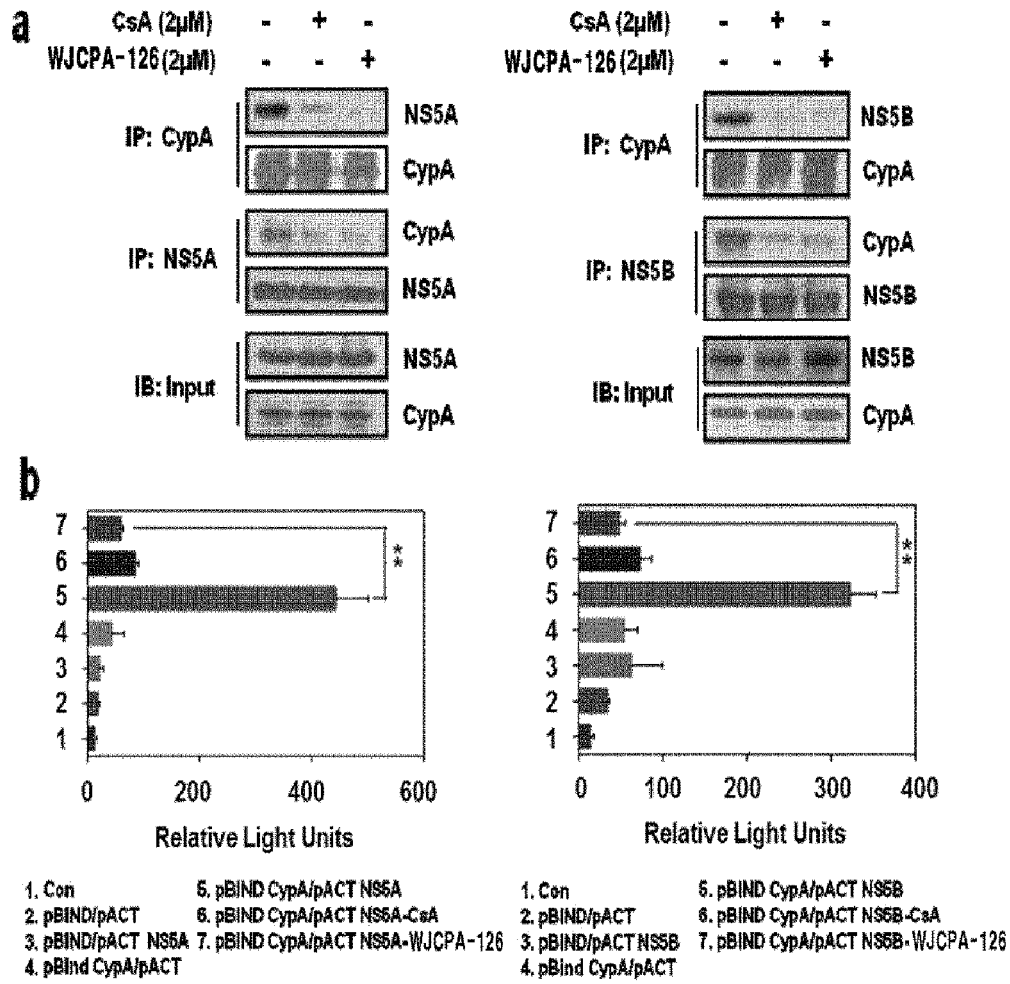

[FIG. 14]
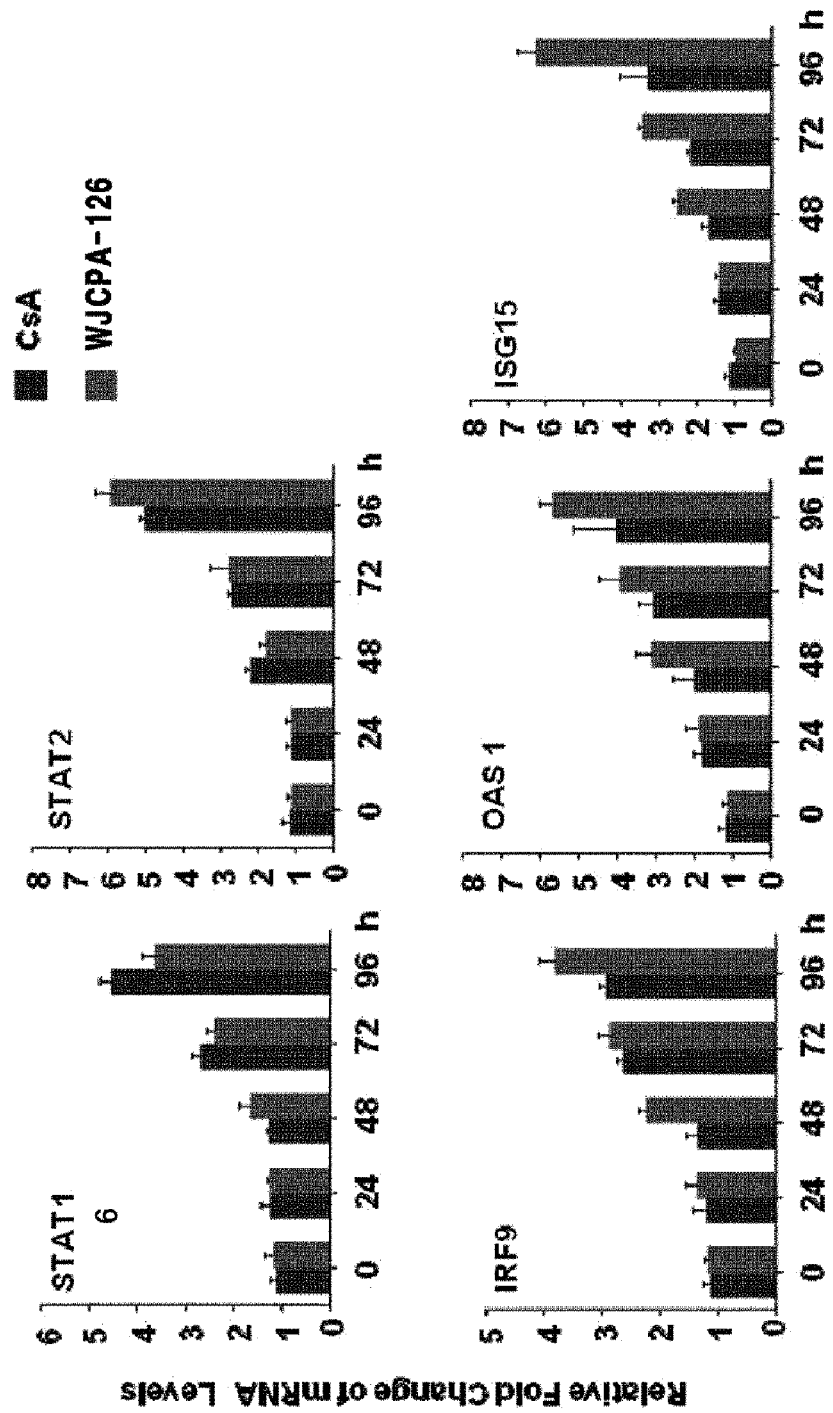

[FIG. 15]
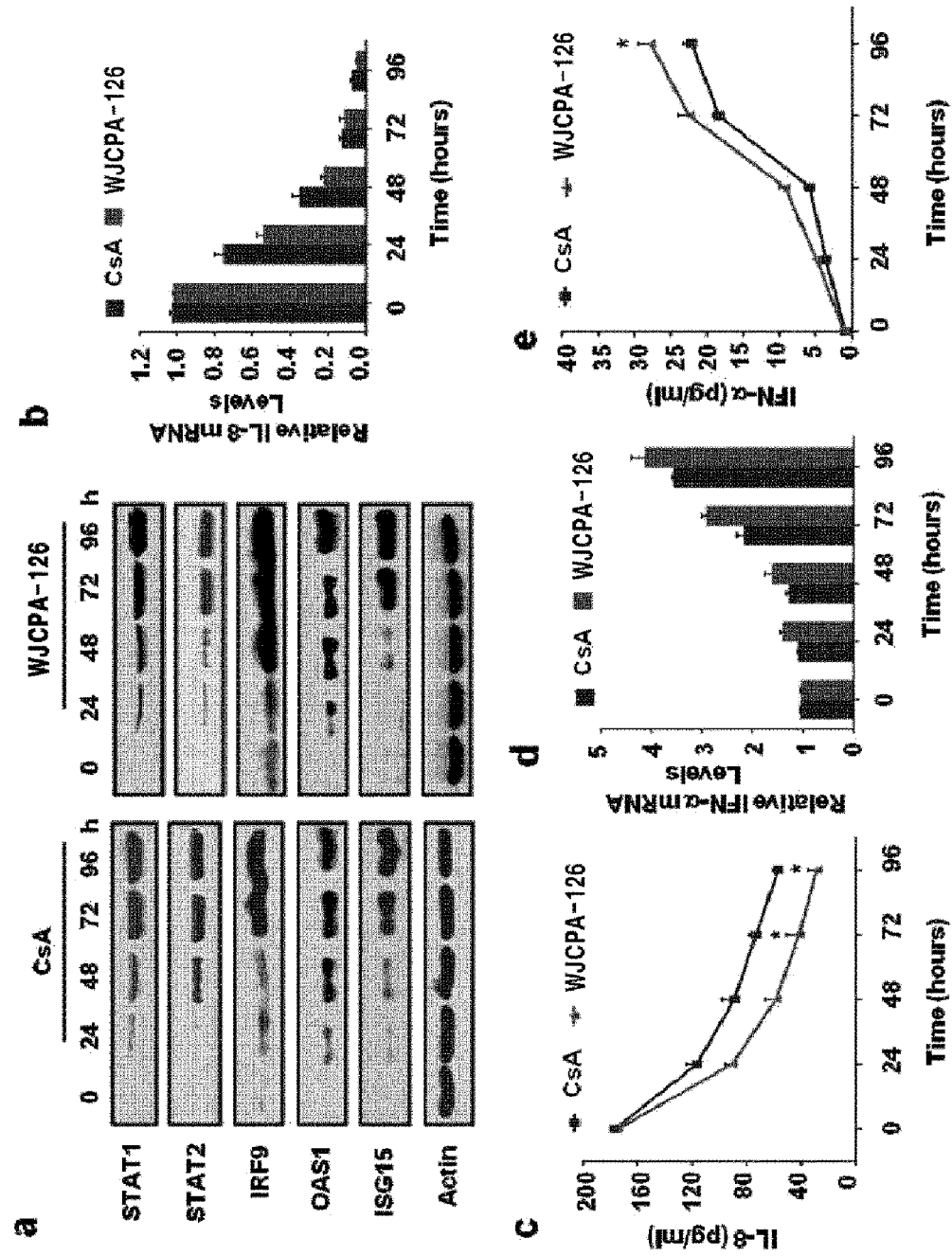

[FIG. 16]
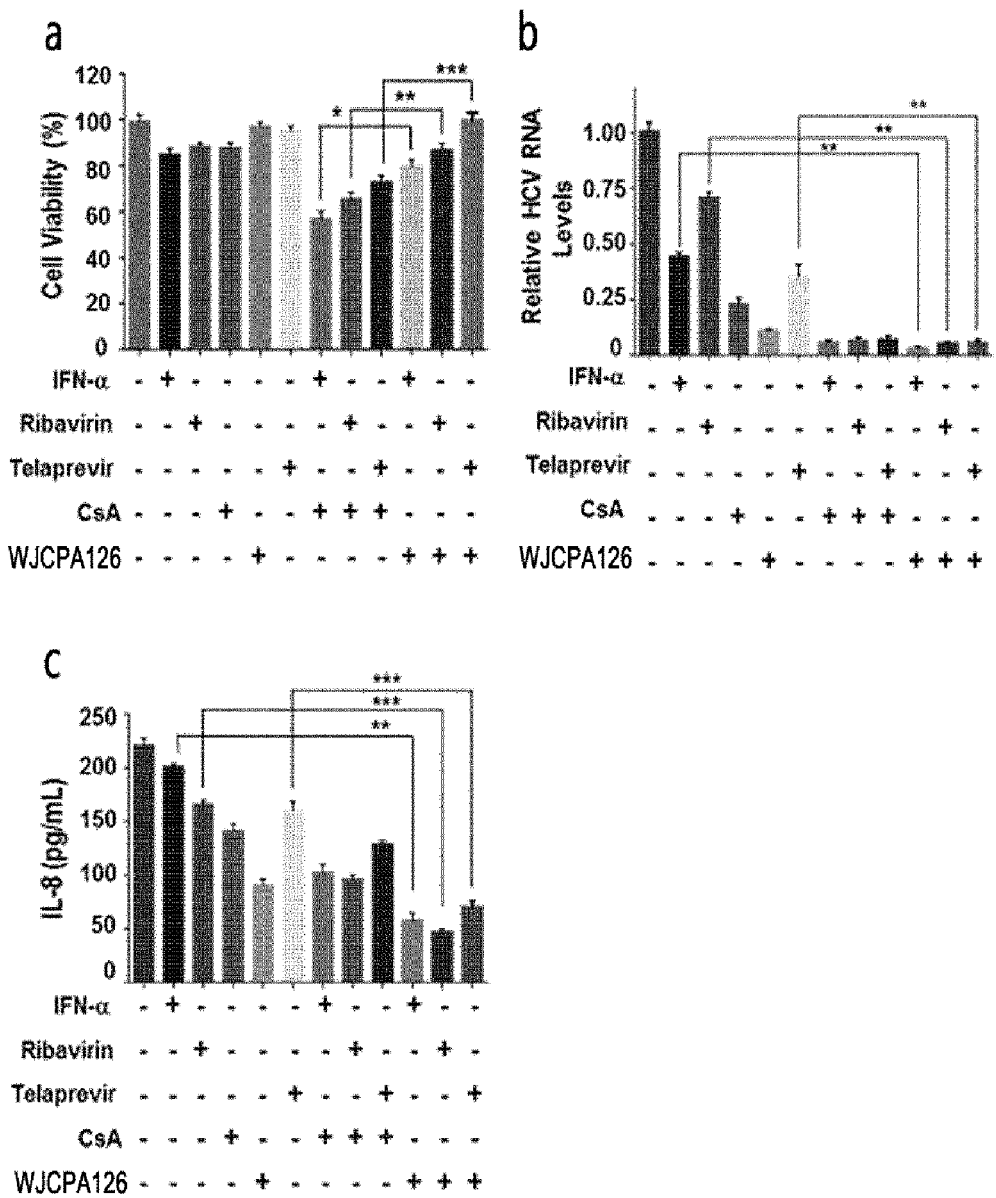

[FIG. 17]
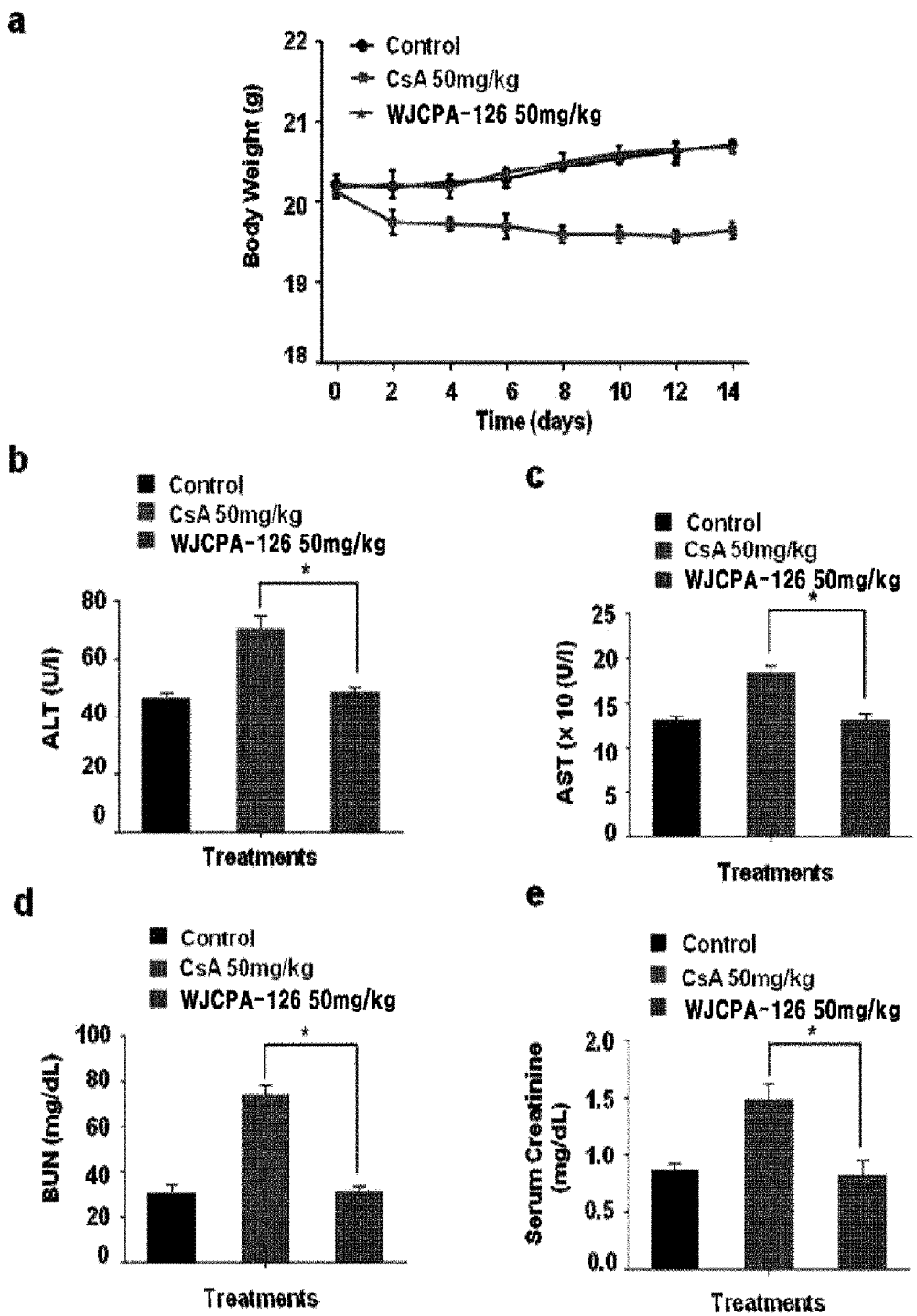

[FIG. 18]
a
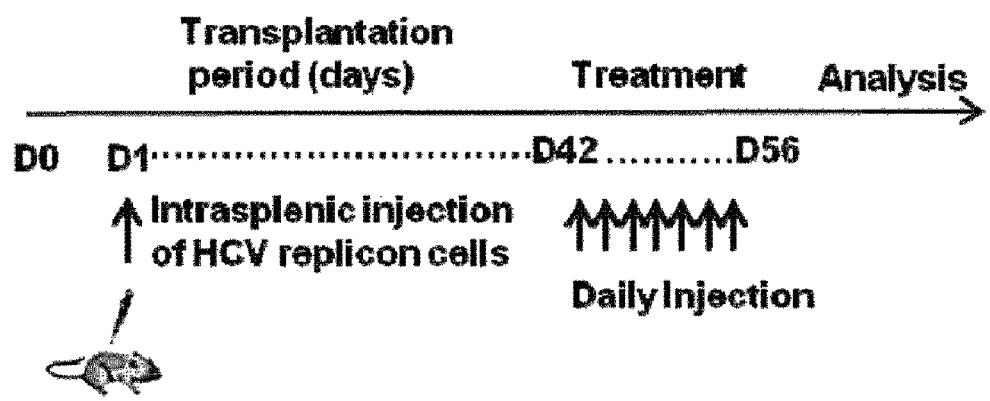
b
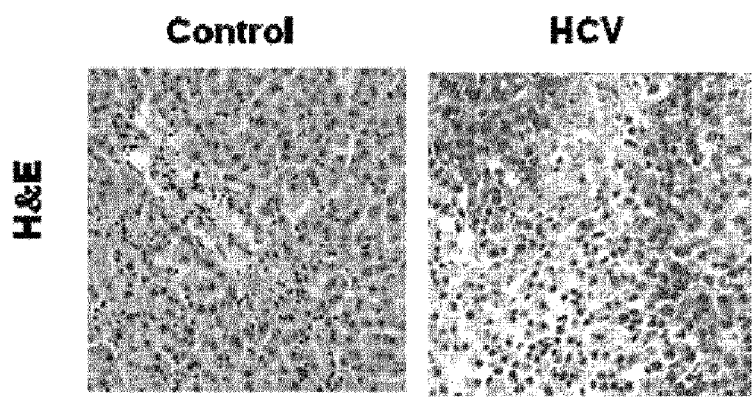

[FIG. 19]
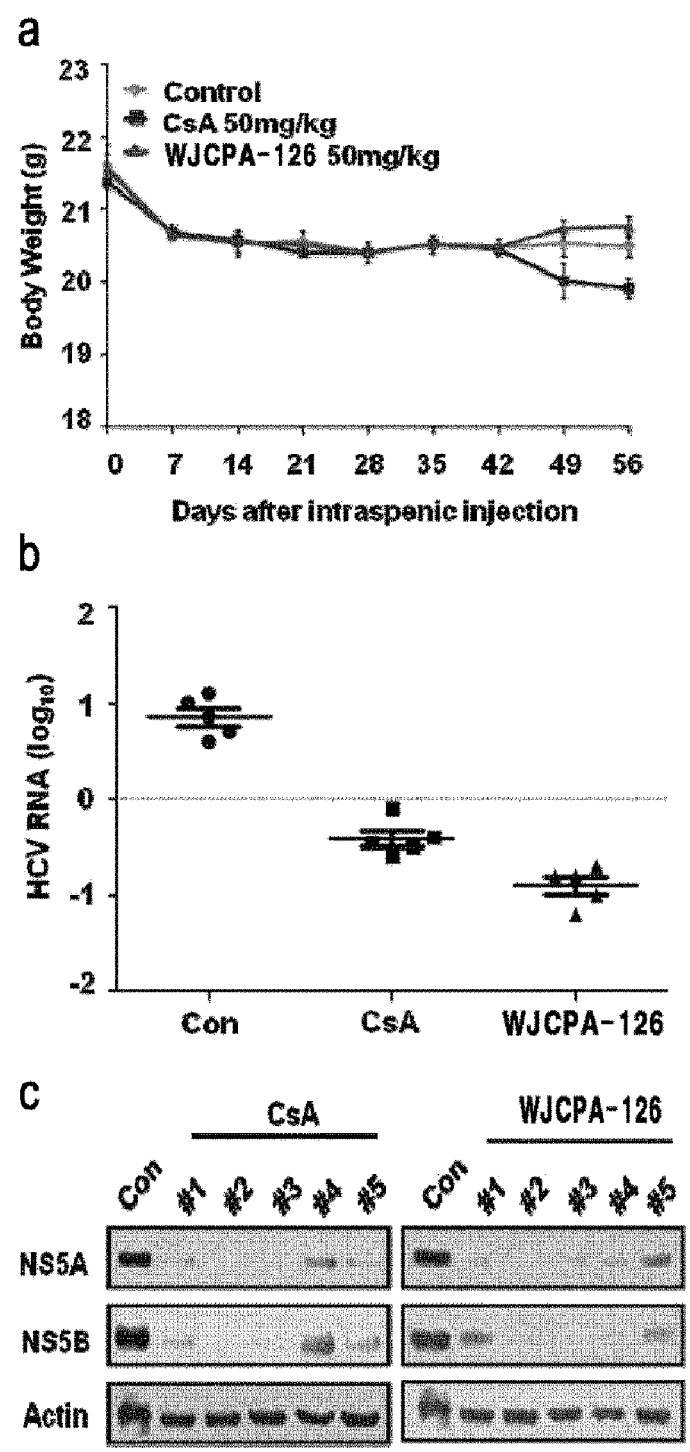

[FIG. 20]
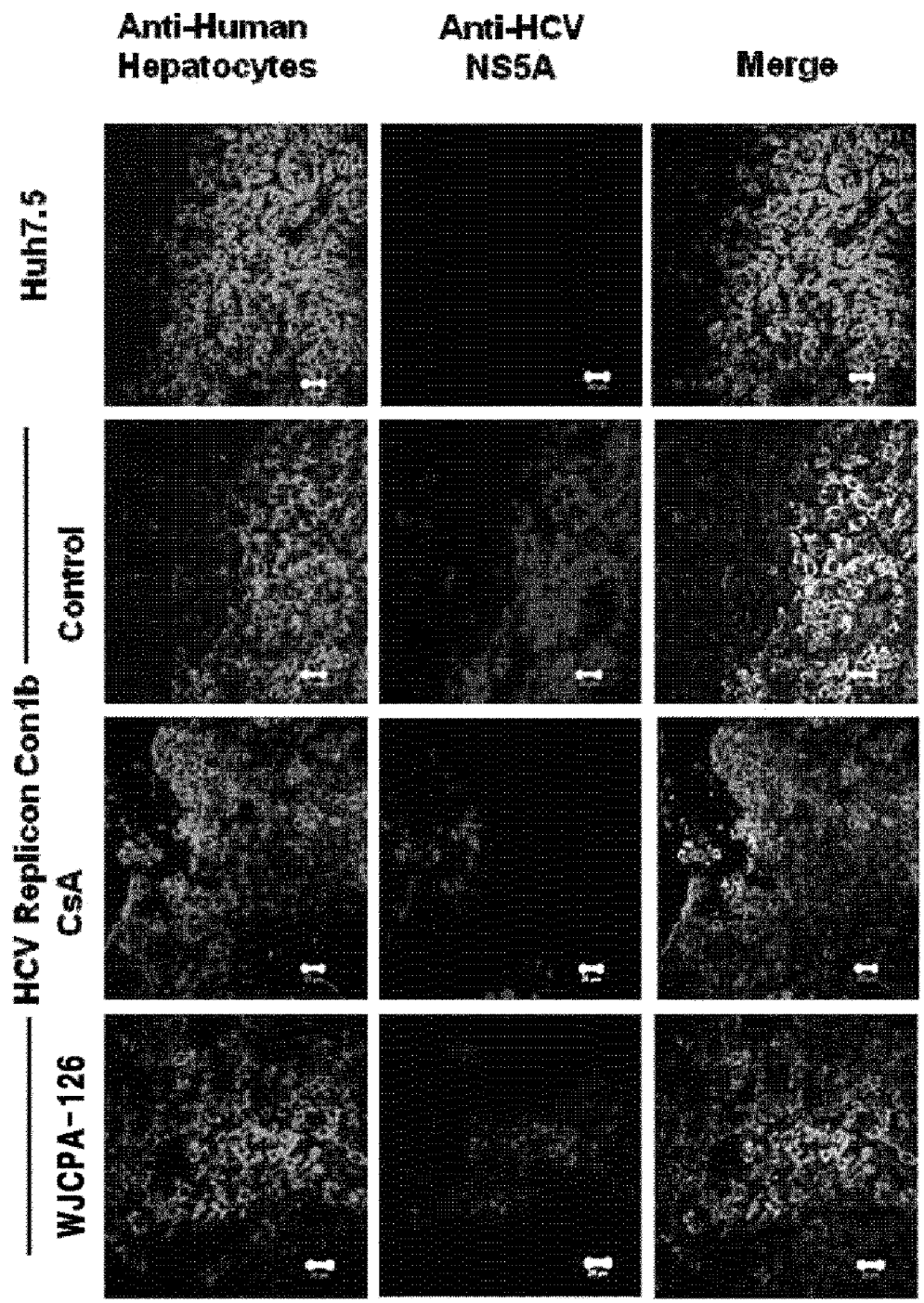

BIS-AMIDE DERIVATIVE AND USE THEREOF

PRIORITY CLAIMS AND RELATED APPLICATIONS

This application is the national stage of International Application No. PCT/KR2014/008402, filed Sep. 5, 2014, which claims the benefit of Korean Application No. 10-2013-0108748, filed Sep. 10, 2013, the entire content of which is expressly incorporated herein by reference.

TECHNICAL FIELD

The present invention relates to a bis-amide derivative compound of the following Formula 1 or a pharmaceutically acceptable salt thereof; a method of preparing the bis-amide derivative compound; and a pharmaceutical composition for preventing or treating diseases caused by hepatitis C virus infection and health functional food for preventing or ameliorating diseases caused by hepatitis C virus infection, containing the bis-amide derivative compound or a pharmaceutically acceptable salt thereof as an active ingredient.

[Formula 1]

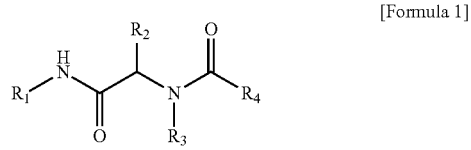

BACKGROUND ART

Hepatitis C virus (HCV) is one of the major factors causing chronic hepatitis and liver cirrhosis, and is an important factor from the etiological point of view in terms of hepatocellular carcinoma. Despite the development of a triple therapy using the combination of interferon-α (IFN-α), ribavirin (RBV), and telaprevir or boceprevir as direct acting antivirals (DAA), sustained virological response rates, toxicity, and resistance still remain as major problems to be solved. Accordingly, there is a need for the development of a novel antivirus that can intervene in several steps of the viral life cycle while exhibiting lower side effects.

HCV relies on host machineries through its life cycle. Among various cellular factors, cyclophilin A (CypA) has the activity of peptidyl-prolyl cis-trans isomerase (PPIase), which catalyzes the isomerization of a prolyl peptide bond, and is thought to be involved in protein folding of nonstructural viral proteins (e.g., NS2, NS5A, and NS5B). Accordingly, CypA is thought to be as an attractive target for potential anti-HCV materials.

Recently, CypA inhibitors were suggested as a therapeutic option for the treatment of hepatitis C virus. The three different kinds of non-immunosuppressive analogs of cyclosporine (CsA), i.e. Alisporivir; Dehio-025, SCY-635, and NIM811, exhibited effects on the HCV replication. The combined use of a virus-specific inhibitor and a CypA inhibitor was shown to minimize toxicities by reducing the administration frequency of individual drugs. The major advantage of the CypA inhibitor is the high genetic barrier to the sustained antiviral responses and resistance, compared to that of DAA. Although CsA analogs have useful effects against the HCV infection, the clinical safety profiles of these analogs are still under analysis. Recently, the Alisporivir test was stopped due to the occurrence of life-threatening pancreatitis observed in a few patients. Accordingly, the safety issue associated with CsA-based inhibitors requires the development of a novel and improved CypA inhibitor, as a strong anti-HCV material.

DISCLOSURE

Technical Problem

Under the circumstances, the present inventors have endeavored to develop a safe antiviral agent which not only has excellent HCV inhibitory activity but also does not exhibit cytotoxicity or immunosuppressive activity. As a result, the present inventors have selected potential compounds showing PPIase inhibitory activities from a random compound library, synthesized a series of novel bis-amide derivatives having chemical structures similar to these selected compounds, and confirmed that these compounds exhibit the activity as a CypA inhibitor and thus can block the HCV replication, thereby completing the present invention.

Technical Solution

An object of the present invention is to provide a novel bis-amide derivative compound or a pharmaceutically acceptable salt thereof.

Another object of the present invention is to provide a method for preparing a bis-amide derivative compound including reacting an isocyanide derivative ($R_1$—NC) and a carboxylic acid derivative ($R_4$—COOH) with an aldehyde derivative ($R_2$—CHO) and an amine derivative ($R_3$—$NH_2$) or an imine derivative ($R_2$—C=N—$R_3$).

Still another object of the present invention is to provide a pharmaceutical composition for preventing or treating diseases caused by hepatitis C virus infection containing the bis-amide derivative compound or a pharmaceutically acceptable salt thereof as an active ingredient.

Still another object of the present invention is to provide a method for preventing or treating diseases caused in a subject by hepatitis C virus infection including administering the bis-amide derivative compound or a pharmaceutically acceptable salt thereof to a subject in need thereof.

Still another object of the present invention is to provide a health functional food for preventing or ameliorating diseases caused by hepatitis C virus infection containing a bis-amide derivative compound or a pharmaceutically acceptable salt thereof as an active ingredient.

Advantageous Effects of the Invention

The novel bis-amide derivative compound of the present invention, particularly WJCPA-126, specifically binds to the catalytic site of CypA to effectively inhibit the activity of an isomerase, and the duration of the inhibitory effect can be increased because WJCPA-126 binds to CypA with high binding affinity exhibiting a low dissociation rate ($K_{off}$). Accordingly, WJCPA-126 has nontoxic and non-immunosuppressive characteristics and can effectively inhibit HCV replication in vitro and in vivo model systems. Additionally, WJCPA-126 reactivates the host interferon response through an increase in the expression of IFN-stimulated genes (ISGs) and the inhibition of interleukin-8 (IL-8) secretion. Therefore, a series of the bis-amide derivatives including WJCPA-126 can be useful as a novel type CypA inhibitor exhibiting antiviral effect.

BRIEF DESCRIPTION OF THE DRAWINGS

FIG. 1 shows the structures of WJCPA-126 according to an exemplary embodiment of the present invention. FIG. 1(a) shows the chemical structure of WJCPA-126 and FIG. 1(b) shows a result of computer docking analysis of WJCPA-126 regarding CypA.

FIG. 2 shows the results of the inhibitory effect of WJCPA-126 against the activity of CypA PPIase. The upper left panel shows a result of an SPR sensogram illustrating the bond between WJCPA-126 or CsA and CypA, and a comparison result of values between association constant ($K_a$) and dissociation constant ($K_d$). The upper right panel shows a result of SPR analysis illustrating the relative reaction of resonance unit at the WJCPA-126 concentration shown in the graph. The $K_d$ values (±S.D.) were calculated based on three independent experiments. The lower left panel shows a result of SPR analysis illustrating the interactions between WJCPA-126 or CsA and CypB. The lower right panel shows a result of SPR analysis illustrating the bond of WJCPA-126 to CypB at different concentrations shown in the graph. The $K_d$ values (±S.D.) were calculated based on three independent experiments.

FIG. 3 shows the results of the inhibitory effect of WJCPA-126 against the activity of CypA PPIase. FIG. 3(a) shows the result of PPIase analysis measured at different time points, respectively, in which the black circle represents the result of a sample containing 20 nM CypA, and square and triangle represent the results of samples additionally containing 1 μM CsA or WJCPA-126 to 20 nM CypA, respectively. Additionally, FIG. 3(b) shows the result of measured enzyme activity and the $IC_{50}$ value calculated therefrom.

FIG. 4 shows the 2D $^1$H TOCSY NMR spectrum of a WJCPA-126 and CypA complex according to an exemplary embodiment of the present invention, in which the spectrum corresponding to the CypA-WJCPA-126 complex was overlapped. The connectivity in the spin system of Arg 55, Trp 121, and Phe 113 of CypA were represented in solid lines of bright grey, medium grey, and dark grey. The resonances shown represent the binding of WJCPA-126 to the Arg 55, Trp 121, and Phe 113 residues of CypA.

FIG. 5 shows the results of immunoblots illustrating the inhibitory activity of a series of bis-amide derivatives (WJCPA-1 to WJCPA-132), which were prepared according to an exemplary embodiment of the present invention, against the NS5A expression. The numbers shown on the top represent the serial numbers of compounds, and in particular, those compounds which exhibited excellent activities were underlined. Huh?-rep cells were treated with each of the compounds at the concentration of 2 μM for 3 days, followed by the immunoblots.

FIG. 6 shows the antiviral effects of a series of his-amide derivatives according to the present invention. HCV replication cells were cultured after treating with a series of bis-amide derivatives, and the total cell lysate was subjected to western blot analysis luciferase activity analysis. All experiments were repeatedly performed 3 times and the representative values are shown.

FIG. 7 shows the results of activity and cytotoxicity of WJCPA-126. FIG. 7(a) represents the inhibitory effect of WJCPA-126 against the PPIase activity, and FIG. 7(b) represents the non-cytotoxicity of the compounds according to the present invention confirmed via MTT assay.

FIG. 8 shows graphs illustrating the effect of WJCPA-126 on calcineurin/NFAT signaling pathway in murine splenocytes. FIG. 8(a) shows a graph illustrating the MTT analysis result, and data were indicated in terms of mean±S.E. (n=3, *P<0.05; ***P<0.001 vs. CsA-treated cells). FIG. 8(b) shows a graph illustrating the calcineurin phosphorylase analysis result. All measurements were performed 3 times. The mean values were indicated in percentage of calcineurin activity, which was calculated relative to the value of the untreated control cells. The data were indicated in terms of mean±S.E. (n=3, *P<0.05; ***P<0.001 vs. CsA-treated cells).

FIG. 9 shows the results illustrating the effect of WJCPA-126 on calcineurin/NFAT signaling pathway in murine splenocytes. FIG. 9(a) shows the result of western blot analysis illustrating the effect of WJCPA-126 on the dephosphorylation of NFAT in murine splenocytes. The highly phosphorylated NFAT1 (p-NFAT1) showed low mobility in SDS-PAGE whereas the dephosphorylated NFAT1 showed an increased mobility. The representative values of the data obtained from at least three individual experiments performed are shown. FIG. 9(b) shows the analysis result of NFAT1 localization by immunofluorescence staining. The representative images obtained from at least three individual experiments are shown. FIG. 9(c) shows the analysis result of ELISA on the IL-2 production. The data were indicated in terms of mean±S.E. (n=3, *P<0.05; ***P<0.001 vs. CsA-treated cells).

FIG. 10 shows the results illustrating the effect of WJCPA-126 in a HCV replication unit (replicon) cell. FIG. 10(a) shows the result of western blot analysis of the expression of NS5A (top panel) and NS5B (center panel) in HCV replicon cells treated with CsA or WJCPA-126 while increasing the concentration. For all experiments, the representative images obtained from at least three individual experiments are shown. FIG. 10(b) shows the analysis result of the replication complex using the total lysate and a subcellular fractionated membrane of HCV Con1b replicon cells treated with 2 μM CsA or WJCPA-126. FIG. 10(c) shows the result of colocalization of NS5A and NS5B by a confocal microscope. The cells were stained with Alexa Red-containing antibody to NS5A, Alexa Green-containing to NS5B, and DAPI for nuclear staining. The copresence of overlapping red and green were represented in yellow (bright grey in figure). The representative images obtained from at least three individual experiments are shown.

FIG. 11 shows the effect of WJCPA-126 in a HCV replicon cell. FIG. 11(a) shows the images as a result of real-time analysis. The effect of WJCPA-126 was determined in percentage of fluorescent cells in each image using sub-genotype 1b replicated cells. $EC_{50}$ and $CC_{50}$ were determined via nonlinear regression analysis using GraphPad Prism (GraphPad Software). The GFP expression level was quantitated and shown in the left panel. The images of GFP at the level of replicated cells were obtained while increasing the concentration of WJCPA-126 and are shown on the right panel. FIG. 11(b) shows the result obtained in the same manner except that JFH1 genotype 2a replicated cells were used.

FIG. 12 shows the results illustrating the disruption of interactions between CypA and HCV non-structural viral proteins by treatment with WJCPA-126. FIG. 12(a) shows the result of in vitro binding to the CypA of NS5A or NS5B. Recombinant GST-CypA and GST-R55A CypA were incubated with thrombin-cleaved NS5A or NS5B and added to glutathione beads. The bound materials were eluted and analyzed by western blot. Wild-type CypA was shown to effectively bind to NS5A or NS5B. CypA mutant R55A did not bind to viral proteins. FIGS. 12(b) to 12(d) show the inhibition of protein-protein interaction determined by the GST pulldown analysis performed while increasing the amount of CsA or WJCPA-126. GST-specific antibody was used as a loading control. The representative images of all data obtained from at least three individual experiments are shown.

FIG. 13 shows the results illustrating the disruption of interactions between CypA and HCV non-structural viral proteins by treatment with WJCPA-126. FIG. 13(a) shows the result of coimmunoprecipitation analysis of CypA with NS5A (left) or NS5B (right) in a HCV replicon cell in the presence or absence of CsA or WJCPA-126. Antibody and western blot analyses were performed using a cell lysate (input). The representative images of all data obtained from at least three individual experiments are shown. FIG. 13(b) shows the result of mammalian two-hybrid analysis of the CypA binding to HCV NS5A (left) or NS5B (right). The data were indicated in terms of mean±S.E. (n=3, **P<0.01 vs. untreated cells).

FIG. 14 shows the results illustrating the effects of WJCPA-126 on stimulation of IFN signaling and inhibition of IL-8 production in a HCV replicon cell. FIG. 14 shows the result of real-time qRT-PCR analysis in a HCV replicon cell incubated along with 2 μM CsA or WJCPA-126 at different time intervals, respectively. The data were indicated in terms of mean±S.E. (n=3).

FIG. 15 shows the results illustrating the effects of WJCPA-126 on stimulation of IFN signaling and inhibition of IL-8 production in a HCV replicon cell. FIG. 15(a) shows the result of western blot analysis with the indicated antibody. The representative images of all data obtained from at least three individual experiments are shown. FIG. 15(b) shows the result of real-time qRT-PCR analysis in a cell treated with 2μM CsA or WJCPA-126 for analyzing the change in the expression level of IL-8 mRNA. The data were indicated in terms of mean±S.E. (n=3). FIG. 15(c) shows the result of ELISA analysis on the level of IL-8 in a culture medium. The data were indicated in terms of mean±S.E. (n=3, *P<0.05 vs. CsA-treated cells). FIG. 15(d) shows the result of real-time qRT-PCR analysis on IFN-α. The result was normalized regarding the human GAPDH. The data were indicated in terms of mean±S.E. (n=3). FIG. 15(e) shows the result of ELISA analysis on IFN-α production analyzed using a culture medium. The data were indicated in terms of mean±S.E. (n=3, *P<0.05 vs. CsA-treated cells).

FIG. 16 shows the results illustrating the effect of the treatment of WJCPA-126 in combination with IFN-α, ribavirin, or telaprevir in a HCV replicon cell. FIG. 16(a) shows the result of MTT analysis. The treatment of WJCPA-126 in combination with IFN-α, ribavirin, or telaprevir showed a lower toxicity. The data were indicated in terms of mean±S.E. (n=3, *P<0.05 vs. cells treated with a combination of IFN-α and CsA; P<0.001 vs. cells treated with a combination of ribavirin and CsA; and *P<0.001 vs. cells treated with a combination of telaprevir and CsA). FIG. 16(b) shows the result of real-time qRT-PCR analysis on the HCV replicon RNA level in a cell treated with CsA, WJCPA-126, 50 U/mL IFN-α, 100 μM ribavirin, and telaprevir alone, or a combination thereof (n=3, P<0.001 vs. cells treated with IFN-α, ribavirin, or telaprevir alone). FIG. 16(c) shows the result of ELISA analysis on IL-8 level. The HCV replicon cell treated with WJCPA-126 in combination of IFN-α or ribavirin showed a synergistic inhibition of IL-8 production (CI=0.6-0.8). The data were indicated in terms of mean±S.E. (n=3, P<0.01 vs. cells treated with IFN-α alone; ***P<0.001 vs. cells treated with ribavirin or telaprevir alone).

FIG. 17 shows the results illustrating the effect of WJCPA-126 on the functions of the liver and the kidney. Fifteen BALB/c mice were classified into three groups (n=5/group), and used as one untreated group (control) and two treated groups (treatment with CsA or WJCPA-126 at a dose of 50 mg/kg for 2 weeks). FIG. 17(a) shows the change in body weight during the experimental period. The data were indicated in terms of mean±S.E. (n=3). FIGS. 17(b) and 17(c) show the serum levels of alanine aminotransferase (ALT) and aspartate aminotransferase (AST) measured in mice after the systemic administration CsA or WJCPA-126, respectively. No difference was observed between the values of AST and ALT between the control group and the group treated with WJCPA-126. The group treated with CsA showed an increase in the level of ALT and AST enzymes. The data were indicated in terms of mean±S.E. (n=3, *P<0.05 vs. cells treated with CsA). FIGS. 17(d) and 17(e) show the levels of blood urea nitrogen (BUN) and serum creatinine measured for the recovered blood samples, respectively. The levels of BUN and creatinine increased in the CsA-treated group compared to that of WJCPA126-treated group. The data were indicated in terms of mean±S.E. (n=3, *P<0.05 vs. CsA regarding the level of BUN or creatinine).

FIG. 18 shows the results illustrating the effect of abolishing viral replication by WJCPA-126 in a HCV mouse model. FIG. 18(a) shows a schematic diagram illustrating the in vivo experiment performed in a NOD/SCID mouse. The mouse was injected intraperitoneally with CsA or WJCPA-126 at a dose of 50 mg/kg daily for two weeks. FIG. 18(b) shows the result of a histological test of HCV replicated cells and a control group transplanted into murine liver tissue shown by H & E staining.

FIG. 19 shows the results illustrating the effect of abolishing viral replication by WJCPA-126 in a HCV mouse model. FIG. 19(a) shows the change in body weight. The data were indicated in terms of mean±S.E. (n=3). FIG. 19(b) shows the result illustrating the HCV RNA level in a mouse model quantitated via real-time qRT-PCR. Experiments were performed using mice (5 mice/group) and the result was normalized by human GAPDH. The data were indicated in terms of mean±S.E. (n=3). FIG. 19(c) shows the result of western blot analysis. Mice (5 mice/group) were tested regarding the expression of HCV NS5A. The representative images of all data obtained from at least three individual experiments are shown.

FIG. 20 shows the stained confocal microscopic images of human hepatocytes (left lane; center grey) and HCV NS5A (center lane; dark grey) of Huh7 cells or Huh7 cells containing HCV-Con1b. Nuclei were stained with DAPI (right lane; light grey). The colocalization of human hepatocytes and HCV NS5A were overlapped and shown in bright grey. The representative images obtained from three individual experiments are shown.

BEST MODE

In an aspect to achieve the above objects of the present invention, the present invention provides a bis-amide derivative compound of the following Formula 1 or a pharmaceutically acceptable salt thereof.

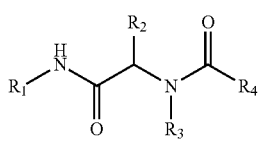

[Formula 1]

In Formula 1 above, $R_1$ is $C_1$-$C_6$ linear or branched alkyl, unsubstituted or substituted cyclohexyl, or unsubstituted or substituted benzyl; $R_2$ is unsubstituted or substituted aryl, in which the substituent may be in multiple number and each substituent is independently $C_1$-$C_4$ alkyl, $C_1$-$C_4$ alkoxy, hydroxy, carboxy, nitro, halogen, or a 5-membered ring comprising a heteroatom formed by an interconnection between two adjacent substituents; $R_3$ is unsubstituted or substituted $C_1$-$C_6$ linear or branched alkyl, cyclohexyl, unsubstituted or substituted phenyl-$C_1$-$C_4$ alkyl, or unsubstituted or substituted aryl, in which the substituent may be in multiple number and each substituent is independently $C_1$-$C_4$ alkoxy or halogen; and $R_4$ is unsubstituted or substituted $C_1$-$C_6$ linear or branched alkyl, unsubstituted or substituted arylalkyl with or without heteroatom(s), or unsubstituted or substituted aryl with or without heteroatom(s), in which the substituent may be in multiple number and each substituent is independently $C_1$-$C_4$ alkoxy, $C_1$-$C_4$ alkoxybenzyl, nitro, or halogen; in which the substituted functional group of $R_1$ and $R_3$ may include one or more substituent(s) selected from the group consisting halogen, CN, $CF_3$, hydroxy, $C_1$-$C_6$ alkyl, and $C_1$-$C_6$ alkoxy.

Preferably, $R_1$ is $C_1$-$C_6$ linear or branched alkyl, cyclohexyl, or benzyl; $R_2$ is unsubstituted or substituted phenyl or naphthyl, in which the number of substituents is in the range of from 1 to 3 and each substituent is independently $C_1$-$C_4$ alkyl, $C_1$-$C_4$ alkoxy, hydroxy, carboxy, nitro, halogen, or a 5-membered ring comprising two oxygen atoms formed by an interconnection between two adjacent substituents; $R_3$ is unsubstituted or substituted $C_1$-$C_6$ linear or branched alkyl, cyclohexyl, unsubstituted or substituted phenyl-$C_1$-$C_4$ alkyl, or unsubstituted or substituted aryl, in which the number of substituents is 1 or 2 and each substituent is independently $C_1$-$C_4$ alkoxy or halogen; and $R_4$ is unsubstituted or substituted $C_1$-$C_6$ linear or branched alkyl, unsubstituted or substituted phenyl, indolyl, or nicotinyl, or unsubstituted or substituted phenylalkyl or indolylalkyl, in which the substituent may be in multiple number and each substituent is independently $C_1$-$C_4$ alkoxy, $C_1$-$C_4$ alkoxybenzyl, nitro, or halogen.

More preferably, $R_1$ is n-pentyl, tert-butyl, cyclohexyl, or benzyl; $R_2$ is phenyl, naphthyl, 4-ethylphenyl, 6-hydroxyphenyl, 4-carboxyphenyl, 4-nitrophenyl, 4-fluorophenyl, 4-chlorophenyl, 3,4-dichlorophenyl, 3-methoxy-4-hydroxyphenyl, 3,4-dimethoxyphenyl, 2,3,4-trimethoxyphenyl, 3,4,5-trimethoxyphenyl, or benzo[1,3]dioxol-5-yl; $R_3$ is n-butyl, 2,2-dimethoxyethyl, cyclohexyl, phenyl, naphthyl, 4-bromophenyl, 4-fluorophenyl, 2-methoxyphenyl, 4-methoxyphenyl, 3,4-dimethoxyphenyl, 4-isopropylphenyl, 4-methoxybenzyl, 3-methoxyphenylethyl, or 3,4-dimethoxyphenylethyl; and $R_4$ is methyl, ethyl, n-propyl, n-butyl, n-pentyl, tert-butyl, chloromethyl, 1-bromopentyl, phenyl, 2-methylphenyl, 2,3-dimethylphenyl, 2,5-dimethylphenyl, 2-methoxy-5-nitrophenyl, 2-nitro-5-methoxy, 2-nitro-4-chlorophenyl, 6-chloronicotinyl, indol-2-yl, indol-3-ylmethyl, 1-(4-methoxybenzyl)-indol-3-yl, 3-methoxyphenylethyl, or 4-methoxyphenylethyl.

As used herein, the term "$C_1$-$C_6$ linear or branched alkyl" refers to a saturated hydrocarbon with a linear or branched structure including 1 to 6 carbon atoms, e.g., methyl, ethyl, n-propyl(n-propyl), i-propyl(isopropyl), n-butyl, i-butyl, t-butyl(tertiary butyl), n-pentyl, n-hexyl, etc.

As used herein, the term "unsubstituted" refers to a state in which only hydrogen atoms are bound to the basic carbon backbone without including any additional substituent. Meanwhile, as used herein, the term "substituted" refers to a state in which at least one atom other than hydrogen or a functional group is bound to the basic carbon backbone.

As used herein, the term "aryl" refers to a functional group or substituent derived from a cyclic aromatic compound. The cyclic compound may be composed of only carbon atoms or may be composed including one or more heteroatom(s) selected from oxygen, sulfur, and/or nitrogen. For example, the aryl group composed of only carbon atoms may include phenyl, naphthyl, anthracenyl, etc., and the aryl group composed including heteroatom(s) may include thienyl, indolyl, pyridinyl, etc. The aryl group containing the heteroatom is also called heteroaryl, and the aryl, as used herein, also includes the heteroaryl.

As used herein, the term "$C_1$-$C_4$ alkoxy" refers to a substituent in which the $C_1$-$C_4$ alkyl is connected to an oxygen atom by a single bond, e.g., all substituents with a linear or branched structure from methoxy to butoxy.

As used herein, the term "halogen" refers to a series of nonmetal atoms in Group XVII of the periodic table, e.g., fluorine (F), chlorine (Cl), bromine (Br), iodine (I), etc.

As used herein, the term "5-membered ring including a heteroatom" may have a structure in which 5 atoms including a carbon atom and one or more heteroatom(s) are connected in a ring shape, and the heteroatom may be oxygen, nitrogen, sulfur, phosphorous, etc. In the present invention, the 5-membered ring is formed on a benzene ring and is thus formed including two or more carbon atoms.

As used herein, the term "phenyl-$C_1$-$C_4$ alkyl" and "aryl-$C_1$-$C_4$ alkyl" refer to a substituent, in which a benzene ring or aryl is bound to an end of a saturated hydrocarbon composed of one to four carbon atoms while the other end is connected to the main backbone, respectively.

As used herein, the term "$C_1$-$C_4$ alkoxybenzyl" refers to a benzyl substituent, in which a benzene ring is substituted with one or more $C_1$-$C_4$ alkoxy, e.g., all benzyl substituents substituted with a linear or branched methoxy, ethoxy, propoxy, or butoxy.

Representative examples of the compounds of Formula 1 are as follows:

1) N-cyclohexyl-2-[(2-1H-indol-3-yl-acetyl)-phenyl-amino]-2-(3,4,5-trimethoxy-phenyl)-acetamide,
2) N-cyclohexyl-2-[(2-1H-indol-3-yl-acetyl)-phenyl-amino]-2-phenyl-acetamide,
3) N-cyclohexyl-2-[(2-1H-indol-3-yl-acetyl)-(4-methoxy-phenyl)-amino]-2-(3,4,5-trimethoxy-phenyl)-acetamide,
4) N-cyclohexyl-2-[(2-1H-indol-3-yl-acetyl)-(2-methoxy-phenyl)-amino]-2-(3,4,5-trimethoxy-phenyl)-acetamide,
5) N-cyclohexyl-2-[(2-1H-indol-3-yl-acetyl)-naphthalen-1-yl-amino]-2-(3,4,5-trimethoxy-phenyl)-acetamide,
6) 2-[butyl-(2-1H-indol-3-yl-acetyl)-amino]-N-cyclohexyl-2-(3,4,5-trimethoxy-phenyl)-acetamide,
7) N-cyclohexyl-2-[[2-(3,4-dimethoxy-phenyl)-ethyl]-(2-1H-indol-3-yl-acetyl)-amino]-2-(3,4,5-trimethoxy-phenyl)-acetamide,
8) N-[cyclohexylcarbamoyl-(3,4,5-trimethoxy-phenyl)-methyl]-N-(4-isopropyl-phenyl)-benzamide,
9) N-cyclohexyl-2-[(2-1H-indol-3-yl-acetyl)-amino]-2-(3,4,5-trimethoxy-phenyl)-acetamide, 10) 2-[(4-bromo-phenyl)-(2-1H-indol-3-yl-acetyl)-amino]-N-cyclohexyl-2-(2,3,4-trimethoxy-phenyl)-acetamide,
11) N-cyclohexyl-2-[(3,4-dimethoxy-phenyl)-(2-1H-indol-3-yl-acetyl)-amino]-2-(3,4,5-trimethoxy-phenyl)-acetamide,
12) N-cyclohexyl-2-[(2-1H-indol-3-yl-acetyl)-(4-isopropyl-phenyl)-amino]-2-(3,4,5-trimethoxy-phenyl)-acetamide,
13) N-[cyclohexylcarbamoyl-(2,3,4-trimethoxy-phenyl)-methyl]-N-(4-isopropyl-phenyl)-benzamide,
14) N-cyclohexyl-2-(3,4-dimethoxy-phenyl)-2-[(2-1H-indol-3-yl-acetyl)-(4-isopropyl-phenyl)-amino]-acetamide,
15) N-cyclohexyl-2-(3,4-dimethoxy-phenyl)-2-[(3,4-dimethoxy-phenyl)-(2-1H-indol-3-yl-acetyl)-amino]-acetamide,
16) N-cyclohexyl-2-[cyclohexyl-(2-1H-indol-3-yl-acetyl)-amino]-2-(3,4-dimethoxy-phenyl)-acetamide,
17) N-cyclohexyl-2-[(2,2-dimethoxy-ethyl)-(2-1H-indol-3-yl-acetyl)-amino]-2-(3,4-dimethoxy-phenyl)-acetamide,
18) N-cyclohexyl-2-[(2-1H-indol-3-yl-acetyl)-phenyl-amino]-2-(4-nitro-phenyl)-acetamide,
19) N-cyclohexyl-2-[(2-1H-indol-3-yl-acetyl)-(4-methoxy-benzyl)-amino]-2-(4-nitro-phenyl)-acetamide,
20) N-cyclohexyl-2-[(3,4-dimethoxy-phenyl)-(2-1H-indol-3-yl-acetyl)-amino]-2-(4-nitro-phenyl)-acetamide,
21) 2-[(4-bromo-phenyl)-(2-1H-indol-3-yl-acetyl)-amino]-N-cyclohexyl-2-(4-nitro-phenyl)-acetamide,
22) N-cyclohexyl-2-[(2-1H-indol-3-yl-acetyl)-(4-isopropyl-phenyl)-amino]-2-(4-nitro-phenyl)-acetamide,
23) N-[cyclohexylcarbamoyl-(4-hydroxy-3-methoxy-phenyl)-methyl]-N-(4-isopropyl-phenyl)-3-(4-methoxy-phenyl)-propionamide,
24) N-cyclohexyl-2-[(3,4-dimethoxy-phenyl)-(2-1H-indol-3-yl-acetyl)-amino]-2-(4-hydroxy-phenyl)-acetamide,
25) 2-bromo-hexanoic acid [cyclohexylcarbamoyl-(4-hydroxy-phenyl)-methyl]-(3,4-dimethoxy-phenyl)-amide,
26) N-[cyclohexylcarbamoyl-(4-hydroxy-phenyl)-methyl]-N-(3,4-dimethoxy-phenyl)-3-(3-methoxy-phenyl)-propionamide,
27) 2-(4-chloro-phenyl)-N-cyclohexyl-2-[(2-1H-indol-3-yl-acetyl)-phenyl-amino]-acetamide,
28) N-[(4-chloro-phenyl)-cyclohexylcarbamoyl-methyl]-N-(4-isopropyl-phenyl)-benzamide,
29) N-[(4-chloro-phenyl)-cyclohexylcarbamoyl-methyl]-N-(4-isopropyl-phenyl)-3-(4-methoxy-phenyl)-propionamide,
30) N-[(4-chloro-phenyl)-cyclohexylcarbamoyl-methyl]-N-(4-isopropyl-phenyl)-2,5-dimethyl-benzamide,
31) 2-[(4-bromo-phenyl)-(2-1H-indol-3-yl-acetyl)-amino]-2-(4-chloro-phenyl)-N-cyclohexyl-acetamide,
32) 2-(4-chloro-phenyl)-N-cyclohexyl-2-[(3,4-dimethoxy-phenyl)-(2-1H-indol-3-yl-acetyl)-amino]-acetamide,
33) 2-(4-chloro-phenyl)-N-cyclohexyl-2-[(2-1H-indol-3-yl-acetyl)-(4-isopropyl-phenyl)-amino]-acetamide,
34) 2-(4-chloro-phenyl)-N-cyclohexyl-2-[(2-1H-indol-3-yl-acetyl)-(4-methoxy-phenyl)-amino]-acetamide,
35) N-[(4-chloro-phenyl)-cyclohexylcarbamoyl-methyl]-N-(3,4-dimethoxy-phenyl)-3-(4-methoxy-phenyl)-propionamide,
36) 2-benzo[1,3]dioxol-5-yl-2-[butyl-(2-1H-indol-3-yl-acetyl)-amino]-N-cyclohexyl-acetamide,
37) N-cyclohexyl-2-(4-ethyl-phenyl)-2-[(2-1H-indol-3-yl-acetyl)-phenyl-amino]-acetamide,
38) 2-[(4-bromo-phenyl)-(2-1H-indol-3-yl-acetyl)-amino]-N-tert-butyl-2-(4-nitro-phenyl)-acetamide,
39) N-(4-bromo-phenyl)-N-[tert-butylcarbamoyl-(4-nitro-phenyl)-methyl]-5-methoxy-2-nitro-benzamide,
40) N-tert-butyl-2-(4-chloro-phenyl)-2-[(2-1H-indol-3-yl-acetyl)-(4-isopropyl-phenyl)-amino]-acetamide,
41) N-[tert-butylcarbamoyl-(4-chloro-phenyl)-methyl]-N-(4-isopropyl-phenyl)-5-methoxy-2-nitro-benzamide,
42) N-[tert-butylcarbamoyl-(4-chloro-phenyl)-methyl]-N-(4-isopropyl-phenyl)-3-(3-methoxy-phenyl)-propionamide,
43) N-cyclohexyl-2-(3,4-dimethoxy-phenyl)-2-[(2-1H-indol-3-yl-acetyl)-(4-methoxy-phenyl)-amino]-acetamide,
44) N-[cyclohexylcarbamoyl-(3,4-dimethoxy-phenyl)-methyl]-3-(3-methoxy-phenyl-N-(4-methoxy-phenyl)-propionamide,
45) N-tert-butyl-2-[(2-1H-indol-3-yl-acetyl)-(4-isopropyl-phenyl)-amino]-2-(3,4,5-trimethoxy-phenyl)-acetamide,
46) N-[tert-butylcarbamoyl-(3,4,5-trimethoxy-phenyl)-methyl]-6-chloro-N-(4-isopropyl-phenyl)-nicotinamide,
47) N-[cyclohexylcarbamoyl-(4-hydroxy-phenyl)-methyl]-N-(3,4-dimethoxy-phenyl)-2-methyl-benzamide,
48) N-(4-bromo-phenyl)-5-methoxy-2-nitro-N-[(4-nitro-phenyl)-pentylcarbamoyl-methyl]-benzamide,
49) 1H-indol-2-carboxylic acid [cyclohexylcarbamoyl-(3,4,5-trimethoxy-phenyl)-methyl]-(4-isopropyl-phenyl)-amide,
50) 6-chloro-N-[cyclohexylcarbamoyl-(3,4,5-trimethoxy-phenyl)-methyl]-N-(4-isopropyl-phenyl)-nicotinamide,
51) N-[cyclohexylcarbamoyl-(3,4,5-trimethoxy-phenyl)-methyl]-N-(4-isopropyl-phenyl)-5-methoxy-2-nitro-benzamide,
52) N-[cyclohexylcarbamoyl-(4-nitro-phenyl)-methyl]-N-(3,4-dimethoxy-phenyl)-5-methoxy-2-nitro-benzamide,
53) N-[cyclohexylcarbamoyl-(4-nitro-phenyl)-methyl]-N-(3,4-dimethoxy-phenyl)-3-(4-methoxy-phenyl)-propionamide,
54) 6-chloro-N-[cyclohexylcarbamoyl-(4-nitro-phenyl)-methyl]-N-(3,4-dimethoxy-phenyl)-nicotinamide,
55) 2-[acetyl-(3,4-dimethoxy-phenyl)-amino]-N-cyclohexyl-2-(4-nitro-phenyl)-acetamide,
56) N-[cyclohexylcarbamoyl-(4-nitro-phenyl)-methyl]-N-(3,4-dimethoxy-phenyl)-2,5-dimethyl-benzamide,
57) N-cyclohexyl-2-[[2-(3,4-dimethoxy-phenyl)-ethyl]-(2-1H-indol-3-yl-acetyl)-amino]-2-(4-nitro-phenyl)-acetamide,
58) 2-{(2-chloro-acetyl)-[2-(3,4-dimethoxy-phenyl)-ethyl]-amino}-N-cyclohexyl-2-(4-nitro-phenyl)-acetamide,
59) N-[cyclohexylcarbamoyl-(4-nitro-phenyl)-methyl]-N-[2-(3,4-dimethoxy-phenyl)-ethyl]-2-methyl-5-nitro-benzamide,
60) N-[cyclohexylcarbamoyl-(4-nitro-phenyl)-methyl]-N-[2-(3,4-dimethoxy-phenyl)-ethyl]-5-methoxy-2-nitro-benzamide,
61) N-[cyclohexylcarbamoyl-(4-nitro-phenyl)-methyl]-N-(3,4-dimethoxy-phenyl)-2-methyl-benzamide,
62) N-[cyclohexylcarbamoyl-(4-nitro-phenyl)-methyl]-N-(3,4-dimethoxy-phenyl)-2,2-dimethyl-propionamide,
63) N-[cyclohexylcarbamoyl-(4-nitro-phenyl)-methyl]-5-methoxy-N-[2-(3-methoxy-phenyl)-ethyl]-2-nitro-benzamide,
64) 2-{acetyl-[2-(3-methoxy-phenyl)-ethyl]-amino}-N-cyclohexyl-2-(4-nitro-phenyl)-acetamide,
65) 6-chloro-N-[cyclohexylcarbamoyl-(4-nitro-phenyl)-methyl]-N-[2-(3-methoxy-phenyl)-ethyl]-nicotinamide,
66) N-[cyclohexylcarbamoyl-(4-nitro-phenyl)-methyl]-N-[2-(3-methoxy-phenyl)-ethyl]-benzamide,
67) N-benzyl-2-(4-nitro-phenyl)-2-[(2-1H-indol-3-yl-acetyl)-(4-isopropyl-phenyl)-amino]-acetamide,
68) N-benzyl-2-[(2-chloro-acetyl)-(4-isopropyl-phenyl)-amino]-2-(4-chloro-phenyl)-acetamide, 69) 2-[(2-chloro-acetyl)-(4-isopropyl-phenyl)-amino]-2-(4-chloro-phenyl)-N-pentyl-acetamide,
70) 2-{(2-chloro-acetyl)-[2-(3,4-dimethoxy-phenyl)-ethyl]-amino}-2-(4-hydroxy-phenyl)-N-pentyl-acetamide,
71) 2-[acetyl-(3,4-dimethoxy-phenyl)-amino]-2-(4-hydroxy-phenyl)-N-pentyl-acetamide,
72) N-(3,4-dimethoxy-phenyl)-N-[(4-hydroxy-phenyl)-pentylcarbamoyl-methyl]-benzamide,
73) N-(3,4-dimethoxy-phenyl)-N-[(4-hydroxy-phenyl)-pentylcarbamoyl-methyl]-butyramide,
74) hexanoic acid (3,4-dimethoxy-phenyl)-[(4-hydroxy-phenyl)-pentylcarbamoyl-methyl]-amide,
75) N-(3,4-dimethoxy-phenyl)-N-[(4-hydroxy-phenyl)-pentylcarbamoyl-methyl]-propionamide,
76) N-benzyl-2-(4-chloro-phenyl)-2-[(2-1H-indol-3-yl-acetyl)-(4-methoxy-phenyl)-amino]-acetamide,
77) 2-(4-fluoro-phenyl)-2-[(2-1H-indol-3-yl-acetyl)-(4-methoxy-phenyl)-amino]-N-pentyl-acetamide,
78) N-cyclohexyl-2-(3,4-dichloro-phenyl)-2-[(2-1H-indol-3-yl-acetyl)-(4-methoxy-phenyl)-amino]-acetamide,
79) N-benzyl-2-(3,4-dichloro-phenyl)-2-[(2-1H-indol-3-yl-acetyl)-(4-methoxy-phenyl)-amino]-acetamide,
80) 2-(3,4-dichloro-phenyl)-2-[(2-1H-indol-3-yl-acetyl)-(4-methoxy-phenyl)-amino]-N-pentyl-acetamide,
81) N-cyclohexyl-2-({2-[1-(4-methoxy-benzyl)-1H-indol-3-yl]-acetyl}-phenyl-amino)-2-phenyl-acetamide,
82) N-cyclohexyl-2-[(3,4-dimethoxy-phenyl)-(2-1H-indol-3-yl-acetyl)-amino]-2-(3,4,5-trimethoxy-phenyl)-acetamide,
83) N-cyclohexyl-2-[(3,4-dimethoxy-phenyl)-2-[(2-1H-indol-3-yl-acetyl)-phenyl-amino]-acetamide,
84) N-cyclohexyl-2-[[(2-1H-indol-3-yl-acetyl)-(4-methoxy-phenyl)-amino]-2-(4-nitro-phenyl)-acetamide,
85) N-(4-bromo-phenyl)-N-[cyclohexylcarbamoyl-(4-nitro-phenyl)-methyl]-3-(3-methoxy-phenyl)-propionamide,
86) N-cyclohexyl-2-(4-hydroxy-3-methoxy-phenyl)-2-[(2-1H-indol-3-yl-acetyl)-(4-isopropyl-phenyl)-amino]-acetamide,
87) N-[cyclohexylcarbamoyl-(4-hydroxy-3-methoxy-phenyl)-methyl]-N-(4-isopropyl-phenyl)-benzamide,
88) N-[tert-butylcarbamoyl-(4-hydroxy-phenyl)-methyl]-N-(3,4-dimethoxy-phenyl)-2,2-dimethyl-propionamide,
89) N-tert-butyl-2-[(3,4-dimethoxy-phenyl)-(2-1H-indol-3-yl-acetyl)-amino]-2-(4-hydroxy-phenyl)-acetamide,
90) N-cyclohexyl-2-[(2-1H-indol-3-yl-acetyl)-(4-isopropyl-phenyl)-amino]-2-naphthalen-1-yl-acetamide,
91) 2-(4-chloro-phenyl)-N-cyclohexyl-2-[(2-1H-indol-3-yl-acetyl)-(4-methoxy-phenyl)-amino]-acetamide,
92) 6-chloro-N-[cyclohexylcarbamoyl-(4-hydroxy-phenyl)-methyl]-N-(3,4-dimethoxy-phenyl)-nicotinamide,
93) N-[cyclohexylcarbamoyl-(4-hydroxy-phenyl)-methyl]-N-(3,4-dimethoxy-phenyl)-2,3-dimethyl-benzamide,
94) N-cyclohexyl-2-(4-hydroxy-phenyl)-2-[(2-1H-indol-3-yl-acetyl)-phenyl-amino]-acetamide,
95) N-[tert-butylcarbamoyl-(4-hydroxy-phenyl)-methyl]-N-(3,4-dimethoxy-phenyl)-3-(3-methoxy-phenyl)-propionamide,
96) 1H-indol-2-carboxylic acid [tert-butylcarbamoyl-(3,4,5-trimethoxy-phenyl)-methyl]-(4-isopropyl-phenyl)-amide,
97) N-(3,4-dimethoxy-phenyl)-N-[(4-hydroxy-phenyl)-pentylcarbamoyl-methyl]-3-(4-methoxy-phenyl)-propionamide,
98) 2-[(3,4-dimethoxy-phenyl)-(2-1H-indol-3-yl-acetyl)-amino]-2-(4-hydroxy-phenyl)-N-pentyl-acetamide,
99) 4-chloro-N-[cyclohexylcarbamoyl-(4-hydroxy-phenyl)-methyl]-N-(3,4-dimethoxy-phenyl)-2-nitro-benzamide,
100) N-[(4-chloro-phenyl)-cyclohexylcarbamoyl-methyl]-N-(4-isopropyl-phenyl)-2-methyl-benzamide,
101) 2-[acetyl-(4-isopropyl-phenyl)-amino]-2-(4-chloro-phenyl)-N-cyclohexyl-acetamide,
102) 2-[(4-bromo-phenyl)-(2-1H-indol-3-yl-acetyl)-amino]-2-(4-nitro-phenyl)-N-pentyl-acetamide,
103) N-(4-bromo-phenyl)-6-chloro-N-[(4-nitro-phenyl)-pentylcarbamoyl-methyl]-nicotinamide,
104) 4-chloro-N-[cyclohexylcarbamoyl-(4-nitro-phenyl)-methyl]-N-(3,4-dimethoxy-phenyl)-2-nitro-benzamide,
105) 2-[(2-chloro-acetyl)-(3,4-dimethoxy-phenyl)-amino]-N-cyclohexyl-2-(4-nitro-phenyl)-acetamide,
106) 1H-indol-2-carboxylic acid [cyclohexylcarbamoyl-(4-nitro-phenyl)-methyl]-(3,4-dimethoxy-phenyl)-amide,
107) N-[cyclohexylcarbamoyl-(4-nitro-phenyl)-methyl]-N-[2-(3,4-dimethoxy-phenyl)-ethyl]-benzamide,
108) 2-{acetyl-[2-(3,4-dimethoxy-phenyl)-ethyl]-amino}-N-cyclohexyl-2-(4-nitro-phenyl)-acetamide,
109) 1H-indol-2-carboxylic acid [cyclohexylcarbamoyl-(4-nitro-phenyl)-methyl]-[2-(3,4-dimethoxy-phenyl)-ethyl]-amide,
110) N-[cyclohexylcarbamoyl-(4-nitro-phenyl)-methyl]-[2-(3,4-dimethoxy-phenyl)-ethyl]-2,2-dimethyl-propionamide,
111) N-cyclohexyl-2-{(2-1H-indol-3-yl-acetyl)-[2-(3-methoxy-phenyl)-ethyl]-amino}-2-(4-nitro-phenyl)-acetamide,
112) 2-{(2-chloro-acetyl)-[2-(3-methoxy-phenyl)-ethyl]-amino}-N-cyclohexyl-2-(4-nitro-phenyl)-acetamide,
113) 2-[(2-chloro-acetyl)-(4-isopropyl-phenyl)-amino]-2-(4-chloro-phenyl)-N-cyclohexyl-acetamide,
114) N-[(4-chloro-phenyl)-pentylcarbamoyl-methyl]-N-(4-isopropyl-phenyl)-benzamide,
115) 2-[(2-chloro-acetyl)-(4-methoxy-phenyl)-amino]-2-(4-hydroxy-phenyl)-N-pentyl-acetamide,
116) 2-bromo-hexanoic acid (3,4-dimethoxy-phenyl)-[(4-hydroxy-phenyl)-pentylcarbamoyl-methyl]-amide,
117) N-(3,4-dimethoxy-phenyl)-N-[(4-hydroxy-phenyl)-pentylcarbamoyl-methyl]-2,2-dimethyl-propionamide,
118) pentanoic acid (3,4-dimethoxy-phenyl)-[(4-hydroxy-phenyl)-pentylcarbamoyl-methyl]-amide,
119) 6-chloro-N-(3,4-dimethoxy-phenyl)-N-[(4-hydroxy-phenyl)-pentylcarbamoyl-methyl]-nicotinamide,
120) 1H-indol-2-carboxylic acid (3,4-dimethoxy-phenyl)-[(4-hydroxy-phenyl)-pentylcarbamoyl-methyl]-amide,
121) pentanoic acid (benzo[1,3]dioxol-5-yl-pentylcarbamoyl-methyl)-(3,4-dimethoxy-phenyl)-amide,
122) N-cyclohexyl-2-(4-fluoro-phenyl)-2-[(2-1H-indol-3-yl-acetyl)-(4-methoxy-phenyl)-amino]-acetamide,
123) N-benzyl-2-(4-fluoro-phenyl)-2-[(2-1H-indol-3-yl-acetyl)-(4-methoxy-phenyl)-amino]-acetamide,
124) 4-{cyclohexylcarbamoyl-[(2-1H-indol-3-yl-acetyl)-(4-methoxy-phenyl)-amino]-methyl}-benzoic acid,
125) 2-(4-chloro-phenyl)-2-[(2-1H-indol-3-yl-acetyl)-(4-methoxy-phenyl)-amino]-N-pentyl-acetic acid,
126) N-cyclohexyl-2-[(2-1H-indol-3-yl-acetyl)-(4-isopropyl-phenyl)-amino]-2-(3,4,5-trimethoxy-phenyl)-acetamide,
127) 2-[(2-chloro-acetyl)-(3,4-dimethoxy-phenyl)-amino]-2-(4-hydroxy-phenyl)-N-pentyl-acetamide,
128) 1H-indol-2-carboxylic acid [cyclohexylcarbamoyl-(4-nitro-phenyl)-methyl-[2-(3-methoxy-phenyl)-ethyl]-amide,
129) 2-[(2-chloro-acetyl)-(3,4-dimethoxy-phenyl)-amino]-2-(4-chloro-phenyl)-N-pentyl-acetamide,
130) 2-[(2-chloro-acetyl)-(4-isopropyl-phenyl)-amino]-2-(4-hydroxy-phenyl)-N-pentyl-acetamide, 131) 2-[(2-chloro-acetyl)-(4-fluoro-phenyl)-amino]-2-(4-hydroxy-phenyl)-N-pentyl-acetamide, 132) 2-benzo[1,3]dioxol-5-yl-2-[(2-chloro-acetyl)-(3,4-dimethoxy-phenyl)-amino]-N-pentyl-acetamide, 133) N-(4-bromo-phenyl)-N-[cyclohexylcarbamoyl-(4-nitro-phenyl)-methyl]-3-(4-methoxy-phenyl)-propionamide, 134) 6-chloro-N-[cyclohexylcarbamoyl-(3,4-dimethoxy-phenyl)-methyl]-N-(4-methoxy-phenyl)-nicotinamide, and 135) N-[(4-chloro-phenyl)-cyclohexylcarbamoyl-methyl]-N-(4-isopropyl-phenyl)-3-(3-methoxy-phenyl)-propionamide.

The compounds 1) to 135) according to the present invention have the chemical structures shown in Tables 1-1 to 1-3 below.

[Table 1-1]

TABLE 1-1

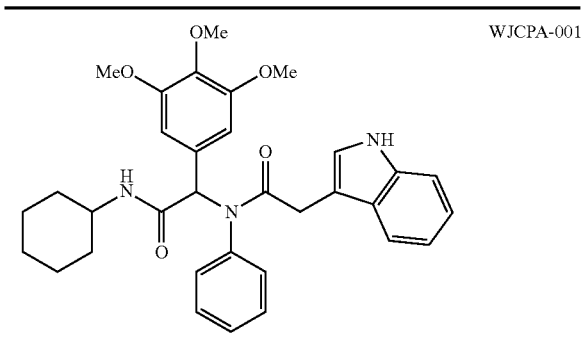
WJCPA-001

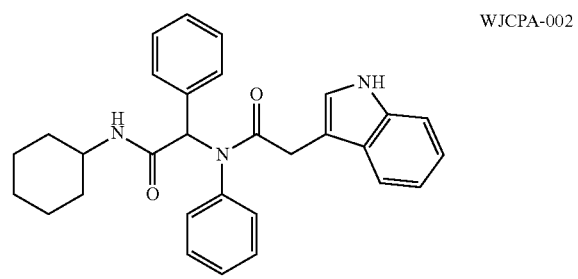
WJCPA-002

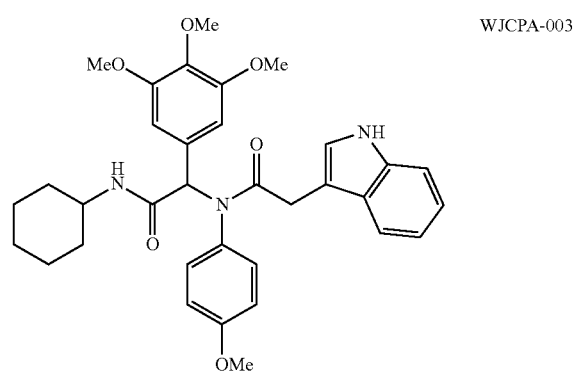
WJCPA-003

TABLE 1-1-continued

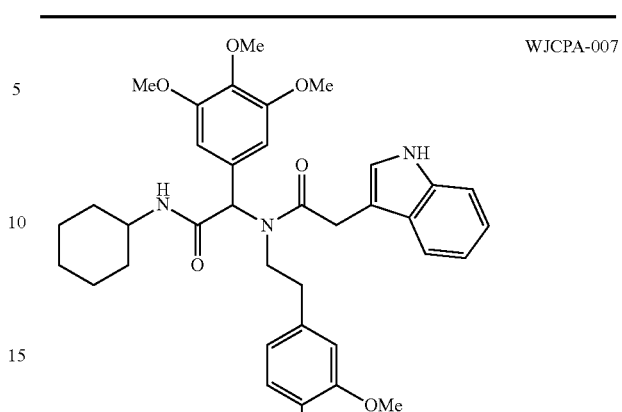
WJCPA-007

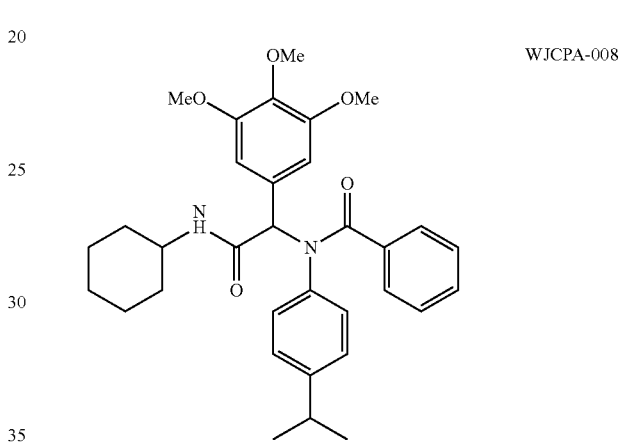
WJCPA-008

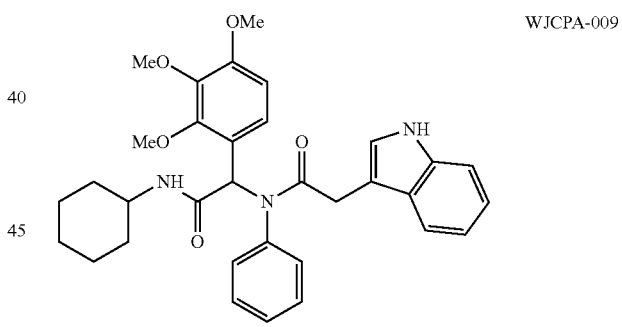
WJCPA-009

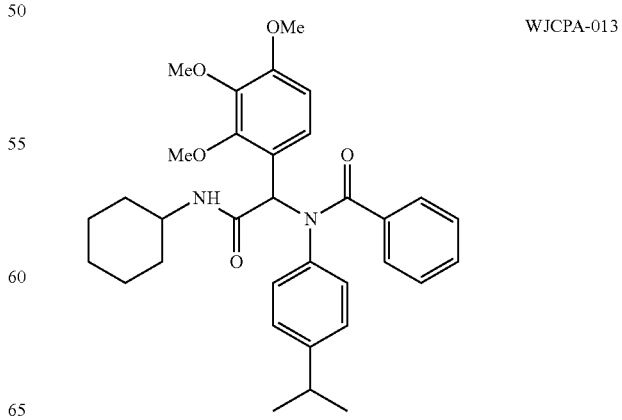
WJCPA-013

TABLE 1-1-continued
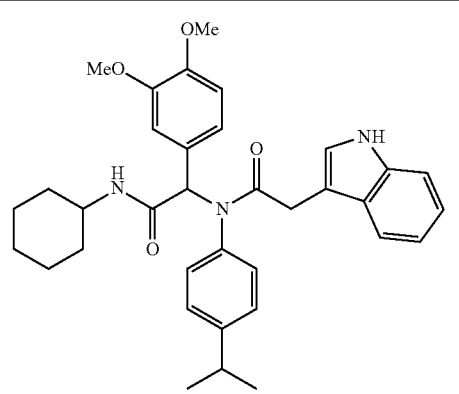
WJCPA-014
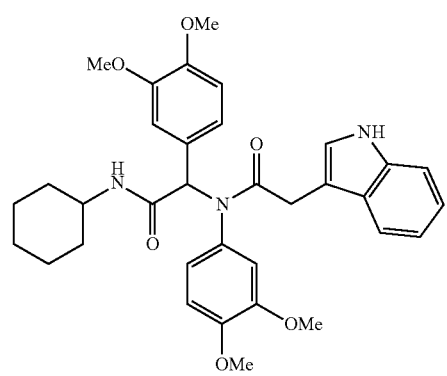 [SMILES: COc1ccc(C(C(=O)NC2CCCCC2)N(C(=O)Cc2c[nH]c3ccccc23)c2ccc(OC)c(OC)c2)cc1OC]
WJCPA-015
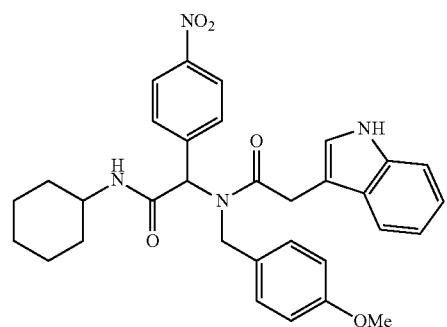 [SMILES: COc1ccc(CN(C(=O)Cc2c[nH]c3ccccc23)C(C(=O)NC2CCCCC2)c2ccc([N+](=O)[O-])cc2)cc1]
WJCPA-019
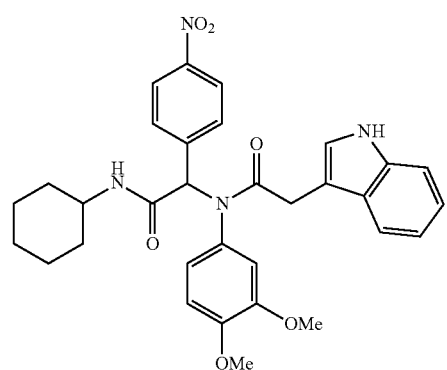 [SMILES: COc1ccc(N(C(=O)Cc2c[nH]c3ccccc23)C(C(=O)NC2CCCCC2)c2ccc([N+](=O)[O-])cc2)cc1OC]
WJCPA-020
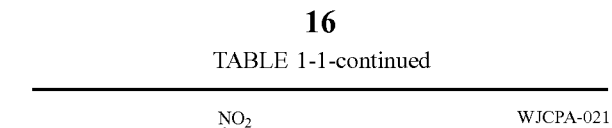
WJCPA-021
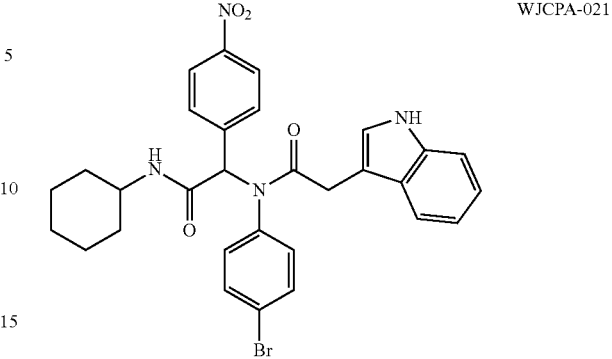
WJCPA-004
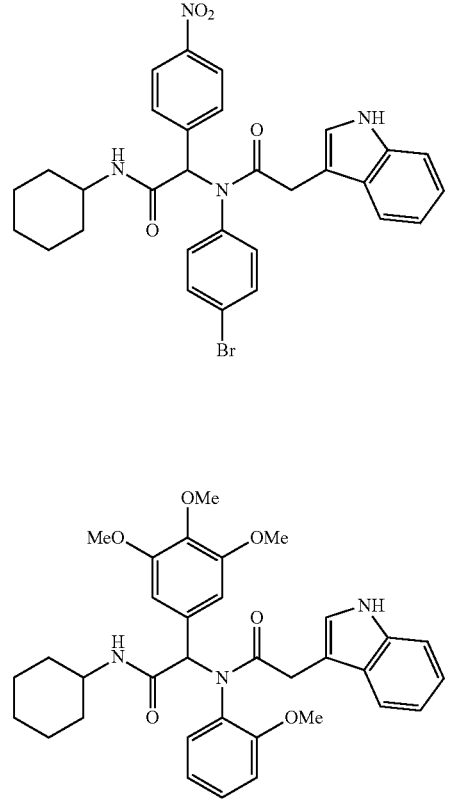
WJCPA-005
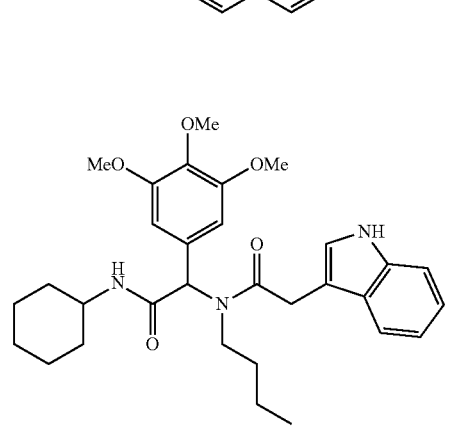
WJCPA-006

TABLE 1-1-continued
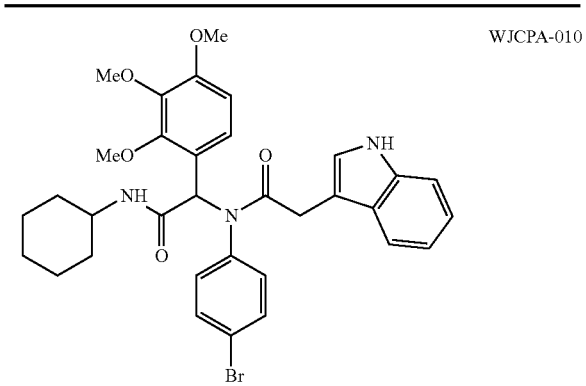
WJCPA-010
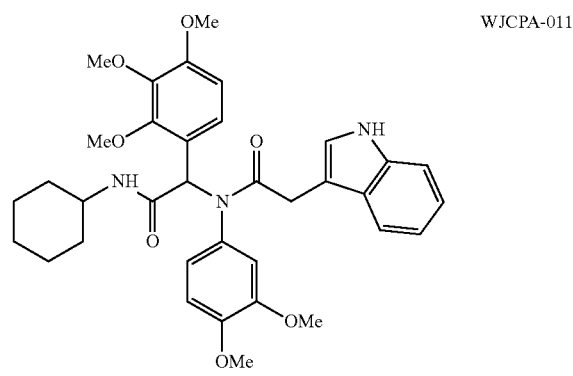
WJCPA-011
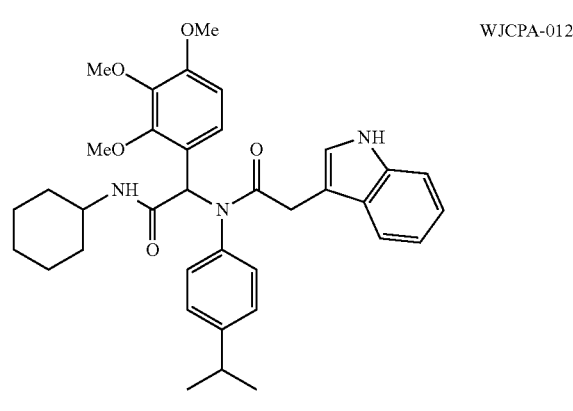
WJCPA-012
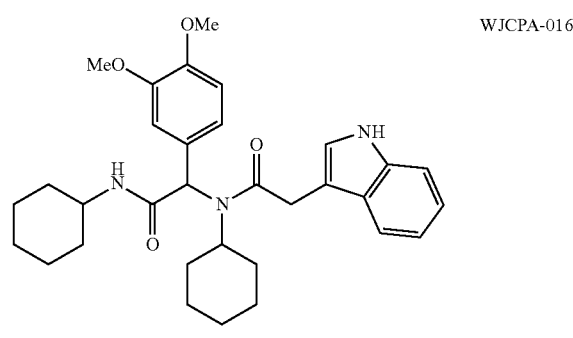
WJCPA-016
TABLE 1-1-continued
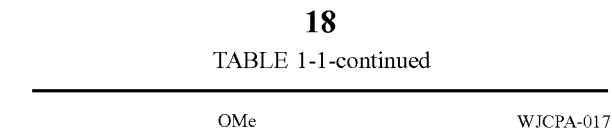
WJCPA-017
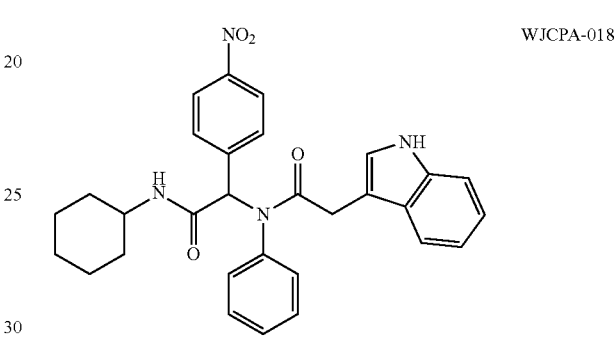
WJCPA-018
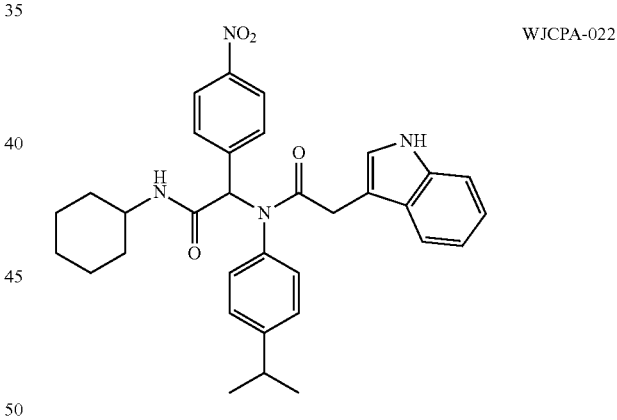
WJCPA-022
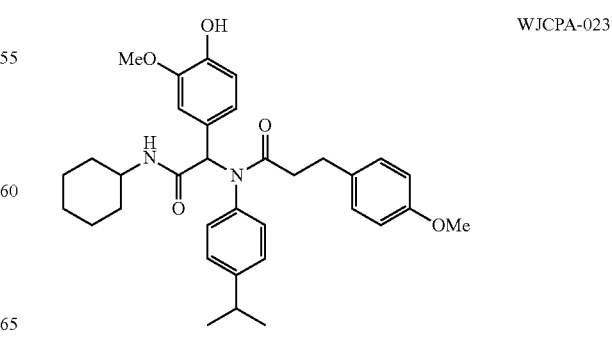
WJCPA-023

TABLE 1-1-continued
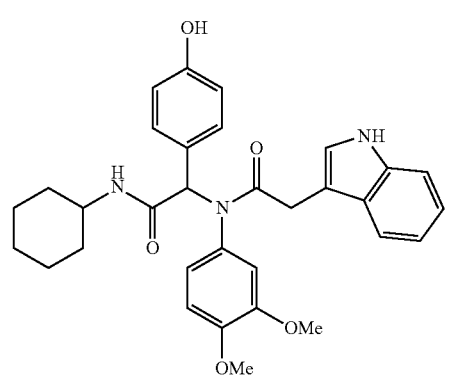 [SMILES: COc1ccc(N(C(=O)Cc2c[nH]c3ccccc23)C(C(=O)NC2CCCCC2)c2ccc(O)cc2)cc1OC]
WJCPA-024
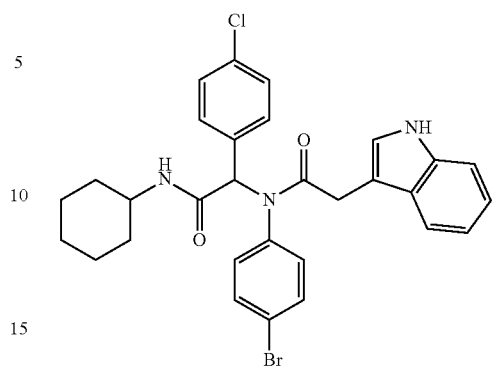
WJCPA-031
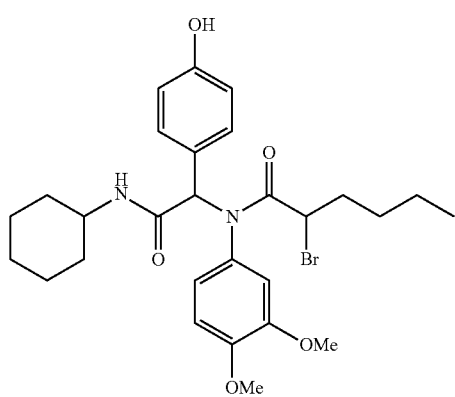 [SMILES: CCCCC(Br)C(=O)N(c1ccc(OC)c(OC)c1)C(C(=O)NC1CCCCC1)c1ccc(O)cc1]
WJCPA-025
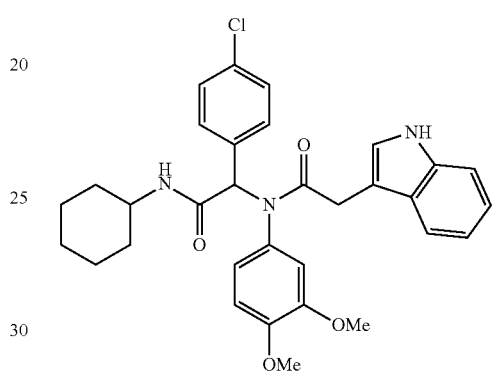
WJCPA-032
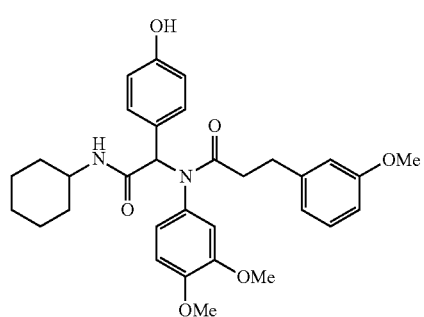 [SMILES: COc1cccc(CCC(=O)N(c2ccc(OC)c(OC)c2)C(C(=O)NC2CCCCC2)c2ccc(O)cc2)c1]
WJCPA-026
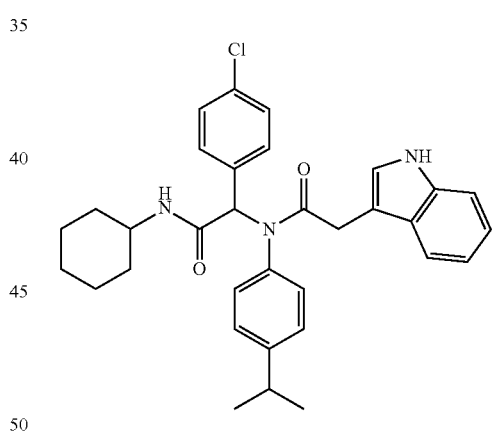
WJCPA-033
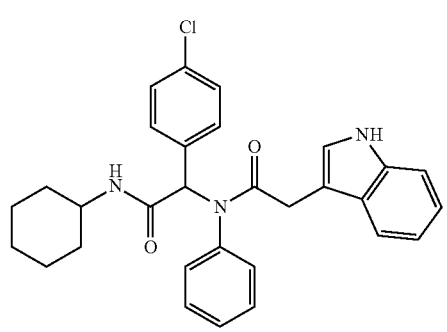
WJCPA-027
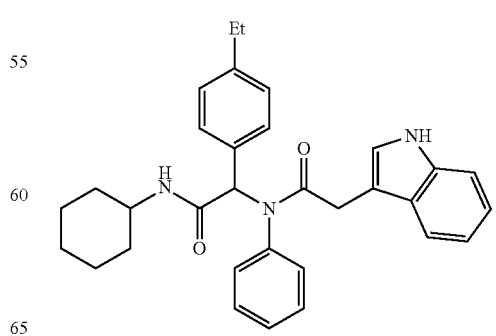
WJCPA-037

TABLE 1-1-continued
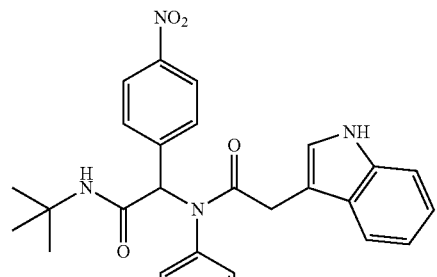
WJCPA-038
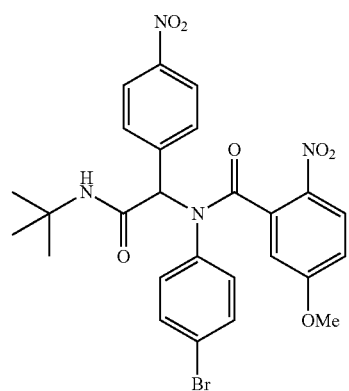 [SMILES: COc1ccc([N+](=O)[O-])c(C(=O)N(c2ccc(Br)cc2)C(C(=O)NC(C)(C)C)c2ccc([N+](=O)[O-])cc2)c1]
WJCPA-039
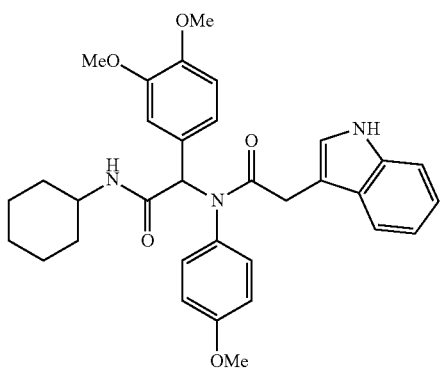 [SMILES: COc1ccc(N(C(=O)Cc2c[nH]c3ccccc23)C(C(=O)NC2CCCCC2)c2ccc(OC)c(OC)c2)cc1]
WJCPA-043
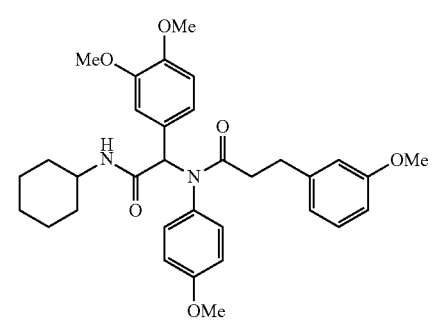 [SMILES: COc1ccc(N(C(=O)CCc2cccc(OC)c2)C(C(=O)NC2CCCCC2)c2ccc(OC)c(OC)c2)cc1]
WJCPA-044
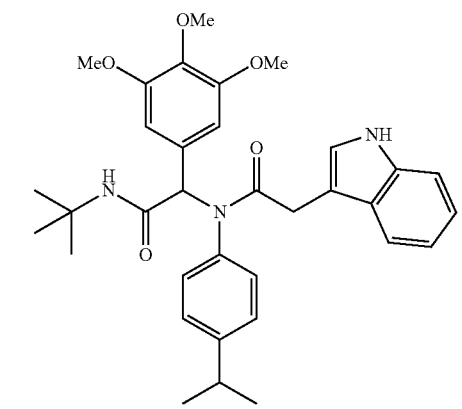 [SMILES: COc1cc(C(C(=O)NC(C)(C)C)N(C(=O)Cc2c[nH]c3ccccc23)c2ccc(C(C)C)cc2)cc(OC)c1OC]
WJCPA-045
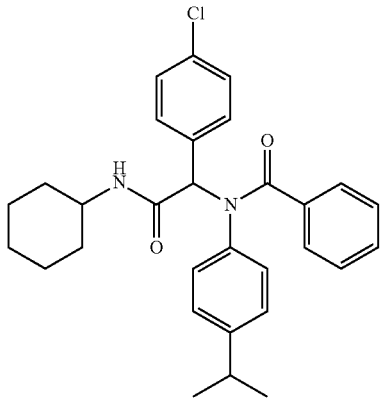 [SMILES: CC(C)c1ccc(N(C(=O)c2ccccc2)C(C(=O)NC2CCCCC2)c2ccc(Cl)cc2)cc1]
WJCPA-028
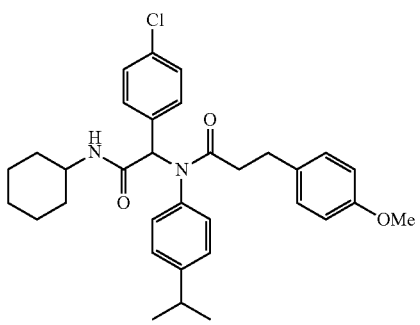 [SMILES: COc1ccc(CCC(=O)N(c2ccc(C(C)C)cc2)C(C(=O)NC2CCCCC2)c2ccc(Cl)cc2)cc1]
WJCPA-029
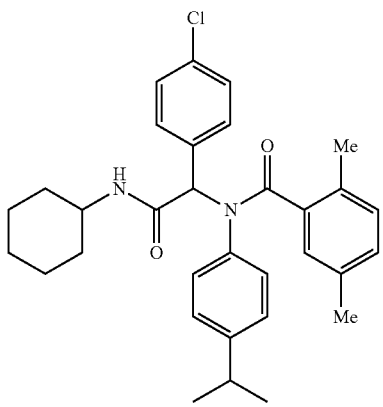 [SMILES: Cc1ccc(C)c(C(=O)N(c2ccc(C(C)C)cc2)C(C(=O)NC2CCCCC2)c2ccc(Cl)cc2)c1]
WJCPA-030

TABLE 1-1-continued
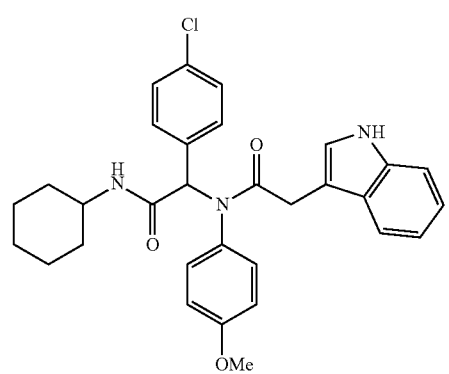
WJCPA-034
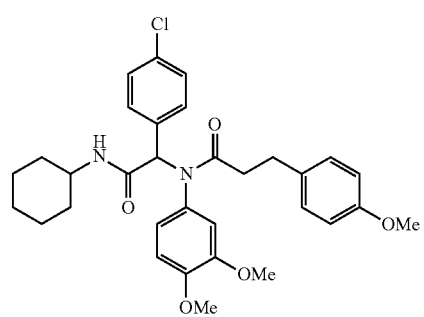 [SMILES: COc1ccc(CCC(=O)N(c2ccc(OC)c(OC)c2)C(C(=O)NC2CCCCC2)c2ccc(Cl)cc2)cc1]
WJCPA-035
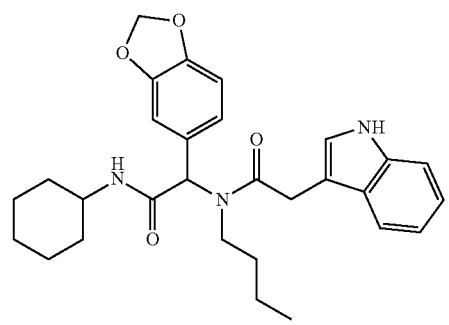 [SMILES: CCCCN(C(=O)Cc1c[nH]c2ccccc12)C(C(=O)NC1CCCCC1)c1ccc2c(c1)OCO2]
WJCPA-036
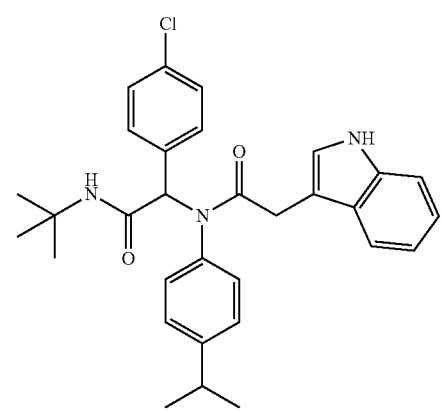 [SMILES: CC(C)c1ccc(N(C(=O)Cc2c[nH]c3ccccc23)C(C(=O)NC(C)(C)C)c2ccc(Cl)cc2)cc1]
WJCPA-040
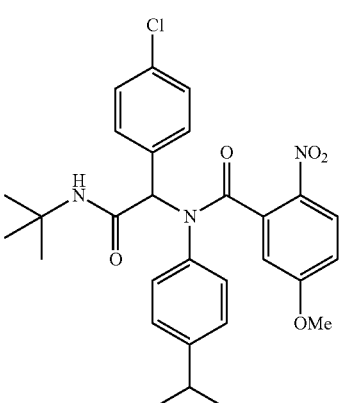
WJCPA-041
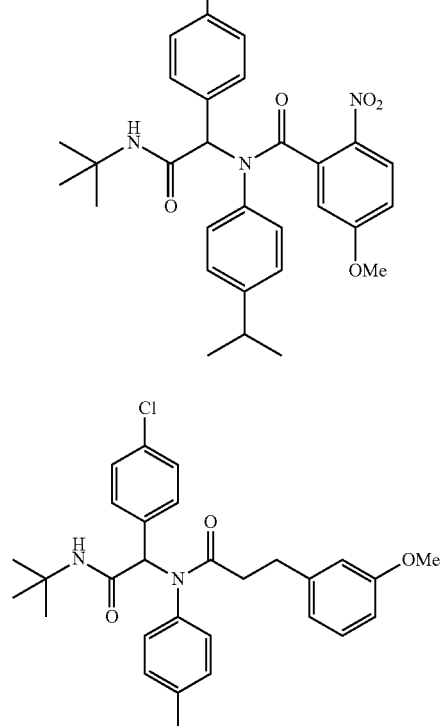
WJCPA-042
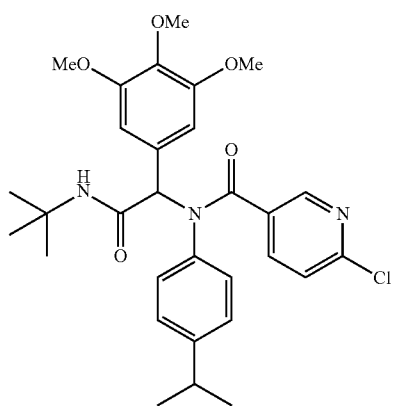 [SMILES: COc1cc(C(C(=O)NC(C)(C)C)N(C(=O)c2ccc(Cl)nc2)c2ccc(C(C)C)cc2)cc(OC)c1OC]
WJCPA-046
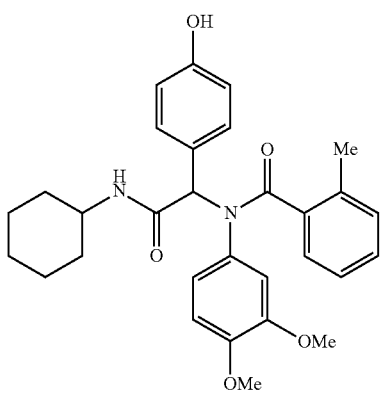 [SMILES: COc1ccc(N(C(=O)c2ccccc2C)C(C(=O)NC2CCCCC2)c2ccc(O)cc2)cc1OC]
WJCPA-047

TABLE 1-1-continued
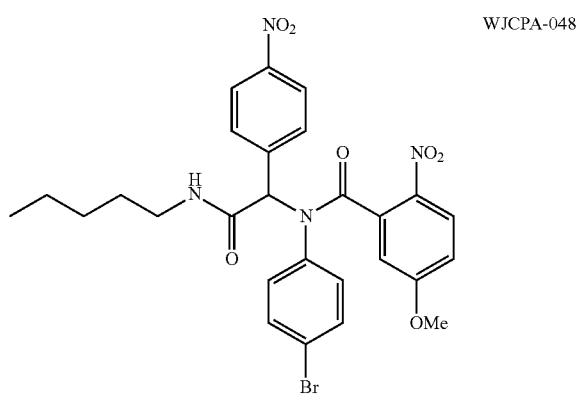
WJCPA-048
TABLE 1-2
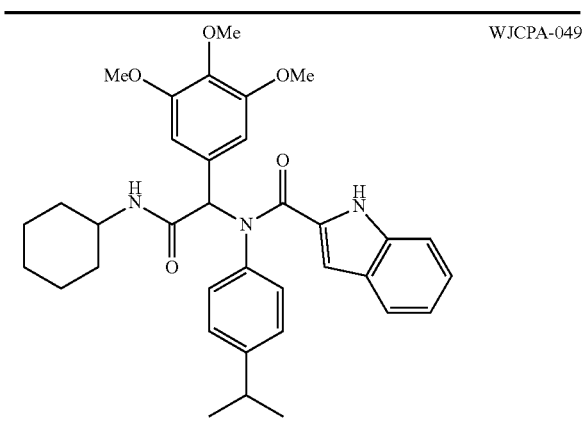
WJCPA-049
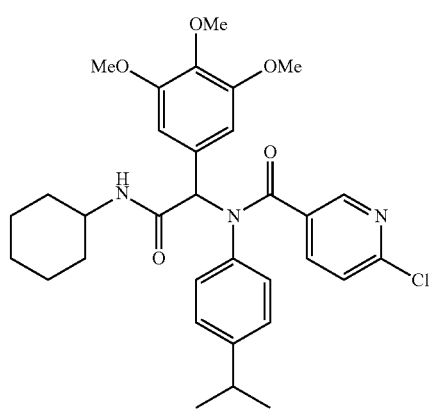 [SMILES: COc1cc(C(C(=O)NC2CCCCC2)N(C(=O)c2ccc(Cl)nc2)c2ccc(C(C)C)cc2)cc(OC)c1OC]
WJCPA-050
TABLE 1-2-continued
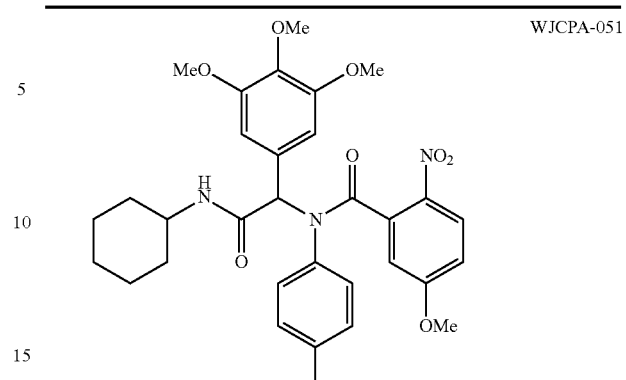
WJCPA-051
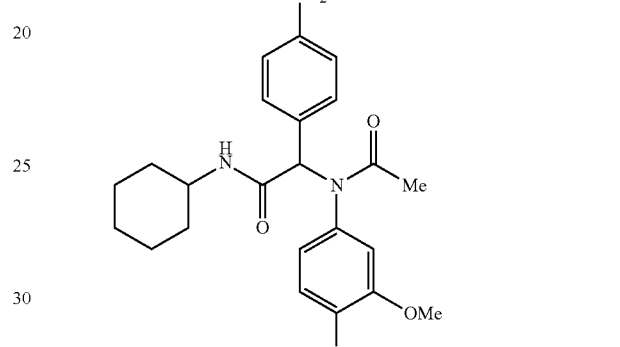
WJCPA-055
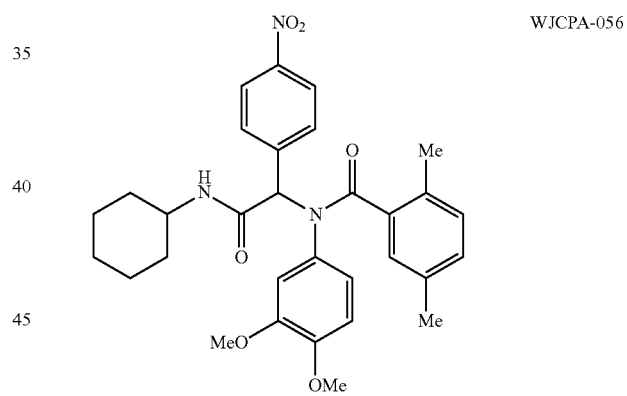
WJCPA-056
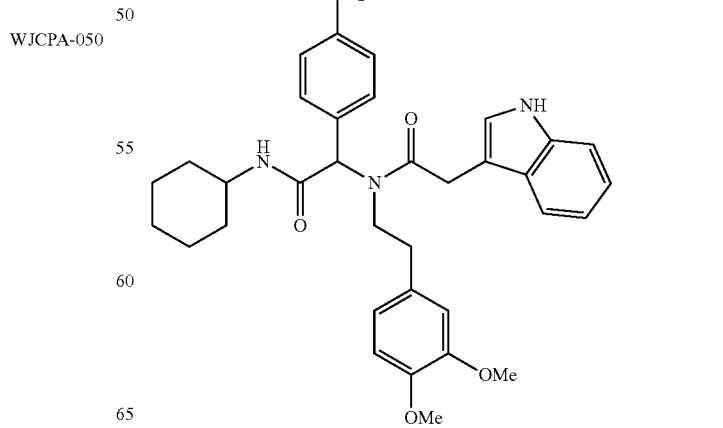
WJCPA-057

TABLE 1-2-continued
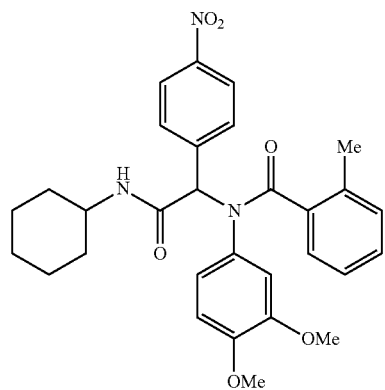 [SMILES: COc1ccc(N(C(=O)c2ccccc2C)C(C(=O)NC2CCCCC2)c2ccc([N+](=O)[O-])cc2)cc1OC]
WJCPA-061
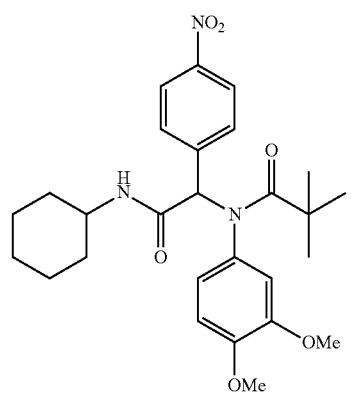 [SMILES: COc1ccc(N(C(=O)C(C)(C)C)C(C(=O)NC2CCCCC2)c2ccc([N+](=O)[O-])cc2)cc1OC]
WJCPA-062
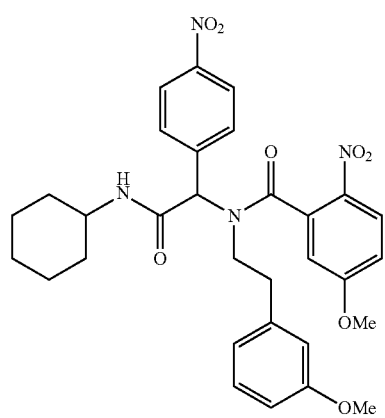 [SMILES: COc1cccc(CCN(C(=O)c2cc(OC)ccc2[N+](=O)[O-])C(C(=O)NC2CCCCC2)c2ccc([N+](=O)[O-])cc2)c1]
WJCPA-063
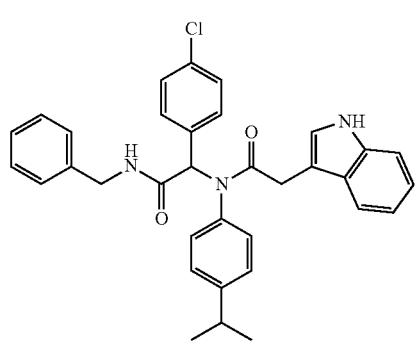 [SMILES: CC(C)c1ccc(N(C(=O)Cc2c[nH]c3ccccc23)C(C(=O)NCc2ccccc2)c2ccc(Cl)cc2)cc1]
WJCPA-067
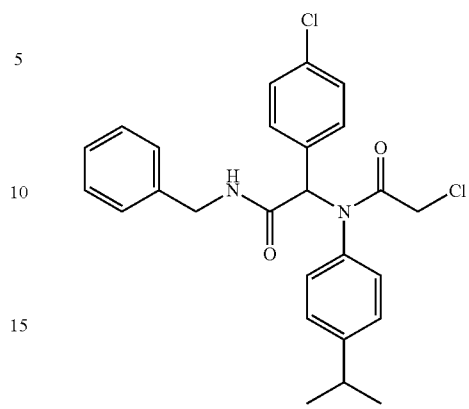
WJCPA-068
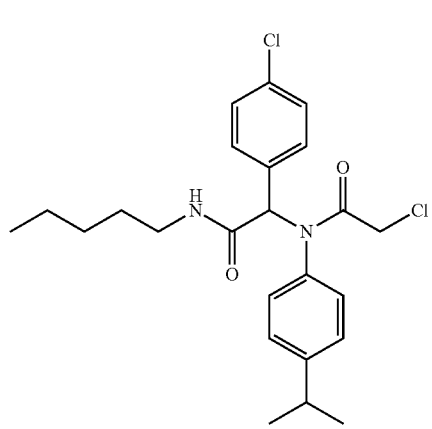 [SMILES: CCCCCNC(=O)C(c1ccc(Cl)cc1)N(C(=O)CCl)c1ccc(C(C)C)cc1]
WJCPA-069
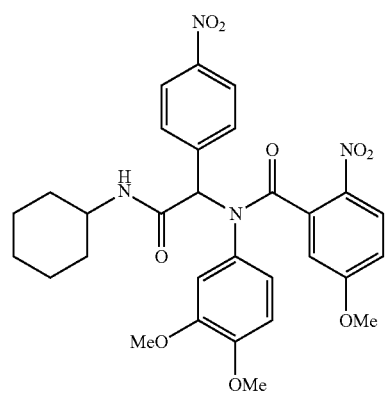 [SMILES: COc1ccc([N+](=O)[O-])c(C(=O)N(c2ccc(OC)c(OC)c2)C(C(=O)NC2CCCCC2)c2ccc([N+](=O)[O-])cc2)c1]
WJCPA-052
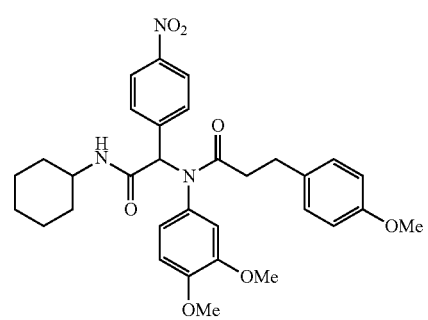
WJCPA-053

TABLE 1-2-continued
WJCPA-054
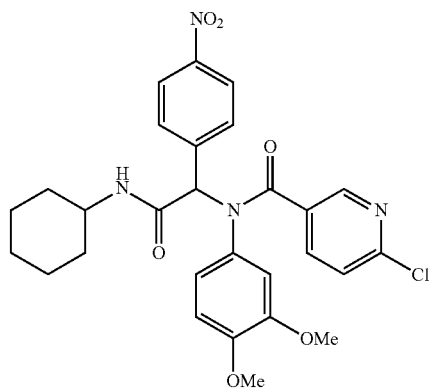 [SMILES: COc1ccc(N(C(=O)c2ccc(Cl)nc2)C(C(=O)NC2CCCCC2)c2ccc([N+](=O)[O-])cc2)cc1OC]
WJCPA-058
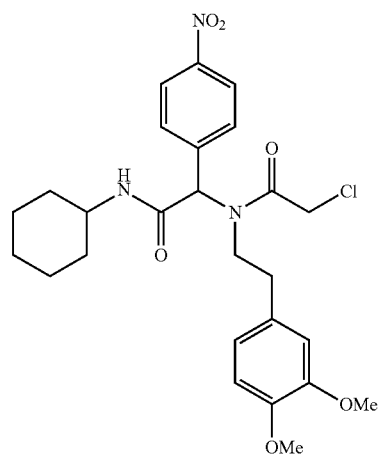 [SMILES: COc1ccc(CCN(C(=O)CCl)C(C(=O)NC2CCCCC2)c2ccc([N+](=O)[O-])cc2)cc1OC]
WJCPA-059
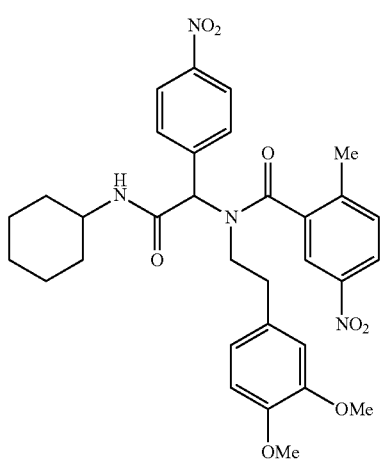 [SMILES: COc1ccc(CCN(C(=O)c2cc([N+](=O)[O-])ccc2C)C(C(=O)NC2CCCCC2)c2ccc([N+](=O)[O-])cc2)cc1OC]
TABLE 1-2-continued
WJCPA-060
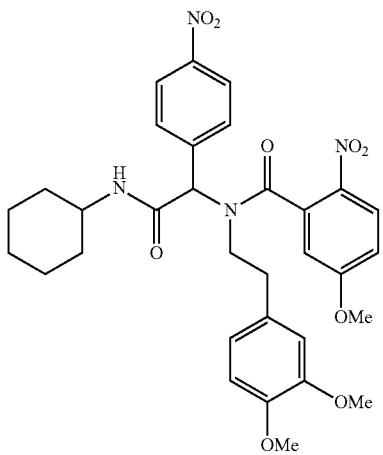 [SMILES: COc1ccc([N+](=O)[O-])c(C(=O)N(CCc2ccc(OC)c(OC)c2)C(C(=O)NC2CCCCC2)c2ccc([N+](=O)[O-])cc2)c1]
WJCPA-064
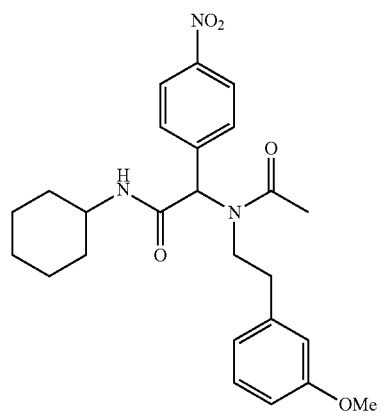 [SMILES: COc1cccc(CCN(C(C)=O)C(C(=O)NC2CCCCC2)c2ccc([N+](=O)[O-])cc2)c1]
WJCPA-065
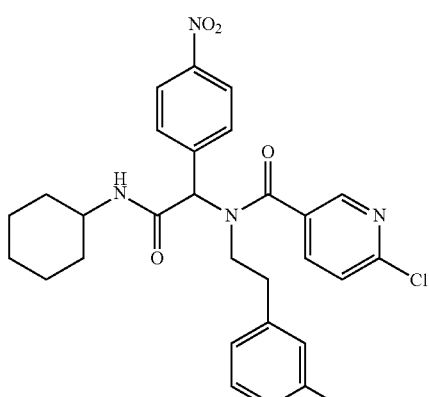

TABLE 1-2-continued
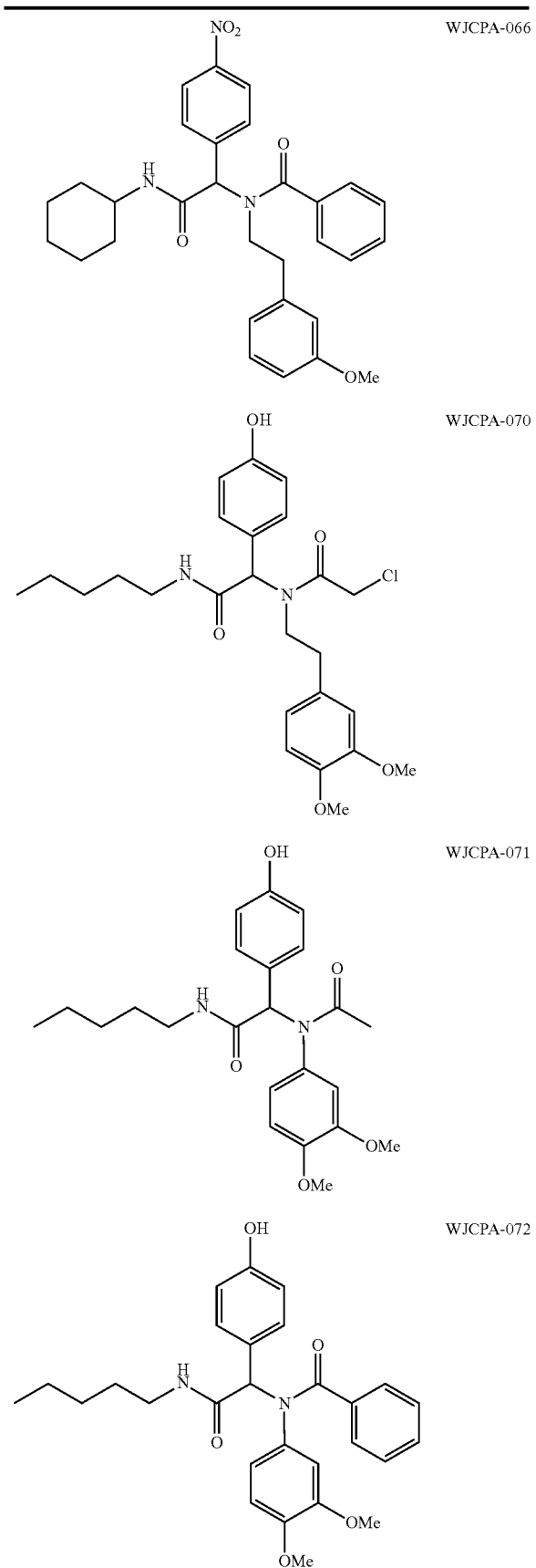
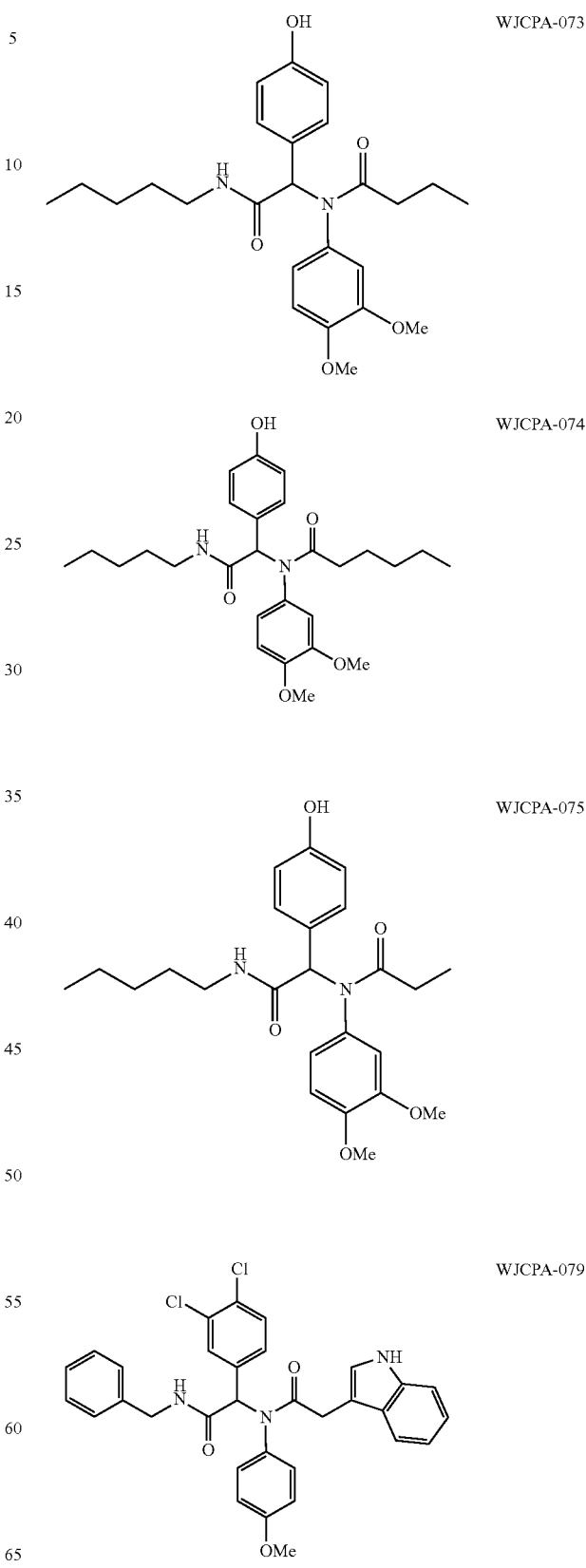

TABLE 1-2-continued
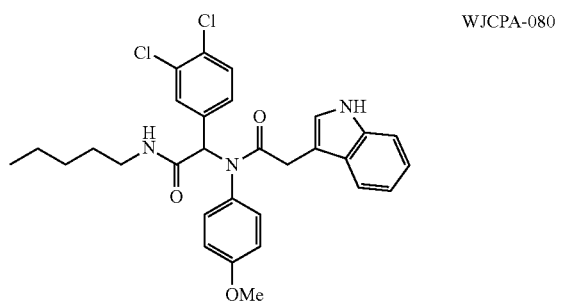
WJCPA-080
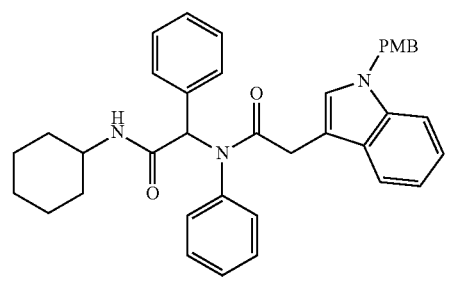
WJCPA-081
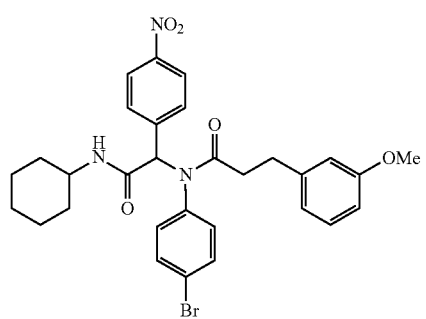 [SMILES: COc1cccc(CCC(=O)N(c2ccc(Br)cc2)C(C(=O)NC2CCCCC2)c2ccc([N+](=O)[O-])cc2)c1]
WJCPA-085
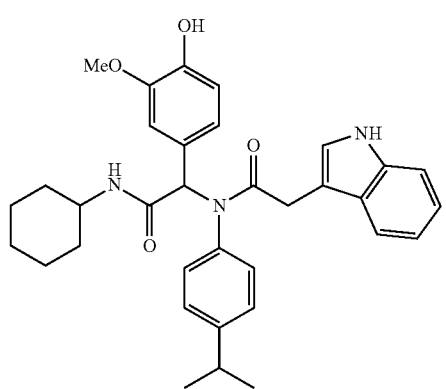 [SMILES: COc1cc(C(C(=O)NC2CCCCC2)N(C(=O)Cc2c[nH]c3ccccc23)c2ccc(C(C)C)cc2)ccc1O]
WJCPA-086
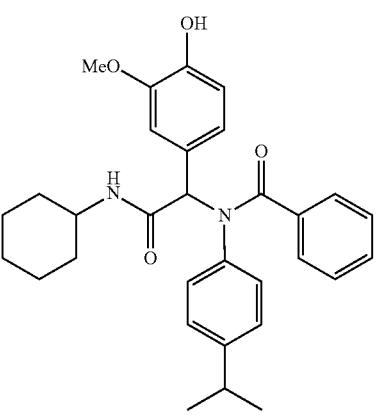 [SMILES: COc1cc(C(C(=O)NC2CCCCC2)N(C(=O)c2ccccc2)c2ccc(C(C)C)cc2)ccc1O]
WJCPA-087
WJCPA-091
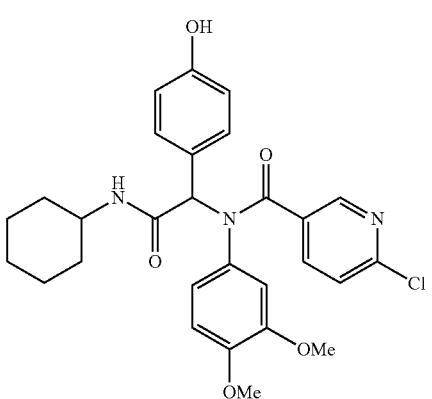 [SMILES: COc1ccc(N(C(=O)c2ccc(Cl)nc2)C(C(=O)NC2CCCCC2)c2ccc(O)cc2)cc1OC]
WJCPA-092
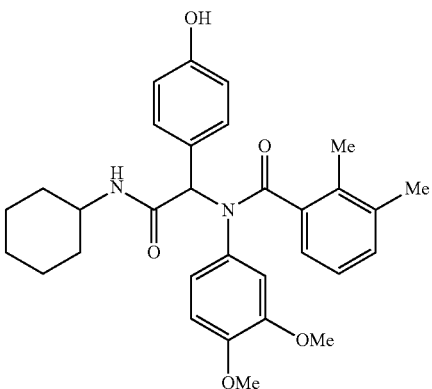 [SMILES: COc1ccc(N(C(=O)c2cccc(C)c2C)C(C(=O)NC2CCCCC2)c2ccc(O)cc2)cc1OC]
WJCPA-093

TABLE 1-2-continued
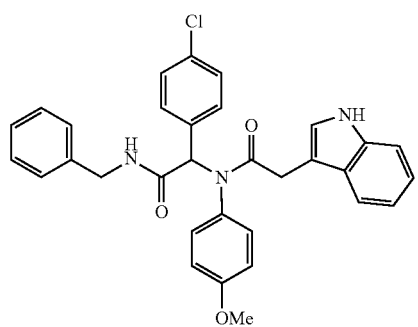 [SMILES: COc1ccc(N(C(=O)Cc2c[nH]c3ccccc23)C(C(=O)NCc2ccccc2)c2ccc(Cl)cc2)cc1]
WJCPA-076
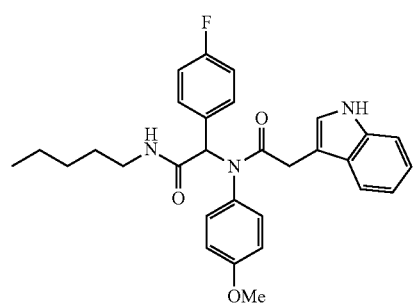 [SMILES: CCCCCNC(=O)C(c1ccc(F)cc1)N(C(=O)Cc1c[nH]c2ccccc12)c1ccc(OC)cc1]
WJCPA-077
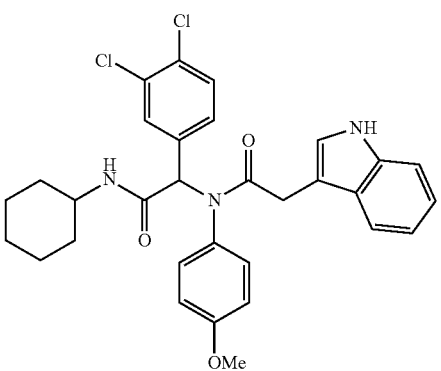 [SMILES: COc1ccc(N(C(=O)Cc2c[nH]c3ccccc23)C(C(=O)NC2CCCCC2)c2ccc(Cl)c(Cl)c2)cc1]
WJCPA-078
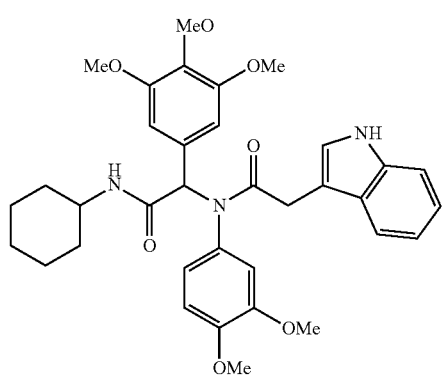 [SMILES: COc1ccc(N(C(=O)Cc2c[nH]c3ccccc23)C(C(=O)NC2CCCCC2)c2cc(OC)c(OC)c(OC)c2)cc1OC]
WJCPA-082
TABLE 1-2-continued
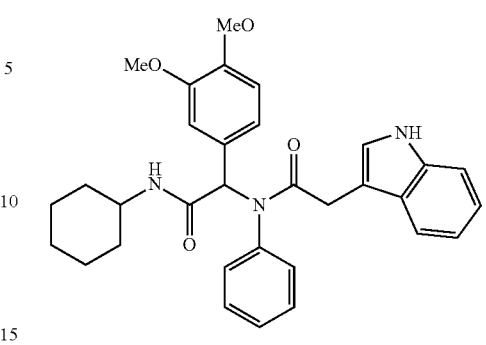
WJCPA-083
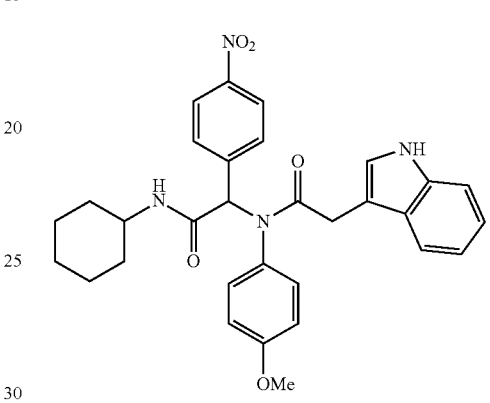
WJCPA-084
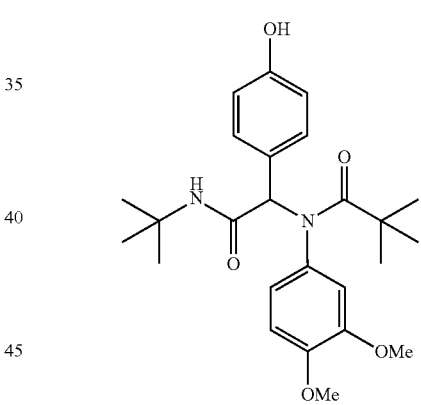
WJCPA-088
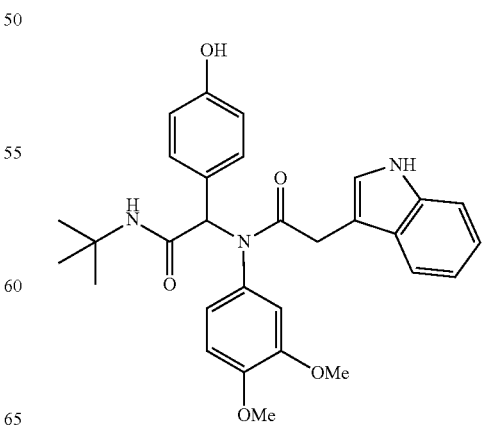
WJCPA-089

TABLE 1-2-continued
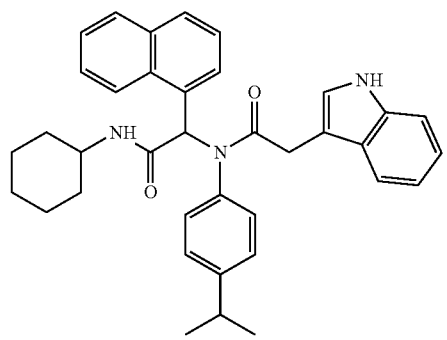 [SMILES: CC(C)c1ccc(N(C(=O)Cc2c[nH]c3ccccc23)C(C(=O)NC2CCCCC2)c2cccc3ccccc23)cc1]
WJCPA-090
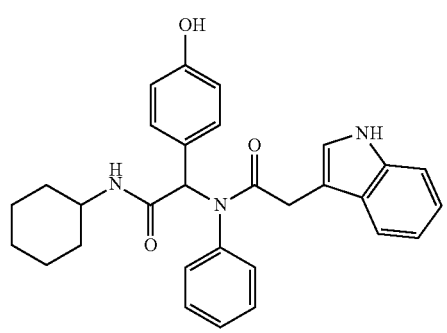 [SMILES: O=C(NC1CCCCC1)C(c1ccc(O)cc1)N(C(=O)Cc1c[nH]c2ccccc12)c1ccccc1]
WJCPA-094
TABLE 1-2-continued
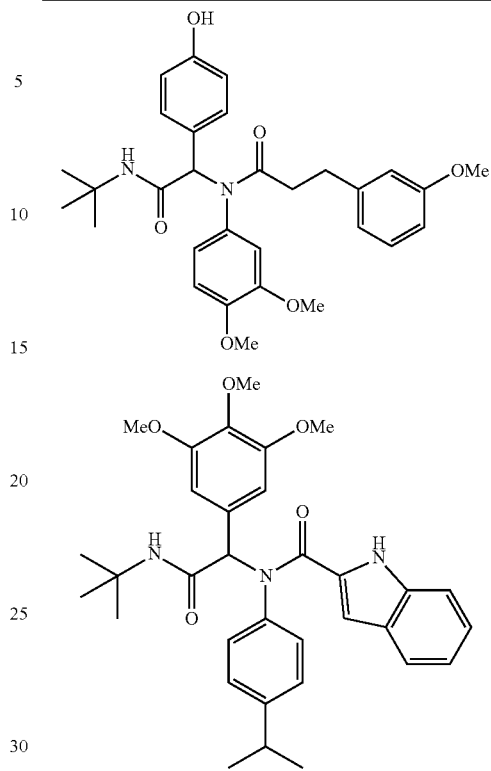
WJCPA-095
WJCPA-096
TABLE 1-3
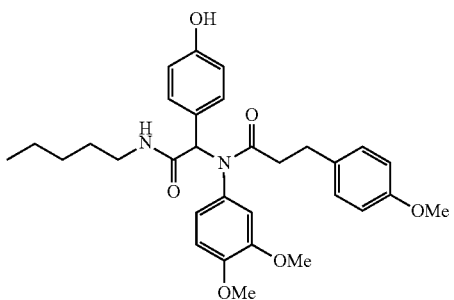 [SMILES: CCCCCNC(=O)C(c1ccc(O)cc1)N(C(=O)CCc1ccc(OC)cc1)c1ccc(OC)c(OC)c1]
WJCPA-097
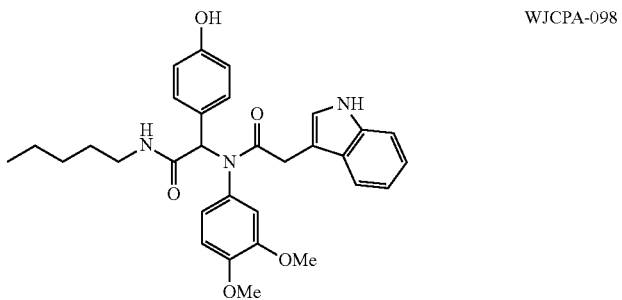
WJCPA-098

TABLE 1-3-continued
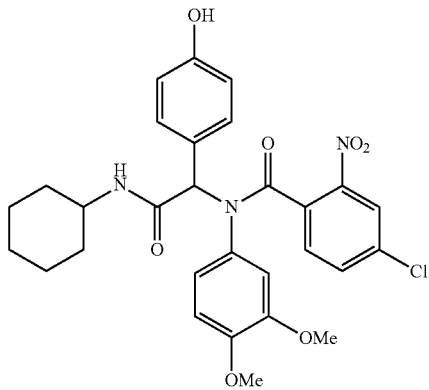 [SMILES: COc1ccc(N(C(=O)c2ccc(Cl)cc2[N+](=O)[O-])C(C(=O)NC2CCCCC2)c2ccc(O)cc2)cc1OC]
WJCPA-099
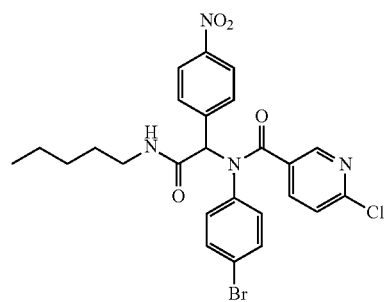 [SMILES: CCCCCNC(=O)C(c1ccc([N+](=O)[O-])cc1)N(C(=O)c1ccc(Cl)nc1)c1ccc(Br)cc1]
WJCPA-103
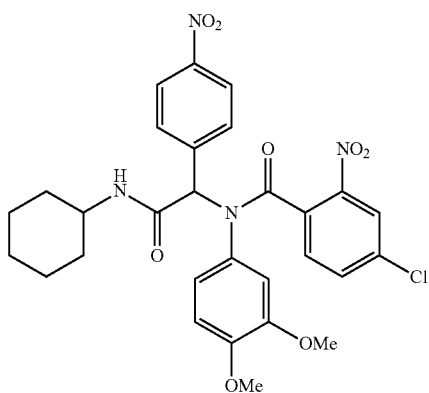 [SMILES: COc1ccc(N(C(=O)c2ccc(Cl)cc2[N+](=O)[O-])C(C(=O)NC2CCCCC2)c2ccc([N+](=O)[O-])cc2)cc1OC]
WJCPA-104
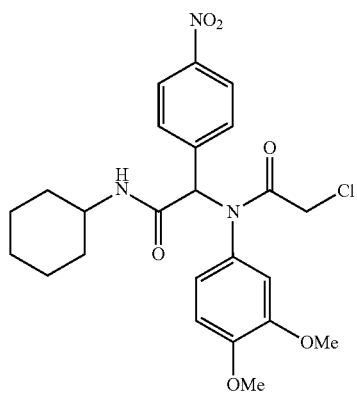 [SMILES: COc1ccc(N(C(=O)CCl)C(C(=O)NC2CCCCC2)c2ccc([N+](=O)[O-])cc2)cc1OC]
WJCPA-105

TABLE 1-3-continued
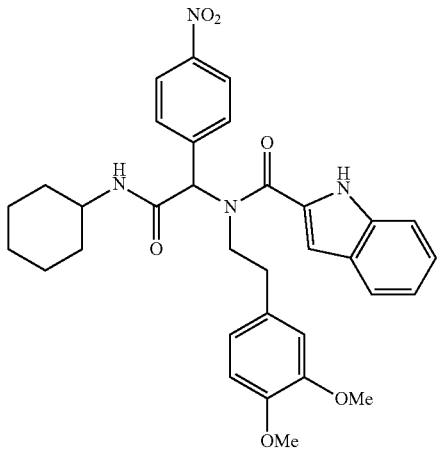 [SMILES: COc1ccc(CCN(C(=O)c2cc3ccccc3[nH]2)C(C(=O)NC2CCCCC2)c2ccc([N+](=O)[O-])cc2)cc1OC]
WJCPA-109
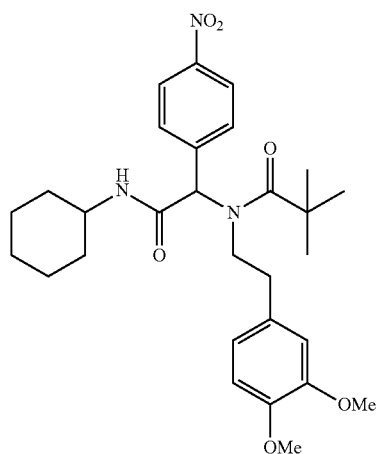 [SMILES: COc1ccc(CCN(C(=O)C(C)(C)C)C(C(=O)NC2CCCCC2)c2ccc([N+](=O)[O-])cc2)cc1OC]
WJCPA-110
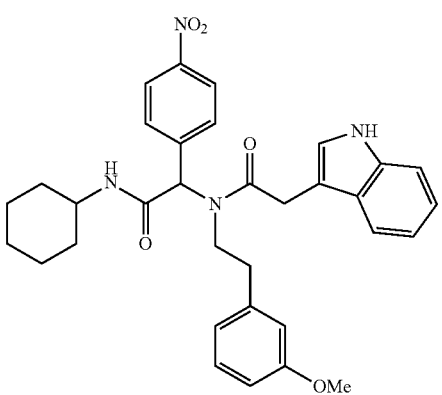 [SMILES: COc1cccc(CCN(C(=O)Cc2c[nH]c3ccccc23)C(C(=O)NC2CCCCC2)c2ccc([N+](=O)[O-])cc2)c1]
WJCPA-111

TABLE 1-3-continued
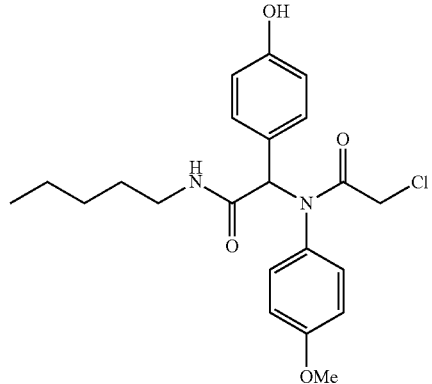 [SMILES: CCCCCNC(=O)C(c1ccc(O)cc1)N(C(=O)CCl)c1ccc(OC)cc1]
WJCPA-115
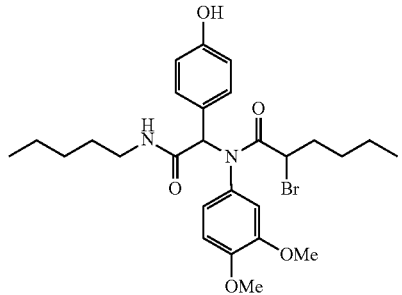 [SMILES: CCCCCNC(=O)C(c1ccc(O)cc1)N(C(=O)C(Br)CCCC)c1ccc(OC)c(OC)c1]
WJCPA-116
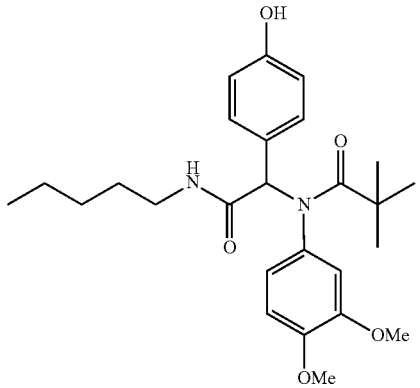 [SMILES: CCCCCNC(=O)C(c1ccc(O)cc1)N(C(=O)C(C)(C)C)c1ccc(OC)c(OC)c1]
WJCPA-117
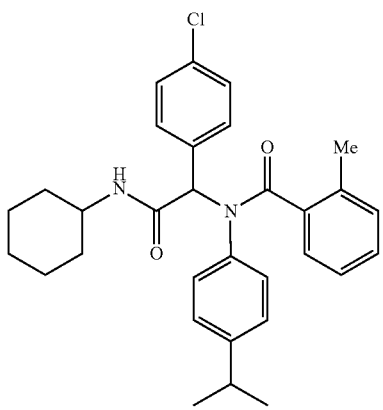 [SMILES: Cc1ccccc1C(=O)N(c1ccc(C(C)C)cc1)C(C(=O)NC1CCCCC1)c1ccc(Cl)cc1]
WJCPA-100

TABLE 1-3-continued
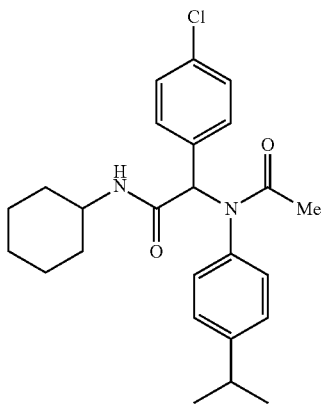 [SMILES: CC(=O)N(c1ccc(C(C)C)cc1)C(C(=O)NC1CCCCC1)c1ccc(Cl)cc1]
WJCPA-101
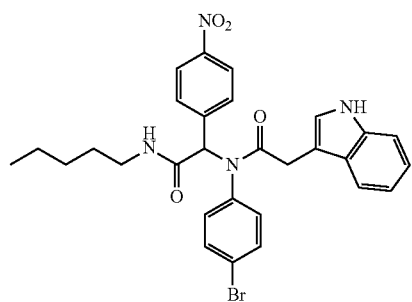 [SMILES: CCCCCNC(=O)C(c1ccc([N+](=O)[O-])cc1)N(C(=O)Cc1c[nH]c2ccccc12)c1ccc(Br)cc1]
WJCPA-102
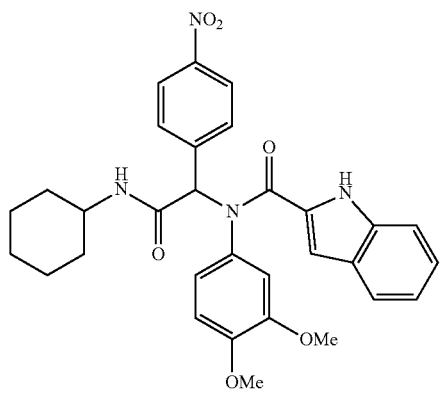 [SMILES: COc1ccc(N(C(=O)c2cc3ccccc3[nH]2)C(C(=O)NC2CCCCC2)c2ccc([N+](=O)[O-])cc2)cc1OC]
WJCPA-106
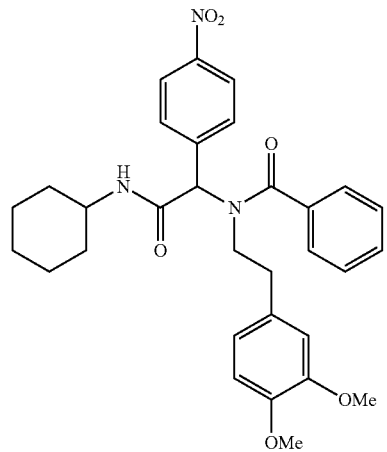 [SMILES: COc1ccc(CCN(C(=O)c2ccccc2)C(C(=O)NC2CCCCC2)c2ccc([N+](=O)[O-])cc2)cc1OC]
WJCPA-107

TABLE 1-3-continued
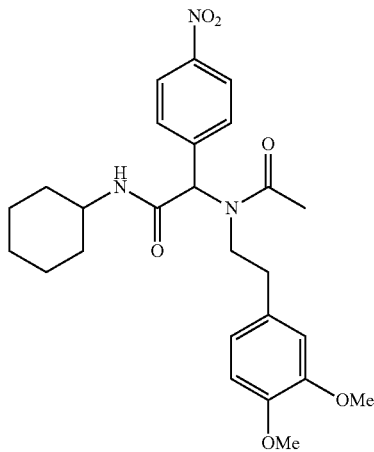 [SMILES: COc1ccc(CCN(C(C)=O)C(C(=O)NC2CCCCC2)c2ccc([N+](=O)[O-])cc2)cc1OC]
WJCPA-108
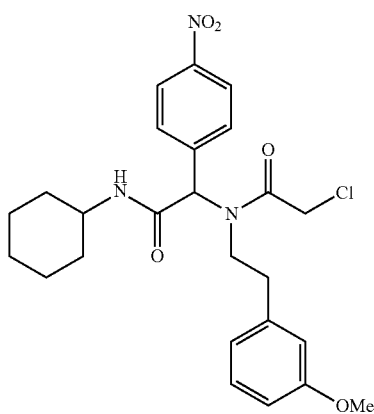 [SMILES: COc1cccc(CCN(C(=O)CCl)C(C(=O)NC2CCCCC2)c2ccc([N+](=O)[O-])cc2)c1]
WJCPA-112
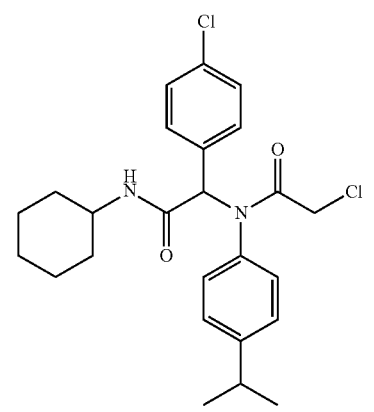 [SMILES: CC(C)c1ccc(N(C(=O)CCl)C(C(=O)NC2CCCCC2)c2ccc(Cl)cc2)cc1]
WJCPA-113

TABLE 1-3-continued
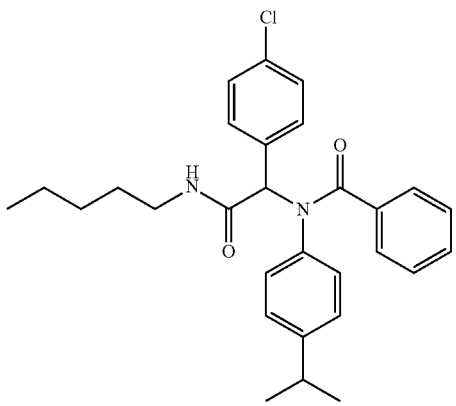 [SMILES: CCCCCNC(=O)C(c1ccc(Cl)cc1)N(C(=O)c1ccccc1)c1ccc(C(C)C)cc1]
WJCPA-114
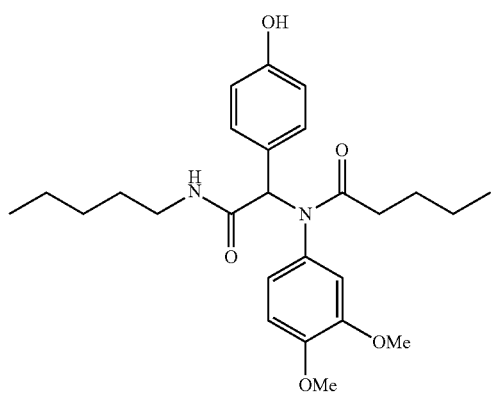 [SMILES: CCCCCNC(=O)C(c1ccc(O)cc1)N(C(=O)CCCC)c1ccc(OC)c(OC)c1]
WJCPA-118
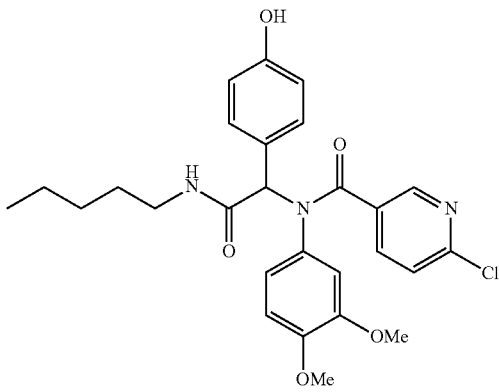 [SMILES: CCCCCNC(=O)C(c1ccc(O)cc1)N(C(=O)c1ccc(Cl)nc1)c1ccc(OC)c(OC)c1]
WJCPA-119
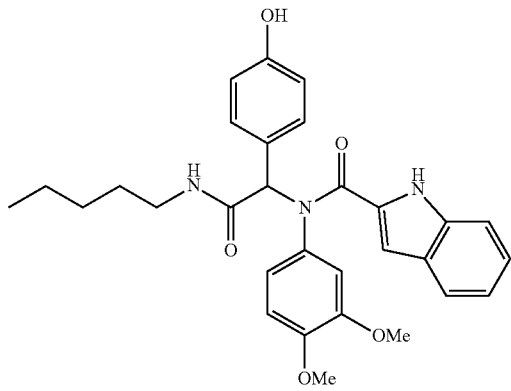 [SMILES: CCCCCNC(=O)C(c1ccc(O)cc1)N(C(=O)c1cc2ccccc2[nH]1)c1ccc(OC)c(OC)c1]
WJCPA-120

TABLE 1-3-continued
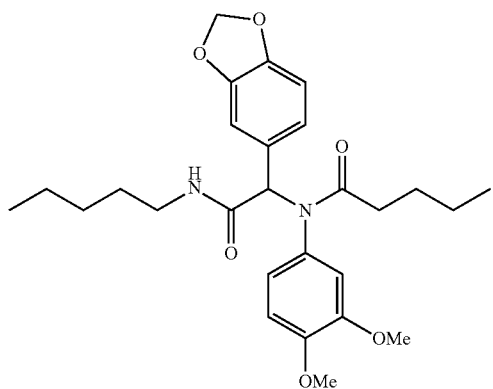 [SMILES: CCCCCNC(=O)C(c1ccc2c(c1)OCO2)N(C(=O)CCCC)c1ccc(OC)c(OC)c1]
WJCPA-121
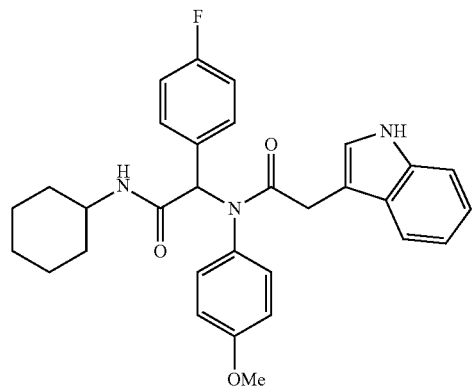 [SMILES: COc1ccc(N(C(=O)Cc2c[nH]c3ccccc23)C(C(=O)NC2CCCCC2)c2ccc(F)cc2)cc1]
WJCPA-122
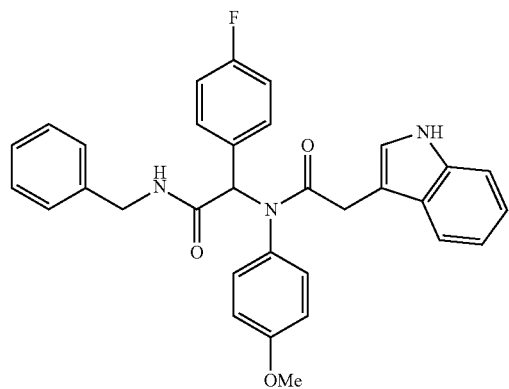 [SMILES: COc1ccc(N(C(=O)Cc2c[nH]c3ccccc23)C(C(=O)NCc2ccccc2)c2ccc(F)cc2)cc1]
WJCPA-123
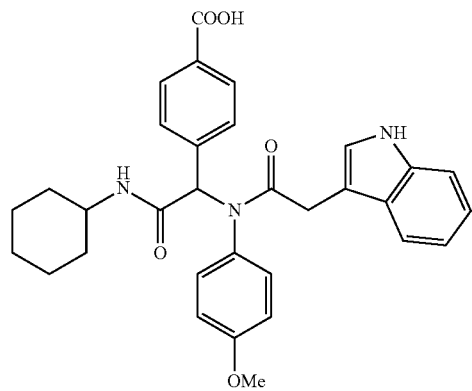 [SMILES: COc1ccc(N(C(=O)Cc2c[nH]c3ccccc23)C(C(=O)NC2CCCCC2)c2ccc(C(=O)O)cc2)cc1]
WJCPA-124

TABLE 1-3-continued
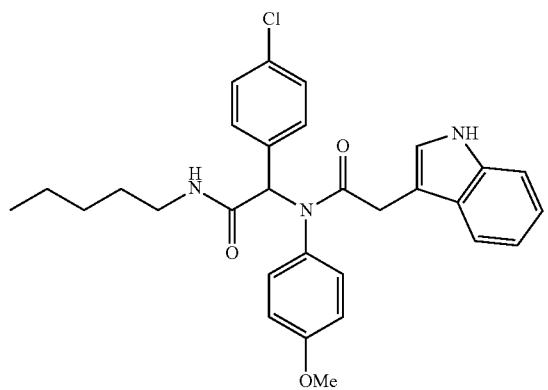 [SMILES: CCCCCNC(=O)C(c1ccc(Cl)cc1)N(C(=O)Cc1c[nH]c2ccccc12)c1ccc(OC)cc1]
WJCPA-125
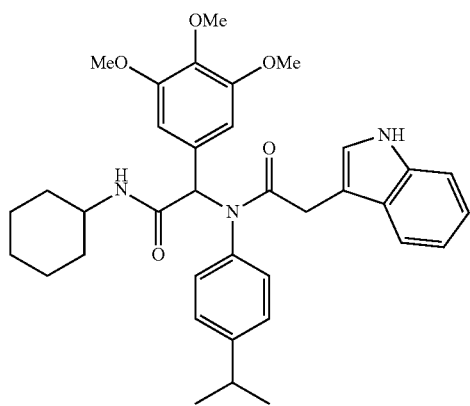 [SMILES: COc1cc(C(C(=O)NC2CCCCC2)N(C(=O)Cc2c[nH]c3ccccc23)c2ccc(C(C)C)cc2)cc(OC)c1OC]
WJCPA-126
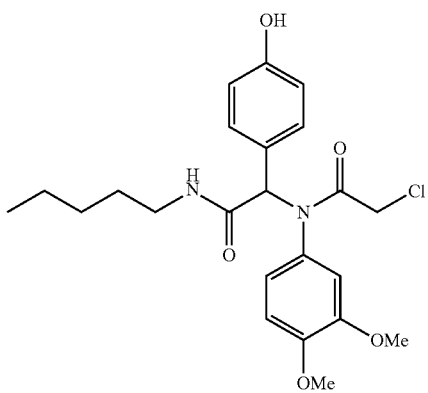 [SMILES: CCCCCNC(=O)C(c1ccc(O)cc1)N(C(=O)CCl)c1ccc(OC)c(OC)c1]
WJCPA-127
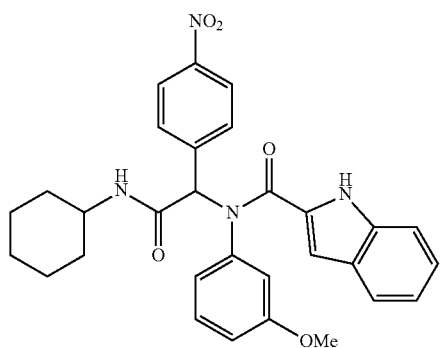 [SMILES: COc1cccc(N(C(=O)c2cc3ccccc3[nH]2)C(C(=O)NC2CCCCC2)c2ccc([N+](=O)[O-])cc2)c1]
WJCPA-128

TABLE 1-3-continued
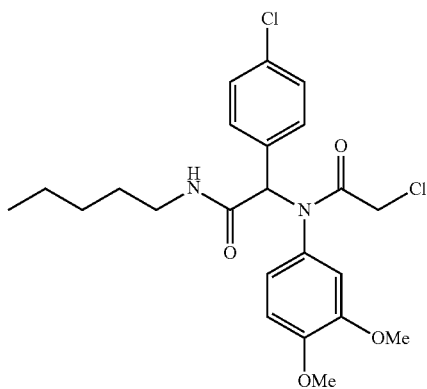 [SMILES: CCCCCNC(=O)C(c1ccc(Cl)cc1)N(C(=O)CCl)c1ccc(OC)c(OC)c1]
WJCPA-129
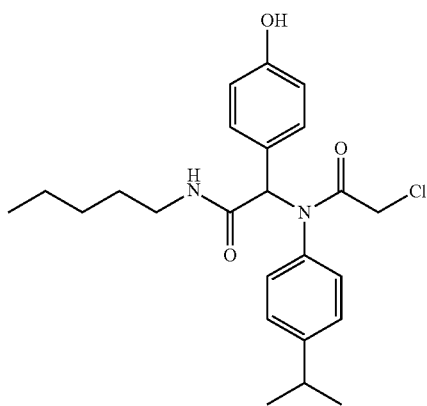 [SMILES: CCCCCNC(=O)C(c1ccc(O)cc1)N(C(=O)CCl)c1ccc(C(C)C)cc1]
WJCPA-130
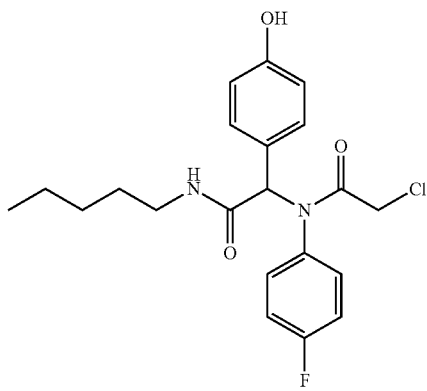 [SMILES: CCCCCNC(=O)C(c1ccc(O)cc1)N(C(=O)CCl)c1ccc(F)cc1]
WJCPA-131
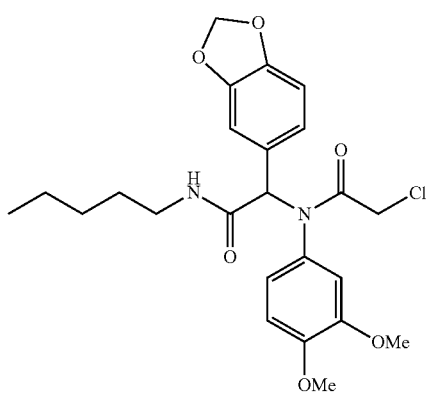 [SMILES: CCCCCNC(=O)C(c1ccc2c(c1)OCO2)N(C(=O)CCl)c1ccc(OC)c(OC)c1]
WJCPA-132

TABLE 1-3-continued

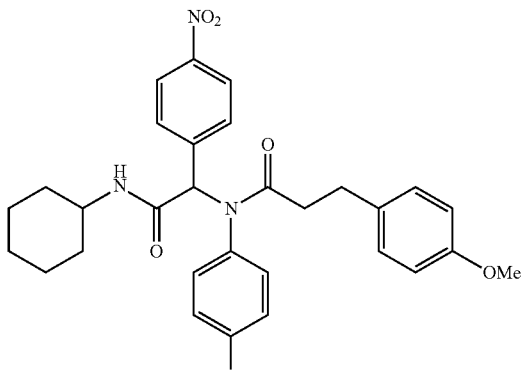

WJCPA-133

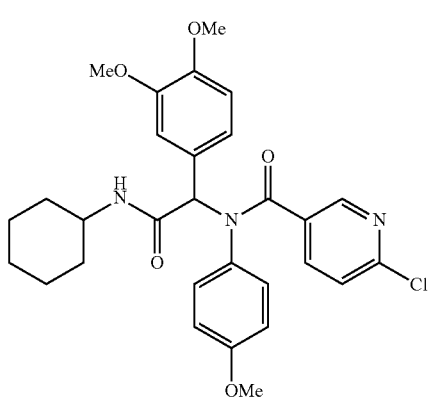 [SMILES: COc1ccc(N(C(=O)c2ccc(Cl)nc2)C(C(=O)NC2CCCCC2)c2ccc(OC)c(OC)c2)cc1]

WJCPA-134

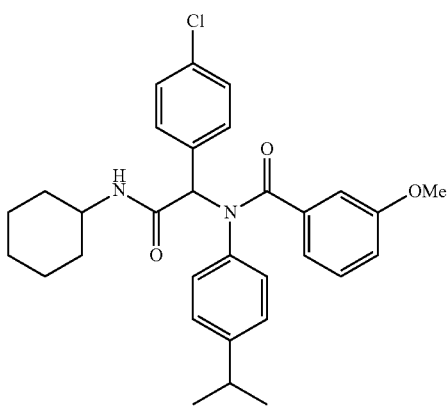 [SMILES: COc1cccc(C(=O)N(c2ccc(C(C)C)cc2)C(C(=O)NC2CCCCC2)c2ccc(Cl)cc2)c1]

WJCPA-135

The bis-amide derivative compound of Formula 1 according to the present invention may be present in the form of a pharmaceutically acceptable salt. For the salt, an acid addition salt formed by a pharmaceutically acceptable free acid is useful. As used herein, the term "a pharmaceutically acceptable salt" refers to any organic or inorganic addition salt of the compounds of Formula 1 shown above, which is at a concentration capable of exhibiting relative non-toxicity and unharmful effective action to patients while not deteriorating advantageous effects of the compounds of Formula 1 due to any side effects caused by the salt.

Acid addition salts are prepared by a conventional method, for example, a method including dissolving a compound in an excess amount of an aqueous acid solution and then precipitating the resultant using a water-miscible organic solvent (e.g. methanol, ethanol, acetone, or acetonitrile). An equimolar amount of the compound and acid or alcohol (e.g., glycol monomethylether) in water are heated and then the mixture is dried by evaporation, or the precipitated salt may be suction-filtered.

In particular, for the free acid, an organic acid or inorganic acid may be used. Examples of the inorganic acid to be used may include hydrochloric acid, phosphoric acid, sulfuric acid, nitric acid, and stannic acid, and examples of the organic acid may include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc., although not limited thereto.

Additionally, a pharmaceutically acceptable metal salt can be prepared using a base. An alkali metal salt or an alkali earth metal salt can be prepared, for example, by dissolving a compound in an excess amount of a solution of an alkali metal hydroxide or an alkali earth metal salt hydroxide, filtering undissolved compound salts, and drying the filtrate by evaporation. In particular, for the metal salt, it is appropriate to prepare a sodium-, potassium-, or calcium salt from the pharmaceutical point of view, but is not limited thereto. Additionally, the silver salt corresponding to the same may be prepared by reacting an alkali metal or alkali earth metal salt with an appropriate silver salt (e.g. silver nitrate).

The pharmaceutically acceptable salt of the compounds of Formula 1 may include an acidic or basic salt that can be present in the compound of Formula 1, unless indicated otherwise. For example, examples of the pharmaceutically acceptable salt may include a sodium-, calcium-, and potassium salt of a hydroxyl group, and examples of other pharmaceutically acceptable salts of an amino group may include hydrogen bromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc., and may be prepared using a salt preparation method known in the art.

In another aspect, the present invention provides a method for preparing a bis-amide derivative compound of Formula 1 including reacting an isocyanide derivative ($R_1$—NC) and a carboxylic acid derivative ($R_4$—COOH) with an aldehyde derivative ($R_2$—CHO) and an amine derivative ($R_3$—$NH_2$) or an imine derivative ($R_2$—C=N—$R_3$).

The above reaction is Ugi multi-component reaction, which includes an imine derivative as an intermediated and produces a bis-amide derivative as the final product by rearrangement via acyl transfer.

Preferably, the above reaction may be performed at 20° C. to 60° C. using $C_1$-$C_4$ alkyl alcohol or haloalcohol as a solvent, but is not limited thereto. More preferably, the above reaction may be performed at a temperature from 20° C. to 30° C. or from 50° C. to 60° C. using methanol or 2,2,2-trifluoroethanol as a solvent, but is not limited thereto.

The method of preparing a bis-amide derivative compound of the present invention, may further include preparing imine derivative ($R_2$—C=N—$R_3$) by reacting aldehyde derivative ($R_2$—CHO) and amine derivative ($R_3$—$NH_2$) according to the types of the reactants, before the above reaction.

Preferably, the above reaction may be performed at a temperature from 20° C. to 30° C. using $C_1$-$C_4$ alkyl alcohol or haloalcohol as a solvent, but is not limited thereto. More preferably, the above reaction may be performed using methanol, ethanol, or 2,2,2-trifluoroethanol.

In an exemplary embodiment of the present invention, when an aldehyde derivative (e.g., 3,4,5-trimethoxy benzaldehyde, 2,3,4-trimethoxybenzaldehyde, 3,4-dimethoxybenzaldehyde, 4-chlorobenzaldehyde, 4-nitrobenzaldehyde, or 4-hydroxybenzaldehyde) and an amine derivative (e.g., 4-isopropylaniline, 4-methoxyaniline, 4-aminoveratrole, 4-bromoaniline, or 3,4-dimethoxyphenylethylamine) were used as reactants, the aldehyde derivative and the amine derivative were reacted first to prepare an imine derivative, which was then mixed with an isocyanide derivative and a carboxylic acid derivative to perform the Ugi multi-component reaction, thereby preparing a bis-amide derivative. In other cases, the reaction was performed by simultaneously mixing the four different reactants, i.e., the isocyanide derivative, the aldehyde derivative, the amine derivative, and the carboxylic acid derivative.

In still another aspect, the present invention provides a pharmaceutical composition for preventing or treating diseases caused by hepatitis C virus infection containing a bis-amide derivative compound of Formula 1 or a pharmaceutically acceptable salt thereof as an active ingredient.

In particular, the composition is characterized in that it achieves antiviral activity by inhibiting the activity of PPIase by the inhibition of the activity of cyclophilin A. Accordingly, the composition can inhibit the replication of hepatitis C virus.

As used herein, the term "hepatitis C virus" refers to a small (55 nm to 65 nm in diameter), enveloped, positive-sense (5' to 3') single-stranded RNA virus of the family Flaviviridae. Hepatitis C virus is the cause of hepatic disease as such as hepatitis C in humans. Specifically, hepatitis C virus belongs to the genus *Hepacivirus*, a member of the family Flaviviridae, and has quasispecies. Hepatitis C virus is predominantly a blood-borne virus. That is, the virus can be transmitted through the contact with contaminated blood and the virus may be transmitted by, for example, injections, straws, transfusion, hemodialysis, or vertical transmission from mother to baby. The detection of vertical transmission requires about 1 to 3 weeks after transmission. The structural proteins formed by the hepatitis C virus include core proteins E1 and E2, and the nonstructural proteins include NS2, NS3, NS4, NS4A, NS4B, NS5, NS5A, and NS5B.

As used herein, the term "cyclophilin A (CypA)", which is cytosolic peptidyl-prolyl isomerase involved in immune regulation having a size of few tens of kDa, refers to a protein binding to cyclophosphorin, belonging to cyclophilin family. Specifically, CypA has a β-barrel structure with two α-helices and a β-sheet. The complex with cyclosporine (cyclosporin, ciclosporin, or cyclosporin A) inhibits a calcium/calmodulin-dependent phosphatase, calcineurin, and the inhibition of which is thought to suppress organ rejection by halting the production of the pro-inflammatory molecules TNF a and interleukin 2. CypA is also known to be recruited by the Gag polyprotein during HIV-1 virus infection and its incorporation into new virus particles is essential for HIV-1 infectivity.

As used herein, the term "peptidyl-prolyl isomerase or peptidyl-prolyl cis/trans isomerase (PPIase)" refers to an enzyme found in both prokayrotes and eukaryotes that interconverts the cis and trans isomers of peptide bonds with the amino acid proline. Proline includes an unusually conformationally restrained peptide bond by forming a cyclic structure with its side chain bonded to its secondary amine nitrogen. Most amino acids have a strong energetic preference for the trans peptide bond conformation due to steric hindrance, however, the proline's unusual structure stabilizes the cis form so that both isomers are present under biologically relevant conditions. Examples of the proteins with prolyl isomerase activity include cyclophilin, FKBP, and parvulin.

As used herein, the term "antiviral activity" refers to an activity of inhibiting or treating viral infection, and as an antibacterial agent is generally specific to a given bacterium, a particular antiviral agent exhibits an antiviral activity against a particular virus. Antibacterial agents, unlike the antibacterial activity, inhibit the development of a target pathogen instead of destroying it. The material exhibiting antiviral activity is called an antiviral agent, and the antiviral agent can be used for the treatment of infection because it is relatively less harmful to a host. Antibacterial agents can be distinguished from viricides which are materials to destroy or inactivate viral particles. Specifically, the bis-amide derivative compound according to the present invention specifically binds to CypA and inhibits the PPIase activity thereby exhibiting an antiviral activity against HCV, i.e., inhibiting HCV replication.

As used herein, the term "prevention" refers to any action which results in suppression or dealy of the onset, spread, and recurrence of diseases caused by hepatitis C virus by administering the composition of the present invention, and the term "treatment" refers to any action which results in improvement or advantageous changes in symptoms of diseases caused by hepatitis C virus by administering the composition of the present invention.

The diseases caused by hepatitis C virus, which can be prevented or treated by the composition of the present invention, include hepatitis, liver cirrhosis, hepatocellular carcinoma, liver hardening, etc.

Additionally, the present invention provides a method for preventing or treating diseases caused by hepatitis C virus infection including administering a bis-amide derivative compound of Formula 1 or a pharmaceutically acceptable salt thereof to a subject in need thereof.

As used herein, the term "subject" refers to any animal including humans, monkeys, cattle, horses, sheep, pigs, chickens, turkeys, quails, cats, dogs, mice, rats, rabbits, and guinea pigs, in which the disease(s) caused by hepatitis C virus has (have) already occurred or can occur, and the disease(s) can be effectively prevented or treated by administering the pharmaceutical composition of the present invention to the subject. The pharmaceutical composition of the present invention may be administered in combination with the existing therapeutic agent.

Preferably, the therapeutic agent to be administered in combination with the pharmaceutical composition of the present invention may be interferon-α, ribavirin, telaprevir, boceprevir, or a combination thereof. More preferably, a pharmaceutical drug(s) exhibiting antiviral activity through a different mechanism(s) may be administered in combination for a synergistic effect.

As used herein, the term "interferon-α" refers to a kind of type I interferon, which is produced by peripheral blood leukocytes or lymphoblastoid cells when exposed to live or inactivated virus, double-stranded RNA, or bacteria products. For example, interferon-α is produced and released by host cells in response to the presence of pathogens such as viruses, bacteria, parasites, and tumor cells. It is a major interferon produced by virus-induced leukocyte culture that triggers protective defenses of the immune system that eliminate pathogens or tumors by intercellular communications. Interferon-α is used for the treatment of hepatitis B- and C viruses, and may be used in combination with other antiviral agents, but interferon-α has been reported to show adverse effects such as depression and severe flu-like symptoms. The most harmful strain, hepatitis C genotype I virus, can be treated with a 60% to 80% success with the standard-of-care treatment of interferon-α, ribavirin and recently approved protease inhibitors such as telaprevir or boceprevir.

As used herein, the term "ribavirin" refers to a guanosine (ribonucleic) analog used to block viral RNA synthesis and viral mRNA capping, i.e., a nucleoside inhibitor. Ribavirin is an antiviral agent used for respiratory syncytial virus (RSV) infection, hepatitis C virus (HCV) infection, and other viral infections, and is sold under the brand name of Copegus, Rebetol, Ribasphere, Vilona, Virazole, etc. Ribavirin is a prodrug, which resembles purine RNA nucleotides when metabolized. Ribavirin interferes with RNA metabolism required for viral replication, however, the exact mechanism of how it affects viral replication is not known. The major serious adverse effect known of ribavirin is hemolytic anemia. Additionally, ribavirin is known as a teratogen in a few animal species, and thus, theoretically, ribavirin may also act as a potential teratogen in humans.

As used herein, the term "telaprevir" refers to an antiviral agent for the treatment of hepatitis C virus, also known as a protease inhibitor. Telaprevir was co-developed by Vertex Pharmaceuticals and Johnson & Johnson and is sold under the brand name of Incivek and Incivo. Specifically, telaprevir inhibits the hepatitis C viral enzyme NS3.4A serine protease. Telaprevir is known to act for only hepatitis C genotype 1 viral infection and has not been proven to have an effect on or being safe when used for other types of the virus. The most common adverse effect of telaprevir is rash, and grade 3 adverse events (mainly anemia and leucopenia/neutropenia) occur more frequently.

As used herein, the term "boceprevir" refers to a protease inhibitor used for the treatment of hepatitis C virus genotype I and it is sold under the brand name of Victrelis. Boceprevir binds to the HCV nonstructural protein 3 (NS3) active site. Boceprevir was developed by Schering-Plough but is now being developed by Merck and approved by the FDA on May 13, 2011. The most common adverse effect of boceprevir is anemia and it occurred about half of the patients administered with boceprevir.

Telaprevir and boceprevir are both antiviral agents targeting HCV NS3-4A proteases, which play an important role in the life cycle of viruses. Both telaprevir and boceprevir exhibit high antiviral effects but they have a major disadvantage of low genetic barrier to resistance in using them in chronic hepatitis C virus patients.

In an exemplary embodiment of the present invention, cytotoxicity, inhibitory activity against HCV replication, and inhibitory activity against IL-8 were confirmed by treating CsA, an existing antiviral agent, or the bis-amide derivative WJCPA-126 according to the present invention alone, or in combination with interferon-α, ribavirin, or telaprevir. As a result, it was confirmed that, when treated with WJCPA-126, the cytotoxicity was lower while exhibiting more excellent inhibitory activities against HCV replication and IL-8 level, compared to when treated with WJCPA-126. Furthermore, in experiments treating in combination with interferon-α, ribavirin, or telaprevir, the combined treatment with CsA showed a decrease of cell viability to a 50% to 60% level, whereas the combined treatment with WJCPA-126 showed that 80% or higher level of cell viability was maintained. Meanwhile, regarding the effect on HCV replication and IL-8 level, the combined treatment with WJCPA-126 showed an improvement in inhibitory activity compared to when WJCPA-126 was treated alone, and also higher inhibitory activity compared to that of combined treatment with CsA (FIG. 6).

The composition of the present invention may be formulated into various forms including oral formulations such as powders, granules, tablets, capsules, suspensions, emulsions, syrups, and aerosols; injections such as sterile injection solutions, etc., according to the conventional method for each purpose of use. Furthermore, the composition of the present invention may be administered via various routes including oral administration, intravenous-, intraperitoneal-, subcutaneous-, intrarectal-, and topical administrations. Examples of suitable carriers, excipients, and diluents to be contained in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition of the present invention may further contain a filler, an anticoagulant, a lubricant, a humectant, a flavoring agent, an emulsifier, a preservative, etc.

Examples of solid formulations for oral administration may include tablets, pills, powders, granules, capsules, etc. These solid formulations may be prepared by mixing with at least one excipient, for example, starch, calcium carbonate, sucrose, lactose, gelatin, etc., to the composition. Additionally, a lubricant such as magnesium stearate and talc may be used, in addition to a simple excipient.

Examples of liquid formulations for oral administration may include suspensions, liquid medicine for internal use, emulsions, syrups, etc., and various kinds of excipients such as humectants, sweeteners, fragrances, preservatives, etc., may be contained, in addition to the frequently used simple diluents such as water and liquid paraffin.

Examples of formulations for parenteral administration may include sterile aqueous solutions, non-aqueous solvents, suspensions, emulsions, freeze-dried formulations, and suppositories. For non-aqueous solvents and suspensions, propylene glycol, polyethylene glycol, a vegetable oil such as olive oil, an injectable ester such as ethyloleate may be used. Examples of bases for suppositories may include Witepsol, macrogol, Tween 61, cacao butter, laurinum, glycerogelatin, etc. Meanwhile, injectional formulations may contain conventional additives such as solubilizers, isotonic agents, suspending agents, emulsifiers, stabilizers, preservatives, etc.

The composition of the present invention is administered in a pharmaceutically effective amount.

As used herein, the term "a pharmaceutically effective amount" refers to an amount sufficient for the treatment of diseases at a reasonable benefit/risk ratio applicable to a medical treatment without causing any adverse effects, and the level of the effective dose may be determined based on the factors including health status of a subject, type of a disease, severity of illness, drug activity, drug sensitivity, administration method, administration time, administration route and dissolution rate, duration of treatment, factors including drug(s) to be concurrently used in combination, and other factors well known in the medical field. The composition of the present invention may be administered as an individual therapeutic agent, in combination with other therapeutic agent(s), or sequentially or simultaneously with a conventional therapeutic agent(s), and may be administered once or multiple times. It is important to administer an amount to obtain the maximum effect with a minimum amount without adverse effects, considering the factors described above, and these factors can easily be determined by one of ordinary skill in the art.

Specifically, the effective amount of the compound in the composition of the present invention may vary depending on the age, sex, and body weight of a patient. In general, 1 mg/kg to 10 mg/kg, preferably 1 mg/kg to 5 mg/kg may be administered daily, every other day, or three times daily with a divided dose. However, the effective amount may increase/decrease according to the administration route, severity of disease(s), sex, body weight, age, etc., and thus the effective amount should not limit the scope of the present invention in any manner.

The composition of the present invention can be administered to mammals including rats, mice, cattle, and humans via various routes. All administration routes may be predicted, e.g., orally or via rectal or intravenous, intramuscular, intradermal, intrauterine or intracerebroventricular injections.

In another aspect, the present invention provides a health functional food for preventing or ameliorating diseases caused by hepatitis C virus infection containing a bis-amide derivative compound of Formula 1 or a pharmaceutically acceptable salt thereof as an active ingredient.

When the composition of the present invention is used as a food additive, the bis-amide derivative compound may be directly added or in combination with other food or food component, and may be appropriately used according to the conventional method. The amount of the active ingredient to be mixed can be determined appropriately according to the purpose of use (prevention, health, or therapeutic treatment).

As used herein, the term "a health functional food" refers to a food which was prepared and processed for the purpose of health supplement by methods of extraction, concentration, purification, mixing, etc., using a particular component(s) as a raw material or a particular component(s) contained in a raw material of food, and also refers to a food, which was designed and processed to sufficiently exhibit biological regulatory functions such as biological defense, regulation of biorhythm, prevention and recovery of diseases, etc., by the above component(s). The composition for the health functional food can perform the functions related to prevention and recovery of diseases, etc.

Additionally, the type of health functional food in which the composition of the present invention can be used is not limited. Furthermore, the composition containing the bis-amide derivative compound of the present invention as an active ingredient may be prepared by mixing with an appropriate supplementary component which can be contained in the health functional food and a known additive, according to the selection of one of ordinary skill in the art. Examples of the food that can added may include meats, sausages, bread, chocolates, candies, snacks, cookies, pizzas, ramens, other noodles, gums, dairy products including ice cream, various kinds of soups, beverages, teas, drinks, alcoholic beverages, vitamin complexes, etc., and may be prepared by adding the compounds according to the present invention as an active ingredient to extracts, teas, jellies, juices, etc.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Synthesis of Bis-Amide Derivative Compounds (WJCPA-001 to WJCPA-135)

The method of synthesizing bis-amide derivatives according to the present invention is schematically shown in Reaction Scheme 1 and Formula 2 below.

[Reaction Scheme 1]

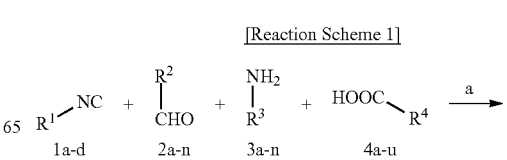

-continued

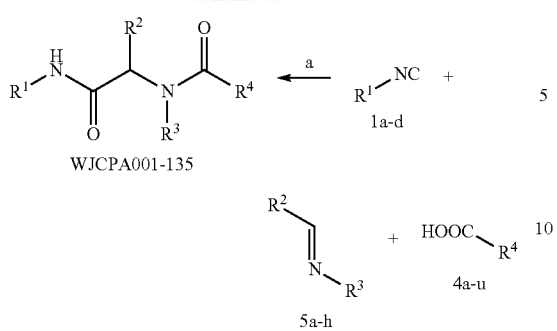

WJCPA001-135

[Reaction Scheme 2]

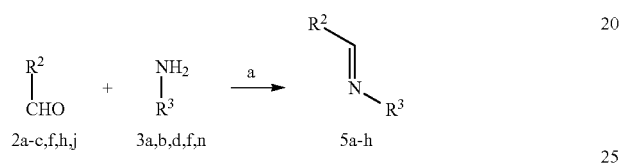

Bis-amide derivatives were prepared by Ugi multi-component reaction. The conventional Ugi 4-component condensation reaction includes the in-situ formation of imine as an intermediate from aldehyde (2) and amine (3). The imine further reacts with isocyanide (1) and carboxylic acid (4) to form an intermediate, and subsequently bis-amide derivatives WJCPA-001 to WJCPA-135 were synthesized by rearrangement through acyl transfer (Reaction Schemes 1 and 2). The reagents used in the reactions are shown in Table 2 below.

[Table 2]

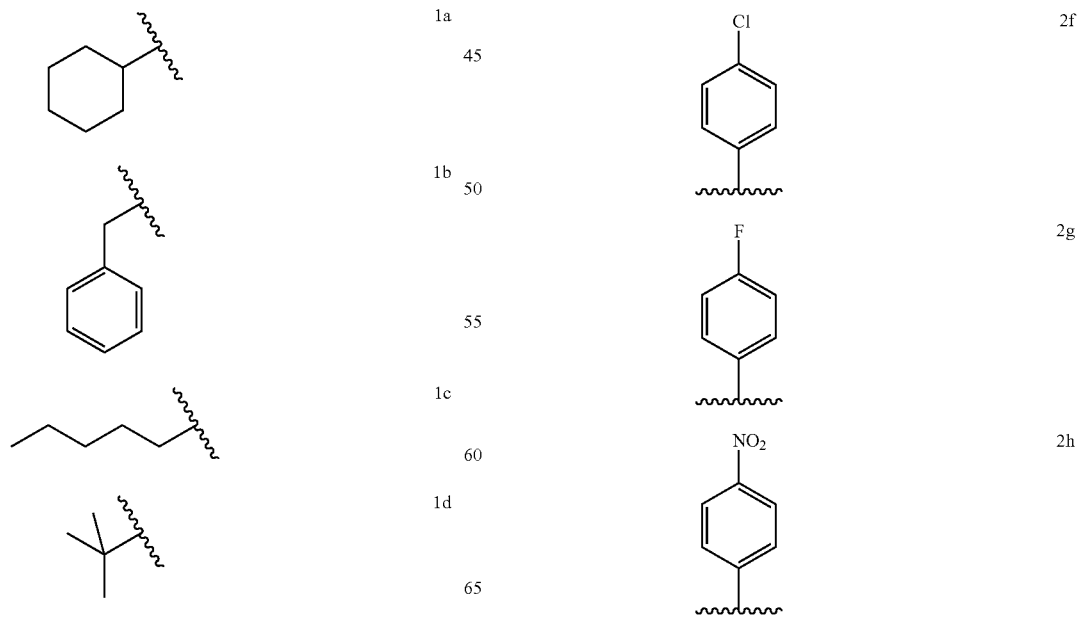

TABLE 2-continued
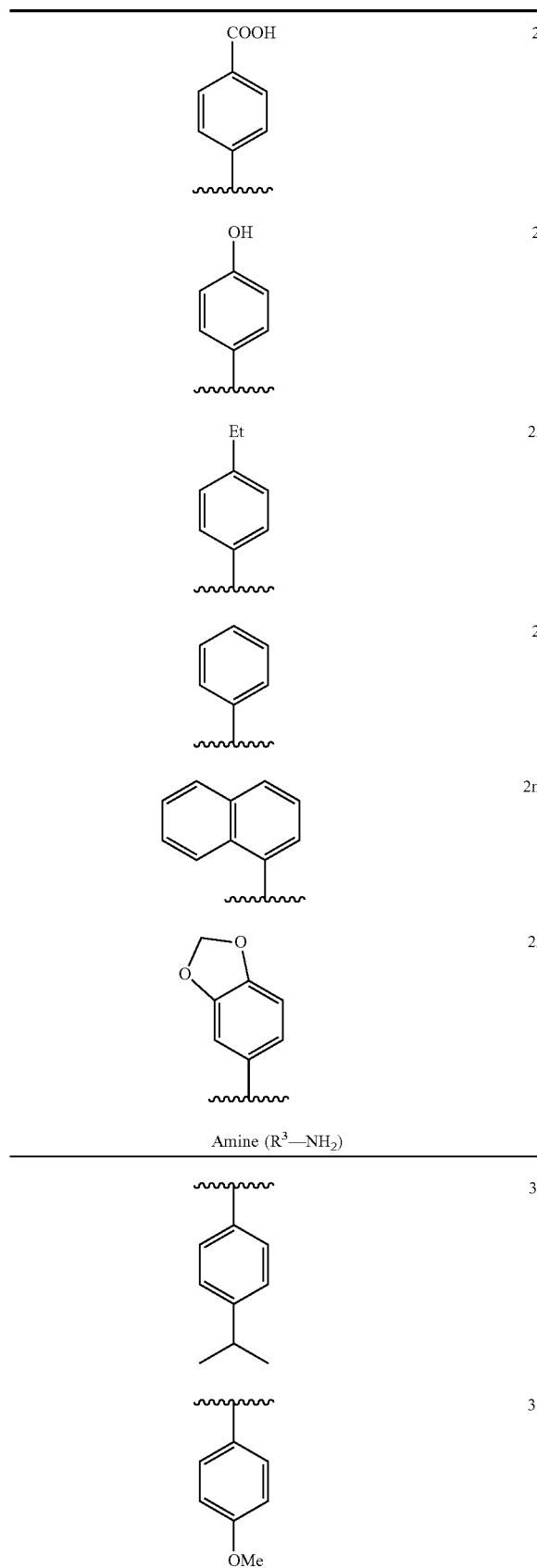
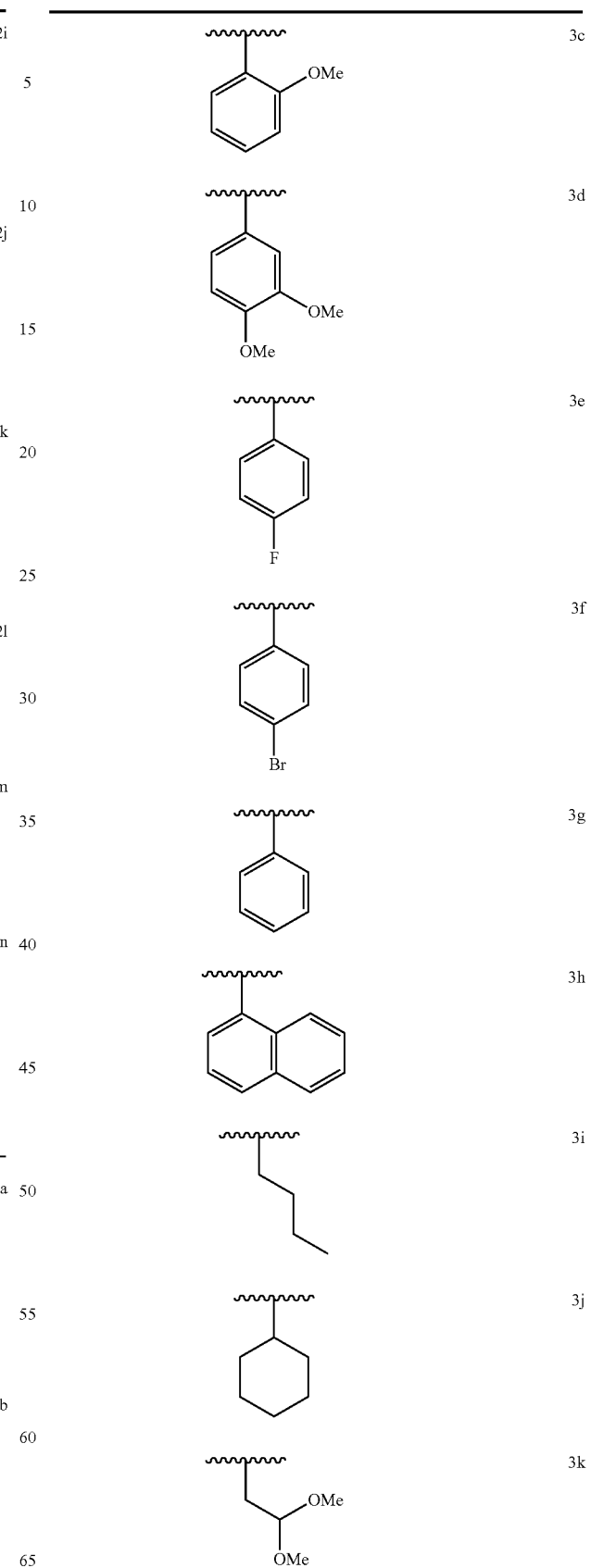

TABLE 2-continued
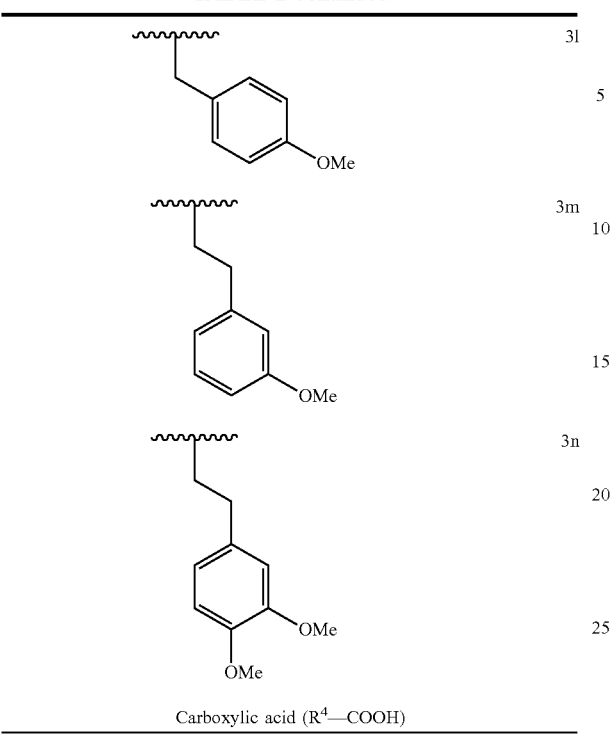
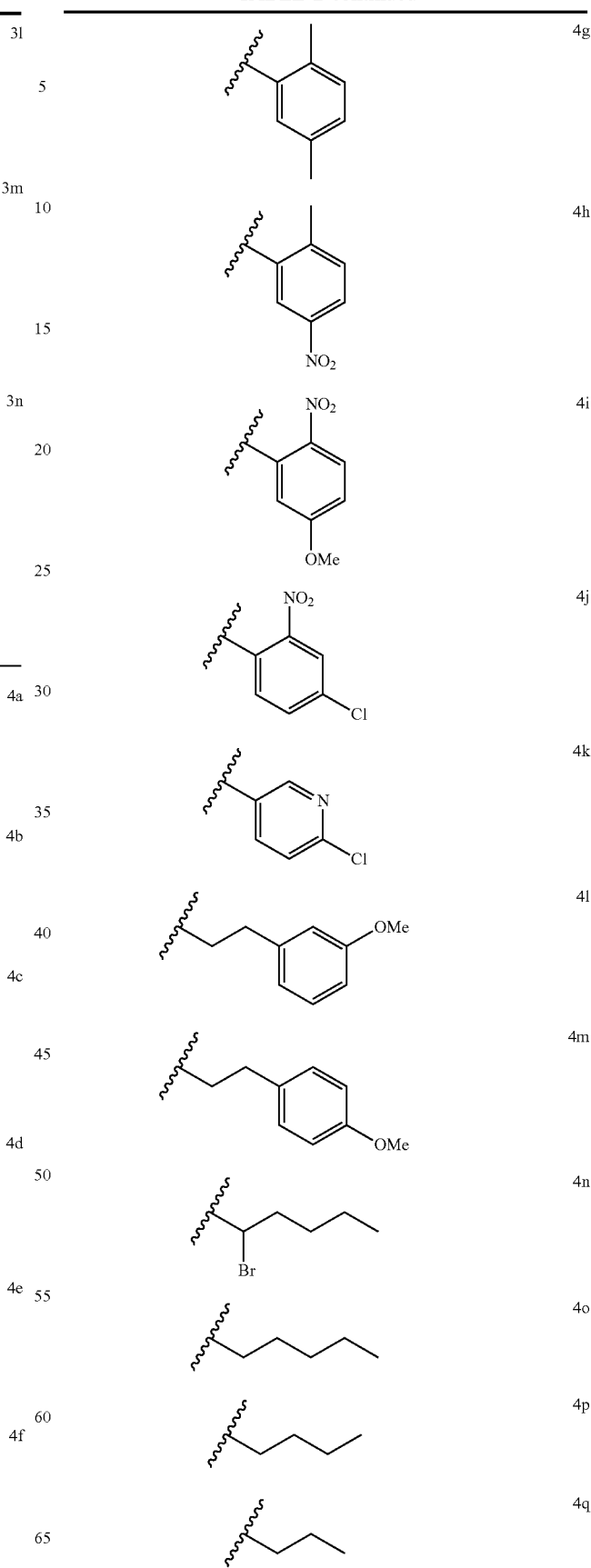

TABLE 2-continued

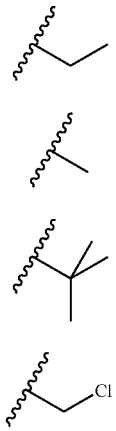

| | |
|---|---|
| 4r | |
| 4s | |
| 4t | |
| 4u | |

1.1. N-cyclohexyl-2-[(2-1H-indol-3-yl-acetyl)-phenyl-amino]-2-(3,4,5-trimethoxy-phenyl)-acetamide (WJCPA-001)

A mixed solution, in which 3,4,5-trimethoxy benzaldehyde (2a; 70 mg, 0.35 mmol) and aniline (3g; 41 mg, 0.44 mmol) were dissolved in a methanol solvent, was stirred at room temperature for 6 hours. The reaction mixture was added with cyclohexyl isocyanide (1a; 38 mg, 0.35 mmol) and 3-indole acetic acid (4a; 130 mg, 0.74 mmol) and heated at 55° C. overnight. The mixture was evaporated to a dry state, washed with saturated aqueous NaHCO3 solution, and extracted with EtOAc. The organic layer was dried over anhydrous magnesium sulfate and concentrated under vacuum. The resulting residue was purified by MPLC (n-hexane:EtOAc=3:1) to obtain the bis-amide compound WJCPA-001.

Beige ash (118 mg, yield 59%), melting point (Mp): 156° C. to 158° C.

IR (cm$^{-1}$) 3261, 1650.

$^1$H NMR (300 MHz, CDCl$_3$) δ: 8.00 (s, 1H), 7.41 (d, J=7.8 Hz, 2H), 7.31 (d, J=8.1 Hz, 2H), 7.24-7.19 (m, 2H), 7.14 (t, J=7.2 Hz, 2H), 7.04 (t, J=7.2 Hz, 1H), 6.95 (s, 1H), 6.30 (s, 2H), 6.07 (s, 1H), 5.75 (d, J=7.8 Hz, 1H), 3.83-3.71 (m, 1H), 3.76 (s, 3H), 3.60 (s, 2H), 3.58 (s, 6H), 1.89-1.80 (m, 2H), 1.68-1.56 (m, 3H), 1.38-1.23 (m, 2H), 1.14-0.92 (m, 3H).

$^{13}$C NMR (125 MHz, CDCl$_3$) δ: 171.9, 168.6, 152.6, 140.0, 137.8, 135.9, 130.5, 129.8, 128.7, 128.1, 127.2, 123.1, 121.8, 119.3, 118.9, 110.9, 109.2, 107.6, 64.5, 60.7, 55.9, 48.6, 32.7, 31.9, 25.4, 24.8, 24.7.

MS (ESI) m/z=578 (M+Na)$^+$, 554 (M−H)$^−$.

HPLC: purity 99.5%.

1.2. N-cyclohexyl-2-[(2-1H-indol-3-yl-acetyl)-phenyl-amino]-2-phenyl-acetamide (WJCPA-002)

A reaction was performed in the same manner as in Example 1.1 using cyclohexyl isocyanide (1a; 51 mg, 0.47 mmol), benzaldehyde (2l; 50 mg, 0.47 mmol), aniline (3g; 53 mg, 0.56 mmol), 3-indole acetic acid (4a; 165 mg, 0.94 mmol), and methanol to obtain the bis-amide compound WJCPA-002 after purification by column chromatography (n-hexane:EtOAc=5:1).

0White solid (163 mg, yield 74%), Mp: 189° C. to 192° C.

IR (cm$^{-1}$) 3319, 1644.

$^1$H NMR (300 MHz, CDCl$_3$) δ: 8.03 (hs, 1H), 7.36 (d, J=8.1 Hz, 1H), 7.31 (d, J=8.1 Hz, 2H), 7.25-7.12 (m, 9H), 7.06-6.99 (m, 3H), 6.06 (s, 1H), 5.68 (d, J=8.7 Hz, 1H), 3.84-3.73 (m, 1H), 3.58 (s, 2H), 1.90-1.80 (m, 2H), 1.63-1.51 (m, 3H), 1.38-1.22 (m, 2H), 1.11-0.89 (m, 3H).

$^{13}$C NMR (125 MHz, CDCl$_3$) δ: 172.0, 168.7, 140.2, 135.9, 134.7, 130.38, 130.3, 128.7, 128.2, 128.0, 127.2, 123.2, 121.7, 119.2, 118.8, 110.9, 109.2, 65.3, 48.6, 32.6, 31.8, 25.4, 24.7, 24.6.

MS (ESI) m/z=488 (M+Na)$^+$, 464 (M−H)$^−$.

HPLC: purity 97.0%.

1.3. N-cyclohexyl-2-[(2-1H-indol-3-yl-acetyl)-(4-methoxy-phenyl)-amino]-2-(3,4,5-trimethoxy-phenyl)-acetamide (WJCPA-003)

A reaction was performed in the same manner as in Example 1.1 using cyclohexyl isocyanide (1a; 56 mg, 0.51 mmol), 3,4,5-trimethoxybenzaldehyde (2a; 100 mg, 0.51 mmol), p-anisidine (3b; 77 mg, 0.63 mmol), 3-indole acetic acid (4a; 186 mg, 1.06 mmol), and methanol to obtain the bis-amide compound WJCPA-003 after purification by column chromatography (n-hexane:EtOAc=3:1).

Ivory solid (217 mg, yield 72%), Mp: 130.5° C. to 134.7° C.

IR (cm$^{-1}$) 3303, 1648.

$^1$H NMR (300 MHz, CDCl$_3$) δ: 8.03 (s, 1H), 7.42 (d, J=7.8 Hz, 2H), 7.31 (d, J=8.1 Hz, 1H), 7.14 (t, J=7.8 Hz, 1H), 7.04 (t, J=8.1 Hz, 1H), 6.98 (s, 1H), 6.79-6.60 (m, 3H), 6.31 (s, 2H), 6.07 (s, 1H), 5.74 (d, J=8.7 Hz, 1H), 3.77 (s, 4H), 3.74 (s, 3H), 3.62-3.54 (m, 8H), 1.19-1.80 (m, 2H), 1.66-1.53 (m, 3H), 1.36-1.23 (m, 2H), 1.10-0.99 (m, 3H).

$^{13}$C NMR (125 MHz, CDCl$_3$) δ: 172.4, 168.6, 159.1, 152.6, 137.7, 135.9, 132.6, 131.5, 129.9, 127.2, 123.1, 121.8, 119.3, 118.9, 110.9, 109.3, 107.7, 64.32, 60.7, 55.9, 55.4, 48.6, 32.7, 31.8, 25.4, 24.8, 24.7.

MS (ESI) m/z=608 (M+Na)$^+$, 584 (M−H)$^−$.

HPLC: purity 99.8%.

1.4. N-cyclohexyl-2-[(2-1H-indol-3-yl-acetyl)-(2-methoxy-phenyl)-amino]-2-(3,4,5-trimethoxy-phenyl)-acetamide (WJCPA-004)

A reaction was performed in the same manner as in Example 1.1 using cyclohexyl isocyanide (1a; 56 mg, 0.51 mmol), 3,4,5-trimethoxybenzaldehyde (2a; 100 mg, 0.51 mmol), o-anisidine (3c; 77 mg, 0.63 mmol), 3-indole acetic acid (4a; 110 mg, 0.63 mmol), and methanol to obtain the bis-amide compound WJCPA-004 after purification by column chromatography (n-hexane:EtOAc=5:1).

Yellow solid (24 mg, yield 8%), Mp: 187.6° C. to 190.3° C.

IR (cm$^{-1}$) 3343, 1630.

$^1$H NMR (300 MHz, CDCl$_3$) δ: 7.97 (s, 1H), 7.46-7.37 (m, 2H), 7.32-7.27 (m, 2H), 7.25-7.11 (m, 3H), 7.07-6.99 (m, 1H), 6.94 (d, J=2.1 Hz, 1H), 6.35 (s, 2H), 6.01 (d, J=8.1 Hz, 1H), 5.94 (s, 1H), 3.81-3.72 (m, 1H), 3.73 (s, 3H), 3.61-3.56 (m, 9H), 3.39 (s, 2H), 1.95-1.79 (m, 2H), 1.65-1.48 (m, 3H), 1.32-1.23 (m, 2H), 1.19-0.94 (m, 3H).

MS (ESI) m/z=608 (M+Na)$^+$, 584 (M−H)$^−$.

HPLC: purity 99.7%.

1.5. N-cyclohexyl-2-[(2-1H-indol-3-yl-acetyl)-naphthalen-1-yl-amino]-2-(3,4,5-trimethoxy-phenyl)-acetamide (WJCPA-005)

A reaction was performed in the same manner as in Example 1.1 using cyclohexyl isocyanide (1a; 56 mg, 0.51 mmol), 3,4,5-trimethoxybenzaldehyde (2a; 100 mg, 0.51 mmol), 1-aminonaphthalene (3h; 95 mg, 0.66 mmol), 3-indole acetic acid (4a; 116 mg, 0.66 mmol), and methanol to obtain the bis-amide compound WJCPA-005 after purification by column chromatography (n-hexane:EtOAc=3:1).

Purple solid (62 mg, yield 20%), Mp: 206.5° C. to 215.1° C. (dec).

$^1$H NMR (300 MHz, CDCl$_3$) δ: 7.99 (s, 1H), 7.87 (d, J=8.4 Hz, 1H), 7.76 (t, J=8.7 Hz, 2H), 7.62 (d, J=6.6 Hz, 1H), 7.40-7.28 (m, 5H), 7.13-7.08 (m, 1H), 7.04-6.96 (m, 1H), 6.85 (d, J=2.1 Hz, 1H), 6.29 (s, 2H), 5.96 (s, 1H), 5.77 (d, J=8.1 Hz, 1H), 3.85-3.79 (m, 1H), 3.73 (s, 3H), 3.49 (s, 2H), 3.47 (s, 6H), 1.91-1.86 (m, 2H), 1.65-1.56 (m, 3H), 1.40-1.23 (m, 2H), 1.14-1.01 (m, 3H).

MS (ESI) m/z=628 (M+Na)$^+$, 604 (M−H)$^−$.

1.6. 2-[butyl-(2-1H-indol-3-yl-acetyl)-amino]-N-cyclohexyl-2-(3,4,5-trimethoxy-phenyl)-acetamide (WJCPA-006)

A reaction was performed at room temperature in the same manner as in Example 1.1 using cyclohexyl isocyanide (1a; 73 mg, 0.67 mmol), 3,4,5-trimethoxybenzaldehyde (2a; 100 mg, 0.51 mmol), butylamine (3i; 61 mg, 0.83 mmol), 3-indole acetic acid (4a; 176 mg, 1.00 mmol), and 2,2,2-trifluoroethanol as a solvent, to obtain the bis-amide compound WJCPA-006 after purification by column chromatography (n-hexane:EtOAc=3:1).

White solid (117 mg, yield 42%), Mp: 173.9° C. to 174.4° C.

$^1$H NMR (300 MHz, CDCl$_3$) δ: 8.09 (s, 1H), 7.63 (d, J=7.5 Hz, 1H), 7.37 (d, J=8.1 Hz, 1H), 7.24-7.09 (m, 3H), 6.63 (s, 2H), 5.88-5.84 (m, 2H), 3.89 (s, 2H), 3.84-3.78 (m, 1H), 3.83 (s, 3H), 3.73 (s, 6H), 3.40-3.35 (m, 2H), 1.86-1.81 (m, 2H), 1.64-1.55 (m, 3H), 1.35-1.23 (m, 3H), 1.11-1.02 (m, 6H), 0.75 (t, J=6.9 Hz, 3H).

MS (ESI) m/z=558 (M+Na)$^+$, 534 (M−H)$^−$.

1.7. N-cyclohexyl-2-[[2-(3,4-dimethoxy-phenyl)-ethyl]-(2-1H-indol-3-yl-acetyl)-amino]-2-(3,4,5-trimethoxy-phenyl)-acetamide (WJCPA-007)

A reaction was performed at room temperature in the same manner as in Example 1.1 using cyclohexyl isocyanide (1a; 55 mg, 0.50 mmol), 3,4,5-trimethoxybenzaldehyde (2a; 100 mg, 0.51 mmol), 3,4-dimethoxyphenylethylamine (3n; 144 mg, 0.63 mmol), 3-indole acetic acid (4a; 133 mg, 0.76 mmol), and 2,2,2-trifluoroethanol as a solvent, to obtain the bis-amide compound WJCPA-007 after purification by column chromatography (n-hexane:EtOAc=3:1).

Bright yellow solid (18 mg, yield 5%), Mp: 177.7° C. to 179.4° C.

$^1$H NMR (300 MHz, CDCl$_3$) δ: 8.11 (s, 1H), 7.60 (d, J=8.1 Hz, 2H), 7.36 (d, J=8.1 Hz, 2H), 7.22-7.08 (m, 3H), 6.70 (s, 2H), 6.42-6.39 (m, 1H), 5.93 (s, 1H), 5.75 (d, J=8.4 Hz, 1H), 3.85-3.72 (m, 18H), 3.58-3.50 (m, 2H), 2.76-2.63 (m, 2H), 1.94-1.82 (m, 2H), 1.68-1.56 (m, 3H), 1.40-1.23 (m, 2H), 1.12-1.03 (m, 3H).

MS (ESI) m/z=666 (M+Na)$^+$.

1.8. N-[cyclohexylcarbamoyl-(3,4,5-trimethoxyphenyl)-methyl]-N-(4-isopropyl-phenyl)-benzamide (WJCPA-008)

A reaction was performed at room temperature in the same manner as in Example 1.1 using cyclohexyl isocyanide (1a; 56 mg, 0.51 mmol), 3,4,5-trimethoxybenzaldehyde (2a; 100 mg, 0.51 mmol), 4-isopropylaniline (3a; 187 mg, 0.64 mmol), benzoic acid (4d; 122 mg, 1.00 mmol), and methanol to obtain the bis-amide compound WJCPA-008 after filtration.

Ivory solid (54 mg, yield 72%), Mp: 178.5° C. to 181.4° C.

IR (cm$^{-1}$) 3331, 1623.

$^1$H NMR (300 MHz, CDCl$_3$) δ: 7.32-7.29 (m, 2H), 7.19-7.09 (m, 3H), 6.90-6.82 (m, 4H), 6.43 (s, 2H), 6.17 (s, 1H), 5.88 (d, J=8.1 Hz, 1H), 3.91-3.82 (m, 1H), 3.80 (s, 3H), 3.68 (s, 6H), 2.73 (heptet, J=7.2 Hz, 1H), 2.01-1.88 (m, 2H), 1.72-1.57 (m, 3H), 1.42-1.30 (m, 2H), 1.24-1.08 (m, 9H).

$^{13}$C NMR (125 MHz, CDCl$_3$) δ: 171.2, 168.5, 152.8, 148.0, 138.4, 137.9, 136.0, 130.2, 130.1, 129.3, 128.4, 127.5, 126.2, 107.6, 65.7, 60.8, 56.0, 48.6, 33.5, 32.8, 25.4, 24.8, 24.7, 23.8, 23.7.

MS (ESI) m/z=567 (M+Na)$^+$.

HPLC: purity 96.8%.

1.9. N-cyclohexyl-2-[(2-1H-indol-3-yl-acetyl)-amino]-2-(3,4,5-trimethoxy-phenyl)-acetamide (WJCPA-009)

A reaction was performed at room temperature in the same manner as in Example 1.1 using cyclohexyl isocyanide (1a; 55 mg, 0.50 mmol), 2,3,4-trimethoxybenzaldehyde (2b; 100 mg, 0.51 mmol), aniline (3g; 59 mg, 0.63 mmol), 3-indole acetic acid (4a; 88 mg, 0.50 mmol), and 2,2,2-trifluoroethanol as a solvent, to obtain the bis-amide compound WJCPA-009 after purification by column chromatography (EtOAc).

Bright yellow solid (75 mg, yield 26%), Mp: 108.5° C. to 112.3° C.

$^1$H NMR (300 MHz, CDCl$_3$) δ: 8.04 (s, 1H), 7.38 (d, J=7.8 Hz, 2H), 7.30 (d, J=8.1 Hz, 1H), 7.15-7.10 (m, 4H), 7.05-6.98 (m, 3H), 6.67 (d, J=8.7 Hz, 1H), 6.39 (s, 1H), 6.32 (d, J=9.0 Hz, 1H), 5.64 (d, J=8.1 Hz, 1H), 3.83-3.79 (m, 1H), 3.81 (s, 3H), 3.76 (s, 3H), 3.75 (s, 3H), 3.57 (s, 2H), 1.89-1.80 (m, 2H), 1.70-1.50 (m, 3H), 1.35-1.23 (m, 2H), 1.12-0.89 (m, 3H).

MS (ESI) m/z=578 (M+Na)$^+$, 554 (M−H)$^{−1}$.

1.10. 2-[(4-bromo-phenyl)-(2-1H-indol-3-yl-acetyl)-amino]-N-cyclohexyl-2-(2,3,4-trimethoxy-phenyl)-acetamide (WJCPA-010)

A reaction was performed at room temperature in the same manner as in Example 1.1 using cyclohexyl isocyanide (1a; 55 mg, 0.50 mmol), 2,3,4-trimethoxybenzaldehyde (2b; 100 mg, 0.51 mmol), 4-bromoaniline (3f; 108 mg, 0.63 mmol), 3-indole acetic acid (4a; 88 mg, 0.50 mmol), and 2,2,2-trifluoroethanol as a solvent, to obtain the bis-amide compound WJCPA-010 after filtration.

White solid (163 mg, yield 50%), Mp: 143.2° C. to 146.5° C.

IR (cm$^{-1}$) 3308, 1644.

$^1$H NMR (300 MHz, CDCl$_3$) δ: 8.00 (s, 1H), 7.37-7.29 (m, 4H), 7.24-7.19 (m, 2H), 7.16-7.11 (m, 1H), 7.07-7.00 (m, 2H), 6.63 (d, J=8.7 Hz, 1H), 6.37-6.34 (m, 2H), 5.51 (d, J=8.4 Hz, 1H), 3.83-3.75 (m, 1H), 3.82 (s, 3H), 3.77 (s, 3H), 3.76 (s, 3H), 3.56 (s, 2H), 1.92-1.82 (m, 2H), 1.68-1.54 (m, 3H), 1.38-1.23 (m, 2H), 1.14-0.91 (m, 3H).

$^{13}$C NMR (125 MHz, CDCl$_3$) δ: 171.5, 169.1, 154.0, 152.2, 141.3, 139.1, 135.9, 132.0, 131.5, 127.1, 125.6, 123.0, 121.9, 121.8, 120.0, 119.3, 118.7, 110.9, 109.2, 106.5, 61.0, 60.5, 58.5, 55.8, 48.7, 32.7, 32.0, 25.4, 24.8, 24.7.

MS (ESI) m/z=656 (M+Na)$^+$.

Anal. Calcd. for C$_{33}$H$_{36}$BrN$_3$O$_5$: C, 62.46; H, 5.72; N, 6.62. Found C, 62.27; H, 5.69; N, 7.01.

HPLC: purity 97.3%.

1.11. N-cyclohexyl-2-[(3,4-dimethoxy-phenyl)-(2-1H-indol-3-yl-acetyl)-amino]-2-(3,4,5-trimethoxy-phenyl)-acetamide (WJCPA-011)

A reaction was performed at room temperature in the same manner as in Example 1.1 using cyclohexyl isocyanide (1a; 55 mg, 0.50 mmol), 2,3,4-trimethoxybenzaldehyde (2b; 100 mg, 0.51 mmol), 4-aminoveratrole (3d; 97 mg, 0.63 mmol), 3-indole acetic acid (4a; 88 mg, 0.50 mmol), and 2,2,2-trifluoroethanol as a solvent, to obtain the bis-amide compound WJCPA-011 after purification by column chromatography (EtOAc).

Bright orange solid (253 mg, yield 80%), Mp: 113.8° C. to 115.8° C.

IR (cm$^{-1}$) 3356, 1647.

$^1$H NMR (300 MHz, CDCl$_3$) δ: 8.20 (s, 1H), 7.34-7.28 (m, 3H), 7.14-7.09 (m, 1H), 7.04-6.98 (m, 2H), 6.69-6.53 (m, 2H), 6.38 (s, 1H), 6.34 (d, J=8.7 Hz, 1H), 5.93 (bs, 1H), 5.64 (d, J=8.1 Hz, 1H), 3.83-3.76 (m, 15H), 3.60 (s, 2H), 3.36 (bs, 1H), 1.90-1.82 (m, 2H), 1.66-1.53 (m, 3H), 1.37-1.23 (m, 2H), 1.13-0.92 (m, 3H).

$^{13}$C NMR (125 MHz, CDCl$_3$) δ: 172.2, 169.3, 153.7, 152.2, 148.3, 141.2, 135.9, 132.9, 127.2, 125.8, 123.0, 121.7, 120.5, 119.2, 118.8, 113.2, 110.8, 110.1, 109.6, 106.4, 61.0, 60.5, 58.3, 55.8, 55.7, 48.5, 32.7, 31.8, 25.4, 24.8, 24.7.

MS (ESI) m/z=638 (M+Na)$^+$, 614 (M−H)$^-$.

HPLC: purity 99.9%.

1.12. N-cyclohexyl-2-[(2-1H-indol-3-yl-acetyl)-(4-isopropyl-phenyl)-amino]-2-(3,4,5-trimethoxy-phenyl)-acetamide (WJCPA-012)

A mixed solution, in which 2,3,4-trimethoxybenzaldehyde (2b; 200 mg, 1.02 mmol) and 4-isopropylaniline (3a; 172 mg, 1.27 mmol) were dissolved in an ethanol solvent, was stirred at room temperature. The thus-formed solid was filtered to obtain an imine compound (5h). The imine (5b; 160 mg, 0.51 mmol) was added into a solution, in which cyclohexyl isocyanide (1a; 56 mg, 0.51 mmol) and 3-indole acetic acid (4a; 112 mg, 0.64 mmol) were dissolved in methanol, and the mixed solution was heated at 55° C. overnight. The mixture was evaporated to a dry state, washed with saturated aqueous NaHCO$_3$ solution, and extracted with EtOAc. The organic layer was dried over anhydrous magnesium sulfate and concentrated under vacuum. The resulting residue was purified by column chromatography (n-hexane:EtOAc=3:1) to obtain the bis-amide compound WJCPA-0012.

Bright yellow solid (187 mg, yield 61%), Mp: 171.3° C. to 175.5° C.

$^1$H NMR (300 MHz, CDCl$_3$) δ: 7.99 (s, 1H), 7.37-7.29 (m, 4H), 7.15-7.10 (m, 1H), 7.04-6.91 (m, 4H), 6.68 (d, J=8.7 Hz, 2H), 6.35-6.31 (m, 2H), 5.67 (d, J=8.1 Hz, 1H), 3.79-3.74 (m, 1H), 3.78 (s, 3H), 3.76 (s, 3H), 3.75 (s, 3H), 3.58 (s, 2H), 2.81 (heptet, J=6.9 Hz, 1H), 1.88-1.80 (m, 2H), 1.66-1.52 (m, 3H), 1.26-1.19 (m, 2H), 1.16 (d, J=6.9 Hz, 6H), 1.08-0.91 (m, 3H).

MS (ESI) m/z=620 (M+Na)$^+$, 596 (M−H)$^-$.

1.13. N-[cyclohexylcarbamoyl-(2,3,4-trimethoxy-phenyl)-methyl]-N-(4-isopropyl-phenyl)-benzamide (WJCPA-013)

A reaction was performed at room temperature in the same manner as in Example 1.12 using cyclohexyl isocyanide (1a; 55 mg, 0.50 mmol), 2,3,4-trimethoxybenzaldehyde (2b; 100 mg, 0.51 mmol), 4-aminoveratrole (3d; 97 mg, 0.63 mmol), 3-indole acetic acid (4a; 88 mg, 0.50 mmol), and 2,2,2-trifluoroethanol as a solvent, to obtain the bis-amide compound WJCPA-013 after purification by column chromatography (n-hexane:EtOAc=3:1).

White solid (120 mg, yield 43%), Mp: 146.5° C. to 147.7° C.

$^1$H NMR (300 MHz, CDCl$_3$) δ: 7.32-7.30 (m, 2H), 7.19-7.07 (m, 3H), 6.98 (d, J=8.7 Hz, 1H), 6.93-6.82 (m, 4H), 6.47 (d, J=9.0 Hz, 1H), 6.34 (s, 1H), 5.79 (d, J=8.1 Hz, 1H), 3.92-3.83 (m, 1H), 3.86 (s, 3H), 3.80 (s, 3H), 3.78 (s, 3H), 2.71 (heptet, J=6.9 Hz, 1H), 1.99-1.91 (m, 2H), 1.72-1.61 (m, 3H), 1.42-1.26 (m, 2H), 1.18-1.06 (m, 3H), 1.07 (d, J=6.9 Hz, 6H).

MS (ESI) m/z=567 (M+Na)$^+$.

1.14. N-cyclohexyl-2-(3,4-dimethoxy-phenyl)-2-[(2-1H-indol-3-yl-acetyl)-(4-isopropyl-phenyl)-amino]-acetamide (WJCPA-014)

A reaction was performed at room temperature in the same manner as in Example 1.1 using cyclohexyl isocyanide (1a; 66 mg, 0.60 mmol), 3,4-dimethoxybenzaldehyde (2c; 100 mg, 0.60 mmol), 4-isopropylaniline (3a; 101 mg, 0.75 mmol), 3-indole acetic acid (4a; 210 mg, 1.20 mmol), and methanol to obtain the bis-amide compound WJCPA-014 after purification by column chromatography (n-hexane:EtOAc=5:1).

White solid (176 mg, yield 51%), Mp: 163.7° C. to 168.4° C.

$^1$H NMR (300 MHz, CDCl$_3$) δ: 8.01 (s, 1H), 7.37-7.29 (m, 3H), 7.16-7.10 (m, 2H), 7.05-6.98 (m, 4H), 6.76 (dd, J=8.4, 1.8 Hz, 1H), 6.68 (d, J=8.4 Hz, 1H), 6.47 (d, J=2.1 Hz, 1H), 6.08 (s, 1H), 5.75 (d, J=8.1 Hz, 1H), 3.82 (s, 3H), 3.80-3.74 (m, 1H), 3.58 (s, 2H), 3.50 (s, 3H), 2.84 (heptet, J=6.9 Hz, 1H), 1.87-1.76 (m, 2H), 1.55-1.52 (m, 3H), 1.40-1.23 (m, 2H), 1.19 (d, J=6.9 Hz, 6H), 1.10-0.87 (m, 3H).

MS (ESI) m/z=590 (M+Na)$^+$, 566 (M−H)$^-$.

1.15. N-cyclohexyl-2-(3,4-dimethoxy-phenyl)-2-[(3,4-dimethoxy-phenyl)-(2-1H-indol-3-yl-acetyl)-amino]-acetamide (WJCPA-015)

A reaction was performed at room temperature in the same manner as in Example 1.1 using cyclohexyl isocyanide (1a; 66 mg, 0.60 mmol), 3,4-dimethoxybenzaldehyde (2c; 100 mg, 0.60 mmol), 4-aminoveratrole (3d; 115 mg, 0.75 mmol), 3-indole acetic acid (4a; 210 mg, 1.20 mmol), and methanol to obtain the bis-amide compound WJCPA-015 after purification by column chromatography (n-hexane: EtOAc=3:1).

Bright yellow solid (234 mg, yield 66%), Mp: 111.7° C. to 114.6° C.

¹H NMR (300 MHz, CDCl₃) δ: 8.10 (s, 1H), 7.35-7.29 (m, 2H), 7.16-7.11 (m, 2H), 7.05-7.00 (m, 2H), 6.72-6.60 (m, 4H), 6.07-5.82 (m, 2H), 5.64 (d, J=7.8 Hz, 1H), 3.87-3.75 (m, 7H), 3.61 (s, 3H), 3.60 (s, 3H), 3.32 (bs, 2H), 1.90-1.80 (m, 2H), 1.63-1.53 (m, 3H), 1.38-1.23 (m, 2H), 1.13-0.88 (m, 3H).
MS (ESI) m/z=584 (M−H)⁻.

1.16. N-cyclohexyl-2-[cyclohexyl-(2-1H-indol-3-yl-acetyl)-amino]-2-(3,4-dimethoxy-phenyl)-acetamide (WJCPA-016)

A reaction was performed at room temperature in the same manner as in Example 1.1 using cyclohexyl isocyanide (1a; 66 mg, 0.60 mmol), 3,4-dimethoxybenzaldehyde (2c; 100 mg, 0.60 mmol), cyclohexylamine (3j; 75 mg, 0.75 mmol), 3-indole acetic acid (4a; 210 mg, 1.20 mmol), and methanol to obtain the bis-amide compound WJCPA-016 after purification by column chromatography (n-hexane: EtOAc=3:1).
White solid (181 mg, yield 56%), Mp: 110.3° C. to 114.8° C.
¹H NMR (300 MHz, DMSO) δ: 10.92-10.84 (m, 1H), 8.06 (bs, 1H), 7.53 (bs, 1H), 7.32-6.73 (m, 6H), 6.39 (s, 1H), 5.56 (s, 1H), 3.84-3.77 (m, 2H), 3.70 (s, 3H), 3.49 (s, 3H), 3.16 (bs, 2H), 1.84-1.49 (m, 9H), 1.52-0.96 (m, 11H).
MS (ESI) m/z=554 (M+Na)⁺, 530 (M−H)⁻.

1.17. N-cyclohexyl-2-[(2,2-dimethoxy-ethyl)-(2-1H-indol-3-yl-acetyl)-amino]-2-(3,4-dimethoxy-phenyl)-acetamide (WJCPA-017)

A reaction was performed at room temperature in the same manner as in Example 1.1 using cyclohexyl isocyanide (1a; 66 mg, 0.60 mmol), 3,4-dimethoxybenzaldehyde (2c; 100 mg, 0.60 mmol), cyclohexylamine (3k; 75 mg, 0.75 mmol), 3-indole acetic acid (4a; 210 mg, 1.20 mmol), and methanol to obtain the bis-amide compound WJCPA-017 after filtration.
White solid (244 mg, yield 75%), Mp: 182.9° C. to 183.7° C.
¹H NMR (300 MHz, DMSO) δ: 10.88 (s, 1H), 7.88 (d, J=7.5 Hz, 1H), 7.47 (d, J=7.5 Hz, 1H), 7.34 (d, J=8.1 Hz, 1H), 7.24-7.20 (m, 1H), 7.09-7.04 (m, 1H), 6.98-6.88 (m, 2H), 6.81 (d, J=8.1 Hz, 1H), 6.74 (s, 1H), 5.94 (s, 1H), 3.74 (s, 3H), 3.62 (s, 3H), 3.54-3.45 (m, 4H), 3.17-3.09 (m, 2H), 3.15 (s, 3H), 3.07 (s, 3H), 1.68-1.51 (m, 5H), 1.26-1.05 (m, 5H).
MS (ESI) m/z=560 (M+Na)⁺, 536 (M−H)⁻.

1.18. N-cyclohexyl-2-[(2-1H-indol-3-yl-acetyl)-phenyl-amino]-2-(4-nitro-phenyl)-acetamide (WJCPA-018)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), aniline (3g; 77 mg, 0.82 mmol), 3-indole acetic acid (4a; 174 mg, 0.99 mmol), and 2,2,2-trifluoroethanol to obtain the bis-amide compound WJCPA-018 after filtration.
White solid (90 mg, yield 26%), Mp: 219.2° C. to 223.6° C.
¹H NMR (300 MHz, CDCl₃) δ: 8.01-7.98 (m, 3H), 7.42 (d, J=7.8 Hz, 2H), 7.35-7.32 (m, 4H), 7.20-7.15 (m, 2H), 7.09-7.04 (m, 2H), 6.80 (d, J=2.0 Hz, 1H), 6.13 (s, 1H), 6.05 (d, J=7.5 Hz, 1H), 3.80-3.70 (m, 1H), 3.62 (s, 2H), 1.84-1.75 (m, 2H), 1.66-1.55 (m, 3H), 1.36-1.22 (m, 2H), 1.11-0.86 (m, 3H).
MS (ESI) m/z=533 (M+Na)⁺, 509 (M−H)⁻.

1.19. N-cyclohexyl-2-[(2-1H-indol-3-yl-acetyl)-(4-methoxy-benzyl)-amino]-2-(4-nitro-phenyl)-acetamide (WJCPA-019)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 4-methoxybenzylamine (3l; 112 mg, 0.82 mmol), 3-indole acetic acid (4a; 116 mg, 0.66 mmol), and 2,2,2-trifluoroethanol to obtain the bis-amide compound WJCPA-019 after filtration.
Yellow solid (140 mg, yield 38%), Mp: 105.1° C. to 111.8° C.
¹H NMR (300 MHz, CDCl₃) δ: 8.46 (s, 1H), 7.98 (d, J=8.7 Hz, 2H), 7.50 (d, J=7.5 Hz, 1H), 7.40-7.32 (m, 3H), 7.18 (t, J=6.9 Hz, 1H), 7.10-7.05 (m, 2H), 6.89 (d, J=8.4 Hz, 2H), 6.72 (d, J=8.4 Hz, 2H), 6.16 (d, J=6.9 Hz, 1H), 5.81 (s, 1H), 4.64 (dd, J=65.5, 17.1 Hz, 2H), 3.87 (s, 2H), 3.73-3.67 (m, 4H), 1.78-1.74 (m, 2H), 1.60-1.51 (m, 3H), 1.32-1.23 (m, 2H), 1.06-0.88 (m, 3H).
MS (ESI) m/z=577 (M+Na)⁺, 553 (M−H)⁻.

1.20. N-cyclohexyl-2-[(3,4-dimethoxy-phenyl)-(2-1H-indol-3-yl-acetyl)-amino]-2-(4-nitro-phenyl)-acetamide (WJCPA-020)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 3,4-methoxybenzylamine (3l; 112 mg, 0.82 mmol), 3-indole acetic acid (4a; 116 mg, 0.66 mmol), and 2,2,2-trifluoroethanol to obtain the bis-amide compound WJCPA-020 after purification by column chromatography (n-hexane:EtOAc=1:1).
Off-white solid (74 mg, yield 19%), Mp: 198.4° C. to 200.2° C.
¹H NMR (300 MHz, CDCl₃) δ: 8.06 (s, 1H), 8.01 (d, J=8.5 Hz, 2H), 7.37-7.32 (m, 4H), 7.17 (t, J=12.5 Hz, 1H), 7.06 (t, J=12.5 Hz, 1H), 6.90 (s, 2H), 6.70 (d, J=8.5 Hz, 1H), 6.24 (dd, J=8.5, 2.5 Hz, 1H), 6.09 (bs, 1H), 5.97 (bs, 1H), 3.83 (bs, 3H), 3.81 (s, 2H), 3.77-3.74 (m, 1H), 3.65 (s, 3H), 1.85-1.77 (m, 2H), 1.64-1.55 (m, 3H), 1.34-1.24 (m, 2H), 1.11-0.92 (m, 3H).
MS (ESI) m/z=593 (M+Na)⁺, 569 (M−H)⁻.

1.21. 2-[(4-bromo-phenyl)-(2-1H-indol-3-yl-acetyl)-amino]-N-cyclohexyl-2-(4-nitro-phenyl)-acetamide (WJCPA-021)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 4-bromoaniline (3f; 141 mg, 0.82 mmol), 3-indole acetic acid (4a; 174 mg, 0.99 mmol), and 2,2,2-trifluoroethanol to obtain the bis-amide compound WJCPA-021 after purification by column chromatography (n-hexane:EtOAc=1:1).
Yellow solid (94 mg, yield 24%), Mp: 256.6° C. to 261.5° C.
¹H NMR (300 MHz, CDCl₃) δ: 8.04-8.01 (m, 3H), 7.40-7.30 (m, 7H), 7.20-7.15 (m, 1H), 7.10-7.05 (m, 1H), 6.84 (d, J=2.4 Hz, 1H), 6.13 (s, 1H), 5.84 (d, J=7.8 Hz, 1H), 3.81-3.68 (m, 1H), 3.60 (s, 2H), 1.86-1.77 (m, 2H), 1.67-1.56 (m, 3H), 1.48-1.23 (m, 2H), 1.12-0.88 (m, 3H).
MS (ESI) m/z=587 (M–H)⁻.

1.22. N-cyclohexyl-2-[(2-1H-indol-3-yl-acetyl)-(4-isopropyl-phenyl)-amino]-2-(4-nitro-phenyl)-acetamide (WJCPA-022)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 4-isopropylaniline (3a; 110 mg, 0.82 mmol), 3-indole acetic acid (4a; 174 mg, 0.99 mmol), and 2,2,2-trifluoroethanol to obtain the bis-amide compound WJCPA-022 after purification by column chromatography (n-hexane:EtOAc=1:1).

Bright yellow solid (96 mg, yield 26%), Mp: 172.2° C. to 175.0° C.

$^1$H NMR (300 MHz, CDCl$_3$) δ: 8.01-7.97 (m, 3H), 7.38-7.31 (m, 4H), 7.19-7.14 (m, 1H), 7.08-7.02 (m, 4H), 6.82 (d, J=2.4 Hz, 2H), 6.14 (d, J=7.8 Hz, 1H), 6.08 (s, 1H), 3.79-3.70 (m, 1H), 3.62 (s, 2H), 2.87 (heptet, J=7.2 Hz, 1H), 1.83-1.74 (m, 2H), 1.62-1.52 (m, 3H), 1.34-1.20 (m, 8H), 1.11-0.88 (m, 3H).
MS (ESI) m/z=551 (M–H)⁻.

1.23. N-[cyclohexylcarbamoyl-(4-hydroxy-3-methoxy-phenyl)-methyl]-N-(4-isopropyl-phenyl)-3-(4-methoxy-phenyl)-propionamide (WJCPA-023)

A reaction was performed at room temperature in the same manner as in Example 1.1 using cyclohexyl isocyanide (1a; 72 mg, 0.66 mmol), vanillin (2d; 100 mg, 0.66 mmol), 4-isopropylaniline (3a; 111 mg, 0.82 mmol), 3-(4-methoxy-phenyl)propionic acid (4m; 238 mg, 1.32 mmol), and 2,2,2-trifluoroethanol to obtain the bis-amide compound WJCPA-023 after filtration.

White solid (17 mg, yield 4%), Mp: 177.6° C. to 179.2° C.

$^1$H NMR (600 MHz, CDCl$_3$) δ: 7.14-7.03 (m, 2H), 6.95 (d, J=16.8 Hz, 3H), 6.74 (d, J=16.8 Hz, 3H), 6.65 (dd, J=16.8, 3.6 Hz, 2H), 6.43 (s, 1H), 5.99 (s, 1H), 5.70 (d, J=15.6 Hz, 1H), 5.55 (bs, 1H), 3.81-3.76 (m, 1H), 3.74 (s, 3H), 3.54 (s, 3H), 2.89-2.80 (m, 3H), 2.38-2.27 (m, 2H), 1.94-1.82 (m, 2H), 1.69-1.55 (m, 3H), 1.38-1.29 (m, 2H), 1.17 (d, J=6.6 Hz, 6H), 1.15-1.01 (m, 3H).
MS (ESI) m/z=581 (M+Na)⁺.

1.24. N-cyclohexyl-2-[(3,4-dimethoxy-phenyl)-(2-1H-indol-3-yl-acetyl)-amino]-2-(4-hydroxy-phenyl)-acetamide (WJCPA-024)

A reaction was performed at room temperature in the same manner as in Example 1.1 using cyclohexyl isocyanide (1a; 90 mg, 0.83 mmol), 4-hydroxybenzaldehyde (2j; 100 mg, 0.83 mmol), 4-aminoveratrole (3d; 160 mg, 1.04 mmol), 3-indole acetic acid (4a; 210 mg, 1.24 mmol), and methanol to obtain the bis-amide compound WJCPA-024 after filtration.

Grey solid (228 mg, yield 51%), Mp: 204.2° C. to 212.0° C. (dec).

$^1$H NMR (300 MHz, DMSO) δ: 10.81 (s, 1H), 9.35 (bs, 1H), 7.80-7.74 (m, 1H), 7.52-7.44 (m, 0.5H), 7.31-7.27 (m, 2.5H), 7.02 (t, J=7.2 Hz, 2H), 6.90 (t, J=7.5 Hz, 1H), 6.81 (bs, 2.5H), 6.61 (bs, 0.5H), 6.47 (d, J=8.4 Hz, 2H), 6.22 (bs, 0.5H), 5.92 (bs, 1.5H), 3.70-3.60 (m, 4H), 3.58-3.50 (m, 3H), 3.28 (bs, 2H), 1.74-1.49 (m, 5H), 1.26-0.92 (m, 5H).
MS (ESI) m/z=564 (M+Na)⁺.

1.25. 2-Bromo-hexanoic acid [cyclohexylcarbamoyl-(4-hydroxy-phenyl)-methyl]-(3,4-dimethoxy-phenyl)-amide (WJCPA-025)

A reaction was performed at room temperature in the same manner as in Example 1.12 using cyclohexyl isocyanide (1a; 66 mg, 0.60 mmol), imine (5d; 150 mg, 0.60 mmol; a compound formed by reacting 4-hydroxybenzaldehyde (2j) and 4-aminoveratrole (3 d) in methanol), 2-bromo-hexanoic acid (4n; 180 mg, 0.90 mmol), and methanol to obtain the bis-amide compound WJCPA-025 after filtration.

White solid (100 mg, yield 30%), Mp: 140.5° C. to 142.7° C.

IR (cm⁻¹) 3295, 1644.
$^1$H NMR (300 MHz, DMSO-d6) δ: 9.38 (s, 1H), 7.86-7.74 (m, 1H), 7.55 (s, 1H), 7.41-7.35 (m, 1H), 6.88-6.81 (m, 2H), 6.63-6.60 (m, 1H), 6.49 (d, J=1.8 Hz, 1H), 5.94 (s, 1H), 5.83 (d, J=5.7 Hz, 1H), 3.94 (t, J=7.5 Hz, 1H), 3.69 (s, 3H), 3.64 (s, 3H), 3.60-3.52 (m, 1H), 2.05-1.96 (m, 1H), 1.77-1.50 (m, 6H), 1.28-1.08 (m, 8H), 0.99-0.91 (m, 1H), 0.84-0.75 (m, 3H).
MS (ESI) m/z=583 (M+Na)⁺.
Anal. Calcd. for C$_{28}$H$_{37}$BrN$_2$O$_5$: C, 59.89; H, 6.64; N, 4.99. Found C, 59.52; H, 6.58; N, 5.33.
HPLC: purity 98.5%.

1.26. N-[cyclohexylcarbamoyl-(4-hydroxy-phenyl)-methyl]-N-(3,4-dimethoxy-phenyl)-3-(3-methoxy-phenyl)-propionamide (WJCPA-026)

A reaction was performed at room temperature in the same manner as in Example 1.12 using cyclohexyl isocyanide (1a; 66 mg, 0.60 mmol), imine (5d; 150 mg, 0.60 mmol; a compound formed by reacting 4-hydroxybenzaldehyde (2j) and 4-aminoveratrole (3 d) in methanol), 3-(3-methoxy-phenyl) propionic acid (4l; 170 mg, 0.90 mmol), and methanol to obtain the bis-amide compound WJCPA-026 after filtration.

White solid (116 mg, yield 36%), Mp: 187.5° C. to 189.1° C.

IR (cm⁻¹) 3293, 1660.
$^1$H NMR (300 MHz, CDCl$_3$) δ: 7.12 (t, J=8.1 Hz, 1H), 6.93 (d, J=8.1 Hz, 2H), 6.70-6.59 (m, 4H), 6.46 (bs, 1H), 6.16 (bs, 1H), 5.95 (bs, 2H), 5.85 (bs, 1H), 5.64-5.62 (m, 1H), 3.79 (bs, 6H), 3.74 (s, 3H), 3.50-3.42 (m, 1H), 2.89 (t, J=7.8 Hz, 2H), 2.42-2.33 (m, 2H), 1.94-1.80 (m, 2H), 1.59-1.56 (m, 3H), 1.35-1.26 (m, 2H), 1.16-0.95 (m, 3H).
$^{13}$C NMR (125 MHz, CDCl$_3$) δ: 173.2, 159.4, 156.3, 148.4, 142.7, 132.5, 131.8, 129.2, 126.2, 122.7, 120.7, 115.2, 114.1, 113.4, 111.2, 110.4, 64.4, 55.7, 55.0, 48.7, 36.4, 32.7, 31.6, 25.4, 24.7, 24.6.
MS (ESI) m/z=569 (M+Na)⁺.
HPLC: purity 99.7%.

1.27. 2-(4-chloro-phenyl)-N-cyclohexyl-2-[(2-1H-indol-3-yl-acetyl)-phenyl-amino]-acetamide (WJCPA-027)

A reaction was performed at room temperature in the same manner as in Example 1.1 using cyclohexyl isocyanide (1a; 78 mg, 0.71 mmol), 4-chlorobenzaldehyde (2f; 100 mg, 0.71 mmol), aniline (3g; 83 mg, 0.89 mmol), 3-indole acetic acid (4a; 187 mg, 1.06 mmol), and 2,2,2-trifluoroethanol to obtain the bis-amide compound WJCPA-027 after purification by column chromatography (n-hexane:EtOAc=3:1).

Bright yellow solid (97 mg, yield 27%), Mp: 203.9° C. to 205.8° C.

IR (cm$^{-1}$) 3267, 1623.

$^1$H NMR (300 MHz, CDCl$_3$) δ: 7.97 (s, 1H), 7.40-7.30 (m, 5H), 7.22-7.02 (m, 8H), 6.92 (d, J=2.4 Hz, 1H), 6.04 (s, 1H), 5.79-5.73 (m, 1H), 3.77-3.75 (m, 1H), 3.58 (s, 2H), 1.87-1.76 (m, 2H), 1.65-1.54 (m, 3H), 1.33-1.19 (m, 2H), 1.09-0.95 (m, 3H).

$^{13}$C NMR (125 MHz, CDCl$_3$) δ: 172.1, 168.3, 139.9, 135.9, 134.2, 133.1, 131.7, 130.2, 128.9, 128.3, 127.1, 123.1, 121.9, 119.4, 118.8, 110.9, 109.1 64.3, 48.6, 32.6, 31.9, 25.3, 24.7, 24.6.

MS (ESI) m/z=522 (M+Na)$^+$, 498 (M−H)$^−$.

HPLC: purity 99.2%.

1.28. N-[(4-chloro-phenyl)-cyclohexylcarbamoyl-methyl]-N-(4-isopropyl-phenyl)-benzamide (WJCPA-028)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-isopropylaniline (3a; 120 mg, 0.89 mmol), benzoic acid (4d; 131 mg, 1.07 mmol), and 2,2,2-trifluoroethanol to obtain the bis-amide compound WJCPA-028 after filtration.

White solid (82 mg, yield 23%), Mp: 181.0° C. to 182.5° C.

$^1$H NMR (300 MHz, CDCl$_3$) δ: 7.31-7.28 (m, 2H), 7.23 (d, J=1.5 Hz, 4H), 7.20-7.09 (m, 3H), 6.91-6.84 (m, 5H), 6.05 (s, 1H), 5.99 (d, J=8.1 Hz, 1H), 3.91-3.82 (m, 1H), 2.74 (heptet, J=6.9 Hz, 1H), 1.98-1.88 (m, 2H), 1.68-1.58 (m, 3H), 1.44-1.29 (m, 2H), 1.24-1.19 (m, 3H), 1.10 (d, J=6.9 Hz, 6H).

$^{13}$C NMR (125 MHz, CDCl$_3$) δ: 171.2, 168.2, 148.2, 138.9, 135.7, 134.2, 133.5, 131.3, 129.6, 128.57, 128.53, 127.5, 126.5, 66.4, 48.6, 33.4, 32.8, 25.4, 24.7, 24.6, 23.77, 23.74.

MS (ESI) m/z=511 (M+Na)$^+$.

HPLC: purity 99.2%.

1.29. N-[(4-chloro-phenyl)-cyclohexylcarbamoyl-methyl]-N-(4-isopropyl-phenyl)-3-(4-methoxy-phenyl)-propionamide (WJCPA-029)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-isopropylaniline (3a; 120 mg, 0.89 mmol), 3-(4-methoxyphenyl)propionic acid (4m; 193 mg, 1.07 mmol), and 2,2,2-trifluoroethanol to obtain the bis-amide compound WJCPA-029 after filtration.

White solid (120 mg, yield 30%), Mp: 205.1° C. to 207.8° C.

IR (cm$^{-1}$) 3258, 1643.

$^1$H NMR (300 MHz, CDCl$_3$) δ: 7.15-7.12 (m, 2H), 7.05-7.02 (m, 5H), 6.96-6.94 (m, 2H), 6.76-6.74 (m, 3H), 5.89 (s, 1H), 5.80-5.77 (m, 1H), 3.80-3.72 (m, 1H), 3.75 (s, 3H), 2.87-2.82 (m, 3H), 2.36-2.30 (m, 2H), 1.93-1.80 (m, 2H), 1.67-1.55 (m, 3H), 1.38-1.26 (m, 2H), 1.20-1.00 (m, 3H), 1.18 (d, J=6.9 Hz, 6H).

$^{13}$C NMR (125 MHz, CDCl$_3$) δ: 173.1, 168.3, 157.8, 149.1, 137.4, 134.1, 133.3, 133.1, 131.5, 129.7, 129.3, 128.2, 127.0, 113.6, 64.6, 55.2, 48.6, 36.8, 33.6, 32.8, 32.7, 30.5, 25.4, 24.7, 23.9, 23.8.

MS (ESI) m/z=569 (M+Na)$^+$.

HPLC: purity 97.1%.

1.30. N-[(4-chloro-phenyl)-cyclohexylcarbamoyl-methyl]-N-(4-isopropyl-phenyl)-2,5-dimethyl-benzamide (WJCPA-030)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-isopropylaniline (3a; 120 mg, 0.89 mmol), 2,5-dimethylbenzoic acid (4g; 161 mg, 1.07 mmol), and 2,2,2-trifluoroethanol to obtain the bis-amide compound WJCPA-030 after filtration.

White solid (94 mg, yield 25%), Mp: 181.3° C. to 182.5° C.

IR (cm$^{-1}$) 3273, 1652.

$^1$H NMR (300 MHz, CDCl$_3$) δ: 7.20 (s, 4H), 6.88-6.80 (m, 7H), 6.09 (s, 1H), 5.92-5.88 (m, 1H), 3.92-3.82 (m, 1H), 2.69 (heptet, J=6.6 Hz, 1H), 2.32 (s, 3H), 2.10 (s, 3H), 2.01-1.90 (m, 2H), 1.69-1.63 (m, 3H), 1.40-1.36 (m, 2H), 1.19-1.05 (m, 3H), 1.07 (d, J=6.9 Hz, 6H).

$^{13}$C NMR (125 MHz, CDCl$_3$) δ: 172.3, 168.4, 148.4, 136.2, 134.5, 134.4, 133.7, 131.7, 131.6, 130.0, 129.7, 129.4, 128.7, 127.9, 126.4, 65.6, 49.0, 33.6, 33.0, 25.7, 25.0, 24.9, 23.94, 23.92.

MS (ESI) m/z=539 (M+Na)$^+$.

HPLC: purity 96.4%.

1.31. 2-[(4-bromo-phenyl)-(2-1H-indol-3-yl-acetyl)-amino]-2-(4-chloro-phenyl)-N-cyclohexyl-acetamide (WJCPA-031)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-bromoaniline (3f; 154 mg, 0.90 mmol), 3-indole acetic acid (4a; 124 mg, 0.71 mmol), and 2,2,2-trifluoroethanol to obtain the bis-amide compound WJCPA-031 after filtration.

White solid (72 mg, yield 17%), Mp: 236.5° C. to 239.8° C.

IR (cm$^{-1}$) 3269, 1655.

$^1$H NMR (300 MHz, CDCl$_3$) δ: 8.02 (s, 1H), 7.36-7.25 (m, 5H), 7.18-7.13 (m, 3H), 7.08-7.02 (m, 3H), 6.93 (d, J=2.4 Hz, 2H), 6.06 (s, 1H), 5.60 (d, J=8.1 Hz, 1H), 3.80-3.71 (m, 1H), 3.56 (s, 2H), 1.88-1.78 (m, 2H), 1.61-1.56 (m, 3H), 1.36-1.23 (m, 2H), 1.13-0.90 (m, 3H).

$^{13}$C NMR (125 MHz, CDCl$_3$) δ: 171.8, 168.2, 138.7, 135.9, 134.5, 132.8, 132.2, 132.0, 131.6, 128.6, 127.0, 123.0, 122.4, 122.0, 119.4, 118.7, 111.0, 108.8, 63.8, 48.8, 32.6, 32.0, 25.3, 24.7, 24.6.

MS (ESI) m/z=576 (M−H)$^−$.

HPLC: purity 99.4%.

1.32. 2-(4-chloro-phenyl)-N-cyclohexyl-2-[(3,4-dimethoxy-phenyl)-(2-1H-indol-3-yl-acetyl)-amino]-acetamide (WJCPA-032)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-aminoveratrole (3d; 128 mg, 0.90 mmol), 3-indole acetic acid (4a; 124 mg, 0.71 mmol), and 2,2,2-trifluoroethanol to obtain the bis-amide compound WJCPA-032 after filtration.

White solid (220 mg, yield 50%), Mp: 210.5° C. to 212.4° C.

IR (cm$^{-1}$) 3263, 1647.

$^1$H NMR (300 MHz, CDCl$_3$) δ: 8.07 (s, 1H), 7.34-7.29 (m, 3H), 7.17-6.97 (m, 8H), 6.69-6.55 (m, 1H), 6.07 (s, 1H), 5.73 (d, J=7.8 Hz, 1H), 3.83 (s, 3H), 3.77-3.71 (m, 1H), 3.61 (s, 3H), 3.35 (bs, 2H), 1.87-1.78 (m, 2H), 1.65-1.53 (m, 3H), 1.37-1.23 (m, 2H), 1.12-0.90 (m, 3H).

$^{13}$C NMR (125 MHz, CDCl$_3$) δ: 172.5, 148.6, 135.9, 134.4, 133.2, 132.4, 131.8, 128.3, 127.1, 123.0, 122.6, 121.9, 119.4, 118.8, 113.5, 110.9, 110.3, 109.3, 63.9, 55.8, 48.6, 32.6, 31.8, 25.3, 24.7, 24.6.

MS (ESI) m/z=582 (M+Na)$^+$, 558 (M−H)$^-$.

Anal. Calcd. for C$_{32}$H$_{34}$ClN$_3$O$_4$: C, 68.62; H, 6.12; N, 7.50. Found C, 68.57; H, 6.05; N, 7.86.

HPLC: purity 99.6%.

1.33. 2-(4-Chloro-phenyl)-N-cyclohexyl-2-[(2-1H-indol-3-yl-acetyl)-(4-isopropyl-phenyl)-amino]-acetamide (WJCPA-033)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-isopropylaniline (3a; 122 mg, 0.90 mmol), 3-indole acetic acid (4a; 186 mg, 1.07 mmol), and methanol to obtain the bis-amide compound WJCPA-033 after filtration.

Bright orange solid (25 mg, yield 6%), Mp: 173.2° C. to 174.6° C.

$^1$H NMR (300 MHz, CDCl$_3$) δ: 8.02 (s, 1H), 7.36-7.30 (m, 3H), 7.17-7.10 (m, 4H), 7.07-7.01 (m, 5H), 6.93 (d, J=2.4 Hz, 1H), 5.99 (s, 1H), 5.86 (d, J=8.4 Hz, 1H), 3.82-3.70 (m, 1H), 3.59 (s, 2H), 2.85 (heptet, J=6.9 Hz, 1H), 1.85-1.76 (m, 2H), 1.64-1.52 (m, 3H), 1.38-1.23 (m, 2H), 1.20 (d, J=6.9 Hz, 6H), 1.08-0.93 (m, 3H).

MS (ESI) m/z=564 (M+Na)$^+$, 540 (M−H)$^-$.

1.34. 2-(4-Chloro-phenyl)-N-cyclohexyl-2-[(2-1H-indol-3-yl-acetyl)-(4-methoxy-phenyl)-amino]-acetamide (WJCPA-034)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-methoxyaniline (3b; 110 mg, 0.90 mmol), 3-indole acetic acid (4a; 192 mg, 1.10 mmol), and methanol to obtain the bis-amide compound WJCPA-034 after filtration.

Bright yellow solid (62 mg, yield 16%), Mp: 199.8° C. to 201.5° C.

IR (cm$^{-1}$) 3264, 1657.

$^1$H NMR (300 MHz, CDCl$_3$) δ: 8.46 (s, 1H), 7.39 (d, J=8.1 Hz, 2H), 7.33 (d, J=8.1 Hz, 2H), 7.16-7.11 (m, 3H), 7.06-7.01 (m, 3H), 6.94 (d, J=2.4 Hz, 1H), 6.73-6.60 (m, 2H), 6.08 (s, 1H), 5.87 (d, J=7.8 Hz, 1H), 3.76 (s, 3H), 3.74-3.68 (m, 1H), 3.57 (s, 2H), 1.85-1.76 (m, 2H), 1.64-1.53 (m, 3H), 1.33-1.23 (m, 2H), 1.11-0.88 (m, 3H).

$^{13}$C NMR (125 MHz, CDCl$_3$) δ: 172.5, 168.4, 159.1, 135.9, 134.2, 133.2, 132.3, 131.8, 131.3, 128.3, 127.2, 123.1, 121.9, 119.3, 118.9, 113.9, 110.9, 109.2, 63.9, 55.3, 48.6, 32.6, 31.8, 25.3, 24.7, 24.6.

MS (ESI) m/z=552 (M+Na)$^+$, 528 (M−H)$^-$.

HPLC: purity 95.9%.

1.35. N-[(4-chloro-phenyl)-cyclohexylcarbamoyl-methyl]-N-(3,4-dimethoxy-phenyl)-3-(4-methoxy-phenyl)-propionamide (WJCPA-035)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-aminoveratrole (3d; 128 mg, 0.91 mmol), 3-(4-methoxyphenyl) propionic acid (4m; 200 mg, 1.10 mmol), and methanol to obtain the bis-amide compound WJCPA-035 after purification by column chromatography (n-hexane:EtOAc=1:1).

White solid (55 mg, yield 14%), Mp: 195.6° C. to 197.3° C.

IR (cm$^{-1}$) 3286, 1650.

$^1$H NMR (300 MHz, CDCl$_3$) δ: 7.15 (d, J=8.1 Hz, 2H), 7.04 (d, J=8.1 Hz, 2H), 6.98 (d, J=8.7 Hz, 3H), 6.96 (d, J=8.7 Hz, 3H), 6.50 (bs, 1H), 5.99 (s, 1H), 5.65 (bs, 1H), 3.82 (s, 6H), 3.76 (s, 3H), 3.51-3.46 (m, 1H), 2.86 (t, J=7.5 Hz, 2H), 2.38-2.31 (m, 2H), 1.96-1.81 (m, 2H), 1.71-1.62 (m, 3H), 1.41-1.26 (m, 2H), 1.18-1.05 (m, 3H).

MS (ESI) m/z=587 (M+Na)$^+$, 563 (M−H)$^-$.

HPLC: purity 99.6%.

1.36. 2-Benzo[1,3]dioxol-5-yl-2-[butyl-(2-1H-indol-3-yl-acetyl)-amino]-N-cyclohexyl-acetamide (WJCPA-036)

A reaction was performed at room temperature in the same manner as in Example 1.1 using cyclohexyl isocyanide (1a; 73 mg, 0.67 mmol), piperonal (2n; 100 mg, 0.67 mmol), butylamine (3i; 61 mg, 0.83 mmol), 3-indole acetic acid (4a; 192 mg, 1.10 mmol), and methanol to obtain the bis-amide compound WJCPA-036 after purification by column chromatography (n-hexane:EtOAc=1:1).

White solid (126 mg, yield 38%), Mp: 171.0° C. to 173.0° C.

IR (cm$^{-1}$) 3234, 1654.

$^1$H NMR (300 MHz, CDCl$_3$) δ: 8.11 (s, 1H), 7.59 (d, J=7.2 Hz, 1H), 7.36 (d, J=8.4 Hz, 1H), 7.24-7.10 (m, 3H), 6.93 (s, 1H), 6.88 (d, J=8.4 Hz, 1H), 6.77 (d, J=7.8 Hz, 1H), 5.96 (s, 2H), 5.82 (d, J=6.9 Hz, 1H), 5.72 (s, 1H), 3.87 (s, 2H), 3.81-3.73 (m, 1H), 3.38-3.29 (m, 2H), 1.86-1.82 (m, 2H), 1.65-1.50 (m, 5H), 1.33-1.23 (m, 2H), 1.14-0.97 (m, 5H), 0.74 (t, J=7.2 Hz, 3H).

MS (ESI) m/z=512 (M+Na)$^+$, 488 (M−H)$^-$.

Anal. Calcd. for C$_{29}$H$_{35}$N$_3$O$_4$: C, 71.14; H, 7.21; N, 8.58. Found C, 71.18; H, 7.24; N, 8.93.

HPLC: purity 98.5%.

1.37. N-cyclohexyl-2-(4-ethyl-phenyl)-2-[(2-1H-indol-3-yl-acetyl)-phenyl-amino]-acetamide (WJCPA-037)

A reaction was performed at room temperature in the same manner as in Example 1.1 using cyclohexyl isocyanide (1a; 82 mg, 0.75 mmol), 4-ethylbenzaldehyde (2k; 100 mg, 0.75 mmol), aniline (3g; 87 mg, 0.93 mmol), 3-indole acetic acid (4a; 196 mg, 1.12 mmol), and 2,2,2-trifluoroethanol to obtain the bis-amide compound WJCPA-037 after filtration.

White solid (30 mg, yield 8%), Mp: 176.0° C. to 177.0° C.

$^1$H NMR (600 MHz, CDCl$_3$) δ: 8.04 (s, 1H), 7.36 (d, J=7.2 Hz, 2H), 7.30 (d, J=8.1 Hz, 2H), 7.17-7.10 (m, 4H), 7.05-6.95 (m, 6H), 6.03 (s, 1H), 5.66 (d, J=7.8 Hz, 1H), 3.83-3.74 (m, 1H), 3.57 (s, 2H), 2.55 (q, J=7.8 Hz, 2H), 1.89-1.80 (m, 2H), 1.66-1.52 (m, 3H), 1.48-1.22 (m, 2H), 1.15 (t, J=7.5 Hz, 3H), 1.08-0.89 (m, 3H).

MS (ESI) m/z=516 (M+Na)$^+$, 492 (M−H)$^-$.

1.38. 2-[(4-Bromo-phenyl)-(2-1H-indol-3-yl-acetyl)-amino]-N-tert-butyl-2-(4-nitro-phenyl)-acetamide (WJCPA-038)

A reaction was performed at room temperature in the same manner as in Example 1.12 using tert-butyl isocyanide (1d; 29 mg, 0.35 mmol), imine (5c; 100 mg, 0.35 mmol; a compound formed by reacting 4-nitrobenzaldehyde (2h) with 4-bromoaniline (3o), 3-indole acetic acid (4a; 75 mg, 0.43 mmol in methanol), and 2,2,2-trifluoroethanol to obtain the bis-amide compound WJCPA-038 after filtration.

Bright yellow solid (52 mg, yield 26%), Mp: 213.2° C. to 215.6° C.

$^1$H NMR (300 MHz, CDCl$_3$) δ: 8.03 (s, 1H), 8.02 (d, J=8.1 Hz, 2H), 7.38-7.26 (m, 7H), 7.17 (d, J=7.2 Hz, 1H), 7.07 (t, J=7.2 Hz, 1H), 6.87 (s, 2H), 6.03 (s, 1H), 5.85 (s, 1H), 3.60 (s, 2H), 1.29 (s, 9H).

MS (ESI) m/z=585 (M+Na)$^+$.

1.39. N-(4-bromo-phenyl)-N-[tert-butylcarbamoyl-(4-nitro-phenyl)-methyl]-5-methoxy-2-nitro-benzamide (WJCPA-039)

A reaction was performed at room temperature in the same manner as in Example 1.12 using tert-butyl isocyanide (1d; 29 mg, 0.35 mmol), imine (5c; 100 mg, 0.35 mmol; a compound formed by reacting 4-nitrobenzaldehyde (2h) with 4-bromoaniline (3o), 5-methoxy-2-nitrobenzoic acid (4i; 103 mg, 0.52 mmol), and 2,2,2-trifluoroethanol to obtain the bis-amide compound WJCPA-039 after purification by column chromatography (n-hexane:EtOAc=3:1).

Brown solid (62 mg, yield 30%), Mp: 111.3° C. to 116.8° C.

$^1$H NMR (300 MHz, CDCl$_3$) δ: 8.12 (d, J=6.9 Hz, 2H), 7.98 (d, J=9.3 Hz, 1H), 7.50 (d, J=8.4 Hz, 2H), 7.14 (d, J=9.0 Hz, 2H), 6.92-6.89 (m, 2H), 6.81-6.74 (m, 2H), 6.25 (s, 1H), 6.02 (bs, 1H), 3.82 (s, 3H), 1.54 (s, 3H), 1.44 (s, 6H).

MS (ESI) m/z=607 (M+Na)$^+$.

1.40. N-tert-butyl-2-(4-chloro-phenyl)-2-[(2-1H-indol-3-yl-acetyl)-(4-isopropyl-phenyl)-amino]-acetamide (WJCPA-040)

A reaction was performed at room temperature in the same manner as in Example 1.12 using tert-butyl isocyanide (1d; 32 mg, 0.39 mmol), imine (5e; 100 mg, 0.39 mmol; a compound formed by reacting 4-chlorobenzaldehyde (2f) and 4-isopropylaniline (3a) in methanol), 3-indole acetic acid (4a; 84 mg, 0.48 mmol), and 2,2,2-trifluoroethanol to obtain the bis-amide compound WJCPA-040 after filtration.

Bright yellow solid (52 mg, yield 25%), Mp: 184.2° C. to 186.6° C.

$^1$H NMR (300 MHz, CDCl$_3$) δ: 7.98 (s, 1H), 7.35-7.30 (m, 3H), 7.17-7.00 (m, 8H), 6.94 (d, J=2.4 Hz, 2H), 5.92 (s, 1H), 5.90 (s, 1H), 3.58 (s, 2H), 2.86 (heptet, J=6.9 Hz, 1H), 1.27 (s, 9H), 1.20 (d, J=6.9 Hz, 6H).

MS (ESI) m/z=538 (M+Na)$^+$, 514 (M−H)$^-$.

1.41. N-[tert-butylcarbamoyl-(4-chloro-phenyl)-methyl]-N-(4-isopropyl-phenyl)-5-methoxy-2-nitro-benzamide (WJCPA-041)

A reaction was performed at room temperature in the same manner as in Example 1.12 using tert-butyl isocyanide (Id; 32 mg, 0.39 mmol), imine (5e; 100 mg, 0.39 mmol; a compound formed by reacting 4-chlorobenzaldehyde (2f) and 4-isopropylaniline (3a) in methanol), 5-methoxy-2-nitrobenzoic acid (4i; 114 mg, 0.58 mmol), and 2,2,2-trifluoroethanol to obtain the bis-amide compound WJCPA-041 after purification by column chromatography (n-hexane:EtOAc=3:1).

Bright yellow solid (84 mg, yield 40%), Mp: 136.0° C. to 138.0° C.

$^1$H NMR (300 MHz, CDCl$_3$) δ: 7.90 (d, J=9.0 Hz, 1H), 7.20 (s, 4H), 6.84 (s, 4H), 6.77-6.70 (m, 2H), 6.11 (bs, 2H), 3.80 (s, 3H), 2.69 (heptet, J=6.9 Hz, 1H), 1.43 (s, 9H), 1.06 (d, J=6.9 Hz, 6H).

MS (ESI) m/z=560 (M+Na)$^+$.

1.42. N-[tert-butylcarbamoyl-(4-chloro-phenyl)-methyl]-N-(4-isopropyl-phenyl)-3-(3-methoxy-phenyl)-propionamide (WJCPA-042)

A reaction was performed at room temperature in the same manner as in Example 1.12 using tert-butyl isocyanide (1d; 32 mg, 0.39 mmol), imine (5e; 100 mg, 0.39 mmol; a compound formed by reacting 4-chlorobenzaldehyde (2f) and 4-isopropylaniline (3a) in methanol), 3-(3-methoxyphenyl)propionic acid (4l; 105 mg, 0.58 mmol), and 2,2,2-trifluoroethanol to obtain the bis-amide compound WJCPA-042 after purification by column chromatography (n-hexane:EtOAc=3:1).

White solid (103 mg, yield 50%), Mp: 124.0° C. to 125.9° C.

$^1$H NMR (300 MHz, CDCl$_3$) δ: 7.15-7.10 (m, 4H), 7.03-7.01 (m, 4H), 6.71-6.59 (m, 4H), 5.83 (s, 1H), 5.81 (s, 1H), 3.74 (s, 3H), 2.88 (t, J=8.1 Hz, 2H), 2.83 (heptet, J=6.6 Hz, 1H), 2.40-2.33 (m, 2H), 1.33 (s, 9H), 1.18 (d, J=6.6 Hz, 6H).

MS (ESI) m/z=543 (M+Na)$^+$.

1.43. N-cyclohexyl-2-(3,4-dimethoxy-phenyl)-2-[(2-1H-indol-3-yl-acetyl)-(4-methoxy-phenyl)-amino]-acetamide (WJCPA-043)

A reaction was performed at room temperature in the same manner as in Example 1.12 using cyclohexyl isocyanide (1a; 60 mg, 0.55 mmol), imine (5f; 150 mg, 0.55 mmol; a compound formed by reacting 3,4-dimethoxybenzaldehyde (2c) and p-anisidine (3b) in methanol), 3-indole acetic acid (4a; 121 mg, 0.69 mmol), and 2,2,2-trifluoroethanol to obtain the bis-amide compound WJCPA-043 after purification by column chromatography (EtOAc).

White solid (235 mg, yield 76%), Mp: 105.1° C. to 108.3° C.

$^1$H NMR (300 MHz, CDCl$_3$) δ: 7.98 (s, 1H), 7.40 (d, J=8.1 Hz, 2H), 7.31 (d, J=8.1 Hz, 2H), 7.14 (t, J=7.8 Hz, 1H), 7.06?7.01 (m, 2H), 6.72-6.53 (m, 5H), 6.09 (s, 1H), 5.66 (d, J=9.0 Hz, 1H), 3.82 (s, 3H), 3.80-3.71 (m, 1H), 3.74 (s, 3H), 3.57 (s, 5H), 1.90-1.79 (m, 2H), 1.69-1.58 (m, 3H), 1.38-1.23 (m, 2H), 1.10-0.95 (m, 3H).

MS (ESI) m/z=578 (M+Na)$^+$, 514 (M−H)$^-$.

1.44. N-[cyclohexylcarbamoyl-(3,4-dimethoxy-phenyl)-methyl]-3-(3-methoxy-phenyl-N-(4-methoxy-phenyl)-propionamide (WJCPA-044)

A reaction was performed at room temperature in the same manner as in Example 1.12 using cyclohexyl isocyanide (1a; 60 mg, 0.55 mmol), imine (5f; 150 mg, 0.55 mmol; a compound formed by reacting 3,4-dimethoxybenzaldehyde (2c) and p-anisidine (3b) in methanol), 3-indole acetic acid (4a; 121 mg, 0.69 mmol), and 2,2,2-trifluoroethanol to obtain the bis-amide compound WJCPA-044 after filtration.

White solid (80 mg, yield 25%), Mp: 129.9° C. to 135.7° C.

$^1$H NMR (300 MHz, CDCl$_3$) δ: 7.12 (t, J=7.8 Hz, 1H), 6.72-6.63 (m, 6H), 6.60-6.58 (m, 2H), 6.49 (bs, 2H), 6.03 (s, 1H), 5.59 (d, J=7.5 Hz, 1H), 3.83 (s, 3H), 3.82?3.76 (m, 1H), 3.74 (s, 3H), 3.73 (s, 3H), 3.61 (s, 3H), 2.89 (t, J=7.5 Hz,

2H), 2.38-2.30 (m, 2H), 1.96-1.81 (m, 2H), 1.71-1.56 (m, 3H), 1.38-1.23 (m, 2H), 1.17-1.00 (m, 3H).
MS (ESI) m/z=583 (M+Na)+.

1.45. N-tert-butyl-2-[(2-1H-indol-3-yl-acetyl)-(4-isopropyl-phenyl)-amino]-2-(3,4,5-trimethoxy-phenyl)-acetamide (WJCPA-045)

A reaction was performed at room temperature in the same manner as in Example 1.1 using tert-butyl isocyanide (1d; 42 mg, 0.51 mmol), 3,4,5-trimethoxybenzaldehyde (2a; 100 mg, 0.51 mmol), 4-isopropylaniline (3a; 86 mg, 0.64 mmol), 3-indole acetic acid (4a; 112 mg, 0.64 mmol), and 2,2,2-trifluoroethanol to obtain the bis-amide compound WJCPA-045 after purification by column chromatography (n-hexane:EtOAc=3:1).

White solid (225 mg, yield 77%), Mp: 88.9° C. to 95.3° C.
$^1$H NMR (300 MHz, CDCl$_3$) δ: 7.98 (s, 1H), 7.38 (d, J=7.8 Hz, 2H), 7.31 (d, J=7.8 Hz, 2H), 7.14 (t, J=8.1 Hz, 1H), 7.03 (t, J=7.8 Hz, 1H), 6.97-6.91 (m, 3H), 6.29 (s, 2H), 5.96 (s, 1H), 5.85 (s, 1H), 3.75 (s, 3H), 3.60 (s, 2H), 3.59 (s, 6H), 2.84 (heptet, J=6.9 Hz, 1H), 1.30 (s, 9H), 1.19 (d, J=6.9 Hz, 6H).
MS (ESI) m/z=594 (M+Na)+.

1.46. N-[tert-butylcarbamoyl-(3,4,5-trimethoxy-phenyl)-methyl]-6-chloro-N-(4-isopropyl-phenyl)-nicotinamide (WJCPA-046)

A reaction was performed at room temperature in the same manner as in Example 1.1 using tert-butyl isocyanide (1d; 42 mg, 0.51 mmol), 3,4,5-trimethoxybenzaldehyde (2a; 100 mg, 0.51 mmol), 4-isopropylaniline (3a; 86 mg, 0.64 mmol), 6-chloronicotinic acid (4k; 101 mg, 0.64 mmol), and 2,2,2-trifluoroethanol to obtain the bis-amide compound WJCPA-046 after purification by column chromatography (n-hexane:EtOAc=1:1).

White solid (132 mg, yield 46%), Mp: 74.6° C. to 80.0° C.
$^1$H NMR (300 MHz, CDCl$_3$) δ: 8.31 (d, J=2.4 Hz, 1H), 7.59 (dd, J=8.1, 2.4 Hz, 1H), 7.10 (d, J=8.1 Hz, 1H), 6.94-6.87 (m, 4H), 6.34 (s, 2H), 6.04 (s, 1H), 5.56 (s, 1H), 3.79 (s, 3H), 3.66 (s, 6H), 2.75 (heptet, J=6.9 Hz, 1H), 1.37 (s, 9H), 1.11 (d, J=6.9 Hz, 6H).
MS (ESI) m/z=576 (M+Na)+.

1.47. N-[cyclohexylcarbamoyl-(4-hydroxy-phenyl)-methyl]-N-(3,4-dimethoxy-phenyl)-2-methyl-benzamide (WJCPA-047)

A reaction was performed at room temperature in the same manner as in Example 1.12 using cyclohexyl isocyanide (1a; 55 mg, 0.48 mmol), imine (5d; 100 mg, 0.39 mmol; a compound formed by reacting 4-hydroxybenzaldehyde (2j) and 4-aminoveratrole (3 d) in methanol), o-toluic acid (4e; 85 mg, 0.60 mmol), and 2,2,2-trifluoroethanol as a solvent to obtain the bis-amide compound WJCPA-047 after filtration.

White solid (56 mg, yield 28%), Mp: 149.4° C. to 154.4° C.
$^1$H NMR (300 MHz, CDCl$_3$) δ: 7.08-6.99 (m, 4H), 6.96-6.91 (m, 1H), 6.67 (d, J=8.7 Hz, 2H), 6.56-6.48 (m, 2H), 6.38 (d, J=8.7 Hz, 1H), 6.20 (s, 1H), 5.65 (bs, 2H), 3.91-3.81 (m, 1H), 3.68 (s, 3H), 3.58 (s, 3H), 2.40 (s, 3H), 1.98-1.87 (m, 2H), 1.72-1.59 (m, 3H), 1.37-1.30 (m, 2H), 1.15-1.04 (m, 3H).
MS (ESI) m/z=525 (M+Na)+.

1.48. N-(4-bromo-phenyl)-5-methoxy-2-nitro-N-[(4-nitro-phenyl)-pentylcarbamoyl-methyl]-benzamide (WJCPA-048)

A reaction was performed at room temperature in the same manner as in Example 1.12 using 1-pentyl isocyanide (1c; 34 mg, 0.35 mmol), imine (5c; 100 mg, 0.35 mmol; a compound formed by reacting 4-nitrobenzaldehyde (2 h) and 4-bromoaniline (3f) in methanol), 5-methoxy-2-nitrobenzoic acid (4i; 85 mg, 0.43 mmol), and 2,2,2-trifluoroethanol to obtain the bis-amide compound WJCPA-048 after purification by column chromatography (n-hexane:EtOAc=3:1).

Brown solid (174 mg, yield 83%), Mp: 91.6° C. to 95.3° C.
$^1$H NMR (300 MHz, CDCl$_3$) δ: 8.12 (d, J=8.7 Hz, 2H), 7.98 (d, J=9.0 Hz, 1H), 7.51 (d, J=8.7 Hz, 2H), 7.14 (d, J=8.7 Hz, 2H), 6.94-6.90 (m, 2H), 6.81-6.76 (m, 2H), 6.34 (s, 1H), 6.16 (bs, 1H), 3.82 (s, 3H), 3.40 (q, J=7.2 Hz, 2H), 1.61-1.56 (m, 2H), 1.34-1.23 (m, 4H), 0.89 (t, J=7.2 Hz, 3H).
MS (ESI) m/z=621 (M+Na)+.

1.49. 1H-indol-2-carboxylic acid [cyclohexylcarbamoyl-(3,4,5-trimethoxy-phenyl)-methyl]-(4-isopropyl-phenyl)-amide (WJCPA-049)

A reaction was performed at room temperature in the same manner as in Example 1.1 using cyclohexyl isocyanide (1a; 70 mg, 0.51 mmol), 3,4,5-trimethoxybenzaldehyde (2a; 100 mg, 0.51 mmol), 4-isopropylaniline (3a; 86 mg, 0.64 mmol), indole-2-carboxylic acid (4c; 103 mg, 0.64 mmol), and 2,2,2-trifluoroethanol to obtain the bis-amide compound WJCPA-049 after filtration.

White solid (120 mg, yield 40%), Mp: 253.7° C. to 255.1° C.
IR (cm$^{-1}$) 3357, 1654.
$^1$H NMR (300 MHz, CDCl$_3$) δ: 9.23 (s, 1H), 7.34-7.28 (m, 3H), 7.23-7.17 (m, 2H), 7.16-7.09 (m, 2H), 7.01-6.96 (m, 2H), 6.39 (s, 2H), 6.19 (s, 1H), 5.79 (d, J=9.0 Hz, 1H), 3.90-3.83 (m, 1H), 3.80 (s, 3H), 3.65 (s, 6H), 2.93 (heptet, J=6.9 Hz, 1H), 2.02-1.85 (m, 2H), 1.68-1.49 (m, 3H), 1.40-1.28 (m, 2H), 1.23 (d, J=6.9 Hz, 6H), 1.19-1.05 (m, 3H).
MS (ESI) m/z=606 (M+Na)+, 582 (M−H)−.
Anal. Calcd. for C$_{35}$H$_{41}$N$_3$O$_5$: C, 72.02; H, 7.08; N, 7.20. Found C, 72.11; H, 7.06; N, 7.57.
HPLC: purity 99.8%.

1.50. 6-Chloro-N-[cyclohexylcarbamoyl-(3,4,5-trimethoxy-phenyl)-methyl]-N-(4-isopropyl-phenyl)-nicotinamide (WJCPA-050)

A reaction was performed at room temperature in the same manner as in Example 1.1 using cyclohexyl isocyanide (1a; 70 mg, 0.51 mmol), 3,4,5-trimethoxybenzaldehyde (2a; 100 mg, 0.51 mmol), 4-isopropylaniline (3a; 86 mg, 0.64 mmol), 6-chloronicotinic acid (4k; 100 mg, 0.64 mmol), and 2,2,2-trifluoroethanol to obtain the bis-amide compound WJCPA-050 after purification by column chromatography (n-hexane:EtOAc=3:1).

White solid (44 mg, yield 14%), Mp: 245.3° C. to 247.6° C.
$^1$H NMR (300 MHz, CDCl$_3$) δ: 8.31 (d, J=2.4 Hz, 1H), 7.60 (dd, J=8.1, 2.4 Hz, 1H), 7.10 (d, J=8.1 Hz, 1H), 6.95-6.89 (m, 4H), 6.34 (s, 2H), 6.13 (s, 1H), 5.56 (d, J=7.2

Hz, 1H), 3.90-3.82 (m, 1H), 3.80 (s, 3H), 3.66 (s, 6H), 2.76 (heptet, J=6.9 Hz, 1H), 2.00-1.86 (m, 2H), 1.73-1.62 (m, 3H), 1.40-1.31 (m, 2H), 1.18-0.92 (m, 3H), 1.11 (d, J=6.9 Hz, 6H).

MS (ESI) m/z=602 (M+Na)$^+$.

1.51. N-[cyclohexylcarbamoyl-(3,4,5-trimethoxy-phenyl)-methyl]-N-(4-isopropyl-phenyl)-5-methoxy-2-nitro-benzamide (WJCPA-051)

A reaction was performed at room temperature in the same manner as in Example 1.1 using cyclohexyl isocyanide (1a; 70 mg, 0.51 mmol), 3,4,5-trimethoxybenzaldehyde (2a; 100 mg, 0.51 mmol), 4-isopropylaniline (3a; 86 mg, 0.64 mmol), 5-methoxy-2-nitrobenzoic acid (4i; 126 mg, 0.64 mmol), and 2,2,2-trifluoroethanol to obtain the bis-amide compound WJCPA-051 after purification by column chromatography (n-hexane:EtOAc=3:1).

Brown solid (224 mg, yield 70%), Mp: 161.3° C. to 163.3° C.

IR (cm$^{-1}$) 3373, 1650.

$^1$H NMR (300 MHz, CDCl$_3$) δ: 7.95 (d, J=9.0 Hz, 1H), 6.94-6.84 (m, 4H), 6.76 (dd, J=9.0, 2.7 Hz, 2H), 6.50 (s, 2H), 6.22 (s, 1H), 5.95 (bs, 1H), 3.97-3.90 (m, 1H), 3.85 (s, 3H), 3.83 (s, 3H), 3.73 (s, 6H), 2.72 (heptet, J=6.9 Hz, 1H), 2.05-1.96 (m, 2H), 1.74-1.68 (m, 3H), 1.45-1.38 (m, 2H), 1.32-1.18 (m, 3H), 1.08 (d, J=6.9 Hz, 6H).

MS (ESI) m/z=642 (M+Na)$^+$.

HPLC: purity 97.3%.

1.52. N-[cyclohexylcarbamoyl-(4-nitro-phenyl)-methyl]-N-(3,4-dimethoxy-phenyl)-5-methoxy-2-nitro-benzamide (WJCPA-052)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), 5-methoxy-2-nitrobenzoic acid (4i; 87 mg, 0.44 mmol), and 2,2,2-trifluoroethanol to obtain the bis-amide compound WJCPA-052 after purification by column chromatography (n-hexane:EtOAc=3:1).

White solid (174 mg, yield 84%), Mp: 118.0° C. to 120.5° C.

IR (cm$^{-1}$) 3348, 1658.

$^1$H NMR (300 MHz, CDCl$_3$) δ: 8.11 (d, J=8.7 Hz, 2H), 7.94 (d, J=9.6 Hz, 1H), 7.51 (d, J=8.7 Hz, 2H), 6.79-6.74 (m, 2H), 6.47-6.38 (m, 2H), 6.34 (s, 1H), 6.18 (bs, 1H), 5.30 (s, 1H), 3.93-3.89 (m, 1H), 3.82 (s, 3H), 3.71 (s, 3H), 3.58 (s, 3H), 2.08-1.94 (m, 2H), 1.74-1.61 (m, 3H), 1.39-1.33 (m, 2H), 1.26-1.17 (m, 3H).

MS (ESI) m/z=615 (M+Na)$^+$.

Anal. Calcd. for C$_{30}$H$_{32}$N$_4$O$_9$. 0.03 CH$_2$Cl$_2$: C, 60.59; H, 5.43; N, 9.41. Found C, 60.39; H, 5.41; N, 9.61.

HPLC: purity 99.3%.

1.53. N-[cyclohexylcarbamoyl-(4-nitro-phenyl)-methyl]-N-(3,4-dimethoxy-phenyl)-3-(4-methoxy-phenyl)-propionamide (WJCPA-053)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), 3-(4-methoxyphenyl)propionic acid (4m; 79 mg, 0.44 mmol), and 2,2,2-trifluoroethanol to obtain the bis-amide compound WJCPA-053 after filtration.

White solid (47 mg, yield 23%), Mp: 182.0° C. to 185.5° C.

IR (cm$^{-1}$) 3265, 1653.

$^1$H NMR (300 MHz, CDCl$_3$) δ: 8.03 (d, J=8.7 Hz, 2H), 7.32 (d, J=8.7 Hz, 2H), 6.99 (d, J=8.7 Hz, 4H), 6.80-6.75 (m, 3H), 6.05 (s, 1H), 5.90 (bs, 1H), 3.82 (s, 6H), 3.76 (s, 3H), 3.62-3.50 (m, 1H), 2.86 (t, J=7.5 Hz, 2H), 2.40-2.35 (m, 2H), 1.97-1.83 (m, 2H), 1.70-1.64 (m, 3H), 1.39-1.34 (m, 2H), 1.20-1.04 (m, 3H).

MS (ESI) m/z=598 (M+Na)$^+$, 574 (M−H)$^-$.

Anal. Calcd. for C$_{32}$H$_{37}$N$_3$O$_7$. 0.07 CH$_2$Cl$_2$: C, 66.21; H, 6.43; N, 7.22. Found C, 65.90; H, 6.47; N, 7.52.

HPLC: purity 98.6%.

1.54. 6-Chloro-N-[cyclohexylcarbamoyl-(4-nitro-phenyl)-methyl]-N-(3,4-dimethoxy-phenyl)-nicoti-namide (WJCPA-054)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), 6-chloronicotinic acid (4k; 69 mg, 0.44 mmol), and 2,2,2-trifluoroethanol to obtain the bis-amide compound WJCPA-054 after purification by column chromatography (n-hexane:EtOAc=3:1).

Grey solid (131 mg, yield 67%), Mp: 196.3° C. to 198.5° C.

IR (cm$^{-1}$) 3266, 1636.

$^1$H NMR (300 MHz, CDCl$_3$) δ: 8.33 (dd, J=2.4, 0.6 Hz, 1H), 8.10 (d, J=9.0 Hz, 2H), 7.59 (dd, J=8.4, 2.4 Hz, 1H), 7.46 (d, J=8.7 Hz, 2H), 7.14 (dd, J=8.4, 0.6 Hz, 1H), 6.72 (bs, 1H), 6.50-6.46 (m, 2H), 6.22 (s, 1H), 5.69 (d, J=7.8 Hz, 1H), 3.90-3.84 (m, 1H), 3.75 (s, 3H), 3.65 (s, 3H), 2.04-1.87 (m, 2H), 1.75-1.59 (m, 3H), 1.40-1.32 (m, 2H), 1.22-1.06 (m, 3H).

MS (ESI) m/z=575 (M+Na)$^+$, 551 (M−H)$^-$.

Anal. Calcd. for C$_{28}$H$_{29}$ClN$_4$O$_6$: C, 60.81; H, 5.29; N, 10.13. Found C, 61.00; H, 5.23; N, 10.43.

HPLC: purity 99.7%.

1.55. 2-[acetyl-(3,4-dimethoxy-phenyl)-amino]-N-cyclohexyl-2-(4-nitro-phenyl)-acetamide (WJCPA-055)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), acetic acid (4s; 26 mg, 0.44 mmol), and methanol to obtain the bis-amide compound WJCPA-055 after filtration.

Bright yellow solid (18 mg, yield 11%), Mp: 178.8° C. to 180.8° C.

$^1$H NMR (300 MHz, CDCl$_3$) δ: 8.05 (d, J=8.7 Hz, 2H), 7.39 (d, J=8.7 Hz, 2H), 7.32-7.26 (m, 1H), 6.67-6.63 (m, 2H), 6.08 (s, 1H), 5.85 (d, J=6.9 Hz, 1H), 3.88-3.79 (m, 1H), 3.83 (s, 3H), 3.73 (bs, 3H), 2.00-1.84 (m, 2H), 1.91 (s, 3H), 1.69-1.51 (m, 3H), 1.40-1.33 (m, 2H), 1.27-1.15 (m, 3H).
MS (ESI) m/z=478 (M+Na)$^+$.

1.56. N-[cyclohexylcarbamoyl-(4-nitro-phenyl)-methyl]-N-(3,4-dimethoxy-phenyl)-2,5-dimethyl-benzamide (WJCPA-056)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), 2,5-dimethylbenzoic acid (4g; 66 mg, 0.44 mmol), and methanol to obtain the bis-amide compound WJCPA-056 after purification by column chromatography (n-hexane:EtOAc=3:1).

Dark green solid (48 mg, yield 25%), Mp: 175.9° C. to 177.9° C.

$^1$H NMR (300 MHz, CDCl$_3$) δ: 8.13 (d, J=9.0 Hz, 2H), 7.53 (d, J=8.7 Hz, 2H), 6.90 (s, 3H), 6.66 (s, 1H), 6.51-6.43 (m, 2H), 6.32 (s, 1H), 6.08 (d, J=8.7 Hz, 1H), 3.95-3.89 (m, 1H), 3.74 (s, 3H), 3.65 (s, 3H), 2.35 (s, 3H), 2.17 (s, 3H), 2.08-1.94 (m, 2H), 1.78-1.63 (m, 3H), 1.47-1.35 (m, 2H), 1.27-1.13 (m, 3H).
MS (ESI) m/z=544 (M–H)$^-$.

1.57. N-cyclohexyl-2-[[2-(3,4-dimethoxy-phenyl)-ethyl]-(2-1H-indol-3-yl-acetyl)-amino]-2-(4-nitro-phenyl)-acetamide (WJCPA-057)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), 3-indole acetic acid (4a; 70 mg, 0.40 mmol), and methanol to obtain the bis-amide compound WJCPA-057 after filtration.

Yellow solid (94 mg, yield 49%), Mp: 100.2° C. to 104.3° C.

$^1$H NMR (600 MHz, CDCl$_3$) δ: 8.16 (d, J=8.7 Hz, 2H), 8.15 (s, 1H), 7.63-7.54 (m, 1H), 7.55 (d, J=7.8 Hz, 2H), 7.40-7.36 (m, 1H), 7.26-7.20 (m, 2H), 7.14-7.10 (m, 1H), 6.72 (d, J=8.1 Hz, 1H), 6.49 (d, J=8.1 Hz, 1H), 6.44 (s, 1H), 6.31 (d, J=7.8 Hz, 1H), 5.82 (s, 1H), 3.86 (s, 2H), 3.82 (s, 3H), 3.76 (s, 3H), 3.66-3.56 (m, 3H), 2.77-2.69 (m, 1H), 2.49-2.44 (m, 1H), 1.88-1.83 (m, 2H), 1.67-1.58 (m, 3H), 1.35-1.23 (m, 2H), 1.12-0.99 (m, 3H).
MS (ESI) m/z=597 (M–H)$^-$.

1.58. 2-{(2-Chloro-acetyl)-[2-(3,4-dimethoxy-phenyl)-ethyl]-amino}-N-cyclohexyl-2-(4-nitro-phenyl)-acetamide (WJCPA-058)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), chloroacetic acid (4u; 38 mg, 0.40 mmol), and methanol to obtain the bis-amide compound WJCPA-058 after filtration.

Bright yellow solid (124 mg, yield 75%), Mp: 227.2° C. to 229.0° C.

$^1$H NMR (300 MHz, CDCl$_3$) δ: 8.25 (d, J=8.7 Hz, 2H), 7.61 (d, J=8.1 Hz, 2H), 6.77 (d, J=8.7 Hz, 1H), 6.61 (d, J=8.7 Hz, 1H), 6.60 (s, 1H), 6.10 (d, J=8.7 Hz, 1H), 5.70 (s, 1H), 3.90-3.82 (m, 1H), 3.88 (s, 2H), 3.85 (s, 3H), 3.84 (s, 3H), 3.63 (t, J=8.1 Hz, 2H), 2.80-2.73 (m, 1H), 2.65-2.58 (m, 1H), 1.96-1.91 (m, 2H), 1.72-1.63 (m, 3H), 1.43-1.31 (m, 2H), 1.22-1.14 (m, 3H).
MS (ESI) m/z=516 (M–H)$^-$.

1.59. N-[cyclohexylcarbamoyl-(4-nitro-phenyl)-methyl]-N-[2-(3,4-dimethoxy-phenyl)-ethyl]-2-methyl-5-nitro-benzamide (WJCPA-059)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), 2-methyl-5-nitrobenzoic acid (4h; 73 mg, 0.40 mmol), and methanol to obtain the bis-amide compound WJCPA-059 after purification by column chromatography (n-hexane: EtOAc=3:1).

Yellow solid (188 mg, yield 97%), Mp: 108.4° C. to 113.5° C.

IR (cm$^{-1}$) 3336, 1646.

$^1$H NMR (300 MHz, CDCl$_3$) δ: 8.33 (d, J=8.7 Hz, 2H), 8.19 (dd, J=8.4, 2.4 Hz, 1H), 8.08 (d, J=2.4 Hz, 1H), 7.78 (d, J=8.7 Hz, 2H), 7.44 (d, J=8.4 Hz, 1H), 6.58 (d, J=8.1 Hz, 2H), 6.09 (d, J=7.2 Hz, 1H), 5.97 (bs, 1H), 5.30 (s, 1H), 3.89-3.83 (m, 2H), 3.77 (s, 3H), 3.63 (s, 3H), 3.49-3.42 (m, 1H), 2.54-2.50 (m, 2H), 2.42 (s, 3H), 2.00-1.92 (m, 2H), 1.74-1.65 (m, 3H), 1.46-1.33 (m, 2H), 1.28-1.13 (m, 3H).
MS (ESI) m/z=603 (M–H)$^-$.
HPLC: purity 97.4%.

1.60. N-[cyclohexylcarbamoyl-(4-nitro-phenyl)-methyl]-N-[2-(3,4-dimethoxy-phenyl)-ethyl]-5-methoxy-2-nitro-benzamide (WJCPA-060)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), 5-methoxy-2-nitrobenzoic acid (4i; 79 mg, 0.40 mmol), and methanol to obtain the bis-amide compound WJCPA-060 after purification by column chromatography (n-hexane: EtOAc=3:1).

Yellow solid (196 mg, yield 99%), Mp: 104.5° C. to 107.6° C.

IR (cm$^{-1}$) 3327, 1642.

$^1$H NMR (300 MHz, CDCl$_3$) δ: 8.31-8.22 (m, 3H), 7.78 (bs, 2H), 7.02 (dd, J=9.3, 2.7 Hz, 1H), 6.77-6.62 (m, 3H), 6.24 (d, J=7.8 Hz, 1H), 6.14 (s, 1H), 5.94-5.83 (m, 1H), 3.97-3.91 (m, 1H), 3.92 (s, 3H), 3.79 (s, 3H), 3.69 (s, 3H), 3.38-3.32 (m, 2H), 2.70-2.57 (m, 2H), 2.04-1.98 (m, 2H), 1.75-1.64 (m, 3H), 1.41-1.32 (m, 2H), 1.28-1.19 (m, 3H).
MS (ESI) m/z=643 (M+Na)$^+$, 619 (M–H)$^-$.
HPLC: purity 99.3%.

1.61. N-[cyclohexylcarbamoyl-(4-nitro-phenyl)-methyl]-N-(3,4-dimethoxy-phenyl)-2-methyl-benzamide (WJCPA-061)

A reaction was performed at room temperature in the same manner as in Example 1.12 using cyclohexyl isocyanide (1a; 48 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), o-toluic acid (4e; 60 mg, 0.44 mmol), and methanol to obtain the bis-amide compound WJCPA-061 after filtration.

Yellow solid (49 mg, yield 26%), Mp: 101.3° C. to 105.5° C.

¹H NMR (300 MHz, CDCl₃) δ: 8.10 (d, J=8.7 Hz, 2H), 7.49 (d, J=8.7 Hz, 2H), 7.08-6.92 (m, 4H), 6.63 (s, 1H), 6.45-6.38 (m, 2H), 6.28 (s, 1H), 6.03 (d, J=7.8 Hz, 1H), 3.95-3.85 (m, 1H), 3.69 (s, 3H), 3.61 (s, 3H), 2.38 (s, 3H), 2.04-1.92 (m, 2H), 1.71-1.58 (m, 3H), 1.47-1.32 (m, 2H), 1.19-1.11 (m, 3H).

MS (ESI) m/z=530 (M−H)⁻.

1.62. N-[cyclohexylcarbamoyl-(4-nitro-phenyl)-methyl]-N-(3,4-dimethoxy-phenyl)-2,2-dimethyl-propionamide (WJCPA-062)

A reaction was performed at room temperature in the same manner as in Example 1.12 using cyclohexyl isocyanide (1a; 48 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), pivalic acid (4t; 45 mg, 0.44 mmol), and methanol to obtain the bis-amide compound WJCPA-062 after purification by column chromatography (n-hexane:EtOAc=3:1).

Grey solid (9 mg, yield 5%), Mp: 153.0° C. to 154.6° C.

¹H NMR (300 MHz, CDCl₃) δ: 8.05 (d, J=8.7 Hz, 2H), 7.36 (d, J=8.4 Hz, 2H), 6.67-6.54 (m, 3H), 6.01 (d, J=7.8 Hz, 1H), 5.91 (s, 1H), 3.78-3.70 (m, 1H), 3.83 (s, 6H), 2.00-1.86 (m, 2H), 1.72-1.62 (m, 3H), 1.43-1.31 (m, 2H), 1.20-1.10 (m, 3H), 1.05 (s, 9H).

MS (ESI) m/z=496 (M−H)⁻.

1.63. N-[cyclohexylcarbamoyl-(4-nitro-phenyl)-methyl]-5-methoxy-N-[2-(3-methoxy-phenyl)-ethyl]-2-nitro-benzamide (WJCPA-063)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), 5-methoxy-2-nitrobenzoic acid (4i; 164 mg, 0.83 mmol), and methanol to obtain the bis-amide compound WJCPA-063.

Yellow solid (340 mg, yield 86%), Mp: 97.9° C. to 101.8° C.

¹H NMR (300 MHz, CDCl₃) δ: 8.29-8.19 (m, 3H), 7.85-7.73 (m, 2H), 7.09-7.00 (m, 2H), 6.80-6.62 (m, 3H), 6.25 (d, J=7.2 Hz, 1H), 6.17 (s, 1H), 6.00-5.87 (m, 1H), 3.93-3.82 (m, 1H), 3.92 (s, 3H), 3.67 (s, 3H), 3.44-3.33 (m, 2H), 2.75-2.56 (m, 2H), 2.04-1.98 (m, 2H), 1.75-1.64 (m, 3H), 1.41-1.32 (m, 2H), 1.28-1.23 (m, 3H).

MS (ESI) m/z=613 (M+Na)⁺, 589 (M−H)⁻.

1.64. 2-{Acetyl-[2-(3-methoxy-phenyl)-ethyl]-amino}-N-cyclohexyl-2-(4-nitro-phenyl)-acetamide (WJCPA-064)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), acetic acid (4s; 50 mg, 0.83 mmol), and methanol to obtain the bis-amide compound WJCPA-064 after filtration.

White solid (198 mg, yield 65%), Mp: 172.2° C. to 174.2° C.

¹H NMR (300 MHz, CDCl₃) δ: 8.22 (d, J=8.7 Hz, 2H), 7.59 (d, J=8.7 Hz, 2H), 7.17 (t, J=7.8 Hz, 1H), 6.73 (d, J=7.8 Hz, 1H), 6.61 (d, J=6.9 Hz, 1H), 6.54 (bs, 1H), 6.21 (d, J=7.5 Hz, 1H), 5.88 (s, 1H), 3.85-3.80 (m, 1H), 3.75 (s, 3H), 3.57 (t, J=8.1 Hz, 2H), 2.85-2.76 (m, 1H), 2.54-2.44 (m, 1H), 2.19 (s, 3H), 1.97-1.89 (m, 2H), 1.71-1.63 (m, 3H), 1.43-1.31 (m, 2H), 1.22-1.10 (m, 3H).

MS (ESI) m/z=452 (M−H)⁻.

1.65. 6-Chloro-N-[cyclohexylcarbamoyl-(4-nitro-phenyl)-methyl]-N-[2-(3-methoxy-phenyl)-ethyl]-nicotinamide (WJCPA-065)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), 6-chloronicotinic acid (4k; 131 mg, 0.83 mmol), and methanol to obtain the bis-amide compound WJCPA-065.

Yellow solid (296 mg, yield 81%), Mp: 87.5° C. to 90.8° C.

¹H NMR (300 MHz, CDCl₃) δ: 8.40 (d, J=2.1 Hz, 1H), 8.27 (d, J=9.0 Hz, 2H), 7.67 (bs, 2H), 7.57 (d, J=7.5 Hz, 1H), 7.35 (d, J=8.1 Hz, 1H), 7.08 (t, J=7.5 Hz, 1H), 6.70 (dd, J=8.4, 1.8 Hz, 1H), 6.37-6.32 (m, 1H), 6.21 (s, 2H), 5.80 (s, 1H), 3.93-3.82 (m, 1H), 3.69 (s, 3H), 3.61 (t, J=7.8 Hz, 2H), 2.65-2.60 (m, 1H), 2.44-2.37 (m, 1H), 1.98-1.92 (m, 2H), 1.73-1.64 (m, 3H), 1.45-1.33 (m, 2H), 1.28-1.13 (m, 3H).

MS (ESI) m/z=549 (M−H)⁻.

1.66. N-[cyclohexylcarbamoyl-(4-nitro-phenyl)-methyl]-N-[2-(3-methoxy-phenyl)-ethyl]-benzamide (WJCPA-066)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), benzoic acid (4d; 101 mg, 0.83 mmol), and methanol to obtain the bis-amide compound WJCPA-066.

White solid (246 mg, yield 72%), Mp: 157.9° C. to 160.7° C.

¹H NMR (300 MHz, CDCl₃) 8.24 (d, J=9.0 Hz, 2H), 7.66 (bs, 2H), 7.50-7.43 (m, 5H), 7.05 (t, J=8.1 Hz, 1H), 6.66 (dd, J=8.1, 2.1 Hz, 1H), 6.31-6.21 (m, 2H), 5.88 (bs, 1H), 3.90-3.84 (m, 1H), 3.67 (s, 3H), 3.62-3.53 (m, 2H), 2.73 (bs, 1H), 2.45-2.36 (m, 1H), 2.02-1.90 (m, 2H), 1.73-1.68 (m, 3H), 1.47-1.35 (m, 2H), 1.28-1.17 (m, 3).

MS (ESI) m/z=514 (M−H)⁻.

1.67. N-benzyl-2-(4-nitro-phenyl)-2-[(2-1H-indol-3-yl-acetyl)-(4-isopropyl-phenyl)-amino]-acetamide (WJCPA-067)

A reaction was performed at room temperature in the same manner as in Example 1.1 using benzyl isocyanide (1b; 67 mg, 0.57 mmol), 4-chlorobenzaldehyde (2f; 80 mg, 0.57 mmol), 4-isopropylaniline (3a; 96 mg, 0.71 mmol), 3-indole acetic acid (4a; 124 mg, 0.71 mmol), and methanol to obtain the bis-amide compound WJCPA-067 after filtration.

White solid (144 mg, yield 55%), Mp: 158.0° C. to 160.1° C.

¹H NMR (300 MHz, CDCl₃) δ: 8.01 (s, 1H), 7.31-7.22 (m, 6H), 7.19-6.99 (m, 10H), 6.92 (d, J=2.4 Hz, 2H), 6.31 (d, J=5.7 Hz, 1H), 6.01 (s, 1H), 4.43-4.40 (m, 2H), 3.57 (s, 2H), 2.84 (heptet, J=6.9 Hz, 1H), 1.20 (d, J=6.9 Hz, 6H).

MS (ESI) m/z=572 (M+Na)⁺, 588 (M+K)⁺, 548 (M−H)⁻.

1.68. N-benzyl-2-[(2-chloro-acetyl)-(4-isopropyl-phenyl)-amino]-2-(4-chloro-phenyl)-acetamide (WJCPA-068)

A reaction was performed at room temperature in the same manner as in Example 1.1 using benzyl isocyanide (1b; 67 mg, 0.57 mmol), 4-chlorobenzaldehyde (2f; 80 mg, 0.57 mmol), 4-isopropylaniline (3a; 96 mg, 0.71 mmol), chloroacetic acid (4u; 67 mg, 0.71 mmol), and methanol to obtain the bis-amide compound WJCPA-068.

White solid (136 mg, yield 51%), Mp: 158.6° C. to 160.6° C.

$^1$H NMR (300 MHz, CDCl$_3$) δ: 7.33-7.22 (m, 8H), 7.17-7.13 (m, 2H), 7.10-7.07 (m, 3H), 6.14 (bs, 1H), 5.95 (s, 1H), 4.48 (t, J=5.6 Hz, 2H), 3.86 (d, J=1.5 Hz, 2H), 2.86 (heptet, J=6.9 Hz, 1H), 1.20 (d, J=6.9 Hz, 6H).

MS (ESI) m/z=507 (M+K)$^+$, 469 (M+H)$^+$.

1.69. 2-[(2-Chloro-acetyl)-(4-isopropyl-phenyl)-amino]-2-(4-chloro-phenyl)-N-pentyl-acetamide (WJCPA-069)

A reaction was performed at room temperature in the same manner as in Example 1.1 using 1-pentyl isocyanide (1c; 55 mg, 0.57 mmol), 4-chlorobenzaldehyde (2f; 80 mg, 0.57 mmol), 4-isopropylaniline (3a; 96 mg, 0.71 mmol), chloroacetic acid (4u; 67 mg, 0.71 mmol), and methanol to obtain the bis-amide compound WJCPA-069 after filtration.

White solid (49 mg, yield 19%), Mp: 157.4° C. to 159.4° C.

$^1$H NMR (300 MHz, CDCl$_3$) δ: 7.19-7.15 (m, 3H), 7.10-7.07 (m, 5H), 5.91 (s, 1H), 5.78 (bs, 1H), 3.86 (d, J=1.8 Hz, 2H), 3.27 (q, J=6.9 Hz, 2H), 2.86 (t, J=6.9 Hz, 1H), 1.48 (pentet, J=6.9 Hz, 2H), 1.34-1.23 (m, 4H), 1.20 (dd, J=6.9, 0.9 Hz, 6H), 0.86 (t, J=6.9 Hz, 3H).

MS (ESI) m/z=487 (M+K)$^+$, 449 (M+H)$^+$.

1.70. 2-{(2-Chloro-acetyl)-[2-(3,4-dimethoxy-phenyl)-ethyl]-amino}-2-(4-hydroxy-phenyl)-N-pentyl-acetamide (WJCPA-070)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), 3,4-dimethoxyphenylethylamine (3n; 149 mg, 0.82 mmol), chloroacetic acid (4u; 77 mg, 0.82 mmol), and methanol to obtain the bis-amide compound WJCPA-070.

White solid (150 mg, yield 48%), Mp: 157.1° C. to 161.1° C.

$^1$H NMR (300 MHz, CDCl$_3$) δ: 7.29 (d, J=8.4 Hz, 1H), 6.86 (d, J=8.4 Hz, 3H), 6.73 (d, J=8.1 Hz, 1H), 6.54 (d. J=8.1 Hz, 1H), 6.43 (s, 1H), 5.93 (t, J=5.7 Hz, 1H), 5.67 (s, 1H), 5.30 (s, 1H), 3.93 (s, 2H), 3.82 (s, 3H), 3.80 (s, 3H), 3.51 (t, J=7.2 Hz, 2H), 3.27-3.22 (m, 2H), 2.63-2.56 (m, 1H), 2.39-2.32 (m, 1H), 1.75 (bs, 2H), 1.47 (pentet, J=6.6 Hz, 2H), 1.31-1.23 (m, 2H), 0.85 (t, J=6.6 Hz, 3H).

MS (ESI) m/z=499 (M+Na)$^+$.

1.71. 2-[Acetyl-(3,4-dimethoxy-phenyl)-amino]-2-(4-hydroxy-phenyl)-N-pentyl-acetamide (WJCPA-071)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), 4-aminoveratrole (3d; 126 mg, 0.82 mmol), acetic acid (4s; 49 mg, 0.82 mmol), and methanol to obtain the bis-amide compound WJCPA-071.

Bright brown solid (181 mg, yield 67%), Mp: 86.7° C. to 90.5° C.

$^1$H NMR (300 MHz, CDCl$_3$) δ: 6.97 (d, J=8.7 Hz, 2H), 6.65 (d, J=8.7 Hz, 3H), 6.56-6.30 (m, 2H), 5.96 (s, 1H), 5.76 (t, J=5.7 Hz, 1H), 3.81 (s, 3H), 3.69 (bs, 3H), 3.25 (q, J=7.2 Hz, 2H), 1.88 (s, 3H), 1.46 (pentet, J=7.2 Hz, 2H), 1.32-1.20 (m, 4H), 0.85 (t, J=6.6 Hz, 3H).

MS (ESI) m/z=415 (M+H)$^+$.

1.72. N-(3,4-dimethoxy-phenyl)-N-[(4-hydroxy-phenyl)-pentylcarbamoyl-methyl]-benzamide (WJCPA-072)

A reaction was performed at room temperature in the same manner as in Example 1.12 using 1-pentyl isocyanide (1c; 56 mg, 0.58 mmol), imine (5d; 150 mg, 0.58 mmol; a compound formed by reacting 4-hydroxybenzaldehyde (2j) and 4-aminoveratrole (3 d) in methanol), benzoic acid (4d; 89 mg, 0.73 mmol), and methanol to obtain the bis-amide compound WJCPA-072.

Brown solid (152 mg, yield 30%), Mp: 100.9° C. to 105.7° C.

$^1$H NMR (300 MHz, CDCl$_3$) δ: 7.33-7.29 (m, 2H), 7.22-7.08 (m, 5H), 6.70-6.67 (m, 2H), 6.55 (bs, 1H), 6.46 (s, 2H), 6.09 (s, 1H), 5.88 (t, J=5.4 Hz, 1H), 3.71 (s, 3H), 3.57 (s, 3H), 3.34-3.26 (m, 2H), 1.49 (pentet, J=7.5 Hz, 2H), 1.32-1.20 (m, 4H), 0.86 (t, J=6.6 Hz, 3H).

MS (ESI) m/z=515 (M+K)$^+$, 499 (M+Na)$^+$.

1.73. N-(3,4-dimethoxy-phenyl)-N-[(4-hydroxy-phenyl)-pentylcarbamoyl-methyl]-butyramide (WJCPA-073)

A reaction was performed at room temperature in the same manner as in Example 1.12 using 1-pentyl isocyanide (1c; 56 mg, 0.58 mmol), imine (5d; 150 mg, 0.58 mmol; a compound formed by reacting 4-hydroxybenzaldehyde (2j) and 4-aminoveratrole (3 d) in methanol), butyric acid (4q; 64 mg, 0.73 mmol), and methanol to obtain the bis-amide compound WJCPA-073.

Dark red solid (195 mg, yield 76%), Mp: 81.5° C. to 83.7° C.

$^1$H NMR (300 MHz, CDCl$_3$) δ: 6.97 (d, J=8.4 Hz, 2H), 6.64 (d, J=8.4 Hz, 3H), 6.46-6.25 (m, 2H), 5.96 (s, 1H), 5.79 (bs, 1H), 5.30 (s, 1H), 3.86-3.62 (m, 6H), 3.25 (q, J=6.6 Hz, 2H), 2.11-1.99 (m, 2H), 1.64-1.54 (m, 2H), 1.45 (pentet, J=7.2 Hz, 2H), 1.31-1.17 (m, 4H), 0.87-0.80 (m, 6H).

MS (ESI) m/z=481 (M+K)$^+$, 465 (M+Na)$^+$.

1.74. Hexanoic acid (3,4-dimethoxy-phenyl)-[(4-hydroxy-phenyl)-pentylcarbamoyl-methyl]-amide (WJCPA-074)

A reaction was performed at room temperature in the same manner as in Example 1.12 using 1-pentyl isocyanide (1c; 56 mg, 0.58 mmol), imine (5d; 150 mg, 0.58 mmol; a compound formed by reacting 4-hydroxybenzaldehyde (2j) and 4-aminoveratrole (3 d) in methanol), hexanoic acid (4o; 85 mg, 0.73 mmol), and methanol to obtain the bis-amide compound WJCPA-074.

Bright brown solid (131 mg, yield 48%), Mp: 71.0° C. to 74.0° C.

$^1$H NMR (300 MHz, CDCl$_3$) δ: 6.97 (d, J=8.1 Hz, 2H), 6.63 (d, J=8.4 Hz, 3H), 5.96-5.90 (m, 3H), 5.76 (s, 1H), 3.87 (s, 1.5H), 3.82 (s, 3H), 3.57 (bs, 1.5H), 3.25 (q, J=6.3 Hz,

2H), 2.09-2.01 (m, 2H), 1.62-1.55 (m, 2H), 1.45 (pentet, J=7.2 Hz, 2H), 1.30-1.14 (m, 8H), 0.90-0.80 (m, 6H).
MS (ESI) m/z=509 (M+K)⁺, 493 (M+Na)⁺.

1.75. N-(3,4-dimethoxy-phenyl)-N-[(4-hydroxy-phenyl)-pentylcarbamoyl-methyl]-propionamide (WJCPA-075)

A reaction was performed at room temperature in the same manner as in Example 1.12 using 1-pentyl isocyanide (1c; 56 mg, 0.58 mmol), imine (5d; 150 mg, 0.58 mmol; a compound formed by reacting 4-hydroxybenzaldehyde (2j) and 4-aminoveratrole (3 d) in methanol), propionic acid (4r; 85 mg, 0.73 mmol), and methanol to obtain the bis-amide compound WJCPA-075.
Bright brown solid (120 mg, yield 48%), Mp: 88.5° C. to 91.6° C.
$^1$H NMR (300 MHz, CDCl$_3$) δ: 6.97 (d, J=8.4 Hz, 2H), 6.64 (d, J=8.7 Hz, 3H), 6.30-5.91 (m, 2H), 5.95 (s, 1H), 5.75 (bs, 1H), 3.81 (s, 6H), 3.25 (q, J=7.2 Hz, 2H), 2.14-2.07 (m, 2H), 1.45 (pentet, J=7.5 Hz, 2H), 1.28-1.20 (m, 4H), 1.05 (t, J=7.2 Hz, 3H), 0.85 (t, J=6.6 Hz, 3H).
MS (ESI) in/z=467 (M+K)⁺, 451 (M+Na)⁺.

1.76. N-benzyl-2-(4-chloro-phenyl)-2-[(2-1H-indol-3-yl-acetyl)-(4-methoxy-phenyl)-amino]-acetamide (WJCPA-076)

A reaction was performed at room temperature in the same manner as in Example 1.1 using benzyl isocyanide (1b; 83 mg, 0.71 mmol), 4-chlorobenzaldehyde (2f; 100 mg, 0.71 mmol), p-anisidine (3b; 109 mg, 0.89 mmol), 3-indole acetic acid (4a; 156 mg, 0.89 mmol), and methanol to obtain the bis-amide compound WJCPA-076 after purification by column chromatography (n-hexane:EtOAc=3:1).
White solid (104 mg, yield 27%), Mp: 160.2° C. to 163.4° C.
$^1$H NMR (300 MHz, CDCl$_3$) δ: 8.01 (s, 1H), 7.35-7.29 (m, 3H), 7.26-7.22 (m, 4H), 7.18-7.10 (m, 5H), 7.06-7.00 (m, 3H), 6.94 (d, J=2.4 Hz, 1H), 6.70-6.60 (m, 2H), 6.28 (t, J=5.4 Hz, 1H), 6.10 (s, 1H), 4.42 (dd, J=5.7, 2.7 Hz, 2H), 3.75 (s, 3H), 3.57 (s, 2H).
MS (ESI) m/z=576 (M+K)⁺.

1.77. 2-(4-Fluoro-phenyl)-2-[(2-1H-indol-3-yl-acetyl)-(4-methoxy-phenyl)-amino]-N-pentyl-acetamide (WJCPA-077)

A reaction was performed at room temperature in the same manner as in Example 1.1 using 1-pentyl isocyanide (1c; 78 mg, 0.80 mmol), 4-fluorobenzaldehyde (2g; 100 mg, 0.80 mmol), p-anisidine (3b; 124 mg, 1.00 mmol), 3-indole acetic acid (4a; 176 mg, 1.00 mmol), and methanol to obtain the bis-amide compound WJCPA-077 after filtration.
White solid (199 mg, yield 49%), Mp: 140.2° C. to 144.5° C.
$^1$H NMR (300 MHz, CDCl$_3$) δ: 8.04 (s, 1H), 7.54-7.36 (m, 2H), 7.33-7.30 (m, 1H), 7.17-6.98 (m, 5H), 6.88-6.81 (m, 2H), 6.76-6.58 (m, 2H), 6.50-6.38 (m, 1H), 6.08 (s, 1H), 5.86 (bs, 1H), 3.75 (s, 3H), 3.57 (s, 2H), 3.22 (q, J=7.2 Hz, 2H), 1.40 (pentet, J=7.2 Hz, 2H), 1.30-1.17 (m, 4H), 0.84 (1, J=6.9 Hz, 3H).
MS (ESI) m/z=540 (M+K)⁺, 524 (M+Na)⁺, 500 (M−H)⁻.

1.78. N-cyclohexyl-2-(3,4-dichloro-phenyl)-2-[(2-1H-indol-3-yl-acetyl)-(4-methoxy-phenyl)-amino]-acetamide (WJCPA-078)

A reaction was performed at room temperature in the same manner as in Example 1.1 using cyclohexyl isocyanide (1a; 62 mg, 0.57 mmol), 3,4-dichlorobenzaldehyde (2e; 100 mg, 0.57 mmol), p-anisidine (3h; 88 mg, 0.71 mmol), 3-indole acetic acid (4a; 125 mg, 0.71 mmol), and methanol to obtain the bis-amide compound WJCPA-078 after purification by column chromatography (n-hexane:EtOAc=1:1).
White solid (199 mg, yield 62%), Mp: 186.3° C. to 187.7° C.
$^1$H NMR (300 MHz, CDCl$_3$) δ: 8.04 (s, 1H), 7.40 (d, J=7.5 Hz, 1H), 7.32 (d, J=8.1 Hz, 1H), 7.27-7.26 (m, 1H), 7.21 (d, J=8.4 Hz, 1H), 7.18-7.13 (m, 1.5H), 7.08-7.03 (m, 1.5H), 6.96-6.90 (m, 2H), 6.71 (bs, 3H), 6.04 (s, 1H), 5.91 (d, J=8.1 Hz, 1H), 3.77 (s, 3H), 3.76-3.68 (m, 1H), 3.59 (s, 2H), 1.84-1.76 (m, 2H), 1.63-1.53 (m, 3H), 1.35-1.23 (m, 2H), 1.11-0.88 (m, 3H).
MS (ESI) m/z=586 (M+Na)⁺.

1.79. N-benzyl-2-(3,4-dichloro-phenyl)-2-[(2-1H-indol-3-yl-acetyl)-(4-methoxy-phenyl)-amino]-acetamide (WJCPA-079)

A reaction was performed at room temperature in the same manner as in Example 1.1 using benzyl isocyanide (1b; 67 mg, 0.57 mmol), 3,4-dichlorobenzaldehyde (2e; 100 mg, 0.57 mmol), p-anisidine (3b; 88 mg, 0.71 mmol), 3-indole acetic acid (4a; 125 mg, 0.71 mmol), and methanol to obtain the bis-amide compound WJCPA-079 after filtration.
White solid (72 mg, yield 22%), Mp: 180.8° C. to 183.0° C.
$^1$H NMR (300 MHz, CDCl$_3$) δ: 7.99 (s, 1H), 7.35-7.30 (m, 2H), 7.28-7.23 (m, 5H), 7.21-7.12 (m, 4H), 7.06-7.00 (m, 1H), 6.96-6.89 (m, 3H), 6.73-6.61 (m, 2H), 6.44 (t, J=5.7 Hz, 1H), 6.06 (s, 1H), 4.41-4.38 (m, 2H), 3.76 (s, 3H), 3.57 (s, 2H).
MS (ESI) m/z=610 (M+K)⁺, 594 (M+Na)⁺.

1.80. 2-(3,4-Dichloro-phenyl)-2-[(2-1H-indol-3-yl-acetyl)-(4-methoxy-phenyl)-amino]-N-pentyl-acetamide (WJCPA-080)

A reaction was performed at room temperature in the same manner as in Example 1.1 using 1-pentyl isocyanide (1c; 55 mg, 0.57 mmol), 3,4-dichlorobenzaldehyde (2e; 100 mg, 0.57 mmol), p-anisidine (3b; 88 mg, 0.71 mmol), 3-indole acetic acid (4a; 125 mg, 0.71 mmol), and methanol to obtain the bis-amide compound WJCPA-080 after purification by column chromatography (n-hexane:EtOAc=1:1).
Bright yellow solid (201 mg, yield 64%), Mp: 80.6° C. to 84.7° C.
$^1$H NMR (300 MHz, CDCl$_3$) δ: 8.04 (s, 1H), 7.37 (d, J=7.8 Hz, 1H), 7.33-7.30 (m, 1H), 7.27-7.26 (m, 1H), 7.23-7.20 (m, 1H), 7.18-7.12 (m, 1H), 7.07-7.02 (m, 1H), 6.97-6.90 (m, 3H), 6.62-6.51 (m, 3H), 6.02 (bs, 1H), 6.00 (s, 1H), 3.77 (s, 3H), 3.59 (s, 2H), 2.20 (q, J=7.2 Hz, 2H), 1.39 (pentet, J=7.2 Hz, 2H), 1.30-1.16 (m, 4H), 0.85 (t, J=6.9 Hz, 3H).
MS (ESI) m/z=590 (M+K)⁺, 574 (M+Na)⁺.

1.81. N-cyclohexyl-2-({2-[1-(4-methoxy-benzyl)-1H-indol-3-yl]-acetyl}-phenyl-amino)-2-phenyl-acetamide (WJCPA-081)

A reaction was performed at room temperature in the same manner as in Example 1.1 using cyclohexyl isocyanide (1a; 51 mg, 0.47 mmol), benzaldehyde (2l; 50 mg, 0.47 mmol), aniline (3g; 47 mg, 0.50 mmol), [1-(4-methoxy-benzyl)-1H-indol-3-yl]acetic acid (4b; 149 mg, 0.50 mmol), and 2,2,2-trifluoroethanol to obtain the bis-amide compound WJCPA-081 after purification by column chromatography (n-hexane:EtOAc=3:1).

White solid (33 mg, yield 11%), Mp: 187.3° C. to 191.9° C.

$^1$H NMR (300 MHz, CDCl$_3$) δ: 7.41 (d, J=7.5 Hz, 2H), 7.23-7.00 (m, 14H), 6.82-6.79 (m, 3H), 6.06 (s, 1H), 5.73 (d, J=7.2 Hz, 1H), 5.15 (s, 2H), 3.82-3.72 (m, 1H), 3.77 (s, 3H), 3.58 (s, 2H), 1.87-1.77 (m, 2H), 1.62-1.51 (m, 3H), 1.35-1.21 (m, 2H), 1.10-0.85 (m, 3H).

MS (ESI) m/z=608 (M+Na)$^+$, 584 (M−H)$^-$.

1.82. N-cyclohexyl-2-[(3,4-dimethoxy-phenyl)-(2-1H-indol-3-yl-acetyl)-amino]-2-(3,4,5-trimethoxy-phenyl)-acetamide (WJCPA-082)

A reaction was performed at room temperature in the same manner as in Example 1.1 using cyclohexyl isocyanide (1a; 55 mg, 0.50 mmol), 3,4,5-trimethoxybenzaldehyde (2a; 100 mg, 0.51 mmol), 4-aminoveratrole (3d; 97 mg, 0.63 mmol), 3-indole acetic acid (4a; 133 mg, 0.76 mmol), and 2,2,2-trifluoroethanol to obtain the bis-amide compound WJCPA-082 after purification by column chromatography (n-hexane:EtOAc=3:1).

Bright orange solid (239 mg, yield 76%), Mp: 113.5° C. to 115.6° C.

$^1$H NMR (300 MHz, CDCl$_3$) δ: 7.99 (s, 1H), 7.39-7.37 (m, 1H), 7.31 (d, J=7.8 Hz, 4H), 7.17-7.12 (m, 1H), 7.06-7.01 (m, 2H), 6.34 (s, 2H), 6.05 (s, 1H), 5.70 (d, J=8.7 Hz, 1H), 3.82 (s, 4H), 3.77 (s, 4H), 3.63-3.61 (m, 9H), 3.40-3.31 (m, 1H), 1.92-1.81 (m, 2H), 1.68-1.60 (m, 3H), 1.35-1.23 (m, 2H), 1.18-1.03 (m, 3H).

MS (ESI) m/z=638 (M+Na)$^+$, 614 (M−H)$^-$.

1.83. N-cyclohexyl-2-(3,4-dimethoxy-phenyl)-2-[(2-1H-indol-3-yl-acetyl)-phenyl-amino]-acetamide (WJCPA-083)

A reaction was performed at room temperature in the same manner as in Example 1.1 using cyclohexyl isocyanide (1a; 65 mg, 0.60 mmol), 3,4-dimethoxybenzaldehyde (2c; 100 mg, 0.60 mmol), aniline (3g; 70 mg, 0.75 mmol), 3-indole acetic acid (4a; 126 mg, 0.72 mmol), and methanol, to obtain the bis-amide compound WJCPA-083.

White solid (86 mg, yield 27%), Mp: 183.0° C. to 187.9° C.

IR (cm$^{-1}$) 3293, 1661.

$^1$H NMR (300 MHz, CDCl$_3$) δ: 8.06 (s, 1H), 7.39 (d, J=7.8 Hz, 1H), 7.30 (d, J=8.1 Hz, 1H), 7.19-7.11 (m, 5H), 7.06-6.97 (m, 2H), 6.77-6.64 (m, 3H), 6.52 (s, 1H), 6.07 (s, 1H), 5.69 (d, J=8.1 Hz, 1H), 3.81 (s, 3H), 3.79-3.73 (m, 1H), 3.58 (s, 2H), 3.53 (s, 3H), 1.89-1.79 (m, 2H), 1.63-1.53 (m, 3H), 1.34-1.23 (m, 2H), 1.13-0.91 (m, 3H).

MS (ESI) m/z=548 (M+Na)$^+$, 524 (M−H)$^-$.

Anal. Calcd. for C$_{32}$H$_{35}$N$_3$O$_4$. 0.05 CH$_2$Cl$_2$: C, 72.66; H, 6.68; N, 7.93. Found C, 72.68; H, 6.68; N, 8.20.

HPLC: purity 99.9%.

1.84. N-cyclohexyl-2-[[(2-1H-indol-3-yl-acetyl)-(4-methoxy-phenyl)-amino]-2-(4-nitro-phenyl)-acetamide (WJCPA-084)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 4-methoxyaniline (3b; 123 mg, 0.82 mmol), 3-indole acetic acid (4a; 103 mg, 0.66 mmol), and 2,2,2-trifluoroethanol to obtain the bis-amide compound WJCPA-084 after filtration.

Bright yellow solid (30 mg, yield 8%), Mp: 205.5° C. to 207.9° C.

IR (cm$^{-1}$) 3310, 1634.

$^1$H NMR (300 MHz, CDCl$_3$) δ: 8.03-7.98 (m, 3H), 7.42 (d, J=7.5 Hz, 2H), 7.34-7.31 (m, 4H), 7.19-7.14 (m, 1H), 7.09-7.04 (m, 1H), 6.85 (d, J=2.4 Hz, 1H), 6.70 (bs, 2H), 6.17 (s, 1H), 6.02 (d, J=8.4 Hz, 1H), 3.77 (s, 3H), 3.74-3.69 (m, 1H), 3.61 (s, 2H), 1.80-1.75 (m, 2H), 1.64-1.53 (m, 3H), 1.30-1.23 (m, 2H), 1.11-0.86 (m, 3H).

$^{13}$C NMR (125 MHz, CDCl$_3$) δ: 172.8, 167.8, 159.3, 147.4, 141.8, 135.9, 132.0, 131.2, 131.0, 127.0, 123.0, 122.0, 119.5, 118.8, 114.2, 111.0, 108.7, 63.9, 55.3, 48.6, 32.48, 32.45, 31.8, 25.2, 24.68, 24.62.

MS (ESI) m/z=563 (M+Na)$^+$, 539 (M−H)$^-$.

Anal. Calcd. for C$_{31}$H$_{32}$N$_4$O$_5$. 0.02 CH$_2$Cl$_2$: C, 68.69; H, 5.95; N, 10.33. Found C, 68.44; H, 5.86; N, 10.58.

HPLC: purity 99.9%. HPLC: purity 99.6%.

1.85. N-(4-bromo-phenyl)-N-[cyclohexylcarbamoyl-(4-nitro-phenyl)-methyl]-3-(3-methoxy-phenyl)-propionamide (WJCPA-085)

A reaction was performed at room temperature in the same manner as in Example 1.12 using cyclohexyl isocyanide (1a; 66 mg, 0.60 mmol), imine (5c; 100 mg, 0.35 mmol; a compound formed by reacting 4-nitrobenzaldehyde (2 h) and 4-bromoaniline (3f) in methanol), 3-(3-methoxyphenyl) propionic acid (41; 140 mg, 0.75 mmol), and methanol to obtain the bis-amide compound WJCPA-085 after filtration.

Bright green solid (160 mg, yield 54%), Mp: 163.0° C. to 167.0° C.

IR (cm$^{-1}$) 3272, 1665.

$^1$H NMR (300 MHz, CDCl$_3$) δ: 8.53 (s, 0.5H), 8.34 (d, J=9.0 Hz, 1H), 8.06 (t, J=9.0 Hz, 2.5H), 7.55 (d, J=8.4 Hz, 1.5H), 7.30 (d, J=8.7 Hz, 2H), 7.18-7.13 (m, 1.5H), 6.73 (dd, J=8.4, 2.7 Hz, 1H), 6.65-6.59 (m, 2H), 6.06 (s, 1H), 5.77 (d, J=8.1 Hz, 1H), 3.85-3.78 (m, 1H), 3.76 (s, 3H), 2.89 (t, J=7.5 Hz, 2H), 2.37-2.30 (m, 2H), 1.97-1.82 (m, 2H), 1.75-1.64 (m, 3H), 1.40-1.29 (m, 2H), 1.19-0.99 (m, 3H).

$^{13}$C NMR (150 MHz, CDCl$_3$) δ: 172.8, 167.5, 159.5, 147.6, 142.1, 141.4, 138.2, 132.4, 131.8, 131.0, 129.4, 123.4, 122.8, 120.7, 114.3, 111.3, 63.7, 55.1, 48.9, 36.3, 32.7, 31.4, 25.3, 24.7, 24.6.

MS (ESI) m/z=592 (M−H)$^-$.

Anal. Calcd. for C$_{30}$H$_{32}$BrN$_3$O$_5$: C, 60.61; H, 5.43; N, 7.07. Found C, 60.46; H, 5.28; N, 7.19.

HPLC: purity 97.1%.

1.86. N-cyclohexyl-2-(4-hydroxy-3-methoxy-phenyl)-2-[(2-1H-indol-3-yl-acetyl)-(4-isopropyl-phenyl)-amino]-acetamide (WJCPA-086)

A reaction was performed at room temperature in the same manner as in Example 1.1 using cyclohexyl isocyanide (1a; 72 mg, 0.66 mmol), vanillin (2d; 100 mg, 0.66 mmol), 4-isopropylaniline (3a; 111 mg, 0.82 mmol), 3-indole acetic acid (4a; 144 mg, 0.82 mmol), and 2,2,2-trifluoroethanol to obtain the bis-amide compound WJCPA-086 after purification by column chromatography (n-hexane:EtOAc=3:1).

Bright yellow solid (146 mg, yield 40%), Mp: 112.5° C. to 116.0° C.

$^1$H NMR (300 MHz, CDCl$_3$) δ: 8.00 (s, 1H), 7.37-7.29 (m, 3H), 7.16-7.11 (m, 2H), 7.05-6.98 (m, 4H), 6.75-6.66 (m, 2H), 6.48 (d, J=1.8 Hz, 1H), 6.04 (s, 1H), 5.76 (d, J=8.1

Hz, 1H), 3.77-3.75 (m, 1H), 3.58 (s, 2H), 3.51 (s, 3H), 2.84 (heptet, J=6.6 Hz, 1H), 1.84-1.78 (m, 2H), 1.63-1.58 (m, 3H), 1.34-1.18 (m, 2H), 1.19 (d, J=6.9 Hz, 6H), 1.09-0.94 (m, 3H).

MS (ESI) m/z=576 (M+Na)$^+$.

1.87. N-[cyclohexylcarbamoyl-(4-hydroxy-3-methoxy-phenyl)-methyl]-N-(4-isopropyl-phenyl)-benzamide (WJCPA-087)

A reaction was performed at room temperature in the same manner as in Example 1.1 using cyclohexyl isocyanide (1a; 72 mg, 0.66 mmol), vanillin (2d; 100 mg, 0.66 mmol), 4-isopropylaniline (3a; 111 mg, 0.82 mmol), benzoic acid (4d; 72 mg, 0.66 mmol), and 2,2,2-trifluoroethanol to obtain the bis-amide compound WJCPA-087 after purification by column chromatography (n-hexane:EtOAc=3:1).

White solid (18 mg, yield 5%), Mp: 109.9° C. to 114.1° C.

$^1$H NMR (300 MHz, CDCl$_3$) δ: 7.31-7.28 (m, 1H), 7.20-7.08 (m, 4H), 6.91-6.79 (m, 6H), 6.62 (d, J=1.5 Hz, 1H), 6.11 (s, 1H), 5.82 (d, J=8.1 Hz, 1H), 5.57 (s, 1H), 3.92-3.81 (m, 1H), 3.62 (s, 3H), 2.73 (heptet, J=6.9 Hz, 1H), 2.00-1.85 (m, 2H), 1.71-1.55 (m, 3H), 1.40-1.26 (m, 2H), 1.19-1.08 (m, 3H), 1.09 (d, J=6.9 Hz, 6H).

MS (ESI) m/z=523 (M+Na)$^+$.

1.88. N-[tert-butylcarbamoyl-(4-hydroxy-phenyl)-methyl]-N-(3,4-dimethoxy-phenyl)-2,2-dimethyl-propionamide (WJCPA-088)

A reaction was performed at room temperature in the same manner as in Example 1.12 using tert-butyl isocyanide (1d; 33 mg, 0.40 mmol), imine (5d; 100 mg, 0.40 mmol; a compound formed by reacting 4-hydroxybenzaldehyde (2j) and 4-aminoveratrole (3 d) in methanol), pivalic acid (4t; 51 mg, 0.50 mmol), and 2,2,2-trifluoroethanol to obtain the bis-amide compound WJCPA-088 after filtration.

White solid (69 mg, yield 40%), Mp: 221.0° C. to 224.0° C.

$^1$H NMR (600 MHz, CDCl$_3$) δ: 7.18 (bs, 0.5H), 7.10 (bs, 0.5H), 6.93 (s, 2H), 6.69 (bs, 0.5H), 6.63 (d, J=15.6 Hz, 2H), 6.46 (bs, 1.5H), 6.16 (bs, 0.5H), 6.11 (bs, 0.5H), 5.74 (bs, 2H), 3.81 (bs, 4.5H), 3.53 (bs, 1.5H), 1.31 (s, 9H), 1.03 (s, 9H).

MS (ESI) m/z=465 (M+Na)$^+$.

1.89. N-tert-butyl-2-[(3,4-dimethoxy-phenyl)-(2-1H-indol-3-yl-acetyl)-amino]-2-(4-hydroxy-phenyl)-acetamide (WJCPA-089)

A reaction was performed at room temperature in the same manner as in Example 1.12 using tert-butyl isocyanide (1d; 33 mg, 0.40 mmol), imine (5d; 100 mg, 0.40 mmol; a compound formed by reacting 4-hydroxybenzaldehyde (2j) and 4-aminoveratrole (3 d) in methanol), 3-indole acetic acid (4a; 88 mg, 0.50 mmol), and 2,2,2-trifluoroethanol to obtain the bis-amide compound WJCPA-089 after filtration.

Bright yellow solid (135 mg, yield 67%), Mp: 154.3° C. to 159.2° C.

$^1$H NMR (600 MHz, CDCl$_3$) δ: 8.04 (s, 1H), 7.32-7.26 (m, 3H), 7.15-7.11 (m, 2H), 7.04-7.01 (m, 3H), 6.94 (d, J=8.4 Hz, 2H), 6.58 (d, J=8.7 Hz, 2H), 5.96 (s, 1H), 5.72 (s, 1H), 3.83 (s, 3H), 3.60 (s, 3H), 3.31 (bs, 2H), 1.29 (s, 9H).

MS (ESI) m/z=538 (M+Na)$^+$.

1.90. N-cyclohexyl-2-[(2-1H-indol-3-yl-acetyl)-(4-isopropyl-phenyl)-amino]-2-naphthalen-1-yl-acetamide (WJCPA-090)

A reaction was performed at room temperature in the same manner as in Example 1.1 using cyclohexyl isocyanide (1a; 70 mg, 0.64 mmol), 1-naphthaldehyde (2m; 100 mg, 0.64 mmol), 4-isopropylaniline (3a; 108 mg, 0.80 mmol), 3-indole acetic acid (4a; 168 mg, 0.96 mmol), and 2,2,2-trifluoroethanol to obtain the bis-amide compound WJCPA-090 after purification by column chromatography (n-hexane:EtOAc=5:1).

White solid (142 mg, yield 39%), Mp: 109.9° C. to 15.0° C.

$^1$H NMR (300 MHz, CDCl$_3$) δ: 8.05-8.02 (m, 2H), 7.83-7.80 (m, 1H), 7.69-7.66 (m, 1H), 7.54-7.47 (m, 3H), 7.37 (d, J=7.8 Hz, 1H), 7.31 (d, J=7.8 Hz, 2H), 7.25-7.01 (m, 8H), 5.48 (d, J=8.1 Hz, 1H), 3.91-3.80 (m, 1H), 3.60 (s, 2H), 2.69 (heptet, J=6.9 Hz, 1H), 1.92-1.85 (m, 2H), 1.66-1.54 (m, 3H), 1.34-1.21 (m, 2H), 1.09-0.89 (m, 3H), 1.08 (dd, J=6.9, 2.4 Hz, 6H).

MS (ESI) m/z=580 (M+Na)$^+$, 556 (M−H)$^−$.

1.91. 2-(4-Chloro-phenyl)-N-cyclohexyl-2-[(2-1H-indol-3-yl-acetyl)-(4-methoxy-phenyl)-amino]-acetamide (WJCPA-091)

A reaction was performed at room temperature in the same manner as in Example 1.1 using cyclohexyl isocyanide (1a; 77 mg, 0.71 mmol), 4-chlorobenzaldehyde (2f; 100 mg, 0.71 mmol), 4-methoxybenzylamine (3l; 124 mg, 0.90 mmol), 3-indole acetic acid (4a; 124 mg, 0.71 mmol), and 2,2,2-trifluoroethanol to obtain the bis-amide compound WJCPA-091 after filtration.

Bright yellow solid (50 mg, yield 12%), Mp: 155.6° C. to 158.9° C.

$^1$H NMR (300 MHz, CDCl$_3$) δ: 8.13 (s, 1H), 7.48 (d, J=7.5 Hz, 1H), 7.35 (d, J=7.8 Hz, 1H), 7.23-7.06 (m, 7H), 6.90-6.83 (m, 2H), 6.74-6.71 (m, 2H), 5.77 (s, 1H), 5.69 (d, J=7.5 Hz, 1H), 4.58 (dd, J=51, 17.4 Hz, 2H), 3.85-3.79 (m, 1H), 3.82 (s, 2H), 3.76 (s, 3H), 1.88-1.77 (m, 2H), 1.65-1.52 (m, 3H), 1.32-1.23 (m, 2H), 1.10-0.99 (m, 3H).

MS (ESI) m/z=566 (M+Na)$^+$, 542 (M−H)$^−$.

1.92. 6-Chloro-N-[cyclohexylcarbamoyl-(4-hydroxy-phenyl)-methyl]-N-(3,4-dimethoxy-phenyl)-nicotinamide (WJCPA-092)

A reaction was performed at room temperature in the same manner as in Example 1.12 using cyclohexyl isocyanide (1a; 66 mg, 0.60 mmol), imine (5d; 150 mg, 0.60 mmol; a compound formed by reacting 4-hydroxybenzaldehyde (2j) and 4-aminoveratrole (3 d) in methanol), 6-chloronicotinic acid (4k; 144 mg, 0.90 mmol), and methanol to obtain the bis-amide compound WJCPA-092 after filtration.

White solid (85 mg, yield 27%), Mp: 123.5° C. to 131.4° C. (dec).

$^1$H NMR (300 MHz, CDCl$_3$) δ: 8.29 (d, J=1.8 Hz, 1H), 7.60 (dd, J=8.2, 2.7 Hz, 1H), 7.11 (d, J=8.1 Hz, 1H), 7.04 (d, J=8.4 Hz, 2H), 6.69 (d, J=9.3 Hz, 2H), 6.47 (d, J=7.5 Hz, 2H), 6.09 (s, 1H), 5.87 (s, 1H), 5.57 (d, J=8.1 Hz, 1H), 3.89-3.79 (m, 1H), 3.74 (s, 3H), 3.60 (s, 3H), 1.97-1.85 (m, 2H), 1.70-1.56 (m, 3H), 1.40-1.28 (m, 2H), 1.19-1.01 (m, 3H).

MS (ESI) m/z=546 (M+Na)$^+$.

1.93. N-[cyclohexylcarbamoyl-(4-hydroxy-phenyl)-methyl]-N-(3,4-dimethoxy-phenyl)-2,3-dimethyl-benzamide (WJCPA-093)

A reaction was performed at room temperature in the same manner as in Example 1.12 using cyclohexyl isocyanide (1a; 66 mg, 0.60 mmol), imine (5d; 150 mg, 0.60 mmol; a compound formed by reacting 4-hydroxybenzaldehyde (2j) and 4-aminoveratrole (3 d) in methanol), 2,3-dimethylbenzoic acid (4f; 135 mg, 0.90 mmol), and methanol to obtain the bis-amide compound WJCPA-093 after filtration.

White solid (170 mg, yield 56%), Mp: 157.2° C. to 161.2° C.

$^1$H NMR (300 MHz, CDCl$_3$) δ: 7.05 (d, J=8.1 Hz, 2H), 6.89-6.80 (m, 2H), 6.06 (d, J=8.1 Hz, 2H), 6.56-6.46 (m, 2H), 6.39-6.35 (m, 2H), 6.18 (s, 1H), 5.69 (d, J=8.4 Hz, 1H), 3.91-3.81 (m, 1H), 3.68 (s, 3H), 3.58 (s, 3H), 2.28 (s, 3H), 2.11 (s, 3H), 1.97-1.87 (m, 2H), 1.66-1.56 (m, 3H), 1.42-1.29 (m, 2H), 1.18-1.04 (m, 3H).

MS (ESI) m/z=539 (M+Na)$^+$.

1.94. N-cyclohexyl-2-(4-hydroxy-phenyl)-2-[(2-1H-indol-3-yl-acetyl)-phenyl-amino]-acetamide (WJCPA-094)

A reaction was performed at room temperature in the same manner as in Example 1.1 using cyclohexyl isocyanide (1a; 90 mg, 0.83 mmol), 4-hydroxybenzaldehyde (2j; 100 mg, 0.83 mmol), aniline (3g; 94 mg, 1.04 mmol), 3-indole acetic acid (4a; 145 mg, 0.83 mmol), and 2,2,2-trifluoroethanol to obtain the bis-amide compound WJCPA-094 after purification by column chromatography (n-hexane:EtOAc=3:1).

Bright yellow solid (70 mg, yield 17%), Mp: 140.0° C. to 142.0° C.

$^1$H NMR (600 MHz, CDCl$_3$) δ: 8.46 (s, 1H), 7.30-6.94 (m, 8H), 6.85-6.82 (m, 4H), 6.55 (d, J=8.4 Hz, 2H), 5.92-5.88 (m, 2H), 3.75-3.68 (m, 1H), 3.53 (s, 2H), 1.79-1.71 (m, 2H), 1.50-1.48 (m, 3H), 1.28-1.20 (m, 2H), 0.98-0.80 (m, 3H).

MS (ESI) m/z=504 (M+Na)$^+$.

1.95. N-[tert-butylcarbamoyl-(4-hydroxy-phenyl)-methyl]-N-(3,4-dimethoxy-phenyl)-3-(3-methoxy-phenyl)-propionamide (WJCPA-095)

A reaction was performed at room temperature in the same manner as in Example 1.12 using tert-butyl isocyanide (1d; 33 mg, 0.40 mmol), imine (5d; 100 mg, 0.40 mmol; a compound formed by reacting 4-hydroxybenzaldehyde (2j) and 4-aminoveratrole (3 d) in methanol), 3-(3-methoxyphenyl)propionic acid (4l; 90 mg, 0.50 mmol), and 2,2,2-trifluoroethanol to obtain the bis-amide compound WJCPA-095 after filtration.

White solid (136 mg, yield 67%), Mp: 211.4° C. to 213.5° C.

$^1$H NMR (300 MHz, CDCl$_3$) δ: 7.13 (t, J=8.1 Hz, 1H), 6.93 (d, J=8.4 Hz, 2H), 6.70-6.60 (m, 8H), 5.93 (bs, 1H), 5.61 (bs, 1H), 3.80 (s, 4H), 3.74 (s, 3H), 3.45 (bs, 2H), 2.90 (t, J=7.8 Hz, 2H), 2.41-2.36 (m, 2H), 1.32 (s, 9H).

MS (ESI) m/z=543 (M+Na)$^+$.

1.96. 1H-indol-2-carboxylic acid [tert-butylcarbamoyl-(3,4,5-trimethoxy-phenyl)-methyl]-(4-isopropyl-phenyl)-amide (WJCPA-096)

A reaction was performed at room temperature in the same manner as in Example 1.1 using tert-butyl isocyanide (1d; 42 mg, 0.51 mmol), 3,4,5-trimethoxybenzaldehyde (2a; 100 mg, 0.51 mmol), 4-isopropylaniline (3a; 86 mg, 0.64 mmol), indole-2-carboxylic acid (4c; 103 mg, 0.64 mmol), and 2,2,2-trifluoroethanol to obtain the bis-amide compound WJCPA-096 after filtration.

White solid (130 mg, yield 45%), Mp: 242.4° C. to 244.0° C.

$^1$H NMR (300 MHz, CDCl$_3$) δ: 9.23 (s, 1H), 7.34-7.28 (m, 4H), 7.23-7.18 (m, 2H), 7.13 (bs, 2H), 6.98 (t, J=6.9 Hz, 1H), 6.38 (s, 2H), 6.10 (s, 1H), 5.80 (s, 1H), 3.79 (s, 3H), 3.66 (s, 6H), 2.93 (heptet, J=6.9 Hz, 1H), 1.37 (s, 9H), 1.27 (d, J=6.9 Hz, 6H).

MS (ESI) m/z=580 (M+Na)$^+$, 556 (M−H)$^-$.

1.97. N-(3,4-dimethoxy-phenyl)-N-[(4-hydroxy-phenyl)-pentylcarbamoyl-methyl]-3-(4-methoxy-phenyl)-propionamide (WJCPA-097)

A reaction was performed at room temperature in the same manner as in Example 1.12 using 1-pentyl isocyanide (1c; 38 mg, 0.39 mmol), imine (5d; 100 mg, 0.39 mmol; a compound formed by reacting 4-hydroxybenzaldehyde (2j) and 4-aminoveratrole (3 d) in methanol), 3-(4-methoxyphenyl) propionic acid (4m; 88 mg, 0.49 mmol), and 2,2,2-trifluoroethanol to obtain the bis-amide compound WJCPA-097 after filtration.

White solid (98 mg, yield 47%), Mp: 150.6° C. to 153.0° C.

$^1$H NMR (300 MHz, CDCl$_3$) δ: 6.96 (t, J=8.7 Hz, 5H), 6.76 (d, J=8.7 Hz, 3H), 6.62 (d, J=8.7 Hz, 3H), 5.97 (s, 1H), 5.70 (bs, 1H), 5.17 (s, 1H), 3.81 (s, 4H), 3.75 (s, 3H), 3.48 (bs, 2H), 3.25 (q, J=6.9 Hz, 2H), 2.86 (t, J=7.5 Hz, 2H), 2.39-2.30 (m, 2H), 1.46 (pentet, J=7.2 Hz, 2H), 1.30-1.22 (m, 4H), 0.86 (t, J=6.9 Hz, 3H).

MS (ESI) m/z=557 (M+Na)$^+$.

1.98. 2-[(3,4-Dimethoxy-phenyl)-(2-1H-indol-3-yl-acetyl)-amino]-2-(4-hydroxy-phenyl)-N-pentyl-acetamide (WJCPA-098)

A reaction was performed at room temperature in the same manner as in Example 1.12 using 1-pentyl isocyanide (1c; 38 mg, 0.39 mmol), imine (5d; 100 mg, 0.39 mmol; a compound formed by reacting 4-hydroxybenzaldehyde (2j) and 4-aminoveratrole (3 d) in methanol), 3-indole acetic acid (4a; 86 mg, 0.49 mmol), and 2,2,2-trifluoroethanol to obtain the bis-amide compound WJCPA-098 after purification by column chromatography (n-hexane:EtOAc=3:1).

Bright orange solid (176 mg, yield 85%), Mp: 110.5° C. to 114.6° C.

$^1$H NMR (300 MHz, CDCl$_3$) δ: 8.09 (s, 1H), 7.30-7.27 (m, 2H), 7.15-7.10 (m, 3H), 7.04-7.00 (m, 3H), 6.94 (d, J=8.4 Hz, 2H), 6.58 (d, J=8.4 Hz, 2H), 5.99 (s, 1H), 5.78 (s, 1H), 3.83 (s, 3H), 3.60 (s, 3H), 3.33 (bs, 2H), 3.22 (q, J=6.9 Hz, 2H), 1.40 (pentet, J=6.9 Hz, 2H), 1.28-1.18 (m, 4H), 0.83 (t, J=6.9 Hz, 3H).

MS (ESI) m/z=552 (M+Na)$^+$.

1.99. 4-Chloro-N-[cyclohexylcarbamoyl-(4-hydroxy-phenyl)-methyl]-N-(3,4-dimethoxy-phenyl)-2-nitro-benzamide (WJCPA-099)

A reaction was performed at room temperature in the same manner as in Example 1.12 using cyclohexyl isocyanide (1a; 55 mg, 0.48 mmol), imine (5d; 100 mg, 0.39 mmol; a compound formed by reacting 4-hydroxybenzaldehyde (2j) and 4-aminoveratrole (3 d) in methanol), 4-chloro-2- nitrobenzoic acid (4j; 180 mg, 0.60 mmol), and methanol to obtain the bis-amide compound WJCPA-099 after filtration.

Bright yellow solid (170 mg, yield 76%), Mp: 153.2° C. to 155.5° C.

$^1$H NMR (300 MHz, CDCl$_3$) δ: 7.90 (s, 1H), 7.43 (s, 2H), 7.08 (d, J=8.4 Hz, 2H), 6.67 (d, J=8.4 Hz, 3H), 6.40 (d, J=8.4 Hz, 2H), 6.20 (s, 1H), 5.79 (d, J=8.4 Hz, 1H), 3.93-3.81 (m, 1H), 3.70 (s, 3H), 3.54 (s, 3H), 2.00-1.90 (m, 2H), 1.69-1.58 (m, 3H), 1.39-1.31 (m, 2H), 1.21-1.10 (m, 3H).

MS (ESI) m/z=590 (M+Na)$^+$.

1.100. N-[(4-chloro-phenyl)-cyclohexylcarbamoyl-methyl]-N-(4-isopropyl-phenyl)-2-methyl-benzamide (WJCPA-100)

A reaction was performed at room temperature in the same manner as in Example 1.12 using cyclohexyl isocyanide (1a; 55 mg, 0.48 mmol), imine (5e; 100 mg, 0.38 mmol; a compound formed by reacting 4-chlorobenzaldehyde (2f) and 4-isopropylaniline (3a) in methanol), o-toluic acid (4e; 82 mg, 0.57 mmol), and methanol to obtain the bis-amide compound WJCPA-100 after filtration.

White solid (40 mg, yield 21%), Mp: 153.3° C. to 155.2° C.

$^1$H NMR (300 MHz, CDCl$_3$) δ: 7.20 (s, 4H), 7.04-6.97 (m, 3H), 6.92-6.80 (m, 5H), 6.10 (s, 1H), 5.90 (d, J=8.1 Hz, 1H), 3.92-3.82 (m, 1H), 2.68 (heptet, J=6.9 Hz, 1H), 2.38 (s, 3H), 2.00-1.89 (m, 2H), 1.72-1.57 (m, 3H), 1.44-1.30 (m, 2H), 1.25-1.12 (m, 3H), 1.06 (d, J=6.9 Hz, 6H).

MS (ESI) m/z=525 (M+Na)$^+$.

1.101. 2-[Acetyl-(4-isopropyl-phenyl)-amino]-2-(4-chloro-phenyl)-N-cyclohexyl-acetamide (WJCPA-101)

A reaction was performed at room temperature in the same manner as in Example 1.12 using cyclohexyl isocyanide (1a; 55 mg, 0.48 mmol), imine (5e; 100 mg, 0.38 mmol; a compound formed by reacting 4-chlorobenzaldehyde (2f) and 4-isopropylaniline (3a) in methanol), acetic acid (4s; 35 mg, 0.57 mmol), and methanol to obtain the bis-amide compound WJCPA-101 after filtration.

White solid (40 mg, yield 24%), Mp: 184.7° C. to 186.0° C.

$^1$H NMR (300 MHz, CDCl$_3$) δ: 7.17-7.13 (m, 2H), 7.10-7.05 (m, 4H), 6.96 (bs, 2H), 5.93 (s, 1H), 5.74 (d, J=8.1 Hz, 1H), 3.85-3.75 (m, 1H), 2.85 (heptet, J=6.9 Hz, 1H), 2.17-1.83 (m, 2H), 1.86 (s, 3H), 1.70-1.56 (m, 3H), 1.41-1.27 (m, 2H), 1.19 (d, J=6.9 Hz, 6H), 1.18-1.07 (m, 3H).

MS (ESI) m/z=449 (M+Na)$^+$.

1.102. 2-[(4-Bromo-phenyl)-(2-1H-indol-3-yl-acetyl)-amino]-2-(4-nitro-phenyl)-N-pentyl-acetamide (WJCPA-102)

A reaction was performed at room temperature in the same manner as in Example 1.12 using 1-pentyl isocyanide (1c; 34 mg, 0.35 mmol), imine (5c; 100 mg, 0.35 mmol; a compound formed by reacting 4-nitrobenzaldehyde (2 h) and 4-bromoaniline (3f) in methanol), 3-indole acetic acid (4a; 75 mg, 0.43 mmol), and 2,2,2-trifluoroethanol to obtain the bis-amide compound WJCPA-102 after filtration.

Bright yellow solid (60 mg, yield 30%), Mp: 188.4° C. to 190.2° C.

$^1$H NMR (300 MHz, CDCl$_3$) δ: 8.03 (d, J=9.0 Hz, 3H), 7.38-7.28 (m, 7H), 7.18 (t, J=7.8 Hz, 1H), 7.08 (t, J=7.8 Hz, 1H), 6.87 (s, 2H), 6.11 (s, 1H), 5.96 (bs, 1H), 3.61 (s, 2H), 3.22 (q, J=6.9 Hz, 2H), 1.40 (pentet, J=7.5 Hz, 2H), 1.28-1.19 (m, 4H), 0.85 (t, J=6.9 Hz, 3H).

MS (ESI) m/z=599 (M+Na)$^+$.

1.103. N-(4-bromo-phenyl)-6-chloro-N-[(4-nitro-phenyl)-pentylcarbamoyl-methyl]-nicotinamide (WJCPA-103)

A reaction was performed at room temperature in the same manner as in Example 1.12 using 1-pentyl isocyanide (1c; 34 mg, 0.35 mmol), imine (5c; 100 mg, 0.35 mmol; a compound formed by reacting 4-nitrobenzaldehyde (2 h) and 4-bromoaniline (30 in methanol), 6-chloronicotinic acid (4k; 68 mg, 0.43 mmol), and 2,2,2-trifluoroethanol to obtain the bis-amide compound WJCPA-103 after filtration.

White solid (116 mg, yield 59%), Mp: 177.7° C. to 179.6° C.

$^1$H NMR (300 MHz, CDCl$_3$) δ: 8.29 (d, J=1.8 Hz, 1H), 8.12 (d, J=8.7 Hz, 2H), 7.56 (dd, J=8.4, 2.1 Hz, 1H), 7.44 (d, J=8.7 Hz, 2H), 7.26-7.22 (m, 2H), 7.17 (d, J=8.7 Hz, 1H), 6.94-6.90 (m, 2H), 6.24 (s, 1H), 5.82 (s, 1H), 3.34 (q, J=7.2 Hz, 2H), 1.54 (pentet, J=7.2 Hz, 2H), 1.33-1.26 (m, 4H), 0.87 (t, J=7.2 Hz, 3H).

MS (ESI) m/z=559 (M+H)$^+$, 557 (M−H)$^−$.

1.104. 4-Chloro-N-[cyclohexylcarbamoyl-(4-nitro-phenyl)-methyl]-N-(3,4-dimethoxy-phenyl)-2-nitro-benzamide (WJCPA-104)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), 4-chloro-2-nitrobenzoic acid (4j; 89 mg, 0.44 mmol), and 2,2,2-trifluoroethanol to obtain the bis-amide compound WJCPA-104 after filtration.

White solid (51 mg, yield 24%), Mp: 189.3° C. to 194.0° C.

$^1$H NMR (300 MHz, CDCl$_3$) δ: 8.11 (d, J=8.7 Hz, 2H), 7.94 (d, J=1.8 Hz, 1H), 7.51 (d, J=8.7 Hz, 2H), 7.45 (dd, J=8.1, 1.8 Hz, 1H), 7.34 (d, J=8.1 Hz, 1H), 6.60 (bs, 1H), 6.43-6.39 (m, 2H), 6.30 (s, 1H), 5.99 (d, J=7.5 Hz, 1H), 3.94-3.88 (m, 1H), 3.71 (s, 3H), 3.60 (s, 3H), 2.04-1.93 (m, 2H), 1.78-1.67 (m, 3H), 1.43-1.32 (m, 2H), 1.28-1.15 (m, 3H).

MS (ESI) m/z=619 (M+Na)$^+$.

1.105. 2-[(2-Chloro-acetyl)-(3,4-dimethoxy-phenyl)-amino]-N-cyclohexyl-2-(4-nitro-phenyl)-acetamide (WJCPA-105)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), chloroacetic acid (4u; 42 mg, 0.44 mmol), and methanol to obtain the bis-amide compound WJCPA-105 after filtration.

White solid (145 mg, yield 84%), Mp: 239.0° C. to 241.9° C.

$^1$H NMR (300 MHz, CDCl$_3$) δ: 8.06 (d, J=8.7 Hz, 2H), 7.39 (d, J=8.1 Hz, 2H), 6.71-6.59 (m, 2H), 6.04 (bs, 2H), 5.71 (d, J=7.8 Hz, 1H), 3.91 (s, 3H), 3.88 (s, 5H), 3.66-3.55

(m, 1H), 2.00-1.83 (m, 2H), 1.73-1.60 (m, 3H), 1.41-1.29 (m, 2H), 1.10-1.00 (m, 3H).

MS (ESI) m/z=512 (M+Na)$^+$, 488 (M−H)$^-$.

1.106. 1H-indol-2-carboxylic acid [cyclohexylcarbamoyl-(4-nitro-phenyl)-methyl]-(3,4-dimethoxy-phenyl)-amide (WJCPA-106)

A reaction was performed at room temperature in the same manner as in Example 1.12 using cyclohexyl isocyanide (1a; 47 mg, 0.35 mmol), imine (5g; 100 mg, 0.35 mmol; a compound formed by reacting 4-nitrobenzaldehyde (2 h) and 4-aminoveratrole (3 d) in 2,2,2-trifluoroethanol), indole-2-carboxylic acid (4c; 71 mg, 0.44 mmol), and methanol to obtain the bis-amide compound WJCPA-106 after filtration.

Bright yellow solid (81 mg, yield 41%), Mp: 218.3° C. to 219.9° C.

$^1$H NMR (300 MHz, CDCl$_3$) δ: 9.25 (s, 1H), 8.01 (d, J=8.7 Hz, 2H), 7.49 (d, J=8.4 Hz, 2H), 7.40-7.32 (m, 2H), 7.26-7.19 (m, 3H), 7.02 (t, J=7.5 Hz, 1H), 6.72 (bs, 1H), 6.23 (s, 1H), 6.03 (d, J=7.2 Hz, 1H), 5.28 (s, 1H), 3.91 (s, 3H), 3.88-3.80 (m, 1H), 3.74 (bs, 3H), 2.01-1.87 (m, 2H), 1.74-1.64 (m, 3H), 1.40-1.30 (m, 2H), 1.27-1.04 (m, 3H).

MS (ESI) m/z=579 (M+Na)$^+$.

1.107. N-[cyclohexylcarbamoyl-(4-nitro-phenyl)-methyl]-N-[2-(3,4-dimethoxy-phenyl)-ethyl]-benzamide (WJCPA-107)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), benzoic acid (4d; 49 mg, 0.44 mmol), and methanol to obtain the bis-amide compound WJCPA-107 after filtration.

White solid (112 mg, yield 64%), Mp: 194.3° C. to 198.0° C.

$^1$H NMR (300 MHz, CDCl$_3$) δ: 8.26 (d, J=9.0 Hz, 2H), 7.67 (bs, 2H), 7.50-7.43 (m, 5H), 6.63 (d, J=8.1 Hz, 2H), 6.26 (bs, 1H), 6.10 (bs, 1H), 5.88 (bs, 1H), 3.94-3.85 (m, 1H), 3.79 (s, 3H), 3.69 (s, 3H), 3.54 (bs, 2H), 2.76-2.63 (m, 1H), 2.42-2.32 (m, 1H), 2.00-1.92 (m, 2H), 1.74-1.64 (m, 3H), 1.47-1.35 (m, 2H), 1.28-1.19 (m, 3H).

MS (ESI) m/z=568 (M+Na)$^+$.

1.108. 2-{acetyl-[2-(3,4-dimethoxy-phenyl)-ethyl]-amino}-N-cyclohexyl-2-(4-nitro-phenyl)-acetamide (WJCPA-108)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), acetic acid (4s; 24 mg, 0.40 mmol), and methanol to obtain the bis-amide compound WJCPA-108 after filtration.

Bright yellow solid (55 mg, yield 35%), Mp: 196.6° C. to 198.5° C.

$^1$H NMR (300 MHz, CDCl$_3$) δ: 8.23 (d, J=8.7 Hz, 2H), 7.60 (d, J=8.4 Hz, 2H), 6.74 (d, J=8.1 Hz, 1H), 6.58-6.52 (m, 2H), 6.21 (d, J=8.7 Hz, 1H), 5.87 (s, 1H), 3.90-3.82 (m, 1H), 3.83 (s, 3H), 3.82 (s, 3H), 3.55 (t, J=8.1 Hz, 1H), 2.83-2.73 (m, 1H), 2.52-2.45 (m, 1H), 2.19 (s, 3H), 1.96-1.91 (m, 2H), 1.71-1.67 (m, 3H), 1.43-1.31 (m, 2H), 1.22-1.14 (m, 3H).

MS (ESI) m/z=482 (M−H)$^-$.

1.109. 1H-indol-2-carboxylic acid [cyclohexylcarbamoyl-(4-nitro-phenyl)-methyl]-[2-(3,4-dimethoxy-phenyl)-ethyl]-amide (WJCPA-109)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), indole-2-carboxylic acid (4c; 64 mg, 0.40 mmol), and methanol to obtain the bis-amide compound WJCPA-109 after purification by column chromatography (n-hexane:EtOAc=3:1).

Bright yellow solid (161 mg, yield 86%), Mp: 191.6° C. to 192.7° C.

$^1$H NMR (300 MHz, CDCl$_3$) δ: 9.18 (s, 1H), 8.24 (d, J=8.7 Hz, 2H), 7.68-7.62 (m, 3H), 7.44-7.42 (m, 1H), 7.34 (t, J=8.1 Hz, 1H), 7.17 (t, J=8.1 Hz, 1H), 7.02 (s, 1H), 6.76 (d, J=8.1 Hz, 1H), 6.64-6.60 (m, 1H), 6.56-6.55 (m, 1H), 6.48 (bs, 1H), 6.01 (s, 1H), 4.06-3.97 (m, 2H), 3.90-3.82 (m, 1H), 3.84 (s, 3H), 3.78 (s, 3H), 3.03-2.93 (m, 1H), 2.71-2.66 (m, 1H), 2.00-1.91 (m, 2H), 1.72-1.63 (m, 3H), 1.45-1.33 (m, 2H), 1.26-1.15 (m, 3H).

MS (ESI) m/z=583 (M−H)$^-$.

1.110. N-[cyclohexylcarbamoyl-(4-nitro-phenyl)-methyl]-[2-(3,4-dimethoxy-phenyl)-ethyl]-2,2-dimethyl-propanamide (WJCPA-110)

A reaction was performed at room temperature in the same manner as in Example 1.12 using cyclohexyl isocyanide (1a; 35 mg, 0.32 mmol), imine (5h; 100 mg, 0.32 mmol; a compound formed by reacting 4-nitrobenzaldehyde (2 h) and 3,4-dimethoxyphenylethylamine (3n) in methanol), pivalic acid (4t; 41 mg, 0.40 mmol), and methanol to obtain the bis-amide compound WJCPA-110 after purification by column chromatography (n-hexane:EtOAc=3:1).

Bright yellow solid (118 mg, yield 70%), Mp: 114.2° C. to 117.2° C.

$^1$H NMR (300 MHz, CDCl$_3$) δ: 8.21 (d, J=8.7 Hz, 2H), 7.49 (d, J=8.4 Hz, 2H), 6.77 (d, J=8.1 Hz, 2H), 6.61 (d, J=8.4 Hz, 1H), 6.58 (s, 1H), 5.30 (s, 1H), 3.88-3.79 (m, 2H), 3.85 (s, 3H), 3.84 (s, 3H), 3.70-3.60 (m, 1H), 2.85-2.79 (m, 2H), 1.98-1.86 (m, 2H), 1.71-1.63 (m, 3H), 1.43-1.33 (m, 2H), 1.36 (s, 9H), 1.28-1.18 (m, 3H).

MS (ESI) m/z=524 (M−H)$^-$.

1.111. N-cyclohexyl-2-{(2-1H-indol-3-yl-acetyl)-[2-(3-methoxy-phenyl)-ethyl]-amino}-2-(4-nitro-phenyl)-acetamide (WJCPA-111)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), 3-indole acetic acid (4a; 145 mg, 0.83 mmol), and methanol to obtain the bis-amide compound WJCPA-111.

Bright yellow solid (153 mg, yield 40%), Mp: 169.5° C. to 171.3° C.

$^1$H NMR (300 MHz, CDCl$_3$) δ: 8.15 (d, J=9.0 Hz, 2H), 7.58 (d, J=8.4 Hz, 1H), 7.53 (d, J=8.7 Hz, 1H), 7.34 (d, J=7.8 Hz, 1H), 7.26-7.10 (m, 5H), 6.74 (d, J=8.4 Hz, 1H), 6.56 (d, J=7.8 Hz, 1H), 6.50 (s, 1H), 6.30 (d, J=7.8 Hz, 1H), 5.81 (s, 1H), 3.85 (s, 2H), 3.80-3.59 (m, 3H), 3.73 (s, 3H), 2.80-2.70

(m, 1H), 2.52-2.42 (m, 1H), 1.85-1.81 (m, 2H), 1.64-1.51 (m, 3H), 1.38-1.23 (m, 2H), 1.11-0.93 (m, 3H).
MS (ESI) m/z=567 (M−H)⁻.

1.112. 2-{(2-Chloro-acetyl)-[2-(3-methoxy-phenyl)-ethyl]-amino}-N-cyclohexyl-2-(4-nitro-phenyl)-acetamide (WJCPA-112)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), chloroacetic acid (4u; 78 mg, 0.83 mmol), and methanol to obtain the bis-amide compound WJCPA-112 after filtration.

White solid (266 mg, yield 82%), Mp: 196.4° C. to 201.8° C.

$^1$H NMR (300 MHz, CDCl$_3$) δ: 8.24 (d, J=8.7 Hz, 2H), 7.61 (d, J=8.7 Hz, 2H), 7.19 (t, J=8.7 Hz, 1H), 6.76 (d, J=6.6 Hz, 1H), 6.64 (d, J=7.5 Hz, 1H), 6.59 (s, 1H), 6.18 (d, J=6.3 Hz, 1H), 5.74 (s, 1H), 3.92 (s, 2H), 3.80-3.72 (m, 1H), 3.76 (s, 3H), 3.65 (t, J=8.1 Hz, 2H), 2.82-2.75 (m, 1H), 2.65-2.59 (m, 1H), 1.98-1.88 (m, 2H), 1.71-1.56 (m, 3H), 1.43-1.31 (m, 2H), 1.22-1.14 (m, 3H).
MS (ESI) m/z=486 (M−H)⁻.

1.113. 2-[(2-Chloro-acetyl)-(4-isopropyl-phenyl)-amino]-2-(4-chloro-phenyl)-N-cyclohexyl-acetamide (WJCPA-113)

A reaction was performed at room temperature in the same manner as in Example 1.1 using cyclohexyl isocyanide (1a; 62 mg, 0.57 mmol), 4-chlorobenzaldehyde (2f; 80 mg, 0.57 mmol), 4-isopropylaniline (3a; 96 mg, 0.71 mmol), chloroacetic acid (4u; 67 mg, 0.71 mmol), and methanol to obtain the bis-amide compound WJCPA-113 after filtration.

White solid (144 mg, yield 55%), Mp: 192.1° C. to 195.5° C.

$^1$H NMR (300 MHz, CDCl$_3$) δ: 7.18-7.14 (m, 3H), 7.09-7.06 (m, 5H), 5.90 (s, 1H), 5.61 (d, J=7.8 Hz, 1H), 3.85-3.75 (m, 3H), 2.85 (heptet, J=6.9 Hz, 1H), 1.96-1.82 (m, 2H), 1.71-1.58 (m, 3H), 1.41-1.26 (m, 2H), 1.19 (d, J=6.9 Hz, 6H), 1.18-1.20 (m, 3H).
MS (ESI) m/z=459 (M−H)⁻.

1.114. N-[(4-Chloro-phenyl)-pentylcarbamoyl-methyl]-N-(4-isopropyl-phenyl)-benzamide (WJCPA-114)

A reaction was performed at room temperature in the same manner as in Example 1.1 using 1-pentyl isocyanide (1c; 55 mg, 0.57 mmol), 4-chlorobenzaldehyde (2f; 80 mg, 0.57 mmol), 4-isopropylaniline (3a; 96 mg, 0.71 mmol), benzoic acid (4d; 87 mg, 0.71 mmol), and methanol to obtain the bis-amide compound WJCPA-114.

Yellow solid (104 mg, yield 38%), Mp: 75.5° C. to 78.6° C.

$^1$H NMR (300 MHz, CDCl$_3$) δ: 8.12-8.08 (m, 1H), 7.49-7.44 (m, 1H), 7.32-7.09 (m, 7H), 6.92-6.85 (m, 4H), 6.16 (bs, 1H), 6.05 (s, 1H), 3.32 (q, J=6.9 Hz, 2H), 2.74 (heptet, J=6.9 Hz, 1H), 1.51 (pentet, J=6.9 Hz, 2H), 1.34-1.23 (m, 4H), 1.10 (d, J=6.9 Hz, 6H), 0.87 (t, J=6.9 Hz, 3H).
MS (ESI) m/z=515 (M+K)⁺, 477 (M+H)⁺.

1.115. 2-[(2-Chloro-acetyl)-(4-methoxy-phenyl)-amino]-2-(4-hydroxy-phenyl)-N-pentyl-acetamide (WJCPA-115)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), p-anisidine (3b; 101 mg, 0.82 mmol), chloroacetic acid (4u; 77 mg, 0.82 mmol), and methanol to obtain the bis-amide compound WJCPA-115.

Grey solid (91 mg, yield 33%), Mp: 155.3° C. to 156.6° C.

$^1$H NMR (300 MHz, CDCl$_3$) δ: 7.56 (bs, 1H), 6.96 (d, J=8.7 Hz, 2H), 6.79 (d, J=7.8 Hz, 1H), 6.68-6.64 (m, 4H), 5.95 (s, 1H), 5.68 (t, J=6.0 Hz, 1H), 3.83 (d, J=3.3 Hz, 2H), 3.76 (s, 3H), 3.25 (q, J=7.5 Hz, 2H), 1.45 (pentet, J=7.5 Hz, 2H), 1.31-1.20 (m, 4H), 0.85 (t, J=6.6 Hz, 3H).
MS (ESI) m/z=157 (M+K)⁺, 419 (M+H)⁺.

1.116. 2-Bromo-hexanoic acid (3,4-dimethoxy-phenyl)-[(4-hydroxy-phenyl)-pentylcarbamoyl-methyl]-amide (WJCPA-116)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), 4-aminoveratrole (3d; 126 mg, 0.82 mmol), 2-bromohexanoic acid (4n; 160 mg, 0.82 mmol), and methanol to obtain the bis-amide compound WJCPA-116 after filtration.

White solid (54 mg, yield 15%), Mp: 179.2° C. to 181.6° C.

$^1$H NMR (300 MHz, CDCl$_3$) δ: 7.34 (d, J=2.4 Hz, 0.5H), 7.19 (d, J=2.1 Hz, 0.5H), 6.95 (t, J=8.7 Hz, 2H), 6.77 (d, J=8.4 Hz, 0.5H), 6.63 (t, J=8.4 Hz, 2H), 6.53 (d, J=8.4 Hz, 0.5H), 6.28-6.25 (m, 0.5H), 6.12 (d, J=2.4 Hz, 0.5H), 6.07 (s, 1H), 5.70-5.61 (m, 1H), 4.08-4.02 (m, 1H), 3.85 (s, 3H), 3.80 (s, 3H), 3.55 (s, 1H), 3.30-3.22 (m, 2H), 2.22-2.14 (m, 1H), 1.94-1.86 (m, 1H), 1.45 (pentet, J=7.2 Hz, 2H), 1.27-1.21 (m, 8H), 0.88-0.83 (m, 6H).
MS (ESI) m/z=587 (M+K)⁺, 571 (M+Na)⁺.

1.117. N-(3,4-dimethoxy-phenyl)-N-[(4-hydroxy-phenyl)-pentylcarbamoyl-methyl]-2,2-dimethyl-propionamide (WJCPA-117)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), 4-aminoveratrole (3d; 126 mg, 0.82 mmol), pivalic acid (4t; 84 mg, 0.82 mmol), and methanol to obtain the bis-amide compound WJCPA-117.

White solid (71 mg, yield 24%), Mp: 192.7° C. to 194.4° C.

$^1$H NMR (300 MHz, CDCl$_3$) δ: 6.94 (d, J=8.4 Hz, 2H), 6.63 (d, J=8.1 Hz, 3H), 6.14-6.04 (m, 2H), 5.75 (bs, 2H), 3.81 (s, 4H), 3.57 (bs, 2H), 3.28-3.21 (m, 2H), 1.44 (pentet, J=7.5 Hz, 2H), 1.31-1.19 (m, 4H), 1.04 (s, 9H), 0.84 (t, J=6.9 Hz, 3H).
MS (ESI) m/z=495 (M+K)⁺, 479 (M+Na)⁺.

1.118. Pentanoic acid (3,4-dimethoxy-phenyl)-[(4-hydroxy-phenyl)-pentylcarbamoyl-methyl]-amide (WJCPA-118)

A reaction was performed at room temperature in the same manner as in Example 1.12 using 1-pentyl isocyanide (1c; 56 mg, 0.58 mmol), imine (5d; 150 mg, 0.58 mmol; a compound formed by reacting 4-hydroxybenzaldehyde (2j) and 4-aminoveratrole (3 d) in methanol), valeric acid (4p; 75 mg, 0.73 mmol), and methanol to obtain the bis-amide compound WJCPA-118.

Pink solid (186 mg, yield 70%), Mp: 77.4° C. to 80.7° C.

¹H NMR (300 MHz, CDCl₃) δ: 6.97 (d, J=8.4 Hz, 2H), 6.64 (d, J=8.4 Hz, 3H), 6.30 (s, 1H), 6.20-6.03 (m, 1H), 5.95 (s, 1H), 5.78 (bs, 1H), 3.82 (s, 4H), 3.57 (bs, 2H), 3.25 (q, J=7.2 Hz, 2H), 2.10-2.04 (m, 2H), 1.60-1.51 (m, 2H), 1.45 (pentet, J=6.6 Hz, 2H), 1.30-1.15 (m, 6H), 0.87-0.77 (m, 6H).
MS (ESI) m/z=495 (M+K)⁺, 479 (M+Na)⁺.

1.119. 6-Chloro-N-(3,4-dimethoxy-phenyl)-N-[(4-hydroxy-phenyl)-pentylcarbamoyl-methyl]-nicotinamide (WJCPA-119)

A reaction was performed at room temperature in the same manner as in Example 1.12 using 1-pentyl isocyanide (1c; 38 mg, 0.39 mmol), imine (5d; 100 mg, 0.39 mmol; a compound formed by reacting 4-hydroxybenzaldehyde (2j) and 4-aminoveratrole (3 d) in methanol), 6-chloronicotinic acid (4k; 77 mg, 0.49 mmol), and methanol to obtain the bis-amide compound WJCPA-119 after purification by column chromatography (n-hexane:EtOAc=1:1).
Bright brown solid (137 mg, yield 69%), Mp: 103.0° C. to 107.1° C.
¹H NMR (300 MHz, CDCl₃) δ: 8.29 (dd, J=2.4, 0.6 Hz, 1H), 7.60 (dd, J=8.1, 2.1 Hz, 1H), 7.11 (dd, J=8.1, 0.6 Hz, 1H), 7.04 (d, J=9.0 Hz, 2H), 6.70 (d, J=8.4 Hz, 3H), 6.48 (d, J=7.8 Hz, 2H), 6.20 (bs, 1H), 6.07 (s, 1H), 5.74 (t, J=6.0 Hz, 1H), 3.75 (s, 4H), 3.61 (bs, 2H), 3.36-3.22 (m, 2H), 1.48 (pentet, J=7.5 Hz, 2H), 1.32-1.19 (m, 4H), 0.85 (t, J=6.9 Hz, 3H).
MS (ESI) m/z=512 (M+H)⁺.

1.120. 1H-indol-2-carboxylic acid (3,4-dimethoxy-phenyl)-[(4-hydroxy-phenyl)-pentylcarbamoyl-methyl]-amide (WJCPA-120)

A reaction was performed at room temperature in the same manner as in Example 1.12 using 1-pentyl isocyanide (1c; 38 mg, 0.39 mmol), imine (5d; 100 mg, 0.39 mmol; a compound formed by reacting 4-hydroxybenzaldehyde (2j) and 4-aminoveratrole (3 d) in methanol), indole-2-carboxylic acid (4c; 79 mg, 0.49 mmol), and methanol to obtain the bis-amide compound WJCPA-120 after filtration.
Grey solid (135 mg, yield 67%), Mp: 210.2° C. to 213.6° C.
¹H NMR (300 MHz, CDCl₃) δ: 9.26 (s, 1H), 7.35 (t, J=8.7 Hz, 3H), 7.23-7.18 (m, 2H), 7.07 (d, J=8.7 Hz, 2H), 7.00 (t, J=7.8 Hz, 1H), 6.68 (d, J=8.4 Hz, 3H), 6.12 (s, 1H), 5.79 (bs, 1H), 5.32 (bs, 1H), 5.24 (s, 1H), 3.90 (s, 3H), 3.65 (bs, 3H), 3.30 (q, J=7.2 Hz, 2H), 1.48 (pentet, J=7.2 Hz, 2H), 1.32-1.19 (m, 4H), 0.85 (t, J=6.6 Hz, 3H).
MS (ESI) m/z=516 (M+H)⁺.

1.121. Pentanoic acid (benzo[1,3]dioxol-5-yl-pentylcarbamoyl-methyl)-(3,4-dimethoxy-phenyl)-amide (WJCPA-121)

A reaction was performed at room temperature in the same manner as in Example 1.1 using 1-pentyl isocyanide (1c; 65 mg, 0.67 mmol), piperonal (2n; 100 mg, 0.67 mmol), 4-aminoveratrole (3d; 128 mg, 0.83 mmol), valeric acid (4p; 85 mg, 0.83 mmol), and methanol to obtain the bis-amide compound WJCPA-121 after purification by column chromatography (n-hexane:EtOAc=1:1).
Yellow solid (178 mg, yield 55%), Mp: 98.9° C. to 100.8° C.
IR (cm⁻¹) 3278, 1651.

¹H NMR (300 MHz, CDCl₃) δ: 6.83-6.50 (m, 5H), 6.32-6.01 (m, 2H), 5.89 (s, 2H), 5.76 (bs, 1H), 3.84 (s, 4H), 3.71 (bs, 2H), 3.26 (q, J=7.2 Hz, 2H), 2.09-2.03 (m, 2H), 1.59-1.51 (m, 2H), 1.49-1.42 (m, 2H), 1.30-1.18 (m, 6H), 0.88-0.78 (m, 6H).
MS (ESI) m/z=507 (M+Na).
Anal. Calcd. for C₂₇H₃₆N₂O₆: C, 66.92; H, 7.49; N, 5.78. Found C, 66.88; H, 7.42; N, 5.92.
HPLC: purity 95.0%.

1.122. N-cyclohexyl-2-(4-fluoro-phenyl)-2-[(2-1H-indol-3-yl-acetyl)-(4-methoxy-phenyl)-amino]-acetamide (WJCPA-122)

A reaction was performed at room temperature in the same manner as in Example 1.1 using cyclohexyl isocyanide (1a; 87 mg, 0.80 mmol), 4-fluorobenzaldehyde (2g; 100 mg, 0.80 mmol), p-anisidine (3b; 124 mg, 1.00 mmol), 3-indole acetic acid (4a; 176 mg, 1.00 mmol), and methanol to obtain the bis-amide compound WJCPA-122 after filtration.
White solid (290 mg, yield 70%), Mp: 209.3° C. to 213.8° C.
IR (cm⁻¹) 3267, 1657.
¹H NMR (300 MHz, CDCl₃) δ: 8.05 (s, 1H), 7.39 (d, J=6.9 Hz, 2H), 7.33-7.30 (m, 1H), 7.17-7.01 (m, 4H), 6.97 (d, J=2.1 Hz, 1H), 6.87-6.81 (m, 2H), 6.77-6.56 (m, 2H), 6.43-6.27 (m, 1H), 6.12 (s, 1H), 5.76 (d, J=8.4 Hz, 1H), 3.79-3.69 (m, 1H), 3.75 (s, 3H), 3.57 (s, 2H), 1.87-1.77 (m, 2H), 1.64-1.53 (m, 3H), 1.35-1.23 (m, 2H), 1.11-0.88 (m, 3H).
MS (ESI) m/z=536 (M+Na)⁺, 514 (M+H)⁺.
Anal. Calcd. for C₃₁H₃₂FN₃O₃: C, 72.49; H, 6.28; N, 8.18. Found C, 72.26; H, 6.12; N, 8.48.
HPLC: purity 96.9%.

1.123. N-benzyl-2-(4-fluoro-phenyl)-2-[(2-1H-indol-3-yl-acetyl)-(4-methoxy-phenyl)-amino]-acetamide (WJCPA-123)

A reaction was performed at room temperature in the same manner as in Example 1.1 using benzyl isocyanide (1b; 87 mg, 0.80 mmol), 4-fluorobenzaldehyde (2g; 100 mg, 0.80 mmol), p-anisidine (3b; 124 mg, 1.00 mmol), 3-indole acetic acid (4a; 176 mg, 1.00 mmol), and methanol to obtain the bis-amide compound WJCPA-123 after purification by column chromatography (n-hexane:EtOAc=1:1).
White solid (180 mg, yield 43%), Mp: 88.5° C. to 91.8° C.
IR (cm⁻¹) 3303, 1632.
¹H NMR (300 MHz, CDCl₃) δ: 8.01 (s, 1H), 7.36-7.22 (m, 6H), 7.19-7.14 (m, 3H), 7.12-7.00 (m, 4H), 6.96-6.95 (m, 1H), 6.86-6.80 (m, 2H), 6.69-6.57 (m, 2H), 6.25 (1, J=5.7 Hz, 1H), 6.14 (s, 1H), 4.42 (dd, J=5.7, 1.8 Hz, 2H), 3.74 (s, 3H), 3.57 (d, J=0.6 Hz, 2H).
MS (ESI) m/z=544 (M+Na)⁺.
HPLC: purity 96.4%.

1.124. 4-{Cyclohexylcarbamoyl-[(2-1H-indol-3-yl-acetyl)-(4-methoxy-phenyl)-amino]-methyl}-benzoic acid (WJCPA-124)

A reaction was performed at room temperature in the same manner as in Example 1.1 using cyclohexyl isocyanide (1a; 73 mg, 0.67 mmol), 4-formylbenzaldehyde (2i; 100 mg, 0.67 mmol), p-anisidine (3b; 103 mg, 0.84 mmol), 3-indole acetic acid (4a; 146 mg, 0.84 mmol), and methanol to obtain the bis-amide compound WJCPA-124 after purification by column chromatography (n-hexane:EtOAc=1:1).

Yellow solid (18 mg, yield 5%), Mp: 170.1° C. to 172.5° C.

$^1$H NMR (300 MHz, CDCl$_3$) δ: 8.03 (s, 1H), 7.87 (d, J=8.7 Hz, 2H), 7.70-7.61 (m, 2H), 7.41-7.37 (m, 2H), 7.33-7.31 (m, 2H), 7.22-7.12 (m, 2H), 7.08-7.02 (m, 1H), 6.95 (d, J=2.1 Hz, 1H), 6.63-6.58 (m, 2H), 6.13 (s, 1H), 5.83 (d, J=7.8 Hz, 1H), 3.82-3.76 (m, 1H), 3.74 (s, 3H), 3.60 (s, 2H), 1.86-1.77 (m, 2H), 1.66 J1.52 (m, 3H), 1.37-1.23 (m, 2H), 1.01-0.85 (m, 3H).

MS (ESI) m/z=578 (M+K)$^+$, 562 (M+Na)$^+$.

1.125. 2-(4-Chloro-phenyl)-2-[(2-1H-indol-3-yl-acetyl)-(4-methoxy-phenyl)-amino]-N-pentyl-acetic acid (WJCPA-125)

A reaction was performed at room temperature in the same manner as in Example 1.1 using 1-pentyl isocyanide (1c; 69 mg, 0.71 mmol), 4-chlorobenzaldehyde (2f; 100 mg, 0.71 mmol), p-anisidine (3b; 109 mg, 0.89 mmol), 3-indole acetic acid (4a; 156 mg, 0.89 mmol), and methanol to obtain the bis-amide compound WJCPA-125 after filtration.

White solid (70 mg, yield 19%), Mp: 153.8° C. to 160.7° C.

$^1$H NMR (300 MHz, CDCl$_3$) δ: 8.07 (s, 1H), 7.38-7.29 (m, 3H), 7.17-7.12 (m, 3H), 7.07-7.01 (m, 3H), 6.97 (d, J=2.4 Hz, 1H), 6.74-6.60 (m, 3H), 6.05 (s, 1H), 5.88 (t, J=6.0 Hz, 1H), 3.76 (s, 3H), 3.57 (s, 2H), 3.21 (q, J=6.9 Hz, 2H), 1.39 (pentet, J=7.2 Hz, 2H), 1.27-1.18 (m, 4H), 0.84 (t, J=6.9 Hz, 3H).

MS (ESI) m/z=556 (M+K)$^+$, 540 (M+Na)$^+$, 516 (M−H)$^−$.

1.126. N-cyclohexyl-2-[(2-1H-indol-3-yl-acetyl)-(4-isopropyl-phenyl)-amino]-2-(3,4,5-trimethoxy-phenyl)-acetamide (WJCPA-126)

A reaction was performed at room temperature in the same manner as in Example 1.1 using cyclohexyl isocyanide (1a; 69 mg, 0.63 mmol), imine (5a; 200 mg, 0.63 mmol; a compound formed by reacting 3,4,5-trimethoxybenzaldehyde (2a) and 4-isopropylaniline (3a) in ethanol), 3-indole acetic acid (4a; 235 mg, 1.34 mmol), and methanol to obtain the bis-amide compound WJCPA-126 after purification by column chromatography (n-hexane:EtOAc=3:1).

Ivory solid (260 mg, yield 69%), Mp: 141.0° C. to 143.0° C.

IR (cm$^{-1}$) 3315, 1644.

$^1$H NMR (300 MHz, CDCl$_3$) δ: 8.04 (s, 1H), 7.37 (d, J=8.1 Hz, 2H), 7.31 (d, J=8.1 Hz, 2H), 7.14 (t, J=7.2 Hz, 2H), 7.03 (t, J=7.2 Hz, 2H), 6.96 (d, J=2.4 Hz, 1H), 6.29 (s, 2H), 6.08 (s, 1H), 5.80 (d, J=8.1 Hz, 1H), 3.76 (s, 4H), 3.60 (s, 2H), 3.58 (s, 6), 2.84 (heptet, J=6.9 Hz, 1H), 1.88-1.78 (m, 2H), 1.64-1.54 (m, 3H), 1.37-1.23 (m, 2H), 1.19 (d, J=6.9 Hz, 6H), 1.14-0.94 (m, 3H).

$^{13}$C NMR (150 MHz, CDCl$_3$) δ: 172.2, 168.6, 152.6, 149.0, 137.6, 137.4, 135.9, 130.2, 129.9, 127.2, 126.7, 123.1, 121.8, 119.3, 118.9, 110.9, 109.3, 107.7, 64.3, 60.7, 55.8, 48.5, 33.7, 32.7, 32.6, 31.8, 25.4, 24.7, 24.7, 23.9, 23.8.

MS (ESI) m/z=636 (M+K)$^+$, 620 (M+Na)$^+$.

HPLC: purity 96.1%.

1.127. 2-[(2-Chloro-acetyl)-(3,4-dimethoxy-phenyl)-amino]-2-(4-hydroxy-phenyl)-N-pentyl-acetamide (WJCPA-127)

A reaction was performed at room temperature in the same manner as in Example 1.12 using 1-pentyl isocyanide (1c; 38 mg, 0.39 mmol), imine (5d; 100 mg, 0.39 mmol; a compound formed by reacting 4-hydroxybenzaldehyde (2j) and 4-aminoveratrole (3 d) in methanol), chloroacetic acid (4u; 46 mg, 0.49 mmol), and 2,2,2-trifluoroethanol to obtain the bis-amide compound WJCPA-127 after filtration.

White solid (52 mg, yield 29%), Mp: 164.0° C. to 166.0° C.

$^1$H NMR (600 MHz, CDCl$_3$) δ: 7.30 (bs, 0.5H), 7.19-7.09 (m, 1.5H), 6.96 (s, 2H), 6.77 (bs, 0.5H), 6.69 (s, 2H), 6.55 (bs, 0.5H), 6.18 (bs, 0.5H), 6.12 (bs, 0.5H), 5.96 (bs, 0.5H), 5.88 (bs, 0.5H), 5.86 (t, J=5.4 Hz, 1H), 3.86-3.79 (m, 6.5H), 3.54 (bs, 1.5H), 3.29-3.21 (m, 2H), 1.45 (pentet, J=7.2 Hz, 2H), 1.29-1.19 (m, 4H), 0.84 (t, J=7.2 Hz, 3H).

MS (ESI) m/z=471 (M+Na)$^+$.

1.128. 1H-indol-2-carboxylic acid [cyclohexylcarbamoyl-(4-nitro-phenyl)-methyl-[2-(3-methoxy-phenyl)-ethyl]-amide (WJCPA-128)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 2-(3-methoxyphenyl) ethylamine (3m; 125 mg, 0.83 mmol), indole-2-carboxylic acid (4c; 134 mg, 0.83 mmol), and methanol to obtain the bis-amide compound WJCPA-128 after filtration.

White solid (340 mg, yield 92%), Mp: 208.8° C. to 211.9° C.

$^1$H NMR (300 MHz, CDCl$_3$) δ: 9.21 (s, 1H), 8.23 (d, J=9.0 Hz, 2H), 7.68 (d, J=8.1 Hz, 1H), 7.62 (d, J=8.7 Hz, 2H), 7.44-7.42 (m, 1H), 7.36-7.31 (m, 1H), 7.21-7.15 (m, 2H), 7.02 (s, 1H), 6.75 (dd, J=8.1, 1.8 Hz, 1H), 6.67 (d, J=7.8 Hz, 1H), 6.60 (s, 1H), 6.42 (bs, 1H), 6.02 (bs, 1H), 4.03-3.87 (m, 3H), 3.74 (s, 3H), 3.07-2.97 (m, 1H), 2.77-2.68 (m, 1H), 2.01-1.90 (m, 2H), 1.73-1.61 (m, 3H), 1.44-1.32 (m, 2H), 1.24-1.14 (m, 3H).

MS (ESI) m/z=553 (M−H)$^−$.

1.129. 2-[(2-Chloro-acetyl)-(3,4-dimethoxy-phenyl)-amino]-2-(4-chloro-phenyl)-N-pentyl-acetamide (WJCPA-129)

A reaction was performed at room temperature in the same manner as in Example 1.1 using 1-pentyl isocyanide (1c; 55 mg, 0.57 mmol), 4-chlorobenzaldehyde (2f; 80 mg, 0.57 mmol), 4-aminoveratrole (3d; 109 mg, 0.71 mmol), chloroacetic acid (4u; 67 mg, 0.71 mmol), and methanol to obtain the bis-amide compound WJCPA-129 after filtration.

White solid (148 mg, yield 56%), Mp: 165.5° C. to 167.8° C.

$^1$H NMR (300 MHz, CDCl$_3$) δ: 7.19 (d, J=8.4 Hz, 2H), 7.09 (d, J=7.8 Hz, 3H), 6.81-6.48 (m, 2H), 5.98 (s, 1H), 5.70 (bs, 1H), 3.87-3.84 (m, 6H), 3.55 (bs, 2H), 3.27 (q, J=6.3 Hz, 2H), 1.47 (pentet, J=6.9 Hz, 2H), 1.35-1.17 (m, 4H), 0.86 (t, J=6.6 Hz, 3H).

MS (ESI) m/z=505 (M+K)$^+$, 467 (M−H)$^−$.

1.130. 2-[(2-Chloro-acetyl)-(4-isopropyl-phenyl)-amino]-2-(4-hydroxy-phenyl)-N-pentyl-acetamide (WJCPA-130)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), 4-isopropylaniline (3a; 109 mg, 0.71 mmol), chloroacetic acid (4u; 77 mg, 0.82 mmol), and methanol to obtain the bis-amide compound WJCPA-130.

White solid (94 mg, yield 33%), Mp: 133.8° C. to 137.0° C.

¹H NMR (300 MHz, DMSO) δ: 9.32 (s, 1H), 7.95 (t, J=5.4 Hz, 1H), 7.09-7.01 (m, 4H), 6.77 (d, J=8.4 Hz, 2H), 6.46 (d, J=8.7 Hz, 2H), 5.86 (s, 1H), 3.93-3.81 (m, 2H), 3.15-2.96 (m, 2H), 2.79 (heptet, J=6.9 Hz, 1H), 1.35 (pentet, J=7.2 Hz, 2H), 1.26-1.14 (m, 4H), 1.10 (dd, J=6.9, 1.8 Hz, 6H), 0.81 (t, J=6.9 Hz, 3H).

MS (ESI) m/z=469 (M+K)$^+$, 431 (M+H)$^+$.

1.131. 2-[(2-Chloro-acetyl)-(4-fluoro-phenyl)-amino]-2-(4-hydroxy-phenyl)-N-pentyl-acetamide (WJCPA-131)

A reaction was performed at room temperature in the same manner as in Example 1.1 using 1-pentyl isocyanide (1c; 64 mg, 0.66 mmol), 4-hydroxybenzaldehyde (2j; 80 mg, 0.66 mmol), 4-fluoroaniline (3e; 91 mg, 0.82 mmol), chloroacetic acid (4u; 77 mg, 0.82 mmol), and methanol to obtain the bis-amide compound WJCPA-131.

White solid (177 mg, yield 66%), Mp: 134.8° C. to 137.6° C.

¹H NMR (300 MHz, DMSO) δ: 9.40 (s, 1H), 8.03 (t, J=5.7 Hz, 1H), 6.98 (bs, 4H), 6.78 (d, J=8.7 Hz, 2H), 6.48 (d, J=8.4 Hz, 2H), 5.87 (s, 1H), 3.97-3.84 (m, 2H), 3.16-2.97 (m, 2H), 1.35 (pentet, J=7.2 Hz, 2H), 1.26-1.14 (m, 4H), 0.81 (t, J=6.9 Hz, 3H).

MS (ESI) m/z=445 (M+K)$^+$, 429 (M+Na)$^+$, 405 (M–H)$^-$.

1.132. 2-Benzo[1,3]dioxol-5-yl-2-[(2-chloro-acetyl)-(3,4-dimethoxy-phenyl)-amino]-N-pentyl-acetamide (WJCPA-132)

A reaction was performed at room temperature in the same manner as in Example 1.1 using 1-pentyl isocyanide (1c; 65 mg, 0.67 mmol), piperonal (2n; 100 mg, 0.67 mmol), 4-aminoveratrole (3d; 128 mg, 0.83 mmol), chloroacetic acid (4u; 79 mg, 0.83 mmol), and methanol to obtain the bis-amide compound WJCPA-132 after filtration.

White solid (73 mg, yield 23%), Mp: 159.3° C. to 160.8° C.

¹H NMR (300 MHz, CDCl₃) δ: 6.63 (d, J=6.6 Hz, 3H), 6.35-6.02 (m, 1H), 5.90-5.84 (m, 3H), 5.64 (bs, 1H), 5.30 (s, 2H), 3.86 (s, 2H), 3.85 (s, 4.5H), 3.61 (bs, 1.5H), 3.26 (q, J=6.9 Hz, 2H), 1.48 (pentet, J=7.2 Hz, 2H), 1.32-1.22 (m, 4H), 0.86 (t, J=6.6 Hz, 3H).

MS (ESI) m/z=515 (M+K)$^+$, 477 (M+H)$^+$.

1.133. N-(4-bromo-phenyl)-N-[cyclohexylcarbamoyl-(4-nitro-phenyl)-methyl]-3-(4-methoxy-phenyl)-propionamide (WJCPA-133)

A reaction was performed at room temperature in the same manner as in Example 1.1 using cyclohexyl isocyanide (1a; 72 mg, 0.66 mmol), 4-nitrobenzaldehyde (2h; 100 mg, 0.66 mmol), 4-bromoaniline (3f; 141 mg, 0.82 mmol), 3-(4-methoxyphenyl) propionic acid (4m; 180 mg, 1.00 mmol), and methanol to obtain the bis-amide compound WJCPA-133 after filtration.

Bright yellow solid (128 mg, yield 32%), Mp: 255.2° C. to 265.8° C. (dec).

IR (cm$^{-1}$) 3269, 1646.

¹H NMR (600 MHz, CDCl₃) δ: 8.54 (s, 0.5H), 8.34 (d, J=8.7 Hz, 1H), 8.06 (t, J=9.0 Hz, 2.5H), 7.55 (d, J=8.4 Hz, 1.5H), 7.30 (d, J=8.7 Hz, 2H), 7.14 (d, J=8.4 Hz, 1.5H), 6.97 (d, J=8.7 Hz, 1.5H), 6.78 (d, J=8.7 Hz, 1H), 6.06 (s, 1H), 5.76 (d, J=8.4 Hz, 1H), 3.85-3.80 (m, 1H), 3.77 (s, 3H), 2.85 (t, J=7.5 Hz, 2H), 2.34-2.28 (m, 2H), 1.96-1.82 (m, 2H), 1.73-1.64 (m, 3H), 1.39-1.32 (m, 2H), 1.19-1.02 (m, 3H).

¹³C NMR (125 MHz, DMSO-d6) δ: 171.1, 167.5, 157.5, 146.7, 143.2, 141.3, 138.7, 132.9, 132.7, 132.2, 131.1, 129.8, 129.1, 124.0, 123.5, 123.0, 113.7, 54.9, 47.9, 36.6, 32.1, 29.8, 25.1, 24.5, 24.4.

MS (ESI) m/z=592 (M–H)$^-$.

HPLC: purity 97.5%.

1.134. 6-Chloro-N-[cyclohexylcarbamoyl-(3,4-dimethoxy-phenyl)-methyl]-N-(4-methoxy-phenyl)-nicotinamide (WJCPA-134)

A reaction was performed at room temperature in the same manner as in Example 1.12 using cyclohexyl isocyanide (1a; 60 mg, 0.55 mmol), imine (5f; 150 mg, 0.55 mmol; a compound formed by reacting 3,4-dimethoxybenzaldehyde (2c) and p-anisidine (3b) in methanol), 6-chloronicotinic acid (4k; 109 mg, 0.69 mmol), and 2,2,2-trifluoroethanol to obtain the bis-amide compound WJCPA-134 after filtration.

White solid (220 mg, yield 73%), Mp: 210.4° C. to 212.1° C.

¹H NMR (300 MHz, CDCl₃) δ: 8.28 (d, J=1.8 Hz, 1H), 7.58 (dd, J=8.1, 2.1 Hz, 1H), 7.11 (d, J=8.1 Hz, 1H), 6.82-6.72 (m, 3H), 6.56-6.54 (m, 4H), 6.15 (s, 1H), 5.49 (d, J=8.1 Hz, 1H), 3.85 (s, 4H), 3.68 (s, 3H), 3.64 (s, 3H), 1.90-1.77 (m, 2H), 1.67-1.57 (m, 3H), 1.41-1.23 (m, 2H), 1.16-1.02 (m, 3H).

MS (ESI) m/z=560 (M+Na)$^+$.

1.135. N-[(4-chloro-phenyl)-cyclohexylcarbamoyl-methyl]-N-(4-isopropyl-phenyl)-3-(3-methoxy-phenyl)-propionamide (WJCPA-135)

A reaction was performed at room temperature in the same manner as in Example 1.12 using cyclohexyl isocyanide (1a; 55 mg, 0.48 mmol), imine (5e; 100 mg, 0.38 mmol; a compound formed by reacting 4-chlorobenzaldehyde (2o and 4-isopropylaniline (3a) in methanol), 3-(3-methoxyphenyl) propionic acid (4l; 108 mg, 0.57 mmol), and methanol to obtain the bis-amide compound WJCPA-135 after filtration.

White solid (160 mg, yield 77%), Mp: 203.2° C. to 205.5° C.

¹H NMR (300 MHz, CDCl₃) δ: 7.15-7.10 (m, 4H), 7.05-7.02 (m, 5H), 6.71-6.67 (m, 1H), 6.64-6.59 (m, 2H), 5.89 (s, 1H), 5.78 (d, J=8.1 Hz, 1H), 3.81-3.77 (m, 1H), 3.74 (s, 3H), 2.88 (t, J=7.8 Hz, 2H), 2.83 (heptet, J=6.9 Hz, 1H), 2.39-2.33 (m, 2H), 1.95-1.81 (m, 2H), 1.71-1.56 (m, 3H), 1.38-1.30 (m, 2H), 1.18 (d, J=6.9 Hz, 6H), 1.14-1.01 (m, 3H).

MS (ESI) m/z=569 (M+Na)$^+$.

Example 2: Materials

Antibodies specific to CypA, GST (glutathione S-transferase), HCV NS5A, STAT1, STAT2, IRF9, OAS1, and ISG15 were purchased from Santa Cruz Biotechnology (Santa cruz, CA, USA). Antibodies to HCV NS5B and NFAT1 were purchased from Enzo life Science (Plymouth Meeting, Pa., USA) and Abcam (Cambridge, Mass., USA), respectively.

Cyclosporine (CsA) was purchased from Sigma (St. Louis, Mo., USA). Bis-amide derivatives containing WJCPA-126 were synthesized and prepared into 5 mM DMSO solution as a stock solution and stored at −20° C.

Recombinant human IFN-α 2A and ribavirin were purchased from Sigma (St. Louis, Mo., USA) and stored at −20° C. Telaprevir was purchased from Selleck Chemicals (Houston, Tex., USA).

Example 3: Isolation of Splenocytes from Mice and Cell Culture

Seven to eight week-old female Balb/c mice were purchased from Orient Bio, Inc. (Sungnam, Korea). Experimental animals were allowed to maintain at a non-pathogenic environment and adapted before the experiment. Experimental mice were sacrificed by dislocation of spine, and the spleens collected therefrom were removed into petri dishes filled with RPMI containing 10% FBS, 100 units/mL of penicillin, and 100 µg/mL of streptomycin. The spleens were dispersed through a nylon mesh to prepare a single cell suspension, and RBC was depleted by using RBC lysis buffer (Sigma, St. Louis, Mo.). Splenocytes were washed and cultured in RPMI complete medium.

Meanwhile, human liver cancer Huh7 cells were cultured in Dulbecco's modified Eagle's medium (DMEM), which contains a mixture of 10% heat-labile fetal bovine serum (FBS), 100 units/mL of penicillin, 100 µg/L of streptomycin, 1% L-glutamine, and 1× nonessential amino acids (NEAA). The Huh7 cells including subgenomic genotype 1b (Con1/SG-Neo(I) hRluc FMDB2aUb) was kindly provided by Professor Charles Rice (The Rockefeller University and Apath, LLC, St. Louis, Mo., USA). The Huh7 cells including full-length genotype 2a JFH1 were cultured by Professor Mark P. Windisch (Institute Pasteur, Korea). All Huh7-derived replicon cells were proliferated in DMEM containing a mixture of 10% FBS, 100 units/mL of penicillin, 100 µg/mL of streptomycin, and 1×NEAA, and selected using 0.5 mg/mL G4188 (Duchefa Biochemie, Amsterdam, The Netherlands).

Example 4: Molecular Docking Analysis by Surface Plasmon Resonance (SPR)

The direct target binding of WJCPA-126 or CsA was confirmed using a two-channel SPR device (Reichert, Depew, N.Y., USA). CypA protein was fixed on the sensor chip surface via free amine coupling by injecting a mixture of 0.1 M 1-ethyl-3-(3-dimethylaminopropyl) carboimidehydrochloride and 0.05 M N-hydroxysuccinimide thereon, and the extra activated carboxylic acid was inhibited using 1M ethanolamine (pH 8.5). The second reference cell was treated similarly while excluding the target protein. All working peptide dilutions were prepared in running buffer (PBS containing 0.2% DMSO) and injected at a rate of 30 µL/min for 3 minutes (association time) and dissociation phase was performed for 3 minutes. Nonspecific background was substracted from each sensogram using SPR_V4017 data collection and alignment program (Reichert, Depew, N.Y.). The binding rate and constant were irrelevant to the flow rate over a wide range. Optimum kinetic parameters were obtained by global fitting analysis using Scrubber2 (Biologic Software, Australia).

Example 5: Analysis of Peptidyl-Prolyl Cis-Trans Isomerase Activity

The PPIase activity of CypA was determined according to a known method using the coupled chymotrypsin analysis. In brief, 20 nM recombinant CypA, which was produced via thrombin-cleavage by GST-CypA in the presence or absence of a CsA or WJCPA-126 inhibitor, was added into 50 mM HEPES buffer (pH 8.0).

The cis-trans isomerization was measured by absorbance at 390 nm in a spectrophotometer. Additionally, the remaining percentage of enzyme activity was measured at different concentrations of the inhibitor to calculate the 50% inhibition concentration ($IC_{50}$) to the PPIase activity. Data was optimized via graphs by exporting using Graph Pad Prism 5.

Example 6: Analysis of Calcineurin Phosphorylase

Dephosphorylation of RH phosphopeptide was measured using calcineurin cell activity assay kit (Enzo Life sciences, Plymouth Meeting, Pa., USA) to determine calcium-dependent activity of calcineurin. Splenocytes ($2 \times 10^6$/well) were incubated along with or WJCPA-126 for 20 hours, and further untreated or stimulated with 1 µg/mL of ionomycin (Calibiochem, La Jolla, Calif., USA). Then, the cells were used for the measurement of calcineurin activity.

Example 7: Analysis of NFAT Dephosphorylation by Western Blot and Immunofluorescence Murine splenocytes ($2 \times 10^6$/well) were cultured, treated with CsA and WJCPA-126 at 37° C. for 20 hours, and further stimulated with 1 µg/mL of ionomycin (Calibiochem, La Jolla, Calif., USA) for 4 hours. Upon stimulation, the cells were washed with sterile PBS, suspended in lysis buffer (Invitrogen, Carlsbad, Calif., USA), incubated on ice for 10 minutes, and centrifuged at 19,000 g for 15 minutes. The phosphorylation state of the NFAT protein in the supernatant was confirmed by western blot analysis using monoclonal anti-NFATc 1.

For the confirmation of NFAT1 localization using a confocal microscope, the cells were washed and then fixed by treating with 3.7% formaldehyde at room temperature for 20 minutes. Then, the cells were washed 3 times with PBS, provided permeability with PBS solution containing 0.5% Triton X, and additionally washed 3 times before incubating them along with primary antibody diluted in PBS containing 3% BSA at a 1:100 ratio at 4° C. overnight. Upon incubation, the cells were washed twice with PBS and incubated in a dark room at room temperature with secondary antibody, which was conjugated with Alexa 546 (Invitrogen, Carlsbad, Calif., USA) diluted in PBS containing 3% BSA at a 1:200 ratio, for 2 hours. The cells were washed again twice with PBS and subjected to counter staining for 10 minutes with 4',6'-diamidino-2-phenylindole (DAPI). Finally, the cells were washed once with PBS and mounted onto glass slides using a coverslip and a mounting solution (Vector Mount, Calif., USA). The images were captured via Zeiss confocal laser scanning microscope (Zeiss, Germany).

Example 8: Determination of IL-2 Concentration by ELISA

Splenocytes ($2 \times 10^6$/well) were seeded into a 24-well plate, stimulated with ionomycin (1 µg/mL), and treated with CsA and WJCPA-126 in a dose-dependent manner at 37° C. for 24 hours. Upon incubation, the cultures from three different wells were collected and IL-2 concentration was analyzed by ELISA according to the protocol by Enzo life Science (Plymouth Meeting, Pa., USA). IL-2 concentration was calculated based on the IL-2 standard solution.

Example 9: Analysis of Cytotoxicity

Cytotoxicity was analyzed in a 96-well plate using 5 mg/mL of MTT (3-(4,5-dimethylthiasol-2-yl)-2,5-diphenyltetrazolium bromide). The optical density of cells was measured at 550 nm using a microplate reader (Bio-Rad, Richmond, Calif., USA). Cell viability rate was expressed in percentage of the absorbance of treated cells relative to the absorbance of untreated cells.

Example 10: Preparation of a Membrane Fraction

Cells grown to about 80% confluence in a culture dish with a diameter of 10 cm were scraped using PBS. The cells were pelleted by centrifugation at 220 g for 10 minutes. The pellet was resuspended in 1 mL hypotonic buffer (10 mM Tris-HCL pH 7.5, 10 mM KCL, 1.5 mM $MgCl_2$, 0.5 mM PMSF (phenylmethylsulfonyl fluoride), and 2 µg/mL leupeptin), and incubated at 4° C. for 10 minutes. The suspension was homogenized using 75 strokes of a glass dounce homogenizer using a tight-fitting pestle (Sigma, St. Louis, Mo., USA). Nuclei and undestroyed cells were removed by centrifugation at 220 g for 10 minutes at 4° C. The cell membrane in the thus-obtained supernatant was directly centrifuged at 68,000 g for 1 hour at 4° C. using an ultracentrifuge tube in a micro-ultracentrifuge (Hitachi, Japan). Upon centrifugation, the coarse replication complex fraction was recovered from the pellet and used for western blot analysis.

Example 11: Determination of IL-8 and INF-α Concentrations in Cell Culture Media by ELISA HCV replicon Con1b cells ($2 \times 10^6$/well) were seeded into a 6-well plate and treated with 2 µM CsA and WJCPA-126 in a time-dependent manner at 37° C. for up to 4 days. Upon incubation, the cell culture media were collected and the IL-8 and IFN-α concentrations were analyzed according to the protocol of eBioscience (San Diego, Calif., USA) by ELISA.

Example 12: Preparation of a HCV Mouse Model

Five to six-week old immunodeficient NOD/SCID mice (Charles River Laboratories, USA) were used. The use of experimental animals and experimental protocol (KHUASP (SE)-11-045) was approved by the Institutional Animal Care and Use Committee of Kyung Hee University (Seoul, Korea). The control Huh7 cells or the Huh7 cells including the HCV-Con1b replicon were injected into mice intrasplenically ($1 \times 10^6$ cells/200 µL of PBS). Cell transplantation and surgical procedures were performed under anesthesia along with a prophylactic antibiotic. The intraperitoneal administration of CsA and WJCPA-126 (50 mg/kg) started 6 weeks after the cell transplantation and continued for 14 days. Each treatment group consisted of 5 mice. Upon completion of the treatment, the mice were sacrificed and liver tissues were collected from them for analysis.

Example 13: Histological and Immunofluorescent Histochemical Analyses

Murine liver tissues were dissected and then cryoprotected in 30% sucrose for the preparation of paraffin-embedded samples. Paraffin samples for Hematoxylin and Eosin (H&E) staining were prepared. After removing paraffin, rehydrated samples were incubated with monoclonal antibodies to human hepatocytes (Hep par 1) and HCV NS5A (Santa Cruz, Calif., USA), which were diluted at a ratio of 1:50, at 4° C. overnight. After washing 3 times, the samples were incubated with anti-rabbit or anti-mouse IgG antibodies (Invitrogen, Carlsbad, Calif., USA), which were conjugated with Alexa Fluor 488 or Alexa Fluor 546, which were diluted at a ratio of 1:100, for 2 hours. The nuclei were stained with DAPI for 5 minutes and analyzed using a confocal microscope.

Example 14: Western Blot Analysis

Cell extracts were separated by SDS-PAGE and then transferred to a nitrocellulose membrane. After blocking, the membrane was incubated with indicated primary antibody and subsequently incubated with secondary antibody. The samples were detected with enhanced chemiluminescence reagents (Santa Cruz, Calif., USA).

Example 15: Expression and Purification of GST Proteins

A plasmid pGEX-KG was used for the expression of recombinant proteins in *E. coli*. GST-CypA, a mutant GST-CypAR55A (a mutation at PPIase site), GST-CypB, GST-NS5A, and the full length GST-NS5B were prepared by a standard replication process. The bacteria expression vector, pGEX-KG, was transformed into TOP1OF cells (Promega, Madison, Wis., USA). The bacteria culture was grown in LB medium containing 100 µg/mL of ampicillin until the optical density at 600 nm reached 0.8 to 1.0. Then, 0.1 mM isopropyl β-D-1-thiogalactopyranoside (IPTG) was added thereto to induce the expression of a GST fusion protein and incubated further at 30° C. for 4 hours. The resulting bacteria was pelleted by centrifugation at 340 g for 20 minutes at 4° C., resuspended in 10 mL PBST (PBS containing 1% Triton X-100), added with 1 mM PMSF, and subjected to sonication at 25% amplitude with a brake at intervals of 10 seconds for 30 minutes. Upon sonication, the bacteria extract was centrifuged at 340 g for 5 minutes at 4° C. and the supernatant containing GST protein was stored at −80° C. The GST fusion protein was cleaved in thrombin-cleaving buffer containing 50 units of thrombin overnight so that the recombinant proteins could be released from the GST-tagged glutathione resin. The supernatant containing the recombinant proteins was recovered and used for a pull-down assay.

Example 16: GST Pull-Down Assay

Recombinant proteins GST-CypA, GST-NS5A, and GST-NS5B were produced by affinity purification. The GST proteins or the GST-CypA fusion proteins in the amount of 100 µg were incubated with 50 µL of glutathione-agarose beads at 4° C. for 4 hours while rotating. The resultants were washed with phosphate buffer saline containing 1% Triton X-100 (PBST buffer), and the GST-tagged resin was incubated with 10 µg of thrombin-cleaved full-length NS5A or NS5B protein in 500 µL of binding buffer (20 mM Tris pH 7.9, 0.5 M Nacl, 10% glycerol, 10 mM DTT, and 1% NP-40) at 4° C. while rotating overnight. In a similar manner, thrombin-cleaved CypA protein was incubated with purified GST-NS5A or GST-NS5B and the binding was confirmed. The proteins linked to glutathione-agarose beads were eluted using 25 µL. of 5×SDS-PAGE, heated for 5 minutes, and subjected to western blot analysis using anti-GST, anti-CypA, anti-NS5A, and anti-NS5B antibodies.

Example 17: Co-Immunoprecipitation Assay

For co-immunoprecipitation, 4 µg of specific antibody and 1 mg/mL of HCV Con1b replicon protein lysate to a final volume of 500 μL were rotated at 4° C. for 4 hours. Then, 20 μL of the washed protein A/G PLUS agarose (Santa Cruz, Calif., USA) was added thereto and incubated at 4° C. overnight. Subsequently, the sample was washed 3 times with Triton-wash-buffer, resuspended, and denatured in 5×SDS-PAGE buffer at 95° C. for 5 minutes. The resultant was centrifuges at 19,000 g for 1 minute at 4° C. and subjected to western blot analysis.

Example 18: Mammalian Two-Hybrid System

The interaction between intracellular CypA-NS5A and CypA-NS5B was confirmed by the two-hybrid screening technology using CheckMate™ mammalian two-hybrid system (Promega, Madison, Wis., USA) according to the manufacturer's instructions. In brief, pACT- and pBIND-based plasmids were co-transfected (TurboFect, FermentasC) to Huh7 cells along with a pG5luc reporter construct, and incubated at 37° C. After 72 hours, the cell lysate was analyzed regarding the luciferase activity.

Example 19: Real-Time Quantitative Reverse Transcriptase PCR Analysis

Real-time quantitative reverse transcriptase PCR (qRT-PCR) was performed using SYBR Green PCR Master Mix (Invitrogen/Applied Biosystem, Carlsbad, Calif., USA) and ABI Prism 7300 Real-time PCR System (Applied Biosystems, Carlsbad, Calif., USA) according to the manufacturer's instructions. Calculations were performed based on 2-ΔΔCT method using the following equation: R (ratio)=2-[ΔCT (sample)-ΔCT (control group)]. The data were expressed as fold change of the treated group relative to the control group and standardized relative to the glyceraldehyde 3-phosphate dehydrogenase (GAPDH) level. The primers used are shown in Table 3 below.

TABLE 3

| Target Gene | Primer | Nucleotide Sequence | SEQ ID NO |
|---|---|---|---|
| GAPDH | F | 5'-CAACTGGTCGTGGACAACCAT-3' | 1 |
| | R | 5'-GCACGGACACTCACAATGTTC-3' | 2 |
| STAT1 | F | 5'-GTGGAAAGACAGCCCTGC-3' | 3 |
| | R | 5'-TTTACTGTATTTCTCTCATTC-3' | 4 |
| STAT2 | F | 5'-TGCGGAAATTCTGCCGGGAC-3' | 5 |
| | R | 5'-CCAGATTCTCCATCATAGCC-3' | 6 |
| IRF9 | F | 5'-CCCGAAAACTCCGGAACTGGG-3' | 7 |
| | R | 5'-AGGCGAGTCTTCCAGACAGCT-3' | 8 |
| ISG15 | F | 5'-GAGCGTGGCCCACCTGAAGC-3' | 9 |
| | R | 5'-TGAGGCCGTACTCCCCCAGC-3' | 10 |
| OAS1 | F | 5'-CAGCGCCCCACCAAGCTC-3' | 11 |
| | R | 5'-TGCTCCCTCGCTCCCAAGCA-3' | 12 |
| IFNa | F | 5'-TGCAGGAGGAGAGGGTGGGA-3' | 13 |
| | R | 5'-ACCTCCCAGGCACAAGGGCT-3' | 14 |
| Con1b | F | 5'-ACTCCCCGGACGCTGACCTC-3' | 15 |
| | R | 5'-GCAGGATCTCCGCCGGAACG-3' | 16 |

Example 20: Synergy Analysis

In order to confirm whether the combination between NIM811 and IFN-α, ribavirin, or telaprevir is synergistic, additive, or antagonistic, the combination index (CI) was calculated using the CalcuSyn Software (Biosoft). In fact, the combination is additive when CI=1.0, synergistic when CI<1.0, and antagonistic when CI>1.0.

Example 21: Analysis of Toxicity in BALB/c Mice

The toxicity of the administration of WJCPA-126 or CsA was confirmed using 15 female BALB/c mice (6-week old). The experimental animals were divided into three groups (n=5) and one of the groups was used as the untreated control group. The mice groups consisting of five mice were administered intraperitoneally daily with CsA or WJCPA-126 at a dose of 50 mg/kg body weight. Fourteen days after the administration, blood samples were collected from the treat groups and the control group, respectively. The weight of experimental mice was measured for the evaluation of systemic toxicity in mice. For the confirmation of hepatotoxicity, the AST and ALT activities were measured according to the manufacturer's protocols applied to a 96-well microplate using the GOT-GPT kit (Asan Pharm, Korea). The analysis results regarding the AST and ALT activities were shown in IU/L units. For the confirmation of nephrotoxicity, the blood urea nitrogen (BUN) was measured using the Blood Urea Nitrogen Enzymatic Assay kit (Bioo Scientific, Austin, Tex., USA), and the creatine level in the serum was measured using the Mouse Creatine Assay kit (Crystal Chem, Inc., Downers Grove, Ill., USA).

Example 22: RNA Extraction from Liver Tissue

HCV RNA was extracted from liver tissue by Trizol method. Mouse liver tissues were mechanically destroyed and lysed in Trizol (Invitrogen, Carlsbad, Calif., USA). The quantitative analysis of HCV RNA was performed using real-time transcription PCR.

Example 23: Immunofluorescent Analysis

HCV replicon Cells were seeded onto the coverslips within a 12-well plate to about 70% confluence for 24 hours. For fixation, the cells were washed 3 times with PBS and fixed with 4% paraformaldehyde solution for 20 minutes at room temperature. Then, the cells were washed again 3 times with PBS. For providing permeability, the cells were incubated in PBS containing 0.5% Triton X-100 for 15 minutes, and washed 3 times with PBS before incubating with primary antibody. The primary antibody was diluted to a desired concentration with 1×PBS containing 3% BSA, in general at a ratio of 1:100, to prevent non-specific binding of the antibody. After overnight incubation, the cells washed 3 times with PBS, and incubated with secondary antibody, which was conjugated with anti-rabbit or anti-mouse IgG antibodies (Invitrogen, Calif., USA), which was conjugated with Alexa 488 or Alexa 546 diluted with PBS containing 3% BSA at a ratio of 1:250, for 2 hours. The cells were counterstained with DAPI and mounted onto glass slides (Vector Mount, Calif., USA). The thus-prepared samples were photographed using the Zeiss confocal microscope (Zeiss, Germany).

Experimental Example 1: Structure of WJCPA-126 and Effect of Anti-peptidyl-prolyl Cis/Trans Isomerase (PPIase)

In order to discover inhibitors against the activity of CypA peptidyl-prolyl isomerase, about 100,000 compounds in a compound library were screened, and about 100 virtual hit compounds were selected therefrom. Among the tested compounds, WJCPA-126 was shown to block the PPIase activity and also the most promising lead compound. The chemical structure of WJCPA-126 is illustrated in FIG. 1a and WJCPA-126 is 2-(2-(1H-indol-3-yl)-N-(4-isopropylphenyl)acetamide)-N-cyclohexyl-2-(3,4,5-trimethoxyphenyl)acetamide having a molecular weight of 597.74. From the structure-based virtual screening by computer docking analysis, it was confirmed that WJCPA-126 has a potential binding affinity to the catalytic site of CypA (FIG. 1b). The binding affinity of WJCPA-126 for CypA was measured via SPR technique. WJCPA-126 showed an affinity with a slower dissociation rate (Kon: $8.2 \times 10^3$ $M^{-1}$ $S^{-1}$, Koff: $6.0 \times 10^{-4}$ $S^{-1}$) compared to that of CypA, and CsA showed a faster dissociation rate (Kon: $7.6 \times 10^3$ $M^{-1}$ $S^{-1}$, Koff: $2.4 \times 10^{-2}$ $S^{-1}$). From the dissociation constant calculated from the SPR-based kinetic analysis, it was confirmed that WJCPA-126 binds to CypA with a higher affinity (KD=520 nM) than to CypB (KD=2.1 μM) (FIG. 2, lower panel). In enzyme analysis, the addition of CypA promoted the PPIase activity. As expected, 1 μM concentration of WJCPA-126 showed a strong inhibitory effect against the PPIase activity of CypA, which was slightly higher than that of CsA, the positive control (FIG. 3a). The IC50 values for WJCPA-126 and CsA were respectively determined as 3.5 nM and 5.5 nM by optimizing the data to Graph pad Prism 5 (FIG. 3b). The results suggest that WJCPA-126 has high specificity to CypA and thereby inhibit the PPIase of CypA.

In order to reconfirm the binding specificity of WJCPA-126 to CypA, 2D $^1$H TOCSY NMR was measured and the spectrum was illustrated in FIG. 4. In the spin system of Arg 55, Trp 121, and Phe 113 of CypA, the connectivity was shown in yellow-, green-, and red solid lines. This indicates that the WJCPA-126 compound of the present invention binds to Arg 55, Trp 121, and Phe 113 residues of CypA. From the above result, it was confirmed that the bis-amide compounds of the present invention can specifically bind to Arg 55, Trp 121, and Phe 113 residues of CypA thereby inhibiting the PPIase activity of CypA.

Additionally, a series of compounds (WJCPA-1 to WJCPA-135) having the bis-amide structure as a parent structure in common, based on the inhibitory effect of WJCPA-126 against the PPIase activity, were synthesized and their activities were confirmed. Specifically, Huh7-rep cells were treated with each of the compounds at a concentration of 2 μM for 3 days, and the expression level of NS5A was confirmed by performing an immunoblot analysis according to a known method (FIG. 5). The 32 kinds of compounds confirmed to have excellent inhibitory effect especially against the NS5A expression from the immunoblot experiment were measured regarding their inhibitory effect against luciferase activity and the results are illustrated in FIG. 6. In the same manner as in western blot, the HCV replicon cells were treated with each of the compounds at a concentration of 2 μM and incubated for 72 hours, and the total cell lysate of the cultured cells were used for the analyses of western blot and the activity of luciferase. As a result, it was confirmed that the compounds having the inhibitory effect against the NS5A expression exhibited a similar pattern of inhibitory effect against luciferase activity.

In particular, WJCPA30 and WJCPA126 significantly inhibited the luciferase activity of HCV up to 80%. The anti-PPIase activity and cytotoxicity for three different kinds of compounds (WJCPA30, WJCPA126, and WJCPA133) were additionally confirmed in HCV replication cells and the results are illustrated in FIGS. 7a and 7b. Each of the compounds showed excellent inhibitory effect against the PPIase activity of CypA, and the $IC_{50}$ values of the compounds were 10.6 nM, 3.6 nM, and 11.2 nM, respectively (FIG. 7a), and the compounds were confirmed to have low cytotoxicities showing the cell viability of 80% or higher up to 10 μM of concentration (FIG. 7b).

The additional effects of WJCPA-126 as the representative bis-amide compound were confirmed in the following experiments.

Experimental Example 2: Effect of WJCPA-126 on the Calcineurin/NFAT/IL-2 Signaling Pathway in Mouse Splenocytes Calcineurin signaling pathway is essential for the productive adaptive immune response. CsA inhibits calcineurin-dependent NFAT activation and IL-2 secretion. Therefore, CsA cannot be used as an antiviral agent and thus there is a need for the development of a CsA non-immunosuppressive analog as an anti-HCV agent. The present inventors examined the effect of WJCPA-126 on calcineurin/NFAT/IL-2 signaling pathway in mouse splenocytes. As a result, it was confirmed that WJCPA-126 showed no cytotoxicity even at a very high concentration (up to 10 μIV) compared to CsA (FIG. 8a). Additionally, WJCPA-126 showed no inhibitory effect against the activity of ionomycin-stimulating calcineurin phosphorylase (FIG. 8b) and maintained the dephosphorylated state of NFAT1 under stimulated condition (FIG. 9a). The dephosphorylated NFAT1 migrated into the nucleus and the migration was inhibited by CsA, as reported previously. In contrast, the WJCPA-126 treatment followed by ionomycin stimulation showed a significant localization of NFAT1 within the nucleus (FIG. 9b). Conclusively, CsA almost completely inhibited the secretion of IL-2 while WJCPA-126 did not show any inhibitory activity against the ionomycin-induced IL-2 production even at a concentration of 10 μM (FIG. 9c). In summary, all data showed that WJCPA-126, unlike CsA, did not show any inhibitory effect against the calcineurin/NFAT/IL-2 signaling pathway, and this suggests that WJCPA-126 is a novel non-immunosuppressive CypA inhibitor.

Experimental Example 3: Antiviral Effect of WJCPA-126 in HCV Replicon Cells

CsA is known to reduce HCV replication by inhibiting the isomerization of the peptidyl-prolyl binding in NS5A and NS5B. Since WJCPA-126 exhibits an inhibitory effect against the PPIase activity, the effect of WJCPA-126 as a CypA inhibitor on HCV replication was confirmed. As illustrated in FIG. 10a, the increase in the concentration of WJCPA-126 (0.5 μM to 4 μM) caused a decrease in the levels of NS5A and NS5B proteins in a dose-dependent manner.

CypA is known to play an important role in the formation of a membrane-related replication complex and thus the effects of WJCPA-126 regarding the use of not only the total cell lysate but also the fractionated membrane of the replicon cell were examined. WJCPA-126 was shown to decrease the protein levels of NS5A and NS5B in both the total lysate and the membrane fraction. The decrease of the CypA level in the membrane fraction without any effect on the total protein level suggests that WJCPA-126 blocks the introduction of CypA regarding the formation of the replication complex (FIG. 10b). Additionally, WJCPA-126 was shown to mainly decrease the levels of localized NS5A and NS5B in the perinuclear region of the replicon cells (FIG. 10c). WJCPA-12 showed a potential antiviral activity while also showing a low cytotoxicity in genotype 1b (Con1b, $EC_{50}=0.73\pm0.1$ μM)– and 2a (JFH1, $EC_{50}=1.1\pm0.05$ μM) replication cells (12.4±2.1 μM and 22.3±4.23 μM $CC_{50}$, respectively) (FIGS. 11a and 11b). Conclusively, these results support that WJCPA-126 is a strong inhibitor against HCV replication.

Experimental Example 4: Inhibitory Effect of WJCPA-126 Against the Protein-Protein Interaction Between a Viral Non-Structural Protein and Cyclophilin A It is well known that CypA binds to the domains II and III of NS5A and the C-terminus of NS5B. In this regard, the present inventors have studied the biochemical mechanism on the inhibitory actions of WJCPA-126 against HCV replication. The in vitro pull-down analysis suggested an evidence that the PPIase mutant (R55A) of CypA cannot completely bind to NS5A and NS5B, whereas the the isomerase active site of CypA is necessary for the interaction with a viral protein (FIG. 12a). WJCPA-126 at concentrations of 2 μM and 4 μM caused a significant decrease of the binding between GST-CypA and NS5A or NS5B, in a dose-dependent manner (FIG. 12b). The reversed experiment with GST-NS5A and GST-NS5B showed similar results (FIGS. 12c and 12d). Additionally, in light of the coimmunoprecipitation (FIG. 13a) and the mammalian two-hybrid analysis (FIG. 13b), it was confirmed that WJCPA-126 destroys the interactions between CypA and NS5A or NS5B. Conclusively, these results indicate that WJCPA-126 achieves the antiviral effect by the inhibition of CypA PPIase activity, similarly as in the case of CsA.

Experimental Example 5: Effects of WJCPA-126 on Induction of Expression of Interferon-Stimulated Gene (ISG) and Inhibition of IL-8 Production HCV NS5A prevents the IFN-activated JAK-STAT (Janus kinase-signal transducer and activator of transcription) pathway and thereby reduces the expression of the response of downstream interferon-stimulated gene (ISG). Recently, it was reported that a CypA inhibitor exhibits an antiviral activity by controlling the host cell innate immune response. In order to confirm the effect of WJCPA-126 on the host cell innate immune response, the expression of classical antivirus ISG was analyzed. WJCPA-126 was shown to increase the mRNA expression levels of STAT1, STAT2, IRF9, OAS1, and ISG15 in a time-dependent manner (FIG. 14). Additionally, an immunoblot analysis also showed a similar result (FIG. 15a). Additionally, previous studies suggested that NS5A may be involved in the inhibition of interferon antiviral activity by inducing IL-8. The present inventors confirmed that WJCPA-126 causes a significant reduction of mRNA level of IL-8 in a time-dependent manner (FIG. 15b). The present inventors also confirmed that WJCPA-126 significantly reduces the expression of IL-8 production in a HCV replicon cell in a time-dependent manner (FIG. 15c). Additionally, they also confirmed that WJCPA-126 cannot control the mRNA level of IFN-α, 48 hours after the treatment (FIG. 15d). WJCPA-126 was shown to significantly increase the IFN-α production although IFN-α could not be detected in the HCV replicon cell (FIG. 15e). It is known that the combined treatment of a CypA inhibitor and IFN-α can induce a higher level of antiviral response compared to when treated with IFN-α alone. More importantly, the treatment of WJCPA-126 in combination with telaprevir, IFN-α, or ribavirin exhibited a synergistic decrease of the levels of HCV-s-specific RNA and IL-8, compared to when treated with any of telaprevir, IFN-α, or ribavirin alone (FIG. 16). In all the experiments above, WJCPA-126 was shown to be slightly more effective than that of the positive control, CsA. In summary, the above data indicates that WJCPA-126 can improve the host immune response by the ISG stimulation and the inhibition of IL-8.

Experimental Example 6: In Vivo Efficiency of WJCPA-126 in a HCV Mouse Model

The toxicity of WJCPA-126 was tested by measuring the serum enzyme levels (alanine aminotransferase (ALT) and aspartate aminotransferase (AST)) as hepatotoxicity markers and the levels of BUN and creatine as new hepatotoxicity markers using BALB/c mice. Unlike CsA, the WJCPA-126 treatment was tolerated and did not induce any noticeable change on safety parameters, such as body weight and serum concentrations of ALT, AST, BUN, and creanitine, thus confirming that WJCPA-126 does not induce hepatotoxicities or nephrotoxicities (FIG. 17). In order to confirm the in vivo antiviral effect of WJCPA-126, the control Huh7 cells or the Huh7 cells including the HCV-Con1b replicon were injected into the splenocytes of immunodeficient NOD/SCID mice in a method known in the art to be transfected. For six weeks after the cell transplantation, two groups (5 mice/group) were used for the drug treatment, and the drug treatment was continued for additional two weeks (FIG. 18a). Before the drug treatment, the histological examination of the Huh7 and the HCV-Con1b replicon cells transplanted into mouse liver samples were visualized by H&E staining (FIG. 18b). The mice treated with WJCPA-126 did not show any noticeable change in body weight unlike the group treated with CsA, which showed a decrease of body weight (FIG. 19a). Additionally, the WJCPA-126 treatment showed a relatively higher level of inhibition on the HCV RNA level than the CsA treatment (FIG. 19b). The western blot analysis also showed a similar result (FIG. 19c). Finally, the expression level of NS5A was visualized by staining the mouse liver tissues transplanted with the HCV replicon cells with human hepatocytes marker (Hep par 1) and HCV NS5A. As expected, HCV NS5A was detected in human hepatocytes, which was used as a control group. However, HCV NS5A was only faintly detected after the treatment with WJCPA-126 or CsA, and the result indicates the increase of the viral protein level by the two compounds (FIG. 20). In summary, the above results suggest that WJCPA-126 can effectively inhibit HCV replication in human replicon cells transplanted into a mouse liver.

Experimental Example 7: Antiviral Effect by the Combined Treatment of WJCPA-126 and IFN-α, Ribavirin or Telaprevir Due to high rate incidence of viral resistance, a combination of multiple drugs having different action mechanism for the effective treatment of HCV infection. Alisprovir is known to exhibit a slightly syngergistic antiviral effect when treated in combination with IFN-α. Accordingly, the present inventors performed experiments for the identification of antiviral effects of WJCPA-126 in combined treatment with IFN-α, RBV, or telaprevir. WJCPA-126, as a CypA inhibitor, did not show any noticeable cytotoxicity when treated in combination with IFN-α, RBV, or telaprevir (FIG. 16a). As illustrated in FIG. 16b, the treatment of WJCPA-126 in combination with IFN-α, RBV, or telaprevir showed a synergistic inhibitory effect on the HCV RNA level. The combination index represents that the combination is additive when CI=1.0, synergistic when CI<1.0, and antagonistic when CI>1.0. The combination of WJCPA-126 with IFN-α, RBV, or telaprevir induced CI values of from 0.3 to 0.5 reflecting the synergistic property. A similar synergistic effect was also observed in the inhibition on the IL-8 level (FIG. 16c). The absence of antagonistic property indicates that WJCPA-126 can play an important role in combined treatment.

The invention claimed is:

1. A bis-amide derivative compound of the following Formula 1 or a pharmaceutically acceptable salt thereof:

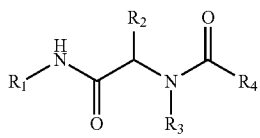

[Formula 1]

wherein:

$R_1$ is $C_1$-$C_6$ linear or branched alkyl, unsubstituted or substituted cyclohexyl, or unsubstituted or substituted benzyl;

$R_2$ is multiply substituted phenyl or unsubstituted or multiply substituted naphthyl, in which each substituent is independently $C_2$-$C_4$ alkyl, $C_1$-$C_4$ alkoxy, hydroxy, carboxy, nitro, halogen, or a 5-membered ring comprising a heteroatom formed by an interconnection between two is adjacent substituents;

$R_3$ is unsubstituted or multiply substituted $C_1$-$C_6$ linear or branched alkyl, cyclohexyl, multiply substituted phenyl-$C_1$-$C_4$ alkyl, or unsubstituted or multiply substituted aryl, in which each substituent is independently $C_1$-$C_4$ alkoxy or halogen; and $R_4$ is unsubstituted or multiply substituted $C_1$-$C_6$ linear or branched alkyl, unsubstituted or multiply substituted phenyl, indolyl, or pyridinyl, or unsubstituted or multiply substituted phenylalkyl or indolylalkyl, in which each substituent is independently $C_1$-$C_4$ alkoxy, $C_1$-$C_4$ alkoxybenzyl, nitro, or halogen, with the proviso that when $R_4$ is unsubstituted or substituted indolyl or pyridinyl, the substituted phenyl of $R_2$ is substituted with $C_2$-$C_4$ alkyl, $C_1$-$C_4$ alkoxy, hydroxy, carboxy, nitro, or a 5-membered ring comprising a heteroatom formed by an interconnection between two adjacent substituents, wherein the substituted functional group of $R_1$ and $R_3$ includes one or more substituents selected from the group consisting of halogen, CN, $CF_3$, hydroxy, $C_1$-$C_6$ alkyl, and $C_1$-$C_6$ alkoxy.

2. The bis-amide derivative compound or a pharmaceutically acceptable salt thereof of claim 1,
wherein:
$R_1$ is $C_1$-$C_6$ linear or branched alkyl, cyclohexyl, or benzyl.

3. The bis-amide derivative compound or a pharmaceutically acceptable salt thereof of claim 1,
wherein:
$R_1$ is n-pentyl, tert-butyl, cyclohexyl, or benzyl;
$R_2$ is naphthyl, 4-ethylphenyl, 4-hydroxyphenyl, 4-carboxyphenyl, 4-nitrophenyl, 4-fluorophenyl, 4-chlorophenyl, 3,4-dichlorophenyl, 3-methoxy-4-hydroxyphenyl, 3,4-dimethoxyphenyl, 2,3,4-trimethoxyphenyl, 3,4,5-trimethoxyphenyl, or benzo[1,3]dioxol-5-yl;
$R_3$ is n-butyl, 2,2-dimethoxyethyl, cyclohexyl, naphthyl, 4-bromophenyl, 4-fluorophenyl, 2-methoxyphenyl, 4-methoxyphenyl, 3,4-dimethoxyphenyl, 4-isopropylphenyl, 4-methoxybenzyl, 3-methoxyphenylethyl, or 3,4-dimethoxyphenylethyl; and $R_4$ is methyl, ethyl, n-propyl, n-butyl, n-pentyl, tert-butyl, chloromethyl, 1-bromopentyl, phenyl, 2-methylphenyl, 2,3-dimethylphenyl, 2,5-dimethylphenyl, 2-methyl-5-nitrophenyl, 2-nitro-5-methoxyphenyl, 2-nitro-4-chlorophenyl, 6-chloropyridin-3-yl, indol-2-yl, indol-3-ylmethyl, (1-(4-methoxybenzyl)-indol-3-yl)methyl, 3-methoxyphenylethyl, or 4-methoxyphenylethyl, with the proviso that when $R_4$ is indol-2-yl or 6-chloropyridinyl, $R_2$ is naphthyl, 4-ethylphenyl, 6-hydroxyphenyl, 4-carboxyphenyl, 4-nitrophenyl, 3-methoxy-4-hydroxyphenyl, 3,4-dimethoxyphenyl, 2,3,4-trimethoxyphenyl, 3,4,5-trimethoxyphenyl, or benzo[1,3]dioxol-5-yl.

4. The bis-amide derivative compound or a pharmaceutically acceptable salt thereof of claim 3, wherein the compound of Formula 1 is selected from the group consisting of:

N-cyclohexyl-2-[(2-1H-indol-3-yl-acetyl)-phenyl-amino]-2-(3,4,5-trimethoxy-phenyl)-acetamide, N-cyclohexyl-2-[(2-1H-indol-3-yl-acetyl)-(4-methoxy-phenyl)-amino]-2-(3,4,5-trimethoxy-phenyl)-acetamide, N-cyclohexyl-2-[(2-1H-indol-3-yl-acetyl)-(2-methoxy-phenyl)-amino]-2-(3,4,5-trimethoxy-phenyl)-acetamide, N-cyclohexyl-2-[(2-1H-indol-3-yl-acetyl)-naphthalen-1-yl-amino]-2-(3,4,5-trimethoxy-phenyl)-acetamide, 2-[butyl-(2-1H-indol-3-yl-acetyl)-amino]-N-cyclohexyl-2-(3,4,5-trimethoxy-phenyl)-acetamide, N-cyclohexyl-2-[[2-(3,4-dimethoxy-phenyl)-ethyl]-(2-1H-indol-3-yl-acetyl)-amino]-2-(3,4,5-trimethoxy-phenyl)-acetamide, N-[cyclohexylcarbamoyl-(3,4,5-trimethoxy-phenyl)-methyl]-N-(4-isopropyl-phenyl)-benzamide, N-cyclohexyl-2-[(2-1H-indol-3-yl-acetyl)-amino]-2-(3,4,5-trimethoxy-phenyl)-acetamide, 2-[(4-bromo-phenyl)-(2-1H-indol-3-yl-acetyl)-amino]-N-cyclohexyl-2-(2,3,4-trimethoxy-phenyl)-acetamide, N-cyclohexyl-2-[(3,4-dimethoxy-phenyl)-(2-1H-indol-3-yl-acetyl)-amino]-2-(3,4,5-trimethoxy-phenyl)-acetamide, N-cyclohexyl-2-[(2-1H-indol-3-yl-acetyl)-(4-isopropyl-phenyl)-amino]-2-(3,4,5-trimethoxy-phenyl)-acetamide, N-[cyclohexylcarbamoyl-(2,3,4-trimethoxy-phenyl)-methyl]-N-(4-isopropyl-phenyl)-benzamide, N-cyclohexyl-2-(3,4-dimethoxy-phenyl)-2-[(2-1H-indol-3-yl-acetyl)-(4-isopropyl-phenyl)-amino]-acetamide, N-cyclohexyl-2-(3,4-dimethoxy-phenyl)-2-[(3,4-dimethoxy-phenyl)-(2-1H-indol-3-yl-acetyl)-amino]-acetamide, N-cyclohexyl-2-[cyclohexyl-(2-1H-indol-3-yl-acetyl)-amino]-2-(3,4-dimethoxy-phenyl)-acetamide, N-cyclohexyl-2-[(2,2-dimethoxy-ethyl)-(2-1H-indol-3-yl-acetyl)-amino]-2-(3,4-dimethoxy-phenyl)-acetamide, N-cyclohexyl-2-[(2-1H-indol-3-yl-acetyl)-phenyl-amino]-2-(4-nitro-phenyl)-acetamide, N-cyclohexyl-2-[(2-1H-indol-3-yl-acetyl)-(4-methoxy-benzyl)-amino]-2-(4-nitro-phenyl)-acetamide, N-cyclohexyl-2-[(3,4-dimethoxy-phenyl)-(2-1H-indol-3-yl-acetyl)-amino]-2-(4-nitro-phenyl)-acetamide, 2-[(4-bromo-phenyl)-(2-1H-indol-3-yl-acetyl)-amino]-N-cyclohexyl-2-(4-nitro-phenyl)-acetamide, N-cyclohexyl-2-[(2-1H-indol-3-yl-acetyl)-(4-isopropyl-phenyl)-amino]-2-(4-nitro-phenyl)-acetamide, N-[cyclohexylcarbamoyl-(4-hydroxy-3-methoxy-phenyl)-methyl]-N-(4-isopropyl-phenyl)-3-(4-methoxy-phenyl)-propionamide, N-cyclohexyl-2-[(3,4-dimethoxy-phenyl)-(2-1H-indol-3-yl-acetyl)-amino]-2-(4-hydroxy-phenyl)-acetamide, 2-bromo-hexanoic acid [cyclohexylcarbamoyl-(4-hydroxy-phenyl)-methyl]-(3,4-dimethoxy-phenyl)-amide, N-[cyclohexylcarbamoyl-(4-hydroxy-phenyl)-methyl]-N-(3,4-dimethoxy-phenyl)-3-(3-methoxy-phenyl)-propionamide, 2-(4-chloro-phenyl)-N-cyclohexyl-2-[(2-1H-indol-3-yl-acetyl)-phenyl-amino]-acetamide, N-[(4-chloro-phenyl)-cyclohexylcarbamoyl-methyl]-N-(4-isopropyl-phenyl)-benzamide, N-[(4-chloro-phenyl)-cyclohexylcarbamoyl-methyl]-N-(4-isopropyl-phenyl)-3-(4-methoxy-phenyl)-propionamide, N-[(4-chloro-phenyl)-cyclohexylcarbamoyl-methyl]-N-(4-isopropyl-phenyl)-2,5-dimethyl-benzamide, 2-[(4-bromo-phenyl)-(2-1H-indol-3-yl-acetyl)-amino]-2-(4-chloro-phenyl)-N-cyclohexyl-acetamide, 2-(4-chloro-phenyl)-N-cyclohexyl-2-[(3,4-dimethoxy-phenyl)-(2-1H-indol-3-yl-acetyl)-amino]-acetamide, 2-(4-chloro-phenyl)-N-cyclohexyl-2-[(2-1H-indol-3-yl-acetyl)-(4-isopropyl-phenyl)-amino]-acetamide, 2-(4-chloro-phenyl)-N-cyclohexyl-2-[(2-1H-indol-3-yl-acetyl)-(4-methoxy-phenyl)-amino]-acetamide, N-[(4-chloro-phenyl)-cyclohexylcarbamoyl-methyl]-N-(3,4-dimethoxy-phenyl)-3-(4-methoxy-phenyl)-propionamide, 2-benzo[1,3]dioxol-5-yl-2-[butyl-(2-1H-indol-3-yl-acetyl)-amino]-N-cyclohexyl-acetamide, N-cyclohexyl-2-(4-ethyl-phenyl)-2-[(2-1H-indol-3-yl-acetyl)-phenyl-amino]-acetamide, 2-[(4-bromo-phenyl)-(2-1H-indol-3-yl-acetyl)-amino]-N-tert-butyl-2-(4-nitro-phenyl)-acetamide, N-(4-bromo-phenyl)-N-[tert-butylcarbamoyl-(4-nitro-phenyl)-methyl]-5-methoxy-2-nitro-benzamide, N-tert-butyl-2-(4-chloro-phenyl)-2-[(2-1H-indol-3-yl-acetyl)-(4-isopropyl-phenyl)-amino]-acetamide, N-[tert-butylcarbamoyl-(4-chloro-phenyl)-methyl]-N-(4-isopropyl-phenyl)-5-methoxy-2-nitro-benzamide, N-[tert-butylcarbamoyl-(4-chloro-phenyl)-methyl]-N-(4-isopropyl-phenyl)-3-(3-methoxy-phenyl)-propionamide, N-cyclohexyl-2-(3,4-dimethoxy-phenyl)-2-[(2-1H-indol-3-yl-acetyl)-(4-methoxy-phenyl)-amino]-acetamide, N-[cyclohexylcarbamoyl-(3,4-dimethoxy-phenyl)-methyl]-3-(3-methoxy-phenyl-N-(4-methoxy-phenyl)-propionamide, N-tert-butyl-2-[(2-1H-indol-3-yl-acetyl)-(4-isopropyl-phenyl)-amino]-2-(3,4,5-trimethoxy-phenyl)-acetamide, N-[tert-butylcarbamoyl-(3,4,5-trimethoxy-phenyl)-methyl]-6-chloro-N-(4-isopropyl-phenyl)-nicotinamide, N-[cyclohexylcarbamoyl-(4-hydroxy-phenyl)-methyl]-N-(3,4-dimethoxy-phenyl)-2-methyl-benzamide, N-(4-bromo-phenyl)-5-methoxy-2-nitro-N-[(4-nitro-phenyl)-pentylcarbamoyl-methyl]-benzamide, 1H-indol-2-carboxylic acid [cyclohexylcarbamoyl-(3,4,5-trimethoxy-phenyl)-methyl]-(4-isopropyl-phenyl)-amide, 6-chloro-N-[cyclohexylcarbamoyl-(3,4,5-trimethoxy-phenyl)-methyl]-N-(4-isopropyl-phenyl)-nicotinamide, N-[cyclohexylcarbamoyl-(3,4,5-trimethoxy-phenyl)-methyl]-N-(4-isopropyl-phenyl)-5-methoxy-2-nitro-benzamide, N-[cyclohexylcarbamoyl-(4-nitro-phenyl)-methyl]-N-(3,4-dimethoxy-phenyl)-5-methoxy-2-nitro-benzamide, N-[cyclohexylcarbamoyl-(4-nitro-phenyl)-methyl]-N-(3,4-dimethoxy-phenyl)-3-(4-methoxy-phenyl)-propionamide, 6-chloro-N-[cyclohexylcarbamoyl-(4-nitro-phenyl)-methyl]-N-(3,4-dimethoxy-phenyl)-nicotinamide, 2-[acetyl-(3,4-dimethoxy-phenyl)-amino]-N-cyclohexyl-2-(4-nitro-phenyl)-acetamide, N-[cyclohexylcarbamoyl-(4-nitro-phenyl)-methyl]-N-(3,4-dimethoxy-phenyl)-2,5-dimethyl-benzamide, N-cyclohexyl-2-[[2-(3,4-dimethoxy-phenyl)-ethyl]-(2-1H-indol-3-yl-acetyl)-amino]-2-(4-nitro-phenyl)-acetamide, 2-{(2-chloro-acetyl)-[2-(3,4-dimethoxy-phenyl)-ethyl]-amino}-N-cyclohexyl-2-(4-nitro-phenyl)-acetamide, N-[cyclohexylcarbamoyl-(4-nitro-phenyl)-methyl]-N-[2-(3,4-dimethoxy-phenyl)-ethyl]-2-methyl-5-nitro-benzamide, N-[cyclohexylcarbamoyl-(4-nitro-phenyl)-methyl]-N-[2-(3,4-dimethoxy-phenyl)-ethyl]-5-methoxy-2-nitro-benzamide, N-[cyclohexylcarbamoyl-(4-nitro-phenyl)-methyl]-N-(3,4-dimethoxy-phenyl)-2-methyl-benzamide, N-[cyclohexylcarbamoyl-(4-nitro-phenyl)-methyl]-N-(3,4-dimethoxy-phenyl)-2,2-dimethyl-propionamide, N-[cyclohexylcarbamoyl-(4-nitro-phenyl)-methyl]-5-methoxy-N-[2-(3-methoxy-phenyl)-ethyl]-2-nitro-benzamide, 2-{acetyl-[2-(3-methoxy-phenyl)-ethyl]-amino}-N-cyclohexyl-2-(4-nitro-phenyl)-acetamide, 6-chloro-N-[cyclohexylcarbamoyl-(4-nitro-phenyl)-methyl]-N-[2-(3-methoxy-phenyl)-ethyl]-nicotinamide, N-[cyclohexylcarbamoyl-(4-nitro-phenyl)-methyl]-N-[2-(3-methoxy-phenyl)-ethyl]-benzamide, N-benzyl-2-(4-nitro-phenyl)-2-[(2-1H-indol-3-yl-acetyl)-(4-isopropyl-phenyl)-amino]-acetamide, N-benzyl-2-[(2-chloro-acetyl)-(4-isopropyl-phenyl)-amino]-2-(4-chloro-phenyl)-acetamide, 2-[(2-chloro-acetyl)-(4-isopropyl-phenyl)-amino]-2-(4-chloro-phenyl)-N-pentyl-acetamide, 2-{(2-chloro-acetyl)-[2-(3,4-dimethoxy-phenyl)-ethyl]-amino}-2-(4-hydroxy-phenyl)-N-pentyl-acetamide, 2-[acetyl-(3,4-dimethoxy-phenyl)-amino]-2-(4-hydroxy-phenyl)-N-pentyl-acetamide, N-(3,4-dimethoxy-phenyl)-N-[(4-hydroxy-phenyl)-pentylcarbamoyl-methyl]-benzamide, N-(3,4-dimethoxy-phenyl)-N-[(4-hydroxy-phenyl)-pentylcarbamoyl-methyl]-butyramide, hexanoic acid (3,4-dimethoxy-phenyl)-[(4-hydroxy-phenyl)-pentylcarbamoyl-methyl]-amide, N-(3,4-dimethoxy-phenyl)-N-[(4-hydroxy-phenyl)-pentylcarbamoyl-methyl]-propionamide, N-benzyl-2-(4-chloro-phenyl)-2-[(2-1H-indol-3-yl-acetyl)-(4-methoxy-phenyl)-amino]-acetamide, 2-(4-fluoro-phenyl)-2-[(2-1H-indol-3-yl-acetyl)-(4-methoxy-phenyl)-amino]-N-pentyl-acetamide, N-cyclohexyl-2-(3,4-dichloro-phenyl)-2-[(2-1H-indol-3-yl-acetyl)-(4-methoxy-phenyl)-amino]-acetamide, N-benzyl-2-(3,4-dichloro-phenyl)-2-[(2-1H-indol-3-yl-acetyl)-(4-methoxy-phenyl)-amino]-acetamide, 2-(3,4-dichloro-phenyl)-2-[(2-1H-indol-3-yl-acetyl)-(4-methoxy-phenyl)-amino]-N-pentyl-acetamide, N-cyclohexyl-2-[(3,4-dimethoxy-phenyl)-(2-1H-indol-3-yl-acetyl)-amino]-2-(3,4,5-trimethoxy-phenyl)-acetamide, N-cyclohexyl-2-[(3,4-dimethoxy-phenyl)-2-[(2-1H-indol-3-yl-acetyl)-phenyl-amino]-acetamide, N-cyclohexyl-2-[[(2-1H-indol-3-yl-acetyl)-(4-methoxy-phenyl)-amino]-2-(4-nitro-phenyl)-acetamide, N-(4-bromo-phenyl)-N-[cyclohexylcarbamoyl-(4-nitro-phenyl)-methyl]-3-(3-methoxy-phenyl)-propionamide, N-cyclohexyl-2-(4-hydroxy-3-methoxy-phenyl)-2-[(2-1H-indol-3-yl-acetyl)-(4-isopropyl-phenyl)-amino]-acetamide, N-[cyclohexylcarbamoyl-(4-hydroxy-3-methoxy-phenyl)-methyl]-N-(4-isopropyl-phenyl)-benzamide, N-[tert-butylcarbamoyl-(4-hydroxy-phenyl)-methyl]-N-(3,4-dimethoxy-phenyl)-2,2-dimethyl-propionamide, N-tert-butyl-2-[(3,4-dimethoxy-phenyl)-(2-1H-indol-3-yl-acetyl)-amino]-2-(4-hydroxy-phenyl)-acetamide, N-cyclohexyl-2-[(2-1H-indol-3-yl-acetyl)-(4-isopropyl-phenyl)-amino]-2-naphthalen-1-yl-acetamide, 2-(4-chloro-phenyl)-N-cyclohexyl-2-[(2-1H-indol-3-yl-acetyl)-(4-methoxy-phenyl)-amino]-acetamide, 6-chloro-N-[cyclohexylcarbamoyl-(4-hydroxy-phenyl)-methyl]-N-(3,4-dimethoxy-phenyl)-nicotinamide, N-[cyclohexylcarbamoyl-(4-hydroxy-phenyl)-methyl]-N-(3,4-dimethoxy-phenyl)-2,3-dimethyl-benzamide, N-cyclohexyl-2-(4-hydroxy-phenyl)-2-[(2-1H-indol-3-yl-acetyl)-phenyl-amino]-acetamide, N-[tert-butylcarbamoyl-(4-hydroxy-phenyl)-methyl]-N-(3,4-dimethoxy-phenyl)-3-(3-methoxy-phenyl)-propionamide, 1H-indol-2-carboxylic acid [tert-butylcarbamoyl-(3,4,5-trimethoxy-phenyl)-methyl]-(4-isopropyl-phenyl)-amide, N-(3,4-dimethoxy-phenyl)-N-[(4-hydroxy-phenyl)-pentylcarbamoyl-methyl]-3-(4-methoxy-phenyl)-propionamide, 2-[(3,4-dimethoxy-phenyl)-(2-1H-indol-3-yl-acetyl)-amino]-2-(4-hydroxy-phenyl)-N-pentyl-acetamide, 4-chloro-N-[cyclohexylcarbamoyl-(4-hydroxy-phenyl)-methyl]-N-(3,4-dimethoxy-phenyl)-2-nitro-benzamide, N-[(4-chloro-phenyl)-cyclohexylcarbamoyl-methyl]-N-(4-isopropyl-phenyl)-2-methyl-benzamide, 2-[acetyl-(4-isopropyl-phenyl)-amino]-2-(4-chloro-phenyl)-N-cyclohexyl-acetamide, 2-[(4-bromo-phenyl)-(2-1H-indol-3-yl-acetyl)-amino]-2-(4-nitro-phenyl)-N-pentyl-acetamide, N-(4-bromo-phenyl)-6-chloro-N-[(4-nitro-phenyl)-pentylcarbamoyl-methyl]-nicotinamide, 4-chloro-N-[cyclohexylcarbamoyl-(4-nitro-phenyl)-methyl]-N-(3,4-dimethoxy-phenyl)-2-nitro-benzamide, 2-[(2-chloro-acetyl)-(3,4-dimethoxy-phenyl)-amino]-N-cyclohexyl-2-(4-nitro-phenyl)-acetamide, 1H-indol-2-carboxylic acid [cyclohexylcarbamoyl-(4-nitro-phenyl)-methyl]-(3,4-dimethoxy-phenyl)-amide, N-[cyclohexylcarbamoyl-(4-nitro-phenyl)-methyl]-N-[2-(3,4-dimethoxy-phenyl)-ethyl]-benzamide, 2-{acetyl-[2-(3,4-dimethoxy-phenyl)-ethyl]-amino}-N-cyclohexyl-2-(4-nitro-phenyl)-acetamide, 1H-indol-2-carboxylic acid [cyclohexylcarbamoyl-(4-nitro-phenyl)-methyl]-[2-(3,4-dimethoxy-phenyl)-ethyl]-amide,
N-[cyclohexylcarbamoyl-(4-nitro-phenyl)-methyl]-[2-(3,4-dimethoxy-phenyl)-ethyl]-2,2-dimethyl-propionamide,
N-cyclohexyl-2-{(2-1H-indol-3-yl-acetyl)-[2-(3-methoxy-phenyl)-ethyl]-amino}-2-(4-nitro-phenyl)-acetamide,
2-{(2-chloro-acetyl)-[2-(3-methoxy-phenyl)-ethyl]-amino}-N-cyclohexyl-2-(4-nitro-phenyl)-acetamide,
2-[(2-chloro-acetyl)-(4-isopropyl-phenyl)-amino]-2-(4-chloro-phenyl)-N-cyclohexyl-acetamide,
N-[(4-chloro-phenyl)-pentylcarbamoyl-methyl]-N-(4-isopropyl-phenyl)-benzamide,
2-[(2-chloro-acetyl)-(4-methoxy-phenyl)-amino]-2-(4-hydroxy-phenyl)-N-pentyl-acetamide,
2-bromo-hexanoic acid (3,4-dimethoxy-phenyl)-[(4-hydroxy-phenyl)-pentylcarbamoyl-methyl]-amide,
N-(3,4-dimethoxy-phenyl)-N-[(4-hydroxy-phenyl)-pentylcarbamoyl-methyl]-2,2-dimethyl-propionamide,
pentanoic acid (3,4-dimethoxy-phenyl)-[(4-hydroxy-phenyl)-pentylcarbamoyl-methyl]-amide,
6-chloro-N-(3,4-dimethoxy-phenyl)-N-[(4-hydroxy-phenyl)-pentylcarbamoyl-methyl]-nicotinamide,
1H-indol-2-carboxylic acid (3,4-dimethoxy-phenyl)-[(4-hydroxy-phenyl)-pentylcarbamoyl-methyl]-amide,
pentanoic acid (benzo[1,3]dioxol-5-yl-pentylcarbamoyl-methyl)-(3,4-dimethoxy-phenyl)-amide,
N-cyclohexyl-2-(4-fluoro-phenyl)-2-[(2-1H-indol-3-yl-acetyl)-(4-methoxy-phenyl)-amino]-acetamide,
N-benzyl-2-(4-fluoro-phenyl)-2-[(2-1H-indol-3-yl-acetyl)-(4-methoxy-phenyl)-amino]-acetamide,
4-{cyclohexylcarbamoyl-[(2-1H-indol-3-yl-acetyl)-(4-methoxy-phenyl)-amino]-methyl}-benzoic acid,
2-(4-chloro-phenyl)-2-[(2-1H-indol-3-yl-acetyl)-(4-methoxy-phenyl)-amino]-N-pentyl-acetic acid,
N-cyclohexyl-2-[(2-1H-indol-3-yl-acetyl)-(4-isopropyl-phenyl)-amino]-2-(3,4,5-trimethoxy-phenyl)-acetamide,
2-[(2-chloro-acetyl)-(3,4-dimethoxy-phenyl)-amino]-2-(4-hydroxy-phenyl)-N-pentyl-acetamide,
1H-indol-2-carboxylic acid [cyclohexylcarbamoyl-(4-nitro-phenyl)-methyl-[2-(3-methoxy-phenyl)-ethyl]-amide,
2-[(2-chloro-acetyl)-(3,4-dimethoxy-phenyl)-amino]-2-(4-chloro-phenyl)-N-pentyl-acetamide,
2-[(2-chloro-acetyl)-(4-isopropyl-phenyl)-amino]-2-(4-hydroxy-phenyl)-N-pentyl-acetamide,
2-[(2-chloro-acetyl)-(4-fluoro-phenyl)-amino]-2-(4-hydroxy-phenyl)-N-pentyl-acetamide,
2-benzo[1,3]dioxol-5-yl-2-[(2-chloro-acetyl)-(3,4-dimethoxy-phenyl)-amino]-N-pentyl-acetamide,
N-(4-bromo-phenyl)-N-[cyclohexylcarbamoyl-(4-nitro-phenyl)-methyl]-3-(4-methoxy-phenyl)-propionamide,
6-chloro-N-[cyclohexylcarbamoyl-(3,4-dimethoxy-phenyl)-methyl]-N-(4-methoxy-phenyl)-nicotinamide, and
N-[(4-chloro-phenyl)-cyclohexylcarbamoyl-methyl]-N-(4-isopropyl-phenyl)-3-(3-methoxy-phenyl)-propionamide.

5. A method for preparing a bis-amide derivative compound of Formula 1 comprising reacting an isocyanide derivative ($R_1$—NC) and a carboxylic acid derivative ($R_4$—COOH) with an aldehyde derivative ($R_2$—CHO) and an amine derivative ($R_3$—$NH_2$) or an imine derivative ($R_2$—C=N—$R_3$):

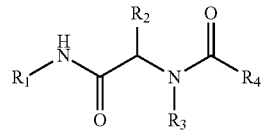

[Formula 1]

wherein:
$R_1$ is $C_1$-$C_6$ linear or branched alkyl, unsubstituted or substituted cyclohexyl, or unsubstituted or substituted benzyl;
$R_2$ is multiply substituted phenyl or unsubstituted or multiply substituted naphthyl, in which each substituent is independently $C_2$-$C_4$ alkyl, $C_1$-$C_4$ alkoxy, hydroxy, carboxy, nitro, halogen, or a 5-membered ring comprising a heteroatom formed by an interconnection between two adjacent substituents;
$R_3$ is unsubstituted or multiply substituted $C_1$-$C_6$ linear or branched alkyl, cyclohexyl, multiply substituted phenyl-$C_1$-$C_4$ alkyl, or unsubstituted or multiply substituted aryl, in which each substituent is independently $C_1$-$C_4$ alkoxy or halogen; and
$R_4$ is unsubstituted or multiply substituted $C_1$-$C_6$ linear or branched alkyl, unsubstituted or multiply substituted phenyl, indolyl, or pyridinyl, or unsubstituted or multiply substituted phenylalkyl or indolylalkyl, in which each substituent is independently $C_1$-$C_4$ alkoxy, $C_1$-$C_4$ alkoxybenzyl, nitro, or halogen,
with the proviso that when $R_4$ is unsubstituted or substituted indolyl or pyridinyl, the substituted phenyl of $R_2$ is substituted with $C_2$-$C_4$ alkyl, $C_1$-$C_4$ alkoxy, hydroxy, carboxy, nitro, or a 5-membered ring comprising a heteroatom formed by an interconnection between two adjacent substituents,
wherein the substituted functional group of $R_1$ and $R_3$ includes one or more substituents selected from the group consisting of halogen, CN, $CF_3$, hydroxy, $C_1$-$C_6$ alkyl, and $C_1$-$C_6$ alkoxy.

6. The method of claim 5, wherein the reaction is performed at a temperature from 20° C. to 60° C. using a $C_1$-$C_4$ alkyl alcohol or haloalcohol as a solvent.

7. The method of claim 6, wherein the solvent is methanol or 2,2,2-trifluoroethanol.

8. The method of claim 5, further comprising preparing an imine derivative ($R_2$—C=N—$R_3$) by reacting an aldehyde derivative ($R_2$—CHO) with an amine derivative ($R_3$—$NH_2$), before the reaction.

9. The method of claim 8, wherein the reaction is performed at a temperature from 20° C. to 30° C. using a $C_1$-$C_4$ alkyl alcohol or haloalcohol as a solvent.

10. The method of claim 9, wherein the solvent is methanol, ethanol, or 2,2,2-trifluoroethanol.

11. A pharmaceutical composition comprising a bis-amide derivative compound of the following Formula 1 or a pharmaceutically acceptable salt thereof as an active ingredient:

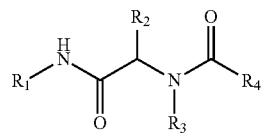

[Formula 1]

wherein:
$R_1$ is $C_1$-$C_6$ linear or branched alkyl, unsubstituted or substituted cyclohexyl, or unsubstituted or substituted benzyl;

$R_2$ is multiply substituted phenyl or unsubstituted or multiply substituted naphthyl, in which each substituent is independently $C_2$-$C_4$ alkyl, $C_1$-$C_4$ alkoxy, hydroxy, carboxy, nitro, halogen, or a 5-membered ring comprising a heteroatom formed by an interconnection between two adjacent substituents;

$R_3$ is unsubstituted or multiply substituted $C_1$-$C_6$ linear or branched alkyl, cyclohexyl, multiply substituted phenyl-$C_1$-$C_4$ alkyl, or unsubstituted or multiply substituted aryl, in which each substituent is independently $C_1$-$C_4$ alkoxy or halogen; and $R_4$ is unsubstituted or multiply substituted $C_1$-$C_6$ linear or branched alkyl, unsubstituted or multiply substituted phenyl, indolyl, or pyridinyl, or unsubstituted or multiply substituted phenylalkyl or indolylalkyl, in which each substituent is independently $C_1$-$C_4$ alkoxy, $C_1$-$C_4$ alkoxybenzyl, nitro, or halogen, with the proviso that when $R_4$ is unsubstituted or substituted indolyl or pyridinyl, the substituted phenyl of $R_2$ is substituted with $C_2$-$C_4$ alkyl, $C_1$-$C_4$ alkoxy, hydroxy, carboxy, nitro, or a 5-membered ring comprising a heteroatom formed by an interconnection between two adjacent substituents, wherein the substituted functional group of $R_1$ and $R_3$ includes one or more substituents selected from the group consisting of halogen, CN, $CF_3$, hydroxy, $C_1$-$C_6$ alkyl, and $C_1$-$C_6$ alkoxy.

12. The pharmaceutical composition of claim 11, further comprising a drug selected from the group consisting of interferon-α, ribavirin, telaprevir, and boceprevir.

13. A method for ameliorating or treating diseases caused in a subject by hepatitis C virus infection comprising administering a bis-amide derivative compound of the following Formula 1 or a pharmaceutically acceptable salt thereof to a subject in need thereof:

[Formula 1]

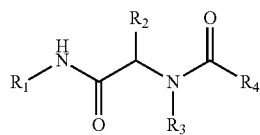

wherein:

$R_1$ is $C_1$-$C_6$ linear or branched alkyl, unsubstituted or substituted cyclohexyl, or unsubstituted or substituted benzyl;

$R_2$ is unsubstituted or multiply substituted aryl, in which each substituent is independently $C_1$-$C_4$ alkyl, $C_1$-$C_4$ alkoxy, hydroxy, carboxy, nitro, halogen, or a 5-membered ring comprising a heteroatom formed by an interconnection between two adjacent substituents;

$R_3$ is unsubstituted or multiply substituted $C_1$-$C_6$ linear or branched alkyl, cyclohexyl, unsubstituted or multiply substituted phenyl-$C_1$-$C_4$ alkyl, or unsubstituted or multiply substituted aryl, in which each substituent is independently $C_1$-$C_4$ alkoxy or halogen; and $R_4$ is unsubstituted or multiply substituted $C_1$-$C_6$ linear or branched alkyl, unsubstituted or multiply substituted arylalkyl with or without heteroatom(s), or unsubstituted or multiply substituted aryl with or without heteroatom(s), in which each substituent is independently $C_1$-$C_4$ alkoxy, $C_1$-$C_4$ alkoxybenzyl, nitro, or halogen, wherein the substituted functional group of $R_1$ and $R_3$ includes one or more substituent(s) selected from the group consisting halogen, CN, $CF_3$, hydroxy, $C_1$-$C_6$ alkyl, and $C_1$-$C_6$ alkoxy, and the diseases caused by hepatitis C virus are selected from the group consisting of hepatitis, liver cirrhosis, hepatocellular carcinoma, and liver hardening.

14. The method of claim 13, wherein the compound exhibits the antiviral activity by inhibiting the activity of PPIase by the inhibition of the activity of cyclophilin A.

15. The method of claim 13, wherein the compound inhibits the replication of hepatitis C virus.

16. The method of claim 13, wherein the compound or the pharmaceutically acceptable salt thereof is administered in combination with a drug selected from the group consisting of interferon-α, ribavirin, telaprevir, and boceprevir.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: forward primer for GAPDH

<400> SEQUENCE: 1
caactggtcg tggacaacca t                                    21

<210> SEQ ID NO 2
<211> LENGTH: 21
<212> TYPE: DNA
<213> ORGANISM: Artificial Sequence
<220> FEATURE:
<223> OTHER INFORMATION: reverse primer for GAPDH

<400> SEQUENCE: 2
gcacggacac tcacaatgtt c                                    21

<210> SEQ ID NO 3
<211> LENGTH: 18
<212> TYPE: DNA
<213> ORGANISM: Artificial Sequence
<220> FEATURE:
<223> OTHER INFORMATION: forward primer for STAT1

<400> SEQUENCE: 3
gtggaaagac agccctgc                                        18

<210> SEQ ID NO 4
<211> LENGTH: 21
<212> TYPE: DNA
<213> ORGANISM: Artificial Sequence
<220> FEATURE:
<223> OTHER INFORMATION: reverse primer for STAT1

<400> SEQUENCE: 4
tttactgtat ttctctcatt c                                    21

<210> SEQ ID NO 5
<211> LENGTH: 20
<212> TYPE: DNA
<213> ORGANISM: Artificial Sequence
<220> FEATURE:
<223> OTHER INFORMATION: forward primer for STAT2

<400> SEQUENCE: 5
tgcggaaatt ctgccgggac                                      20

<210> SEQ ID NO 6
<211> LENGTH: 20
<212> TYPE: DNA
<213> ORGANISM: Artificial Sequence
<220> FEATURE:
<223> OTHER INFORMATION: reverse primer for STAT2

<400> SEQUENCE: 6
ccagattctc catcatagcc                                      20

<210> SEQ ID NO 7
<211> LENGTH: 21
<212> TYPE: DNA
<213> ORGANISM: Artificial Sequence
<220> FEATURE:
<223> OTHER INFORMATION: forward primer for IRF9

<400> SEQUENCE: 7
cccgaaaact ccggaactgg g                                      21

<210> SEQ ID NO 8
<211> LENGTH: 21
<212> TYPE: DNA
<213> ORGANISM: Artificial Sequence
<220> FEATURE:
<223> OTHER INFORMATION: reverse primer for IRF9

<400> SEQUENCE: 8
aggcgagtct tccagacagc t                                      21

<210> SEQ ID NO 9
<211> LENGTH: 20
<212> TYPE: DNA
<213> ORGANISM: Artificial Sequence
<220> FEATURE:
<223> OTHER INFORMATION: forward primer for ISG15

<400> SEQUENCE: 9
gagcgtggcc cacctgaagc                                        20

<210> SEQ ID NO 10
<211> LENGTH: 20
<212> TYPE: DNA
<213> ORGANISM: Artificial Sequence
<220> FEATURE:
<223> OTHER INFORMATION: reverse primer for ISG15

<400> SEQUENCE: 10
tgaggccgta ctcccccagc                                        20

<210> SEQ ID NO 11
<211> LENGTH: 18
<212> TYPE: DNA
<213> ORGANISM: Artificial Sequence
<220> FEATURE:
<223> OTHER INFORMATION: forward primer for OAS1

<400> SEQUENCE: 11
cagcgcccca ccaagctc                                          18

<210> SEQ ID NO 12
<211> LENGTH: 20
<212> TYPE: DNA
<213> ORGANISM: Artificial Sequence
<220> FEATURE:
<223> OTHER INFORMATION: reverse primer for OAS1

<400> SEQUENCE: 12
tgctccctcg ctcccaagca                                        20

<210> SEQ ID NO 13
<211> LENGTH: 20
<212> TYPE: DNA
<213> ORGANISM: Artificial Sequence
<220> FEATURE:

```
<223> OTHER INFORMATION: forward primer for IFN-alpha

<400> SEQUENCE: 13
tgcaggagga gagggtggga                                              20

<210> SEQ ID NO 14
<211> LENGTH: 20
<212> TYPE: DNA
<213> ORGANISM: Artificial Sequence
<220> FEATURE:
<223> OTHER INFORMATION: reverse primer for IFN-alpha

<400> SEQUENCE: 14
acctcccagg cacaagggct                                              20

<210> SEQ ID NO 15
<211> LENGTH: 20
<212> TYPE: DNA
<213> ORGANISM: Artificial Sequence
<220> FEATURE:
<223> OTHER INFORMATION: forward primer for Con1b

<400> SEQUENCE: 15
actccccgga cgctgacctc                                              20

<210> SEQ ID NO 16
<211> LENGTH: 20
<212> TYPE: DNA
<213> ORGANISM: Artificial Sequence
<220> FEATURE:
<223> OTHER INFORMATION: reverse primer for Con1b

<400> SEQUENCE: 16
gcaggatctc cgccggaacg                                              20
```